US009872911B2

(12) United States Patent
Vegas et al.

(10) Patent No.: US 9,872,911 B2
(45) Date of Patent: Jan. 23, 2018

(54) ALPHA-AMINOAMIDINE POLYMERS AND USES THEREOF

(71) Applicant: Massachusetts Institute of Technology, Cambridge, MA (US)

(72) Inventors: Arturo Jose Vegas, Cambridge, MA (US); Kathryn Ann Whitehead, Pittsburgh, PA (US); Daniel Griffith Anderson, Sudbury, MA (US); Robert S. Langer, Newton, MA (US); Joseph R. Dorkin, Somerville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/364,028

(22) PCT Filed: Dec. 15, 2012

(86) PCT No.: PCT/US2012/069961
§ 371 (c)(1),
(2) Date: Jun. 9, 2014

(87) PCT Pub. No.: WO2013/090861
PCT Pub. Date: Jun. 20, 2013

(65) Prior Publication Data
US 2014/0322309 A1 Oct. 30, 2014

Related U.S. Application Data

(60) Provisional application No. 61/576,899, filed on Dec. 16, 2011.

(51) Int. Cl.
*A61K 47/34* (2017.01)
*A61K 9/127* (2006.01)
*A61K 31/713* (2006.01)
*A61K 9/51* (2006.01)
*C08G 73/00* (2006.01)
*C08L 79/00* (2006.01)
*A61K 33/00* (2006.01)
*A61K 38/16* (2006.01)
*A61K 39/00* (2006.01)
*C08G 12/06* (2006.01)
*C08G 12/34* (2006.01)
*C12N 15/113* (2010.01)

(52) U.S. Cl.
CPC ............ *A61K 47/34* (2013.01); *A61K 9/1271* (2013.01); *A61K 9/5146* (2013.01); *A61K 31/713* (2013.01); *A61K 33/00* (2013.01); *A61K 38/16* (2013.01); *A61K 39/00* (2013.01); *C08G 12/06* (2013.01); *C08G 12/34* (2013.01); *C08G 73/00* (2013.01); *C08L 79/00* (2013.01); *C12N 15/113* (2013.01)

(58) Field of Classification Search
CPC ...... A61K 31/713; A61K 33/00; A61K 38/16; A61K 39/00; A61K 47/34; A61K 9/1271; A61K 9/5146; C08G 12/06; C08G 12/34; C08G 73/00; C08L 79/00; C12N 15/113
USPC ............... 435/375; 424/184.1, 450, 451, 600
See application file for complete search history.

(56) References Cited

U.S. PATENT DOCUMENTS

| 5,284,910 | A | 2/1994 | Chang et al. |
| 6,315,981 | B1 | 11/2001 | Unger |
| 7,105,151 | B2 | 9/2006 | Unger et al. |
| 7,375,096 | B1 | 5/2008 | Davis et al. |
| 2003/0211139 | A1* | 11/2003 | Legon .................. A61K 9/1272 424/450 |
| 2005/0059005 | A1 | 3/2005 | Tuschl et al. |

(Continued)

FOREIGN PATENT DOCUMENTS

WO WO 01/37983 A1 5/2001
WO WO 2004/106411 A2 12/2004
(Continued)

OTHER PUBLICATIONS

Cai et al., Dication C(R1)—N(R2)2 Synthons and their use in the synthesis of formamidines, amidines, and α-aminonitriles. *Tetrahedron.* Oct. 13, 2000;56(42):8253-62. doi:10.1016/S0040-4020(00)00785-7.
Keung et al., Novel α-amino amidine synthesis via scandium(III) triflate mediated 3CC Ugi condensation reaction. *Tetrahedron Letts.* Jan. 19, 2004;45(4):733-737. doi:10.1016/j.tetlet.2003.11.051.
Kysil et al., TMSC1-promoted isocyanide-based MCR of ethylenediamines: an efficient assembling of 2-aminopyrazine core. *Tetrahedron Letts.* Sep. 3, 2007;48(36):6239-6244. doi:10.1016/j.tetlet.2007.07.044.
Kysil et al., General multicomponent strategy for the synthesis of 2-amino-1,4-diazaheterocycles: scope, limitations, and utility. *Eur J Org Chem.* Mar. 2010;2010(8):1525-43. Epub Feb. 8, 2010. doi: 10.1002/ejoc.200901360.

(Continued)

Primary Examiner — Janet L Epps-Smith
(74) Attorney, Agent, or Firm — Wolf, Greenfield & Sacks, P.C.

(57) ABSTRACT

α-Aminoamidine polymers and methods of preparing a-aminoamidine polymers by reacting by reacting one or more amines with one or more isocyanides and one or more aldehydes are described. Methods of preparing a-aminoamidine polymers from commercially available starting materials are also provided, wherein the starting materials are racemic or stereochemically pure. a-Aminoamidine polymers or salt forms thereof are preferably biodegradable and biocompatible and may be used in a variety of drug delivery systems and for other purposes as well such as, for example, coatings, additives, excipients, plastics, and materials, etc. Given the amino moiety of these α-aminoamidine polymers, they are particularly suited for the delivery of polynucleotides. Complexes, micelles, liposomes or particles containing the inventive α-aminoamidine polymers and polynucleotides can be prepared. The inventive α-aminoamidine polymers may also be used in preparing microparticles for drug delivery. They are particularly useful in delivering labile agents given their ability to buffer the pH of their surroundings.

40 Claims, 70 Drawing Sheets

(56) References Cited

U.S. PATENT DOCUMENTS

| | | |
|---|---|---|
| 2006/0210527 A1 | 9/2006 | Davis |
| 2007/0025952 A1 | 2/2007 | Davis et al. |
| 2008/0176958 A1 | 7/2008 | Davis et al. |
| 2008/0279954 A1 | 11/2008 | Davis et al. |
| 2009/0191244 A1 | 7/2009 | Kheir et al. |

FOREIGN PATENT DOCUMENTS

| | | | |
|---|---|---|---|
| WO | WO 2006/138380 A2 | 12/2006 | |
| WO | WO 2007/143659 A2 | 12/2007 | |
| WO | WO 2008/011561 A2 | 1/2008 | |
| WO | WO 2010/053572 A2 | 5/2010 | |

OTHER PUBLICATIONS

Akinc et al., A combinatorial library of lipid-like materials for delivery of RNAi therapeutics. Nat Biotechnol. May 2008;26(5):561-9. doi: 10.1038/nbt1402. Epub Apr. 27, 2008.

Byk et al., Synthesis, activity, and structure-activity relationship studies of novel cationic lipids for DNA transfer. J Med Chem. Jan. 15, 1998;41(2):224-35.

Cotten et al., Receptor-mediated transport of DNA into eukaryotic cells. Methods Enzymol. 1993;217:618-44.

Hofland et al., Formation of stable cationic lipid/DNA complexes for gene transfer. Proc Natl Acad Sci U S A. Jul. 9, 1996;93(14):7305-9.

Lukyanov et al., Micelles from lipid derivatives of water-soluble polymers as delivery systems for poorly soluble drugs. Adv Drug Deliv Rev. May 7, 2004;56(9):1273-89.

Mathiowitz et al., Novel microcapsules for delivery systems. Reactive Polymers, Ion Exchangers, Sorbents. Oct. 1987;6(2-3):275-283.

Mathiowitz et al., Polyanhydride microspheres as drug carriers. I. Hot-melt microencapsulation. J Control Rel. Jun. 1987;5(1):13-22.

Mathiowitz et al., Polyanhydride microspheres as drug carriers. II. Microencapsulation by solvent removal. J Appl Poly Sci. Feb. 1988;3:755-774.

McFarland et al., Reactions of Cyclohexylisonitrile and Isobutyraldehyde with Various Nucleophiles and Catalysts. J Org Chem. 1963;28(9):2179-2181.

Narang et al., Cationic lipids with increased DNA binding affinity for nonviral gene transfer in dividing and nondividing cells. Bioconjug Chem. Jan.-Feb. 2005;16(1):156-68.

Phillips et al., Enhanced antibody response to liposome-associated protein antigens: preferential stimulation of IgG2a/b production. Vaccine. 1992;10(3):151-8.

Tranchant et al., Physicochemical optimisation of plasmid delivery by cationic lipids. J Gene Med. Feb. 2004;6 Suppl 1:S24-35.

Van Balen et al., Liposome/water lipophilicity: methods, information content, and pharmaceutical applications. Med Res Rev. May 2004;24(3):299-324.

Wu et al., Cationic lipid polymerization as a novel approach for constructing new DNA delivery agents. Bioconjug Chem. Mar.-Apr. 2001;12(2):251-7.

International Search Report and Written Opinion for PCT/US2012/069961, dated Feb. 14, 2013.

International Preliminary Report on Patentability for PCT/US2012/069961, dated Jun. 26, 2014.

Keung et al., Novel α-amino amidine synthesis via scandium(III) triflate mediated 3CC Ugi condensation reaction. Tetrahedron Lett. 2004;45(4):733-37.

\* cited by examiner wherein each X', Y', and Z' is, independently, a substituent of the formula:

wherein $W^3$ is $R^2$ or a group of formula:

Library ID 104180

| | 1 | 2 | 3 | 4 | 5 | 6 | 7 | 8 | 9 | 10 | 11 | 12 |
|---|---|---|---|---|---|---|---|---|---|---|---|---|
| A | Isocyanide1 / Aldehyde1 / Silane1 | Isocyanide2 / Aldehyde1 / Silane1 | Isocyanide3 / Aldehyde1 / Silane1 | Isocyanide4 / Aldehyde1 / Silane1 | Isocyanide5 / Aldehyde1 / Silane1 | Isocyanide6 / Aldehyde1 / Silane1 | Cells Only Negative Control | Isocyanide8 / Aldehyde1 / Silane1 | Isocyanide9 / Aldehyde1 / Silane1 | Isocyanide10 / Aldehyde1 / Silane1 | Isocyanide1 / Aldehyde3 / Silane1 | Isocyanide7 / Aldehyde1 / Silane1 |
| B | Isocyanide1 / Aldehyde2 / Silane1 | Isocyanide2 / Aldehyde2 / Silane1 | Isocyanide3 / Aldehyde2 / Silane1 | Isocyanide4 / Aldehyde2 / Silane1 | Isocyanide5 / Aldehyde2 / Silane1 | Cells Only Negative Control | Isocyanide7 / Aldehyde2 / Silane1 | Isocyanide8 / Aldehyde2 / Silane1 | Isocyanide9 / Aldehyde2 / Silane1 | Isocyanide10 / Aldehyde2 / Silane1 | Isocyanide2 / Aldehyde4 / Silane1 | Isocyanide8 / Aldehyde2 / Silane1 |
| C | Lipo Positive Control | Isocyanide2 / Aldehyde3 / Silane1 | Isocyanide3 / Aldehyde3 / Silane1 | Isocyanide4 / Aldehyde3 / Silane1 | Cells Only Negative Control | Isocyanide6 / Aldehyde3 / Silane1 | Isocyanide7 / Aldehyde3 / Silane1 | Cells Only Negative Control | Cells Only Negative Control | Isocyanide10 / Aldehyde3 / Silane1 | Isocyanide3 / Aldehyde5 / Silane1 | Isocyanide9 / Aldehyde3 / Silane1 |
| D | Isocyanide1 / Aldehyde4 / Silane1 | Isocyanide2 / Aldehyde4 / Silane1 | Lipo Positive Control | Isocyanide4 / Aldehyde4 / Silane1 | Isocyanide5 / Aldehyde4 / Silane1 | Isocyanide6 / Aldehyde4 / Silane1 | Isocyanide7 / Aldehyde4 / Silane1 | Isocyanide8 / Aldehyde4 / Silane1 | Isocyanide9 / Aldehyde4 / Silane1 | Cells Only Negative Control | Isocyanide4 / Aldehyde6 / Silane1 | Isocyanide10 / Aldehyde4 / Silane1 |
| E | Isocyanide2 / Aldehyde5 / Silane1 | Isocyanide2 / Aldehyde5 / Silane1 | Isocyanide3 / Aldehyde5 / Silane1 | Isocyanide4 / Aldehyde5 / Silane1 | Isocyanide5 / Aldehyde5 / Silane1 | Isocyanide6 / Aldehyde5 / Silane1 | Isocyanide7 / Aldehyde5 / Silane1 | Isocyanide8 / Aldehyde5 / Silane1 | Isocyanide9 / Aldehyde5 / Silane1 | Isocyanide10 / Aldehyde5 / Silane1 | Isocyanide5 / Aldehyde7 / Silane1 | Cells Only Negative Control |
| F | Isocyanide2 / Aldehyde6 / Silane1 | Isocyanide2 / Aldehyde6 / Silane1 | Isocyanide3 / Aldehyde6 / Silane1 | Isocyanide4 / Aldehyde6 / Silane1 | Isocyanide5 / Aldehyde6 / Silane1 | Isocyanide6 / Aldehyde6 / Silane1 | Lipo Positive Control | Lipo Positive Control | Isocyanide9 / Aldehyde6 / Silane1 | Isocyanide10 / Aldehyde6 / Silane1 | Isocyanide6 / Aldehyde6 / Silane1 | Isocyanide8 / Aldehyde6 / Silane1 |
| G | Isocyanide2 / Aldehyde7 / Silane1 | Isocyanide2 / Aldehyde7 / Silane1 | Isocyanide3 / Aldehyde7 / Silane1 | Isocyanide4 / Aldehyde7 / Silane1 | Isocyanide5 / Aldehyde7 / Silane1 | Isocyanide6 / Aldehyde7 / Silane1 | Isocyanide7 / Aldehyde7 / Silane1 | Isocyanide8 / Aldehyde7 / Silane1 | Isocyanide9 / Aldehyde7 / Silane1 | Isocyanide10 / Aldehyde7 / Silane1 | Isocyanide4 / Aldehyde6 / Silane1 | Isocyanide7 / Aldehyde7 / Silane1 |
| H | Isocyanide2 / Aldehyde8 / Silane1 | Isocyanide2 / Aldehyde8 / Silane1 | Isocyanide3 / Aldehyde8 / Silane1 | Isocyanide4 / Aldehyde8 / Silane1 | Isocyanide5 / Aldehyde8 / Silane1 | Isocyanide6 / Aldehyde8 / Silane1 | Isocyanide7 / Aldehyde8 / Silane1 | Isocyanide8 / Aldehyde8 / Silane1 | Isocyanide9 / Aldehyde8 / Silane1 | Isocyanide10 / Aldehyde8 / Silane1 | Isocyanide5 / Aldehyde7 / Silane1 | Isocyanide6 / Aldehyde1 / Silane1 |

Figure 13

|   | 1 | 2 | 3 | 4 | 5 | 6 | 7 | 8 | 9 | 10 | 11 | 12 |
|---|---|---|---|---|---|---|---|---|---|---|---|---|
| A | 1 | 9 | 17 | 25 | 33 | 41 | Cells | 57 | 65 | 73 | 3 | 49 |
| B | 2 | 10 | 18 | 26 | 34 | Cells | 50 | Cells | 66 | 74 | 12 | 58 |
| C | Lipo | 11 | 19 | 27 | Cells | 43 | 51 | 59 | Cells | 75 | 35 | 67 |
| D | 4 | Lipo | 20 | 28 | 36 | 44 | 52 | 60 | 68 | Cells | 42 | 76 |
| E | 5 | 13 | Lipo | 29 | 37 | 45 | 53 | 61 | 69 | 77 | Cells | 62 |
| F | 6 | 14 | 22 | Lipo | 38 | 46 | 54 | Lipo | 70 | 78 | 21 | Cells |
| G | 7 | 15 | 23 | 31 | Lipo | 47 | Lipo | 63 | 71 | 79 | 30 | 55 |
| H | 8 | 16 | 24 | 32 | 40 | Lipo | 56 | 64 | 72 | 80 | 39 | 48 |

Figure 13
continued

Library ID 104181

|   | 1 | 2 | 3 | 4 | 5 | 6 | 7 | 8 | 9 | 10 | 11 | 12 |
|---|---|---|---|---|---|---|---|---|---|----|----|----|
| A | Isocyanide1 Aldehyde9 Silane1 | Isocyanide2 Aldehyde9 Silane1 | Isocyanide3 Aldehyde9 Silane1 | Isocyanide4 Aldehyde9 Silane1 | Isocyanide5 Aldehyde9 Silane1 | Isocyanide6 Aldehyde9 Silane1 | Cells Only Negative Control | Isocyanide8 Aldehyde9 Silane1 | Isocyanide9 Aldehyde9 Silane1 | Isocyanide10 Aldehyde9 Silane1 | Isocyanide1 Aldehyde1 Silane3 | Isocyanide7 Aldehyde1 Silane1 |
| B | Isocyanide1 Aldehyde10 Silane1 | Isocyanide2 Aldehyde10 Silane1 | Isocyanide3 Aldehyde10 Silane1 | Isocyanide4 Aldehyde10 Silane1 | Isocyanide5 Aldehyde10 Silane1 | Isocyanide6 Aldehyde9 Silane1 | Isocyanide7 Aldehyde10 Silane1 | Cells Only Negative Control | Isocyanide9 Aldehyde10 Silane1 | Isocyanide10 Aldehyde10 Silane1 | Isocyanide2 Aldehyde2 Silane3 | Isocyanide8 Aldehyde10 Silane1 |
| C | Isocyanide2 Aldehyde1 Silane3 | Isocyanide2 Aldehyde1 Silane3 | Isocyanide3 Aldehyde1 Silane3 | Isocyanide4 Aldehyde1 Silane3 | Cells Only Negative Control | Isocyanide6 Aldehyde1 Silane3 | Isocyanide7 Aldehyde1 Silane3 | Isocyanide8 Aldehyde1 Silane3 | Cells Only Negative Control | Isocyanide10 Aldehyde1 Silane3 | Isocyanide5 Aldehyde1 Silane3 | Isocyanide9 Aldehyde1 Silane3 |
| D | Isocyanide1 Aldehyde2 Silane3 | Lipo Positive Control | Isocyanide3 Aldehyde2 Silane3 | Isocyanide4 Aldehyde2 Silane3 | Isocyanide5 Aldehyde2 Silane3 | Isocyanide6 Aldehyde2 Silane3 | Isocyanide7 Aldehyde2 Silane3 | Isocyanide8 Aldehyde2 Silane3 | Isocyanide9 Aldehyde2 Silane3 | Cells Only Negative Control | Isocyanide6 Aldehyde10 Silane1 | Isocyanide10 Aldehyde2 Silane3 |
| E | Isocyanide1 Aldehyde3 Silane3 | Isocyanide2 Aldehyde3 Silane3 | Lipo Positive Control | Isocyanide4 Aldehyde3 Silane3 | Isocyanide5 Aldehyde3 Silane3 | Isocyanide6 Aldehyde3 Silane3 | Isocyanide7 Aldehyde3 Silane3 | Isocyanide8 Aldehyde3 Silane3 | Isocyanide9 Aldehyde3 Silane3 | Isocyanide10 Aldehyde3 Silane3 | Isocyanide6 Aldehyde10 Silane1 | Isocyanide10 Aldehyde2 Silane3 |
| F | Isocyanide1 Aldehyde4 Silane3 | Isocyanide2 Aldehyde4 Silane3 | Isocyanide3 Aldehyde4 Silane3 | Lipo Positive Control | Isocyanide5 Aldehyde4 Silane3 | Isocyanide6 Aldehyde4 Silane3 | Isocyanide7 Aldehyde4 Silane3 | Lipo Positive Control | Isocyanide9 Aldehyde4 Silane3 | Isocyanide10 Aldehyde4 Silane3 | Isocyanide3 Aldehyde3 Silane3 | Isocyanide8 Aldehyde4 Silane3 |
| G | Isocyanide2 Aldehyde4 Silane3 | Isocyanide2 Aldehyde5 Silane3 | Isocyanide3 Aldehyde5 Silane3 | Isocyanide4 Aldehyde5 Silane3 | Lipo Positive Control | Isocyanide6 Aldehyde5 Silane3 | Isocyanide7 Aldehyde5 Silane3 | Isocyanide8 Aldehyde5 Silane3 | Isocyanide9 Aldehyde5 Silane3 | Isocyanide10 Aldehyde5 Silane3 | Isocyanide4 Aldehyde4 Silane3 | Isocyanide7 Aldehyde5 Silane3 |
| H | Isocyanide2 Aldehyde6 Silane3 | Isocyanide2 Aldehyde6 Silane3 | Isocyanide3 Aldehyde6 Silane3 | Isocyanide4 Aldehyde6 Silane3 | Isocyanide5 Aldehyde6 Silane3 | Lipo Positive Control | Isocyanide7 Aldehyde6 Silane3 | Isocyanide8 Aldehyde6 Silane3 | Isocyanide9 Aldehyde6 Silane3 | Isocyanide10 Aldehyde6 Silane3 | Isocyanide5 Aldehyde5 Silane3 | Isocyanide6 Aldehyde6 Silane3 |

Figure 14

|   | 1 | 2 | 3 | 4 | 5 | 6 | 7 | 8 | 9 | 10 | 11 | 12 |
|---|---|---|---|---|---|---|---|---|---|----|----|----|
| A | 1 | 9 | 17 | 25 | 33 | 41 | Cells | 57 | 65 | 73 | 3 | 49 |
| B | 2 | 10 | 18 | 26 | 34 | Cells | 50 | Cells | 66 | 74 | 12 | 58 |
| C | Lipo | 11 | 19 | 27 | Cells | 43 | 51 | 59 | Cells | 75 | 35 | 67 |
| D | 4 | Lipo | 20 | 28 | 36 | 44 | 52 | 60 | 68 | Cells | 42 | 76 |
| E | 5 | 13 | Lipo | 29 | 37 | 45 | 53 | 61 | 69 | 77 | Cells | 62 |
| F | 6 | 14 | 22 | Lipo | 38 | 46 | 54 | Lipo | 70 | 78 | 21 | Cells |
| G | 7 | 15 | 23 | 31 | Lipo | 47 | Lipo | 63 | 71 | 79 | 30 | 55 |
| H | 8 | 16 | 24 | 32 | 40 | Lipo | 56 | 64 | 72 | 80 | 39 | 48 |

Library ID 104182

| | 1 | 2 | 3 | 4 | 5 | 6 | 7 | 8 | 9 | 10 | 11 | 12 |
|---|---|---|---|---|---|---|---|---|---|---|---|---|
| A | Isocyanide1 Aldehyde7 Silane3 | Isocyanide2 Aldehyde7 Silane3 | Isocyanide3 Aldehyde7 Silane3 | Isocyanide4 Aldehyde7 Silane3 | Isocyanide5 Aldehyde7 Silane3 | Isocyanide6 Aldehyde7 Silane3 | Cells Only Negative Control | Isocyanide8 Aldehyde7 Silane3 | Isocyanide9 Aldehyde7 Silane3 | Isocyanide10 Aldehyde7 Silane3 | Isocyanide1 Aldehyde9 Silane3 | Isocyanide7 Aldehyde7 Silane3 |
| B | Isocyanide1 Aldehyde8 Silane3 | Isocyanide2 Aldehyde8 Silane3 | Isocyanide3 Aldehyde8 Silane3 | Isocyanide4 Aldehyde8 Silane3 | Isocyanide5 Aldehyde8 Silane3 | Isocyanide6 Aldehyde8 Silane3 | Isocyanide7 Aldehyde8 Silane3 | Cells Only Negative Control | Isocyanide9 Aldehyde8 Silane3 | Isocyanide10 Aldehyde8 Silane3 | Isocyanide2 Aldehyde10 Silane3 | Isocyanide8 Aldehyde8 Silane3 |
| C | Isocyanide1 Aldehyde9 Silane3 | Isocyanide2 Aldehyde9 Silane3 | Isocyanide3 Aldehyde9 Silane3 | Isocyanide4 Aldehyde9 Silane3 | Cells Only Negative Control | Isocyanide6 Aldehyde9 Silane3 | Isocyanide7 Aldehyde9 Silane3 | Isocyanide8 Aldehyde9 Silane3 | Cells Only Negative Control | Isocyanide10 Aldehyde9 Silane3 | Isocyanide5 Aldehyde9 Silane3 | Isocyanide9 Aldehyde9 Silane3 |
| D | Isocyanide1 Aldehyde10 Silane3 | Lipo Positive Control | Isocyanide3 Aldehyde10 Silane3 | Isocyanide4 Aldehyde10 Silane3 | Isocyanide5 Aldehyde10 Silane3 | Isocyanide6 Aldehyde10 Silane3 | Isocyanide7 Aldehyde10 Silane3 | Isocyanide8 Aldehyde10 Silane3 | Isocyanide9 Aldehyde10 Silane3 | Cells Only Negative Control | Isocyanide6 Aldehyde8 Silane3 | Isocyanide10 Aldehyde9 Silane3 |
| E | Isocyanide2 Aldehyde1 Silane4 | Isocyanide2 Aldehyde1 Silane4 | Isocyanide3 Aldehyde1 Silane4 | Isocyanide4 Aldehyde1 Silane4 | Isocyanide5 Aldehyde1 Silane4 | Isocyanide6 Aldehyde1 Silane4 | Isocyanide7 Aldehyde1 Silane4 | Isocyanide8 Aldehyde1 Silane4 | Isocyanide9 Aldehyde1 Silane4 | Isocyanide10 Aldehyde1 Silane4 | Cells Only Negative Control | Isocyanide8 Aldehyde2 Silane4 |
| F | Isocyanide2 Aldehyde2 Silane4 | Isocyanide2 Aldehyde2 Silane4 | Lipo Positive Control | Lipo Positive Control | Lipo Positive Control | Lipo Positive Control | Lipo Positive Control | Lipo Positive Control | Isocyanide9 Aldehyde2 Silane4 | Isocyanide10 Aldehyde2 Silane4 | Isocyanide3 Aldehyde1 Silane4 | Isocyanide2 Aldehyde9 Silane4 |
| G | Isocyanide2 Aldehyde3 Silane4 | Isocyanide2 Aldehyde3 Silane4 | Isocyanide3 Aldehyde3 Silane4 | Isocyanide4 Aldehyde3 Silane4 | Isocyanide5 Aldehyde3 Silane4 | Isocyanide6 Aldehyde3 Silane4 | Isocyanide7 Aldehyde3 Silane4 | Isocyanide8 Aldehyde3 Silane4 | Isocyanide9 Aldehyde3 Silane4 | Isocyanide10 Aldehyde3 Silane4 | Isocyanide4 Aldehyde2 Silane4 | Isocyanide7 Aldehyde3 Silane4 |
| H | Isocyanide2 Aldehyde4 Silane4 | Isocyanide2 Aldehyde4 Silane4 | Isocyanide3 Aldehyde4 Silane4 | Isocyanide4 Aldehyde4 Silane4 | Isocyanide5 Aldehyde4 Silane4 | Isocyanide6 Aldehyde4 Silane4 | Isocyanide7 Aldehyde4 Silane4 | Isocyanide8 Aldehyde4 Silane4 | Isocyanide9 Aldehyde4 Silane4 | Isocyanide10 Aldehyde4 Silane4 | Isocyanide5 Aldehyde3 Silane4 | Isocyanide6 Aldehyde4 Silane4 |

|   | 1 | 2 | 3 | 4 | 5 | 6 | 7 | 8 | 9 | 10 | 11 | 12 |
|---|---|---|---|---|---|---|---|---|---|----|----|----|
| A | 1 | 9 | 17 | 25 | 33 | 41 | Cells | 57 | 65 | 73 | 3 | 49 |
| B | 2 | 10 | 18 | 26 | 34 | Cells | 50 | Cells | 66 | 74 | 12 | 58 |
| C | Lipo | 11 | 19 | 27 | Cells | 43 | 51 | 59 | Cells | 75 | 35 | 67 |
| D | 4 | Lipo | 20 | 28 | 36 | 44 | 52 | 60 | 68 | Cells | 42 | 76 |
| E | 5 | 13 | Lipo | 29 | 37 | 45 | 53 | 61 | 69 | 77 | Cells | 62 |
| F | 6 | 14 | 22 | Lipo | 38 | 46 | 54 | Lipo | 70 | 78 | 21 | Cells |
| G | 7 | 15 | 23 | 31 | Lipo | 47 | Lipo | 63 | 71 | 79 | 30 | 55 |
| H | 8 | 16 | 24 | 32 | 40 | Lipo | 56 | 64 | 72 | 80 | 39 | 48 |

Figure 15
continued

Library ID 104183

| | 1 | 2 | 3 | 4 | 5 | 6 | 7 | 8 | 9 | 10 | 11 | 12 |
|---|---|---|---|---|---|---|---|---|---|---|---|---|
| A | Isocyanide1 Aldehyde5 Silane4 | Isocyanide2 Aldehyde5 Silane4 | Isocyanide3 Aldehyde5 Silane4 | Isocyanide4 Aldehyde5 Silane4 | Isocyanide5 Aldehyde5 Silane4 | Isocyanide6 Aldehyde5 Silane4 | Cells Only Negative Control | Isocyanide8 Aldehyde5 Silane4 | Isocyanide9 Aldehyde5 Silane4 | Isocyanide10 Aldehyde5 Silane4 | Isocyanide1 Aldehyde5 Silane4 | Isocyanide7 Aldehyde5 Silane4 |
| B | Isocyanide1 Aldehyde6 Silane4 | Isocyanide2 Aldehyde6 Silane4 | Isocyanide3 Aldehyde6 Silane4 | Isocyanide4 Aldehyde6 Silane4 | Isocyanide5 Aldehyde6 Silane4 | Cells Only Negative Control | Isocyanide7 Aldehyde6 Silane4 | Cells Only Negative Control | Isocyanide9 Aldehyde6 Silane4 | Isocyanide10 Aldehyde6 Silane4 | Isocyanide2 Aldehyde6 Silane4 | Isocyanide8 Aldehyde6 Silane4 |
| C | Lipo Positive Control | Isocyanide2 Aldehyde7 Silane4 | Isocyanide3 Aldehyde7 Silane4 | Isocyanide4 Aldehyde7 Silane4 | Cells Only Negative Control | Isocyanide6 Aldehyde7 Silane4 | Isocyanide7 Aldehyde7 Silane4 | Isocyanide8 Aldehyde7 Silane4 | Cells Only Negative Control | Isocyanide10 Aldehyde7 Silane4 | Isocyanide5 Aldehyde7 Silane4 | Isocyanide9 Aldehyde7 Silane4 |
| D | Isocyanide1 Aldehyde8 Silane4 | Lipo Positive Control | Isocyanide3 Aldehyde8 Silane4 | Isocyanide4 Aldehyde8 Silane4 | Isocyanide5 Aldehyde8 Silane4 | Isocyanide6 Aldehyde8 Silane4 | Isocyanide7 Aldehyde8 Silane4 | Isocyanide8 Aldehyde6 Silane4 | Isocyanide9 Aldehyde8 Silane4 | Cells Only Negative Control | Isocyanide6 Aldehyde6 Silane4 | Isocyanide10 Aldehyde8 Silane4 |
| E | Isocyanide2 Aldehyde9 Silane4 | Isocyanide2 Aldehyde9 Silane4 | Isocyanide3 Aldehyde9 Silane4 | Isocyanide4 Aldehyde9 Silane4 | Isocyanide5 Aldehyde9 Silane4 | Isocyanide6 Aldehyde9 Silane4 | Isocyanide7 Aldehyde9 Silane4 | Isocyanide8 Aldehyde9 Silane4 | Isocyanide9 Aldehyde10 Silane4 | Isocyanide10 Aldehyde9 Silane4 | Cells Only Negative Control | Isocyanide8 Aldehyde10 Silane4 |
| F | Isocyanide2 Aldehyde10 Silane4 | Isocyanide2 Aldehyde10 Silane4 | Isocyanide3 Aldehyde10 Silane4 | Lipo Positive Control | Isocyanide5 Aldehyde10 Silane4 | Isocyanide6 Aldehyde10 Silane4 | Lipo Positive Control | Lipo Positive Control | Isocyanide9 Aldehyde10 Silane4 | Isocyanide10 Aldehyde10 Silane4 | Isocyanide3 Aldehyde10 Silane4 | Isocyanide7 Aldehyde10 Silane4 |
| G | Isocyanide2 Aldehyde1 Silane5 | Isocyanide2 Aldehyde1 Silane5 | Isocyanide3 Aldehyde1 Silane5 | Isocyanide4 Aldehyde1 Silane5 | Isocyanide5 Aldehyde1 Silane5 | Isocyanide6 Aldehyde1 Silane5 | Isocyanide7 Aldehyde1 Silane5 | Isocyanide8 Aldehyde1 Silane5 | Isocyanide9 Aldehyde1 Silane5 | Isocyanide10 Aldehyde1 Silane5 | Isocyanide4 Aldehyde10 Silane4 | Isocyanide7 Aldehyde1 Silane5 |
| H | Isocyanide2 Aldehyde2 Silane5 | Isocyanide2 Aldehyde2 Silane5 | Isocyanide3 Aldehyde2 Silane5 | Isocyanide4 Aldehyde2 Silane5 | Isocyanide5 Aldehyde2 Silane5 | Isocyanide6 Aldehyde2 Silane5 | Isocyanide7 Aldehyde2 Silane5 | Isocyanide8 Aldehyde2 Silane5 | Isocyanide9 Aldehyde2 Silane5 | Isocyanide10 Aldehyde2 Silane5 | Isocyanide5 Aldehyde1 Silane5 | Isocyanide6 Aldehyde2 Silane5 |

Figure 16

| | 1 | 2 | 3 | 4 | 5 | 6 | 7 | 8 | 9 | 10 | 11 | 12 |
|---|---|---|---|---|---|---|---|---|---|---|---|---|
| A | 1 | 9 | 17 | 25 | 33 | 41 | Cells | 57 | 65 | 73 | 3 | 49 |
| B | 2 | 10 | 18 | 26 | 34 | Cells | 50 | Cells | 66 | 74 | 12 | 58 |
| C | Lipo | 11 | 19 | 27 | Cells | 43 | 51 | 59 | Cells | 75 | 35 | 67 |
| D | 4 | Lipo | 20 | 28 | 36 | 44 | 52 | 60 | 68 | Cells | 42 | 76 |
| E | 5 | 13 | Lipo | 29 | 37 | 45 | 53 | 61 | 69 | 77 | Cells | 62 |
| F | 6 | 14 | 22 | Lipo | 38 | 46 | 54 | Lipo | 70 | 78 | 21 | Cells |
| G | 7 | 15 | 23 | 31 | Lipo | 47 | Lipo | 63 | 71 | 79 | 30 | 55 |
| H | 8 | 16 | 24 | 32 | 40 | Lipo | 56 | 64 | 72 | 80 | 39 | 48 |

Figure 16
continued

Library ID 104184

| | 1 | 2 | 3 | 4 | 5 | 6 | 7 | 8 | 9 | 10 | 11 | 12 |
|---|---|---|---|---|---|---|---|---|---|---|---|---|
| A | Isocyanide1 Aldehyde3 Silane5 | Isocyanide2 Aldehyde3 Silane5 | Isocyanide3 Aldehyde3 Silane5 | Isocyanide4 Aldehyde3 Silane5 | Isocyanide5 Aldehyde3 Silane5 | Isocyanide6 Aldehyde3 Silane5 | Cells Only Negative Control | Isocyanide8 Aldehyde3 Silane5 | Isocyanide9 Aldehyde3 Silane5 | Isocyanide10 Aldehyde3 Silane5 | Isocyanide1 Aldehyde5 Silane5 | Isocyanide7 Aldehyde3 Silane5 |
| B | Isocyanide1 Aldehyde4 Silane5 | Isocyanide2 Aldehyde4 Silane5 | Isocyanide3 Aldehyde4 Silane5 | Isocyanide4 Aldehyde4 Silane5 | Isocyanide5 Aldehyde4 Silane5 | Cells Only Negative Control | Isocyanide7 Aldehyde4 Silane5 | Cells Only Negative Control | Isocyanide9 Aldehyde4 Silane5 | Isocyanide10 Aldehyde4 Silane5 | Isocyanide2 Aldehyde5 Silane5 | Isocyanide8 Aldehyde4 Silane5 |
| C | Isocyanide1 Aldehyde5 Silane5 | Isocyanide2 Aldehyde5 Silane5 | Isocyanide3 Aldehyde5 Silane5 | Isocyanide4 Aldehyde5 Silane5 | Cells Only Negative Control | Isocyanide6 Aldehyde5 Silane5 | Isocyanide7 Aldehyde5 Silane5 | Isocyanide8 Aldehyde5 Silane5 | Cells Only Negative Control | Isocyanide10 Aldehyde5 Silane5 | Isocyanide5 Aldehyde5 Silane5 | Isocyanide9 Aldehyde5 Silane5 |
| D | Isocyanide1 Aldehyde6 Silane5 | Isocyanide2 Aldehyde7 Silane5 | Lipo Positive Control | Isocyanide4 Aldehyde6 Silane5 | Isocyanide5 Aldehyde6 Silane5 | Isocyanide6 Aldehyde6 Silane5 | Isocyanide7 Aldehyde6 Silane5 | Isocyanide8 Aldehyde6 Silane5 | Isocyanide9 Aldehyde6 Silane5 | Cells Only Negative Control | Isocyanide10 Aldehyde6 Silane5 | Isocyanide10 Aldehyde6 Silane5 |
| E | Isocyanide1 Aldehyde7 Silane5 | Isocyanide2 Aldehyde7 Silane5 | Isocyanide3 Aldehyde7 Silane5 | Isocyanide4 Aldehyde7 Silane5 | Isocyanide5 Aldehyde7 Silane5 | Isocyanide6 Aldehyde7 Silane5 | Isocyanide7 Aldehyde7 Silane5 | Isocyanide8 Aldehyde7 Silane5 | Isocyanide9 Aldehyde7 Silane5 | Isocyanide10 Aldehyde7 Silane5 | Cells Only Negative Control | Isocyanide8 Aldehyde5 Silane5 |
| F | Isocyanide2 Aldehyde7 Silane5 | Lipo Positive Control | Isocyanide3 Aldehyde8 Silane5 | Lipo Positive Control | Isocyanide5 Aldehyde8 Silane5 | Isocyanide6 Aldehyde8 Silane5 | Isocyanide7 Aldehyde8 Silane5 | Lipo Positive Control | Isocyanide9 Aldehyde8 Silane5 | Isocyanide10 Aldehyde8 Silane5 | Isocyanide4 Aldehyde5 Silane5 | Isocyanide8 Aldehyde5 Silane5 |
| G | Isocyanide2 Aldehyde8 Silane5 | Isocyanide2 Aldehyde8 Silane5 | Isocyanide3 Aldehyde9 Silane5 | Isocyanide4 Aldehyde9 Silane5 | Lipo Positive Control | Isocyanide6 Aldehyde9 Silane5 | Lipo Positive Control | Isocyanide8 Aldehyde9 Silane5 | Isocyanide9 Aldehyde9 Silane5 | Isocyanide10 Aldehyde9 Silane5 | Isocyanide5 Aldehyde5 Silane5 | Isocyanide7 Aldehyde5 Silane5 |
| H | Isocyanide2 Aldehyde10 Silane5 | Isocyanide2 Aldehyde10 Silane5 | Isocyanide3 Aldehyde10 Silane5 | Isocyanide4 Aldehyde10 Silane5 | Isocyanide5 Aldehyde10 Silane5 | Isocyanide6 Aldehyde10 Silane5 | Isocyanide7 Aldehyde10 Silane5 | Isocyanide8 Aldehyde10 Silane5 | Isocyanide9 Aldehyde10 Silane5 | Isocyanide10 Aldehyde10 Silane5 | Isocyanide4 Aldehyde5 Silane5 | Isocyanide6 Aldehyde5 Silane5 |

Figure 17

|   | 1 | 2 | 3 | 4 | 5 | 6 | 7 | 8 | 9 | 10 | 11 | 12 |
|---|---|---|---|---|---|---|---|---|---|---|---|---|
| A | 1 | 9 | 17 | 25 | 33 | 41 | Cells | 57 | 65 | 73 | 3 | 49 |
| B | 2 | 10 | 18 | 26 | 34 | Cells | 50 | Cells | 66 | 74 | 12 | 58 |
| C | Lipo | 11 | 19 | 27 | Cells | 43 | 51 | 59 | Cells | 75 | 35 | 67 |
| D | 4 | Lipo | 20 | 28 | 36 | 44 | 52 | 60 | 68 | Cells | 42 | 76 |
| E | 5 | 13 | Lipo | 29 | 37 | 45 | 53 | 61 | 69 | 77 | Cells | 62 |
| F | 6 | 14 | 22 | Lipo | 38 | 46 | 54 | Lipo | 70 | 78 | 21 | Cells |
| G | 7 | 15 | 23 | 31 | Lipo | 47 | Lipo | 63 | 71 | 79 | 30 | 55 |
| H | 8 | 16 | 24 | 32 | 40 | Lipo | 56 | 64 | 72 | 80 | 39 | 48 |

Figure 17
continued

ALPHA-AMINOAMIDINE POLYMERS AND USES THEREOF

RELATED APPLICATIONS

The present application claims priority under 35 U.S.C. § 119(e) to U.S. provisional patent application, U.S. Ser. No. 61/576,899, filed Dec. 16, 2011, which is incorporated herein by reference.

GOVERNMENT SUPPORT

This invention was made with Government support under Grant No. EB000244 awarded by the National Institutes of Health. The Government has certain rights in this invention.

BACKGROUND OF THE INVENTION

Therapeutic intervention with nucleic acids is a promising strategy for the treatment of human disease. The safe and effective delivery of nucleic acids into cells, however, remains a significant obstacle. Virus-based delivery has been investigated thoroughly and has shown good efficacy yet concerns about toxicity and immunogenicity limit the clinical potential of this approach. Non-viral vectors such as cationic polymers are now receiving increased attention as effective nucleic acid delivery agents because of their demonstrated delivery potential. In order for these synthetic vectors to be clinically effective, they must meet several criteria: 1) form particles (e.g., nanoparticles) with nucleic acids, 2) mediate delivery into the target cells of interest (transfection) 3) low toxicity, low immunogenicity, and biodegradability. Although much progress has been made, significant challenges remain as to date there are still no FDA approved treatments utilizing RNAi interference (siRNA) or for gene (DNA) therapy. Increasing the chemical diversity of available polymers may assist in the development of new safe and effective materials, and increase the probability of clinical success.

Despite promise in the laboratory, the potential of genetic therapies for the treatment of disease has yet to be realized. Initial attempts to translate genetic materials into cures led to cancer and, in some cases, death to patients involved in the clinical trials. Such deleterious outcomes were attributed not to the genetic material, but to the viral delivery systems utilized in these trials. As a result, there has been intense interest in developing synthetic materials that have the delivery efficiencies of viral vectors but circumvent the mutagenesis that led to the observed side effects (e.g., cancer).

Synthetic materials, or nonviral delivery vectors, come in a variety of forms that work in unique ways. Polymeric materials such as polyethylenimine or poly(beta-amino ester)s have been shown to efficiently complex DNA for delivery into the cell. Polymers in these classes of delivery agents typically contain amine functionalities that serve to electrostatically bind to DNA to form nanoparticles that are then taken up by the cell via endocytosis. Once in the cell, these amine groups serve to buffer the endosome and cause an influx of ions due to the proton-sponge mechanism. The resulting burst of the endocytic vesicle leads to the release of the payload of the particle, which is then free to travel to the nucleus where the DNA is expressed.

While the mechanism of RNA-based therapies is different, the objective of the delivery system remains the same. The RNA must be complexed and internalized by the cell in order to exhibit activity. In many cases, polymeric materials do not work as efficiently for RNA delivery. This is likely due to the difference in chemical structure of the therapeutic RNA being delivered, which are generally short, linear fragments containing additional hydroxyl moieties on each ribose ring. These differences necessitate an alternative nonviral approach that is suited for complexation with short RNA strands. Promising results have been achieved with materials that form liposomes or lipoplexes that entrap the RNA or form nanoparticles, which are efficiently internalized by the cell.

The materials utilized to form a lipid-based delivery system generally consist of a positively charged headgroup and a hydrophobic tail. The charged portion serves to electrostatically bind the negatively charged RNA, while the hydrophobic tail leads to self-assembly into lipophilic particles. Such cationic lipids are promising but still fall short of the transfection efficiency achieved by viral vectors. Few advances have been made in the field, in part due to the limited structural diversity of these lipid or polymeric molecules, which is a result of the difficult synthetic procedures required to access these structures. Therefore, in order to push the area of nonviral particle delivery systems forward, it is necessary to investigate chemical transformations that can lead to diverse molecules capable of complexing RNA and shuttling the material across the cell membrane. The most successful approach to date has been the contribution by Anderson and coworkers, who generated a library of lipid-like cationic materials and polymers using straightforward simple chemical transformations. See, e.g., PCT Application Publication Nos. WO 2004/106411; WO 2006/138380; WO 2007/143659; WO 2008/011561; and WO 2010/053572. The Anderson team generated over 1000 cationic materials that were tested for their ability to complex and deliver RNA in a high throughput assay. This screen led to the identification of a number of lead cationic materials that were more efficient in vitro than the current industry standard, Lipofectamine 2000, and are currently being tested in vivo for potential use in therapeutic applications. See, e.g., Akinc et al., *Nat. Biotech.* 2008 26:561.

SUMMARY OF THE INVENTION

In this invention, the inventors have utilized a combinatorial approach to generate novel polymeric materials that form polyplexes with nucleic acids and can effectuate their delivery. The present invention stems in part from the discovery that α-aminoamidine polymers for drug delivery may be prepared by reacting one or more amines with one or more isocyanides and one or more aldehydes.

In several different aspects, the present invention provides novel α-aminoamidine polymers, e.g.:

polymers of Formula (I):

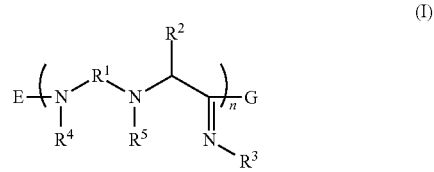

(I)

and pharmaceutically acceptable salts and isomers thereof;

polymers of Formula (II):

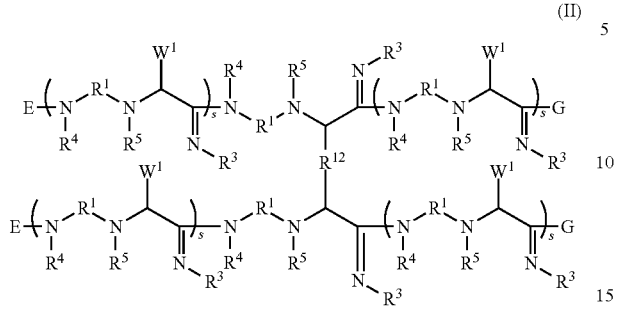

and pharmaceutically acceptable salts and isomers thereof; wherein $W^1$ is $R^2$ or a group of formula:

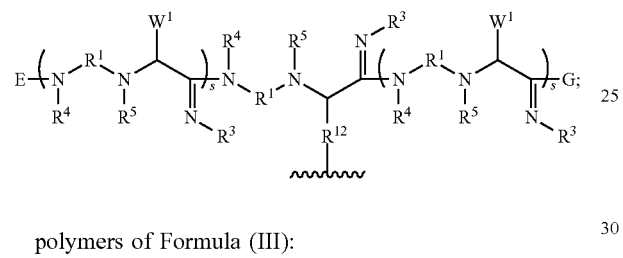

polymers of Formula (III):

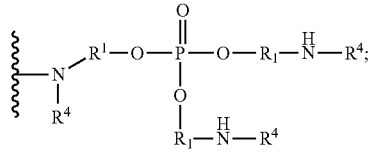

wherein each instance of X', Y', and Z' is, independently, a substituent group of formula:

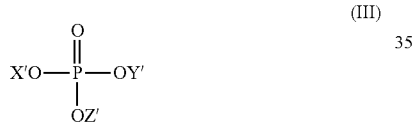

and pharmaceutically acceptable salts and isomers thereof; where $W^2$ is G or a group of formula:

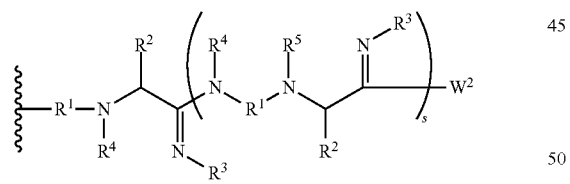

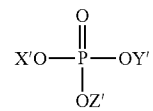

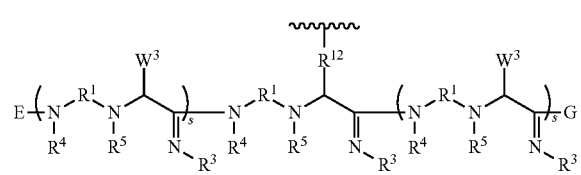

or
polymers of Formula (III):

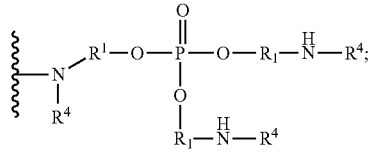

and pharmaceutically acceptable salts and isomers thereof; wherein each instance of X', Y', and Z' is, independently, a substituent group of formula:

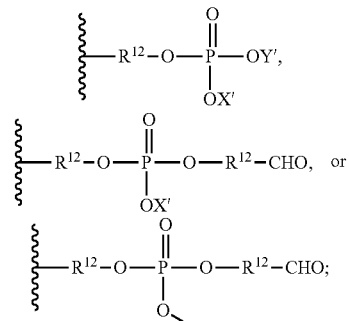

wherein $W^3$ is $R^2$ or a group of formula:

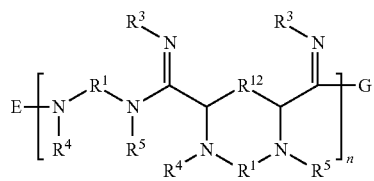

and polymers of Formula (IV):

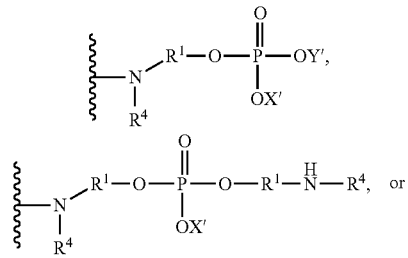

and pharmaceutically acceptable salts and isomers thereof; wherein $R^1$, $R^2$, $R^3$, $R^4$, $R^5$, $R^6$, $R^7$, $R^8$, $R^{10}$, $R^{11}$, $R^{12}$, n, q, s, E and G are as defined herein.

The inventive α-aminoamidine polymers are particularly useful in the delivery of polynucleotides to a cell. The α-aminoamidine polymers of the present invention are amenable to combinatorial synthesis and screening to generate libraries of polymers for use as non-viral drug delivery agents. The inventive polymers may be used for other purposes as well such as, for example, coatings, additives, excipients, plastics, and materials, etc.

These α-aminoamidine polymers may be prepared by reacting one or more amines with one or more isocyanides and one or more aldehydes. See, e.g., FIGS. 1-5. In certain embodiments, the amine is stereochemically pure (e.g., enantiomerically pure). In certain embodiments, the aldehyde is stereochemically pure (e.g., enantiomerically pure). In certain embodiments, the isocyanide is stereochemically pure (e.g., enantiomerically pure). In certain embodiments, one or more amines, one or more isocyanides, and one or more aldehydes are reacted at elevated temperatures in the absence of solvent to prepare the inventive α-aminoamidine polymers.

Typically, the amines chosen contain between two and five amine moieties and the isocyanides and aldehydes include substituents (i.e. tails) of varying chain lengths and optionally feature various functional groups and varying degrees of saturation. The amines chosen preferably contain two primary amino groups, bis(primary amines), or three primary amino groups, tris(primary amines). Alternatively, the amines chosen may contain more than three primary amino groups or any ratio of primary, secondary, and tertiary amino groups. The inventive α-aminoamidine polymers may be used in the delivery of therapeutic agents (e.g., polynucleotide, small molecule, protein, peptide) to a subject (e.g., a human).

The inventive α-aminoamidine polymers are particularly useful in delivering negatively charged agents given the tertiary amines available for protonation or quaternization thus forming a cationic polymer. For example, the α-aminoamidine polymers may be used to delivery DNA, RNA, or other polynucleotides to a subject or to a cell. As would be appreciated by one of skill in the art, the above reaction may result in a mixture with α-aminoamidine polymers having various compositions and molecular weights. Also, two different aldehydes and/or two different amines may be used in the reaction mixture to prepare an α-aminoamidine polymer with different composition. Also, two different isocyanide polymers may be used in the reaction mixture to prepare an α-aminoamidine polymer with different composition. Typically, these polymers are a mixture of various constitutional isomers, are usually isolable (e.g., by chromatography on silica gel, HPLC, etc.); and the identity and purity of the products may be confirmed through $^{1}H/^{13}C$ NMR spectroscopy and/or by MALDI-MS.

In one aspect of the invention, the inventive α-aminoamidine polymers are combined with an agent to be delivered to a cell or a subject to form microparticles, nanoparticles, liposomes, or micelles. The agent to be delivered by the particles, liposomes, or micelles may be in the form of a gas, liquid, or solid, and the agent may be any chemical compound or material (e.g., a polynucleotide, protein, peptide, or small molecule). The inventive α-aminoamidine polymers may be combined with other α-aminoamidine polymers, polymers (synthetic or natural), surfactants, cholesterol, carbohydrates, proteins, peptides, and lipids, etc. to form the particles. In certain embodiments, the particle comprises one or more stabilizing agents. The particles may then optionally be combined with a pharmaceutical excipient to form a pharmaceutical composition.

The details of one or more embodiments of the invention are set forth herein. Other features, objects, and advantages of the invention will be apparent from the description, the figures, the examples, and the claims.

DEFINITIONS

Definitions of specific functional groups and chemical terms are described in more detail below. For purposes of this invention, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito: 1999, the entire contents of which are incorporated herein by reference.

If, for instance, a particular enantiomer of a polymer of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

The "enantiomeric excess" of a substance is a measure of how pure a desired enantiomer is relative to the undesired enantiomer. Enantiomeric excess is defined as the absolute difference between the mole fraction of each enantiomer which is most often expressed as a percent enantiomeric excess. For mixtures of diastereomers, there are analogous definitions and uses for "diastereomeric excess" and percent diastereomeric excess.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" as used herein, includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, and carbocyclyl (cycloalkyl, cycloalkenyl, and cycloalkynyl) moieties. Thus, as used herein, the term "alkyl" includes straight, branched and cyclic alkyl groups. An analogous convention applies to other generic terms such as "alkenyl," "alkynyl," and the like. Furthermore, as used herein, the terms "alkyl," "alkenyl," "alkynyl," and the like encompass both substituted and unsubstituted groups. In certain embodiments, as used herein, "lower alkyl" is used to indicate those alkyl groups (cyclic, acyclic, substituted, unsubstituted, branched or unbranched) having 1-6 carbon atoms.

The term "heteroaliphatic" refers to an aliphatic group, as defined herein, which further comprises 1 or more (e.g., 1, 2, 3, 4, 5, 6, etc. for example, 1 to 25) heteroatoms (e.g., oxygen, sulfur, nitrogen, boron, silicon, phosphorus) included in the parent chain. Exemplary heteroaliphatic groups include heteroalkyl, heteroalkenyl, heteroalkynyl, and heterocyclyl groups as defined herein.

As used herein, "alkyl" refers to a radical of a straight-chain or branched saturated hydrocarbon group having from 1 to 50 carbon atoms ("$C_{1-50}$ alkyl"). In some embodiments, an alkyl group has 1 to 40 carbon atoms ("$C_{1-40}$ alkyl"). In some embodiments, an alkyl group has 1 to 30 carbon atoms ("$C_{1-30}$ alkyl"). In some embodiments, an alkyl group has 1 to 20 carbon atoms ("$C_{1-20}$ alkyl"). In some embodiments, an alkyl group has 1 to 20 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_1$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_2$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-50}$ alkyl. In certain embodiments, the alkyl group is a substituted $C_{1-50}$ alkyl.

As used herein, "heteroalkyl" refers to an alkyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("heteroC$_{1-10}$ alkyl"). In some embodiments, a heteroalkyl group is a saturated group having 1 to 9 carbon atoms and 1 or more heteroatoms within the parent chain ("heteroC$_{1-9}$ alkyl"). In some embodiments, a heteroalkyl group is a saturated group having 1 to 8 carbon atoms and 1 or more heteroatoms within the parent chain ("heteroC$_{1-8}$ alkyl"). In some embodiments, a heteroalkyl group is a saturated group having 1 to 7 carbon atoms and 1 or more heteroatoms within the parent chain ("heteroC$_{1-7}$ alkyl"). In some embodiments, a heteroalkyl group is a saturated group having 1 to 6 carbon atoms and 1 or more heteroatoms within the parent chain ("heteroC$_{1-6}$ alkyl"). In some embodiments, a heteroalkyl group is a saturated group having 1 to 5 carbon atoms and 1 or 2 heteroatoms within the parent chain ("heteroC$_{1-5}$ alkyl"). In some embodiments, a heteroalkyl group is a saturated group having 1 to 4 carbon atoms and for 2 heteroatoms within the parent chain ("heteroC$_{1-4}$ alkyl"). In some embodiments, a heteroalkyl group is a saturated group having 1 to 3 carbon atoms and 1 heteroatom within the parent chain ("heteroC$_{1-3}$ alkyl"). In some embodiments, a heteroalkyl group is a saturated group having 1 to 2 carbon atoms and 1 heteroatom within the parent chain ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms within the parent chain ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-50}$ alkyl. In certain embodiments, the heteroalkyl group is a substituted heteroC$_{1-50}$ alkyl.

As used herein, "alkenyl" refers to a radical of a straight-chain or branched hydrocarbon group having from 2 to 50 carbon atoms and one or more carbon-carbon double bonds ("$C_{2-50}$ alkenyl"). In some embodiments, an alkenyl group has 2 to 40 carbon atoms ("$C_{2-40}$ alkenyl"). In some embodiments, an alkenyl group has 2 to 30 carbon atoms ("$C_{2-30}$ alkenyl"). In some embodiments, an alkenyl group has 2 to 20 carbon atoms ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-50}$ alkenyl. In certain embodiments, the alkenyl group is a substituted $C_{2-50}$ alkenyl.

As used herein, "heteroalkenyl" refers to an alkenyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("heteroC$_{2-10}$ alkenyl"). In some embodiments, a heteroalkenyl group has 2 to 9 carbon atoms at least one double bond, and 1 or more heteroatoms within the parent chain ("heteroC$_{2-9}$ alkenyl"). In some embodiments, a heteroalkenyl group has 2 to 8 carbon atoms, at least one double bond, and 1 or more heteroatoms within the parent chain ("heteroC$_{2-8}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and for 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-50}$ alkenyl. In certain embodiments, the heteroalkenyl group is a substituted heteroC$_{2-50}$ alkenyl.

As used herein, "alkynyl" refers to a radical of a straight-chain or branched hydrocarbon group having from 2 to 50 carbon atoms and one or more carbon-carbon triple bonds ("C$_{2-50}$ alkynyl"). In some embodiments, an alkynyl group has 2 to 40 carbon atoms ("C$_{2-40}$ alkynyl"). In some embodiments, an alkynyl group has 2 to 30 carbon atoms ("C$_{2-30}$ alkynyl"). In some embodiments, an alkynyl group has 2 to 20 carbon atoms ("C$_{2-20}$ alkynyl"). In some embodiments, an alkynyl group has 2 to 10 carbon atoms ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted C$_{2-50}$ alkynyl. In certain embodiments, the alkynyl group is a substituted C$_{2-50}$ alkynyl.

As used herein, "heteroalkynyl" refers to an alkynyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("heteroC$_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl"). In some embodiments, a heteroalkynyl group has 2 to 8 carbon atoms, at least one triple bond, and 1 or more heteroatoms within the parent chain ("heteroC$_{2-8}$ alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and 1 or 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-50}$ alkynyl. In certain embodiments, the heteroalkynyl group is a substituted heteroC$_{2-50}$ alkynyl.

As used herein, "carbocyclyl" or "carbocycle" refers to a radical of a non-aromatic cyclic hydrocarbon group having from 3 to 10 ring carbon atoms ("C$_{3-10}$ carbocyclyl") and zero heteroatoms in the non-aromatic ring system. In some embodiments, a carbocyclyl group has 3 to 8 ring carbon atoms ("C$_{3-8}$ carbocyclyl"). In some embodiments, a carbocyclyl group has 3 to 7 ring carbon atoms ("C$_{3-7}$ carbocyclyl"). In some embodiments, a carbocyclyl group has 3 to 6 ring carbon atoms ("C$_{3-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted C$_{3-10}$ carbocyclyl. In certain embodiments, the carbocyclyl group is a substituted C$_{3-10}$ carbocyclyl.

In some embodiments, "carbocyclyl" or "carbocycle" is a monocyclic, saturated carbocyclyl group having from 3 to 10 ring carbon atoms ("C$_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_6$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-10}$ cycloalkyl. In certain embodiments, the cycloalkyl group is a substituted $C_{3-10}$ cycloalkyl.

As used herein, "heterocyclyl" or "heterocycle" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, thiorenyl. Exemplary 4-membered heterocyclyl groups containing 1 heteroatom include, without limitation, azetidinyl, oxetanyl and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo-[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

As used herein, the term "partially unsaturated" refers to a ring moiety that includes at least one double or triple bond. The term "partially unsaturated" is intended to encompass rings having multiple sites of unsaturation, but is not intended to include aromatic groups (e.g., aryl or heteroaryl moieties) as herein defined.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group, as defined herein, substituted by an aryl group, as defined herein, wherein the point of attachment is on the alkyl moiety.

As used herein, "heteroaryl" or "aromatic heterocyclic" refers to a radical of a 5-14 membered monocyclic or polycyclic (e.g., bicyclic or tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

Specific heterocycyl and heteroaryl groups that may be included in the polymers of the invention include: 3-methyl-4-(3-methylphenyl)piperazine, 3 methylpiperidine, 4-(bis-(4-fluorophenyl)methyl)piperazine, 4-(diphenylmethyl)piperazine, 4-(ethoxycarbonyl)piperazine, 4-(ethoxycarbonylmethyl)piperazine, 4-(phenylmethyl)piperazine, 4-(1-phenylethyl)piperazine, 4-(1,1-dimethylethoxycarbonyl)piperazine, 4-(2-(bis-(2-propenyl) amino) ethyl)piperazine, 4-(2-(diethylamino)ethyl)piperazine, 4-(2-chlorophenyl)piperazine, 4-(2-cyanophenyl)piperazine, 4-(2-ethoxyphenyl)piperazine, 4-(2-ethylphenyl)piperazine, 4-(2-fluorophenyl)piperazine, 4-(2-hydroxyethyl)piperazine, 4-(2-methoxyethyl)piperazine, 4-(2-methoxyphenyl)piperazine, 4-(2-methylphenyl)piperazine, 4-(2-methylthiophenyl) piperazine, 4-(2-nitrophenyl)piperazine, 4-(2-nitrophenyl)piperazine, 4-(2-phenylethyl)piperazine, 4-(2-pyridyl)piperazine, 4-(2-pyrimidinyl)piperazine, 4-(2,3-dimethylphenyl)piperazine, 4-(2,4-difluorophenyl) piperazine, 4-(2,4-dimethoxyphenyl)piperazine, 4-(2,4-dimethylphenyl)piperazine, 4-(2,5-dimethylphenyl)piperazine, 4-(2,6-dimethylphenyl)piperazine, 4-(3-chlorophenyl)piperazine, 4-(3-methylphenyl)piperazine, 4-(3-trifluoromethylphenyl)piperazine, 4-(3,4-dichlorophenyl)piperazine, 4-3,4-dimethoxyphenyl)piperazine, 4-(3,4-dimethylphenyl) piperazine, 4-(3,4-methylenedioxyphenyl)piperazine, 4-(3,4,5-trimethoxyphenyl)piperazine, 4-(3,5-dichlorophenyl) piperazine, 4-(3,5-dimethoxyphenyl)piperazine, 4-(4-(phenylmethoxy)phenyl)piperazine, 4-(4-(3,1-dimethylethyl)phenylmethyl)piperazine, 4-(4-chloro-3-trifluoromethylphenyl)piperazine, 4-(4-chlorophenyl)-3-methylpiperazine, 4-(4-chlorophenyl)piperazine, 4-(4-chlorophenyl)piperazine, 4-(4-chlorophenylmethyl) piperazine, 4-(4-fluorophenyl)piperazine, 4-(4-methoxyphenyl)piperazine, 4-(4-methylphenyl)piperazine, 4-(4-nitrophenyl)piperazine, 4-(4-trifluoromethylphenyl) piperazine, 4-cyclohexylpiperazine, 4-ethylpiperazine, 4-hydroxy-4-(4-chlorophenyl)methylpiperidine, 4-hydroxy- 4-phenylpiperidine, 4-hydroxypyrrolidine, 4-methylpiperazine, 4-phenylpiperazine, 4-piperidinylpiperazine, 4-(2-furanyl)carbonyl)piperazine, 4-((1,3-dioxolan-5-yl)methyl)piperazine, 6-fluoro-1,2,3,4-tetrahydro-2-methylquinoline, 1,4-diazacylcloheptane, 2,3-dihydroindolyl, 3,3-dimethylpiperidine, 4,4-ethylenedioxypiperidine, 1,2,3,4-tetrahydroisoquinoline, 1,2,3,4-tetrahydroquinoline, azacyclooctane, decahydroquinoline, piperazine, piperidine, pyrrolidine, thiomorpholine, and triazole.

The term "alkoxy" or "thioalkyl" as used herein refers to an alkyl group, as previously defined, attached to the parent molecule through an oxygen atom or through a sulfur atom. In certain embodiments, the alkyl, alkenyl, and alkynyl groups contain 1-20 alipahtic carbon atoms. In certain other embodiments, the alkyl, alkenyl, and alkynyl groups contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups contain 1-6 aliphatic carbon atoms. In yet other embodiments, the alkyl, alkenyl, and alkynyl groups contain 1-4 aliphatic carbon atoms. Examples of alkoxy, include but are not limited to, methoxy, ethoxy, propoxy, isopropoxy, n-butoxy, tert-butoxy, neopentoxy, and n-hexoxy. Examples of thioalkyl include, but are not limited to, methylthio, ethylthio, propylthio, isopropylthio, n-butylthio, and the like.

The term "alkylamino" refers to a group having the structure —NHR', wherein R' is aliphatic, as defined herein. In certain embodiments, the aliphatic group contains 1-20 aliphatic carbon atoms. In certain other embodiments, the aliphatic group contains 1-10 aliphatic carbon atoms. In yet other embodiments, the aliphatic group employed in the invention contain 1-8 aliphatic carbon atoms. In still other embodiments, the aliphatic group contains 1-6 aliphatic carbon atoms. In yet other embodiments, the aliphatic group contains 1-4 aliphatic carbon atoms. Examples of alkylamino groups include, but are not limited to, methylamino, ethylamino, n-propylamino, iso-propylamino, cyclopropylamino, n-butylamino, tert-butylamino, neopentylamino, n-pentylamino, hexylamino, cyclohexylamino, and the like.

The term "dialkylamino" refers to a group having the structure —NRR', wherein R and R' are each an aliphatic group, as defined herein. R and R' may be the same or different in an dialkyamino moiety. In certain embodiments, the aliphatic groups contains 1-20 aliphatic carbon atoms. In certain other embodiments, the aliphatic groups contains 1-10 aliphatic carbon atoms. In yet other embodiments, the aliphatic groups employed in the invention contain 1-8 aliphatic carbon atoms. In still other embodiments, the aliphatic groups contains 1-6 aliphatic carbon atoms. In yet other embodiments, the aliphatic groups contains 1-4 aliphatic carbon atoms. Examples of dialkylamino groups include, but are not limited to, dimethylamino, methyl ethylamino, diethylamino, methylpropylamino, di(n-propyl)amino, di(iso-propyl)amino, di(cyclopropyl)amino, di(n-butyl)amino, di(tert-butyl)amino, di(neopentyl)amino, di(n-pentyl)amino, di(hexyl)amino, di(cyclohexyl)amino, and the like. In certain embodiments, R and R' are linked to form a cyclic structure. The resulting cyclic structure may be aromatic or non-aromatic. Examples of cyclic diaminoalkyl groups include, but are not limited to, aziridinyl, pyrrolidinyl, piperidinyl, morpholinyl, pyrrolyl, imidazolyl, 1,3,4-trianolyl, and tetrazolyl.

The term "haloalkyl" denotes an alkyl group, as defined above, having one, two, or three halogen atoms attached thereto and is exemplified by such groups as chloromethyl, bromoethyl, trifluoromethyl, and the like.

"Independently selected": The term "independently selected" is used herein to indicate that the R groups can be identical or different.

"Labeled": As used herein, the term "labeled" is intended to mean that a polymer has at least one element, isotope, or chemical polymer attached to enable the detection of the polymer. In general, labels typically fall into three classes: a) isotopic labels, which may be radioactive or heavy isotopes, including, but not limited to, $^{2}$H, $^{3}$H, $^{32}$P, $^{35}$S, $^{67}$Ga, $^{99m}$Tc (Tc-99m), $^{111}$In, $^{123}$I, $^{125}$I, $^{169}$Yb and $^{186}$Re; b) immune labels, which may be antibodies or antigens, which may be bound to enzymes (such as horseradish peroxidase) that produce detectable agents; and c) colored, luminescent, phosphorescent, or fluorescent dyes. It will be appreciated that the labels may be incorporated into the polymer at any position that does not interfere with the biological activity or characteristic of the polymer that is being detected. In certain embodiments of the invention, photoaffinity labeling is utilized for the direct elucidation of intermolecular interactions in biological systems. A variety of known photophores can be employed, most relying on photoconversion of diazo polymers, azides, or diazirines to nitrenes or carbenes (See, Bayley, H., Photogenerated Reagents in Biochemistry and Molecular Biology (1983), Elsevier, Amsterdam.), the entire contents of which are hereby incorporated by reference. In certain embodiments of the invention, the photoaffinity labels employed are o-, m- and p-azidobenzoyls, substituted with one or more halogen moieties, including, but not limited to 4-azido-2,3,5,6-tetrafluorobenzoic acid.

Groups as described herein, such as alkyl, alkenyl, alkynyl, heteroalkyl, heteroalkenyl, heteroalkynyl, carbocyclyl, heterocyclyl, aryl, and heteroaryl groups, are substituted or unsubstituted, also referred to herein as "optionally substituted". In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, SeH, —SeR$^{aa}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)

NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(C)R$^{cc}$), C$_{1-50}$ alkyl, C$_{2-50}$ alkenyl, C$_{2-50}$ alkynyl, C$_{3-14}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, NNR$^{bb}$C(=O)R$^{aa}$, =NNR$^{bb}$C(=O)OR$^{aa}$, =NNR$^{bb}$S(O)$_2$R$^{aa}$, NR$^{bb}$, or =NOR$^{cc}$;

each instance of R$^{aa}$ is, independently, selected from C$_{1-50}$ alkyl, C$_{2-50}$ alkenyl, C$_{2-50}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, P(=O)(R$^{aa}$)$_2$, —P(=O)(R$^{aa}$)$_2$, —P(=O)(NR$^{cc}$)$_2$, C$_{1-50}$ alkyl, C$_{2-50}$ alkenyl, C$_{2-50}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-50}$ alkyl, C$_{2-50}$ alkenyl, C$_{2-50}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-50}$ alkyl, C$_{2-50}$ alkenyl, C$_{2-50}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-50}$ alkyl, C$_{2-50}$ alkenyl, C$_{2-50}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-50}$ alkyl, C$_{2-50}$ alkenyl, C$_{2-50}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-50}$ alkyl, —ON(C$_{1-50}$ alkyl)$_2$, —N(C$_{1-50}$ alkyl)$_2$, —N(C$_{1-50}$ alkyl)$_3$$^+$X$^-$, —NH(C$_{1-50}$ alkyl)$_2$$^+$X$^-$, —NH$_2$(C$_{1-50}$ alkyl)$^+$X$^-$, —NH$_3$$^+$X$^-$, —N(OC$_{1-50}$ alkyl)(C$_{1-50}$ alkyl), —N(OH)(C$_{1-50}$ alkyl), —NH(OH), —SH, —SC$_{1-50}$ alkyl, —SS(C$_{1-50}$ alkyl), —C(=O)(C$_{1-50}$ alkyl), —CO$_2$H, —CO$_2$(C$_{1-50}$ alkyl), —OC(=O)(C$_{1-50}$ alkyl), —OCO$_2$(C$_{1-50}$ alkyl), —C(=O)NH$_2$, —C(=O)N(C$_{1-50}$ alkyl)$_2$, —OC(=O)NH(C$_{1-50}$ alkyl), —NHC(=O)(C$_{1-50}$ alkyl), —N(C$_{1-50}$ alkyl)C(=O)(C$_{1-50}$ alkyl), —NHCO$_2$(C$_{1-50}$ alkyl), —NHC(=O)N(C$_{1-50}$ alkyl)$_2$, —NHC(=O)NH(C$_{1-50}$ alkyl), —NHC(=O)NH$_2$, —C(=NH)O(C$_{1-50}$ alkyl), —OC(=NH)(C$_{1-50}$ alkyl), —OC(=NH)OC$_{1-50}$ alkyl, —C(=NH)N(C$_{1-50}$ alkyl)$_2$, —C(=NH)NH(C$_{1-50}$ alkyl), —C(=NH)NH$_2$, —OC(=NH)N(C$_{1-50}$ alkyl)$_2$, —OC(NH)NH(C$_{1-50}$ alkyl), —OC(NH)NH$_2$, —NHC(NH)N(C$_{1-50}$ alkyl)$_2$, —NHC(=NH)NH$_2$, —NHSO$_2$ (C$_{1-50}$ alkyl), —SO$_2$N(C$_{1-50}$ alkyl)$_2$, —SO$_2$NH(C$_{1-50}$ alkyl), —SO$_2$NH$_2$, —SO$_2$C$_{1-50}$ alkyl, —SO$_2$OC$_{1-50}$ alkyl, —OSO$_2$C$_{1-6}$ alkyl, —SOC$_{1-6}$ alkyl, —Si(C$_{1-50}$ alkyl)$_3$, —OSi(C$_{1-6}$ alkyl)$_3$-C(=S)N(C$_{1-50}$ alkyl)$_2$, C(=S)NH(C$_{1-50}$ alkyl), C(=S)NH$_2$, —C(=O)S (C$_{1-6}$ alkyl), —C(=S)SC$_{1-6}$ alkyl, —SC(=S)SC$_{1-6}$ alkyl, —P(=O)$_2$(C$_{1-50}$ alkyl), —P(=O)(C$_{1-50}$ alkyl)$_2$, —OP(=O)(C$_{1-50}$ alkyl)$_2$, —OP(=O)(OC$_{1-50}$ alkyl)$_2$, C$_{1-50}$ alkyl, C$_{2-50}$ alkenyl, C$_{2-50}$ alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S;

wherein X$^-$ is a counterion.

As used herein, the term "halo" or "halogen" refers to fluorine (fluoro, —F), chlorine (chloro, —Cl), bromine (bromo, —Br), or iodine (iodo, —I).

As used herein, a "counterion" is a negatively charged group associated with a positively charged quarternary amine in order to maintain electronic neutrality. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

As used herein, the term "sulfonyl" refers to a group selected from —SO$_2$N(R$^{bb}$)$_2$, —SO$_2$R$^{aa}$, and —SO$_2$OR$^{aa}$, wherein R$^{aa}$ and R$^{bb}$ are as defined herein.

As used herein, the term "acyl" refers ketones (—C(=O)R$^{aa}$), carboxylic acids (—CO$_2$H), aldehydes (—CHO), esters (—CO$_2$R$^{aa}$, —C(=O)SR$^{aa}$, —C(=S)SR$^{aa}$), amides (—C(=O)N(R$^{bb}$)$_2$, —C(=O)NR$^{bb}$SO$_2$R$^{aa}$, —C(=S)N ($R^{bb}$)$_2$), and imines (—C(=N$R^{bb}$)$R^{aa}$, —C(=N$R^{bb}$)O$R^{aa}$, —C(=N$R^{bb}$)N($R^{bb}$)$_2$), wherein $R^{aa}$ and $R^{bb}$ are as defined herein.

As used herein, a "leaving group" is an art-understood term referring to a molecular fragment that departs with a pair of electrons in heterolytic bond cleavage, wherein the molecular fragment is an anion or neutral molecule. See, for example, Smith, March *Advanced Organic Chemistry* 6th ed. (501-502). Leaving groups can be anions or neutral molecules. Common anionic leaving groups are halides such as Cl$^-$, Br$^-$, and I$^-$, and sulfonate esters, such as para-toluenesulfonate or "tosylate" (TsO$^-$), mesyl, or besyl. Common neutral molecule leaving groups are water (H$_2$O), ammonia (NH$_3$), and alcohols (ROH).

Nitrogen atoms can be substituted or unsubstituted as valency permits, and include primary, secondary, tertiary, and quarternary nitrogen atoms. Exemplary nitrogen atom substituents include, but are not limited to, hydrogen, —OH, —O$R^{aa}$, —N($R^{cc}$)$_2$, —CN, —C(=O)$R^{aa}$, —C(=O)N($R^{cc}$)$_2$, —CO$_2$$R^{aa}$, —SO$_2$$R^{aa}$, —C(=N$R^{bb}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2$$R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)$_2$$R^{aa}$, —P(=O) ($R^{aa}$)$_2$, —P(=O)$_2$N($R^{cc}$)$_2$, —P(=O)(N$R^{cc}$)$_2$, C$_{1-10}$ alkyl, C$_{1-10}$ perhaloalkyl, C$_{2-10}$ alkenyl, C$_{2-10}$ alkynyl, C$_{1-10}$ heteroalkyl, C$_{2-10}$ heteroalkenyl, C$_{2-10}$ heteroalkynyl, C$_{3-10}$ carbocyclyl, 3-14 membered heterocyclyl, C$_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above In certain embodiments, the substituent present on the nitrogen atom is an nitrogen protecting group (also referred to herein as an "amino protecting group"). Nitrogen protecting groups include, but are not limited to, —OH, —O$R^{aa}$, —N($R^{cc}$)$_2$, —C(=O)$R^{aa}$, —C(=O)N($R^{cc}$)$_2$, —CO$_2$$R^{aa}$, —SO$_2$$R^{aa}$, —C(=N$R^{cc}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2$$R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, C$_{1-10}$ alkyl (e.g., aralkyl, heteroaralkyl), C$_{2-10}$ alkenyl, C$_{2-10}$ alkynyl, C$_{1-10}$ heteroalkyl, C$_{2-10}$ heteroalkenyl, C$_{2-10}$ heteroalkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis, T. W. Greene and P. G. M. Wuts*, 3$^{rd}$ edition, John Wiley & Sons, 1999, incorporated herein by reference.

For example, nitrogen protecting groups such as amide groups (e.g., —C(=O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetyl-methionine derivative, o-nitrobenzamide and o-(benzoyloxymethyl)benzamide.

Nitrogen protecting groups such as carbamate groups (e.g., —C(=O)O$R^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido) ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-34N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Nitrogen protecting groups such as sulfonamide groups (e.g., —S(=O)$_2$$R^{aa}$) include, but are not limited to, p-toluenesulfonamide (Ts), benzenesulfonamide, 2,3,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

These and other exemplary substituents are described in more detail in the Detailed Description, the Examples and in the claims. The invention is not intended to be limited in any manner by the above exemplary listing of substituents.

As used herein, the term "salt" or "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, non-toxic ammonium, quaternary ammonium, and amine cations formed using counterions such as halide, hydroxide, carboxylate, sulfate, phosphate, nitrate, sulfonate and aryl sulfonate. Further pharmaceutically acceptable salts include salts formed from the quarternization of an amine using an appropriate electrophile, e.g., an alkyl halide, to form a quarternized alkylated amino salt.

The term "isomer" refers to stereoisomers and geometric isomers of the inventive polymers, e.g., cis- and trans-isomers, R- and S-enantiomers, diastereomers, (D)-isomers, (L)-isomers, the racemic mixtures thereof, as well as "head-to-tail" and "tail-to-tail" configurational isomers. "Geometric isomers" includes both the E (trans) and Z (cis) imine =N—$R^3$ isomers provided in the polymers described herein. The present invention contemplates all such polymers, and other mixtures thereof, as falling within the scope of the invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex isomer mixtures. For example, a sample with 70% of R isomer and 30% of S will have an enantiomeric excess of 40%. This can also be thought of as a mixture of 40% pure R with 60% of a racemic mixture (which contributes 30% R and 30% S to the overall composition).

Polymers of the present invention for simplicity are depicted in the "head-to-tail" configuration, and the predominate repeating units envisioned (e.g., >50% of the repeating units in the polymer) are "head-to-tail" units. However, polymers of the present invention may further comprise minor amounts (e.g., <50% of the repeating units in the polymer) of "tail-to-tail" and/or "head-to-head" units within the polymer backbone. The term isomer encompasses mixtures of the predominant "head-to-tail" unit with minor amounts of "head-to-head" and/or "tail-to-tail" units within the polymer:

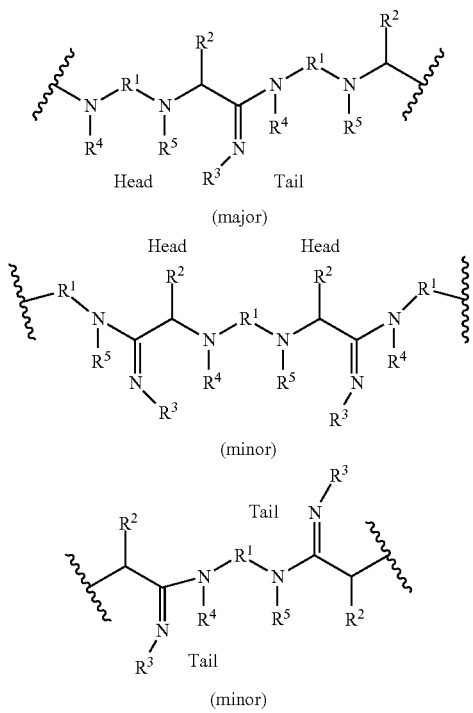

(major)

(minor)

(minor)

"Subject" or "Animal": The term subject or animal, as used herein, refers to humans as well as non-human animals, including, for example, mammals, birds, reptiles, amphibians, and fish. Preferably, the non-human animal is a mammal (e.g., a rodent, a mouse, a rat, a rabbit, a monkey, a dog, a cat, a primate, or a pig). The animal may be of any sex or any stage of development. An animal may be a transgenic animal.

"Associated with": When two entities are "associated with" one another as described herein, they are linked by a direct or indirect covalent or non-covalent interaction. Preferably, the association is covalent. Desirable non-covalent interactions include hydrogen bonding, van der Waals interactions, hydrophobic interactions, magnetic interactions, electrostatic interactions, etc. In certain embodiments, an α-aminoamidine polymer is associated with a polynucleotide through electrostatic interactions.

"Biocompatible": The term "biocompatible," as used herein is intended to describe polymers that are not toxic to cells. Polymers are "biocompatible" if their addition to cells in vitro results in less than or equal to 20% cell death, and their administration in vivo does not induce inflammation or other such adverse effects.

"Biodegradable": As used herein, "biodegradable" polymers are those that, when introduced into cells, are broken down by the cellular machinery or by hydrolysis into components that the cells can either reuse or dispose of without significant toxic effect on the cells (i.e., fewer than about 20% of the cells are killed when the components are added to cells in vitro). The components preferably do not induce inflammation or other adverse effects in vivo. In certain embodiments, the chemical reactions relied upon to break down the biodegradable polymers are uncatalyzed.

"Peptide" or "protein": According to the present invention, a "peptide" or "protein" comprises a string of at least three amino acids linked together by peptide bonds. The terms "protein" and "peptide" may be used interchangeably. Peptide may refer to an individual peptide or a collection of peptides. Inventive peptides preferably contain only natural amino acids, although non-natural amino acids (i.e., polymers that do not occur in nature but that can be incorporated into a polypeptide chain) and/or amino acid analogs as are known in the art may alternatively be employed. Also, one or more of the amino acids in an inventive peptide may be modified, for example, by the addition of a chemical entity such as a carbohydrate group, a phosphate group, a farnesyl group, an isofarnesyl group, a fatty acid group, a linker for conjugation, functionalization, or other modification, etc. In certain embodiments, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide.

"Polynucleotide" or "oligonucleotide": Polynucleotide or oligonucleotide refers to a polymer of nucleotides. Typically, a polynucleotide comprises at least three nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages).

"Small molecule": As used herein, the term "small molecule" refers to organic molecules, whether naturally-occurring or artificially created (e.g., via chemical synthesis) that have relatively low molecular weight and that are not proteins, polypeptides, or nucleic acids. Typically, small molecules have a molecular weight of less than about 1500 g/mol. In certain embodiments, the small molecule is uncharged. In certain embodiments, the small molecule is negatively charged. Also, small molecules typically have multiple carbon-carbon bonds. Known naturally-occurring small molecules include, but are not limited to, penicillin, erythromycin, taxol, cyclosporin, and rapamycin. Known synthetic small molecules include, but are not limited to, ampicillin, methicillin, sulfamethoxazole, and sulfonamides.

"Tail": As used herein, the term "tail" refers to hydrophobic or lipid-like substituents such as substituted or unsubstituted, branched or unbranched, cyclic or acyclic $C_{4-20}$ aliphatic groups optionally interrupted by one or more heteroatoms independently selected from O, S, Si, and $NR^{10}$. Tails can be substituents of any atom or functional group of the α-aminoamidine polymers.

BRIEF DESCRIPTION OF THE DRAWINGS

FIG. 13 depicts plate map 104180.

FIG. 14 depicts plate map 104181.

FIG. 15 depicts plate map 104182.

FIG. 16 depicts plate map 104183.

FIG. 17 depicts plate map 104184.

DETAILED DESCRIPTION OF CERTAIN EMBODIMENTS OF THE INVENTION

Figure 1:
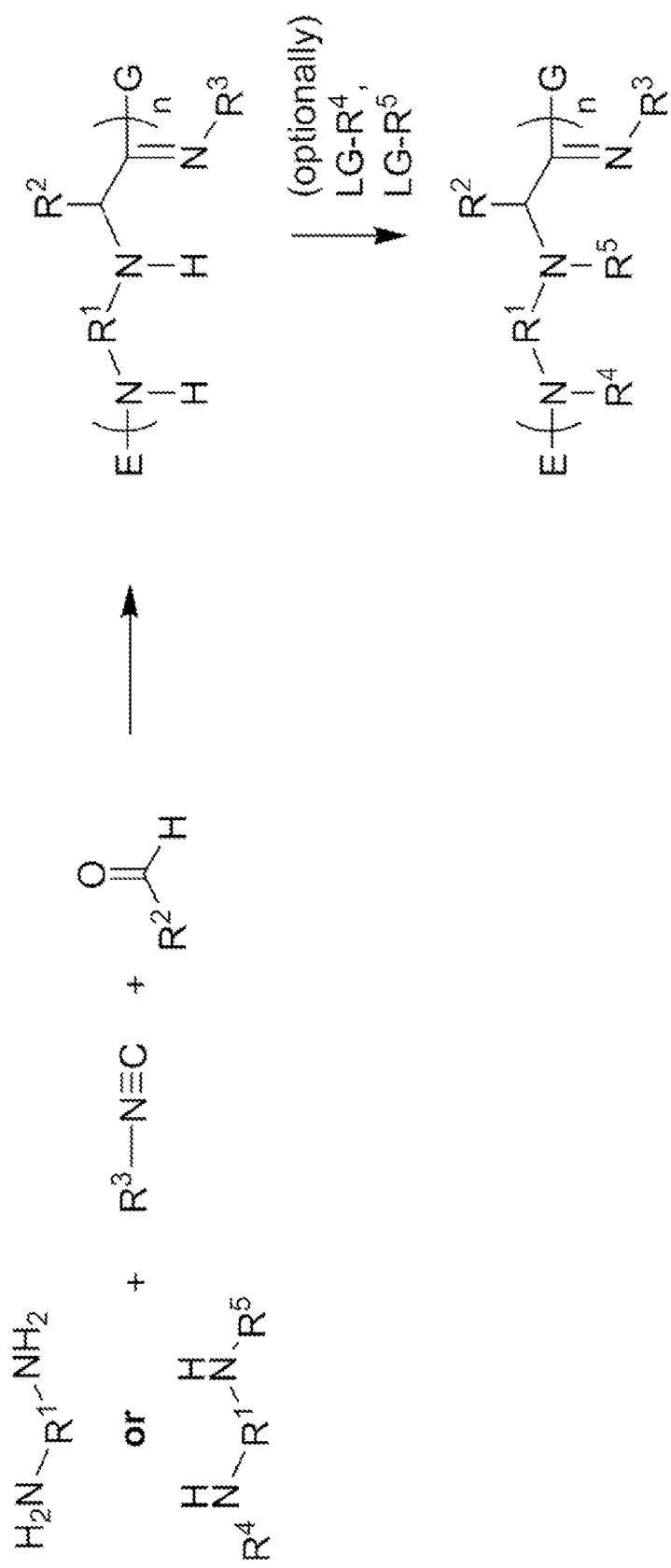
FIGS. 1-5 depicts exemplary synthetic schemes for preparing polymers of Formula (I), (II), (III), and (IV).
Figure 2:
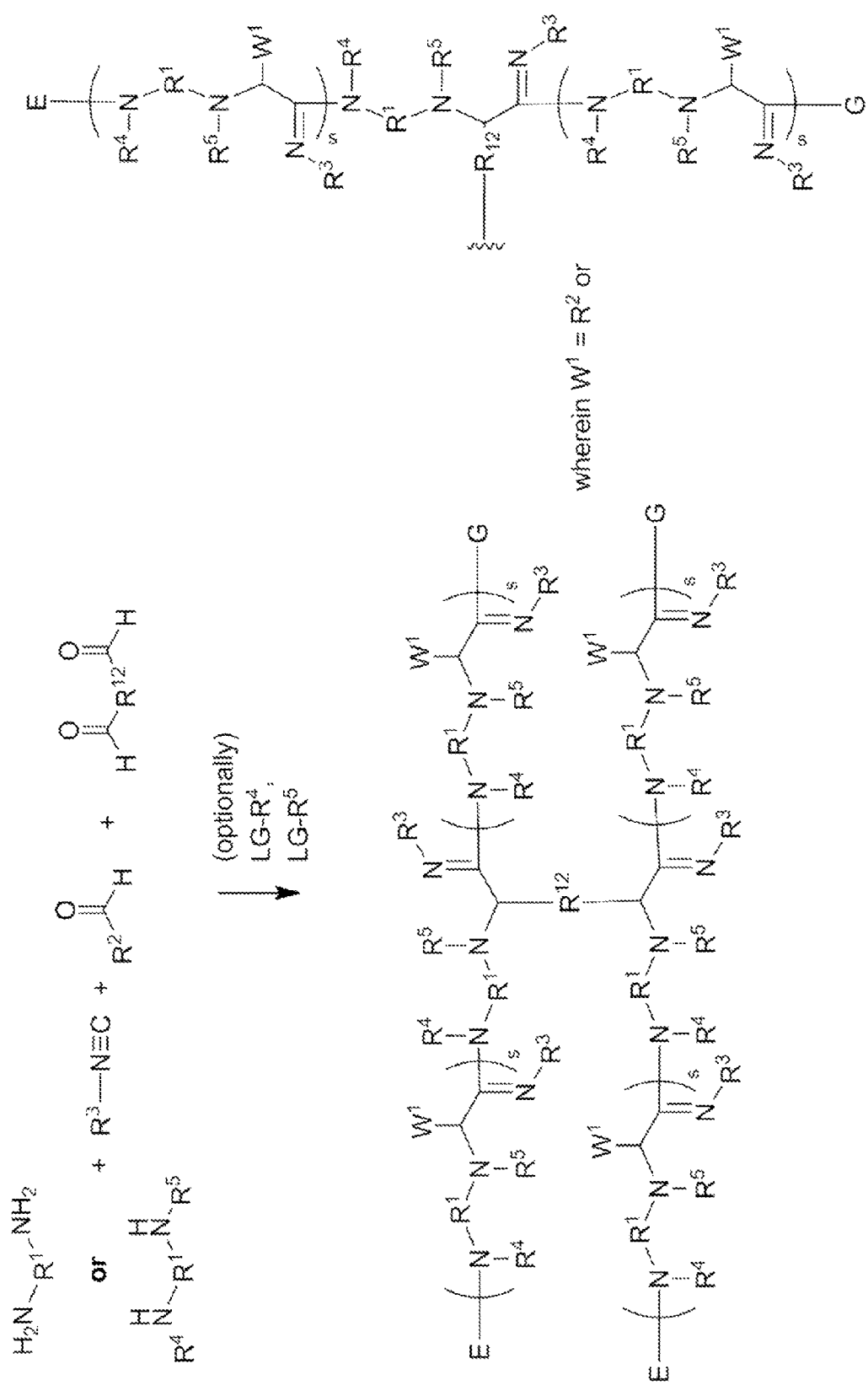
Figure 3:
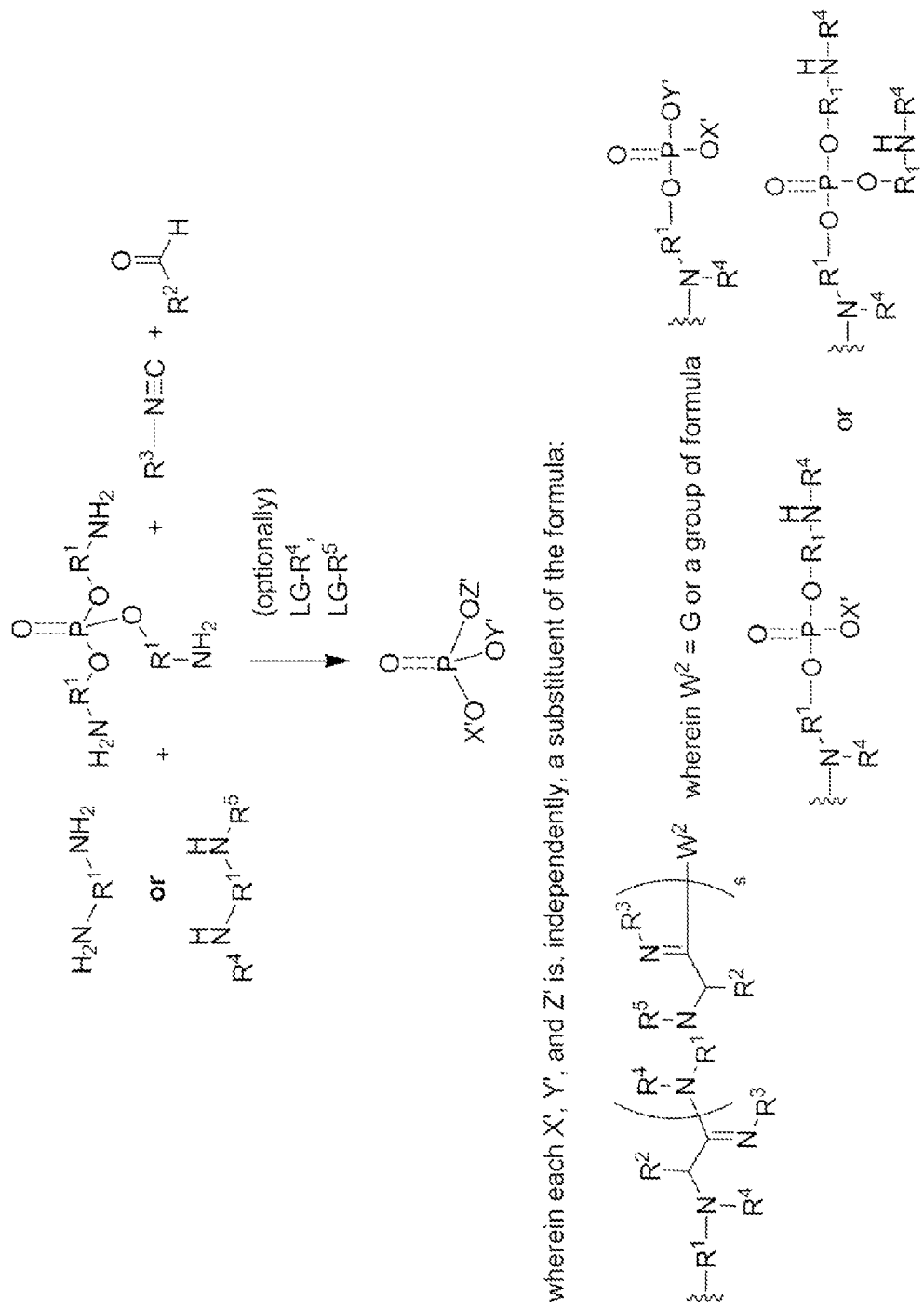
Figure 4:
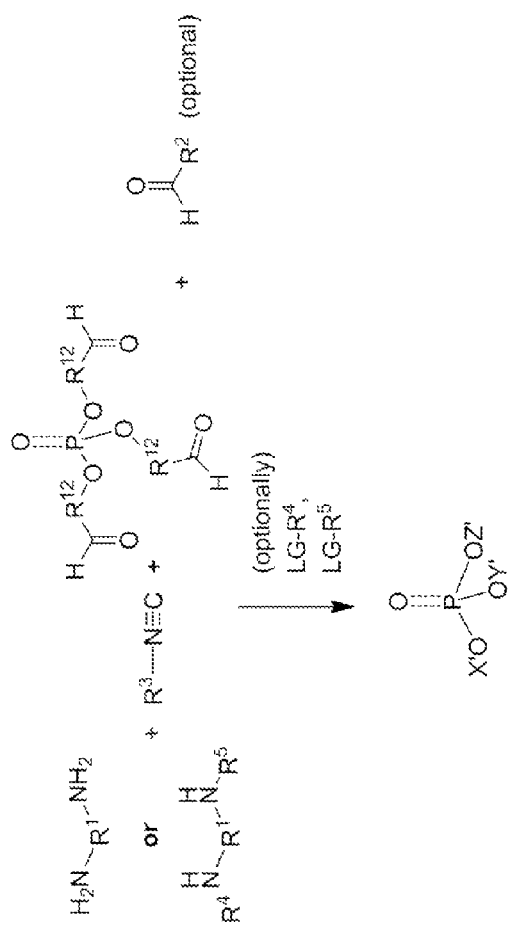
Figure 4:
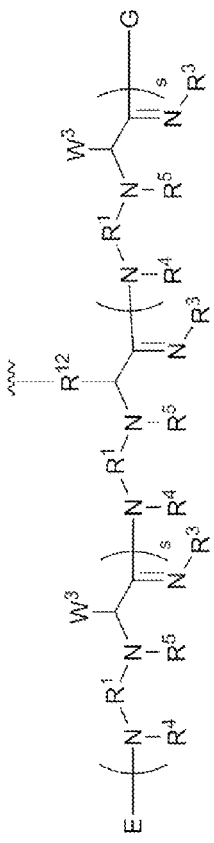
Figure 4:
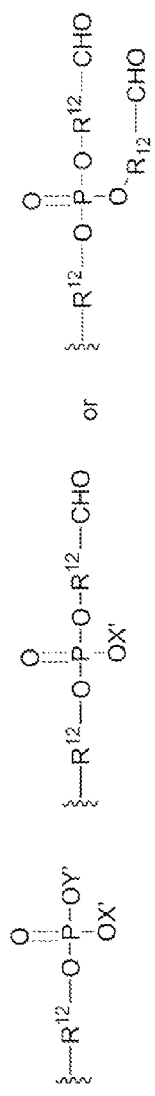
Figure 5:
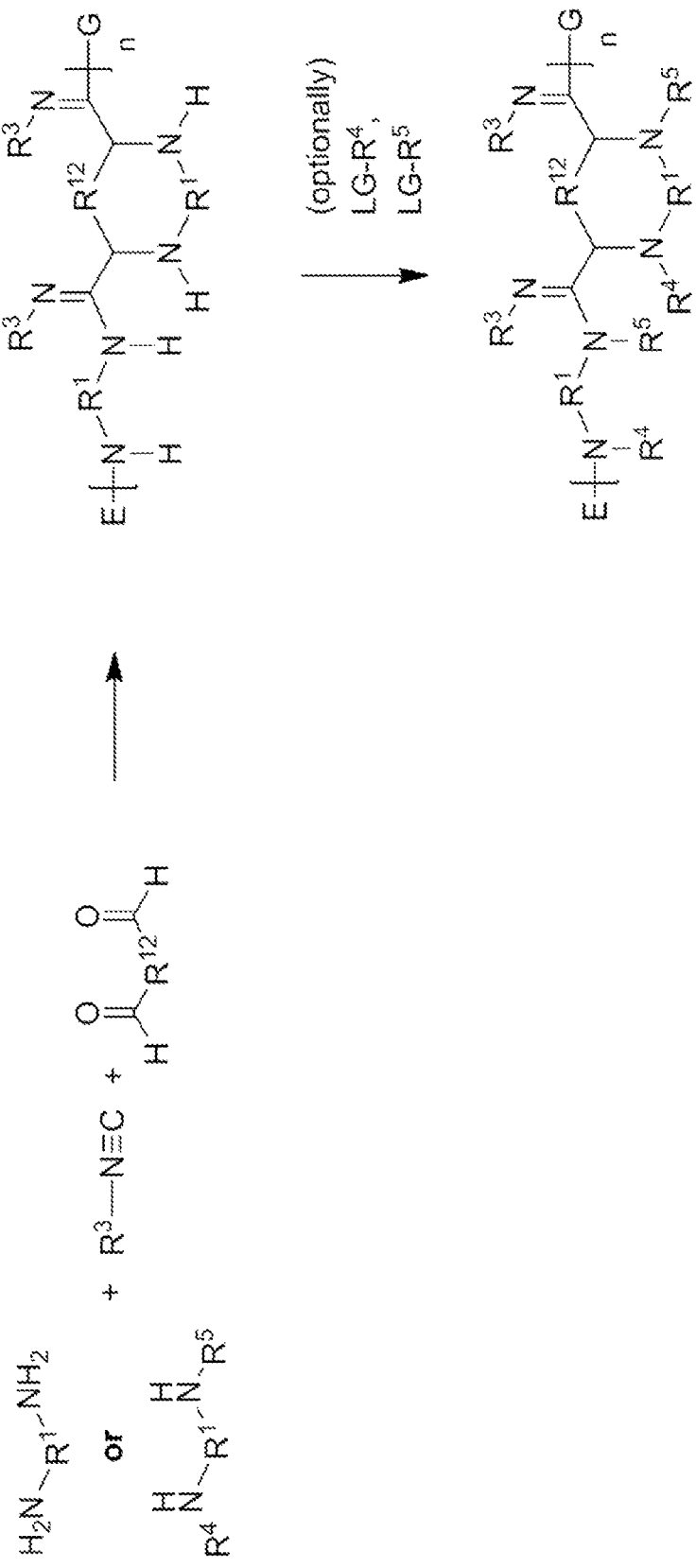
Figure 6:
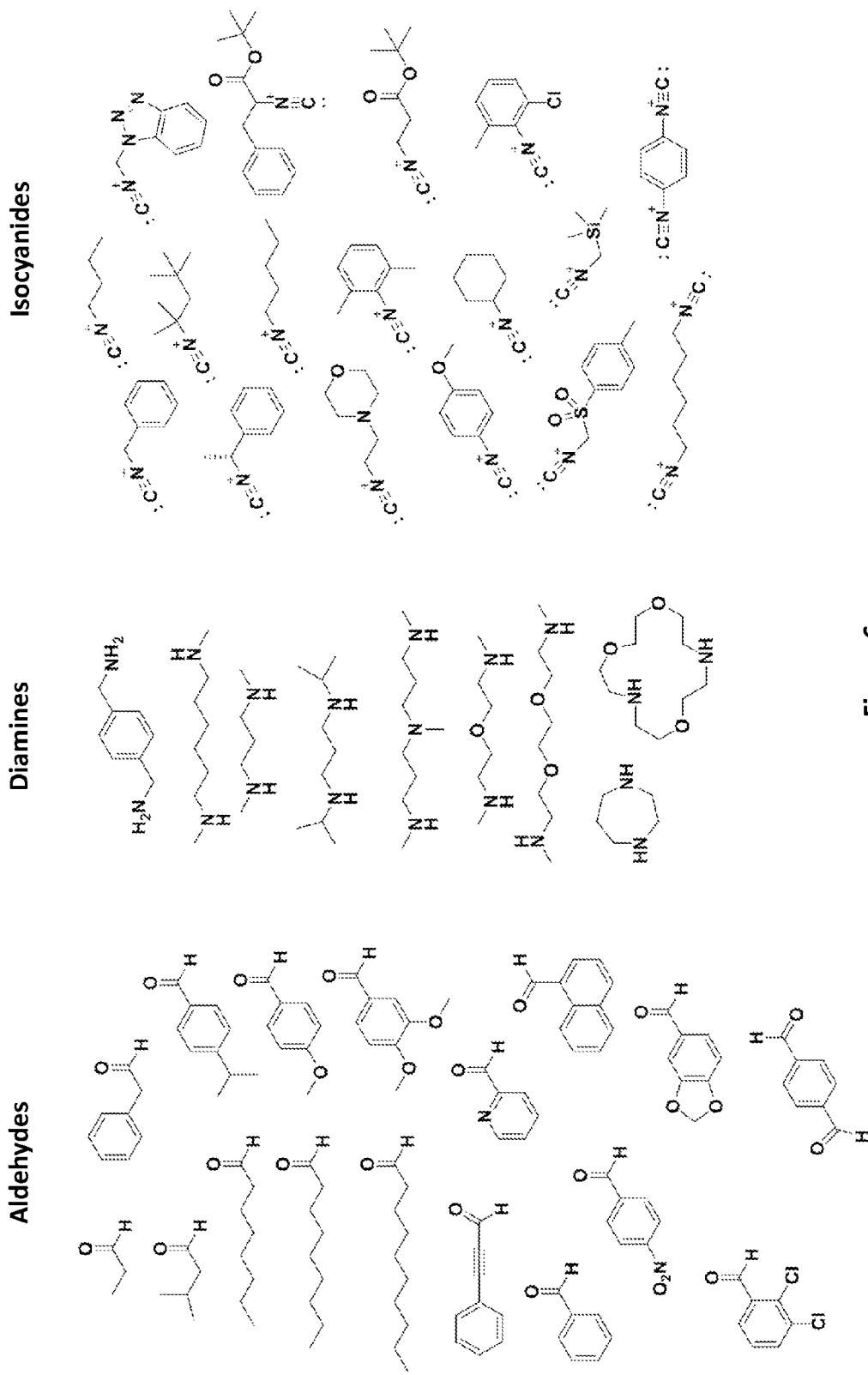
FIG. 6 depicts exemplary aldehyde, amine and isocyanide starting materials.
Figure 7:
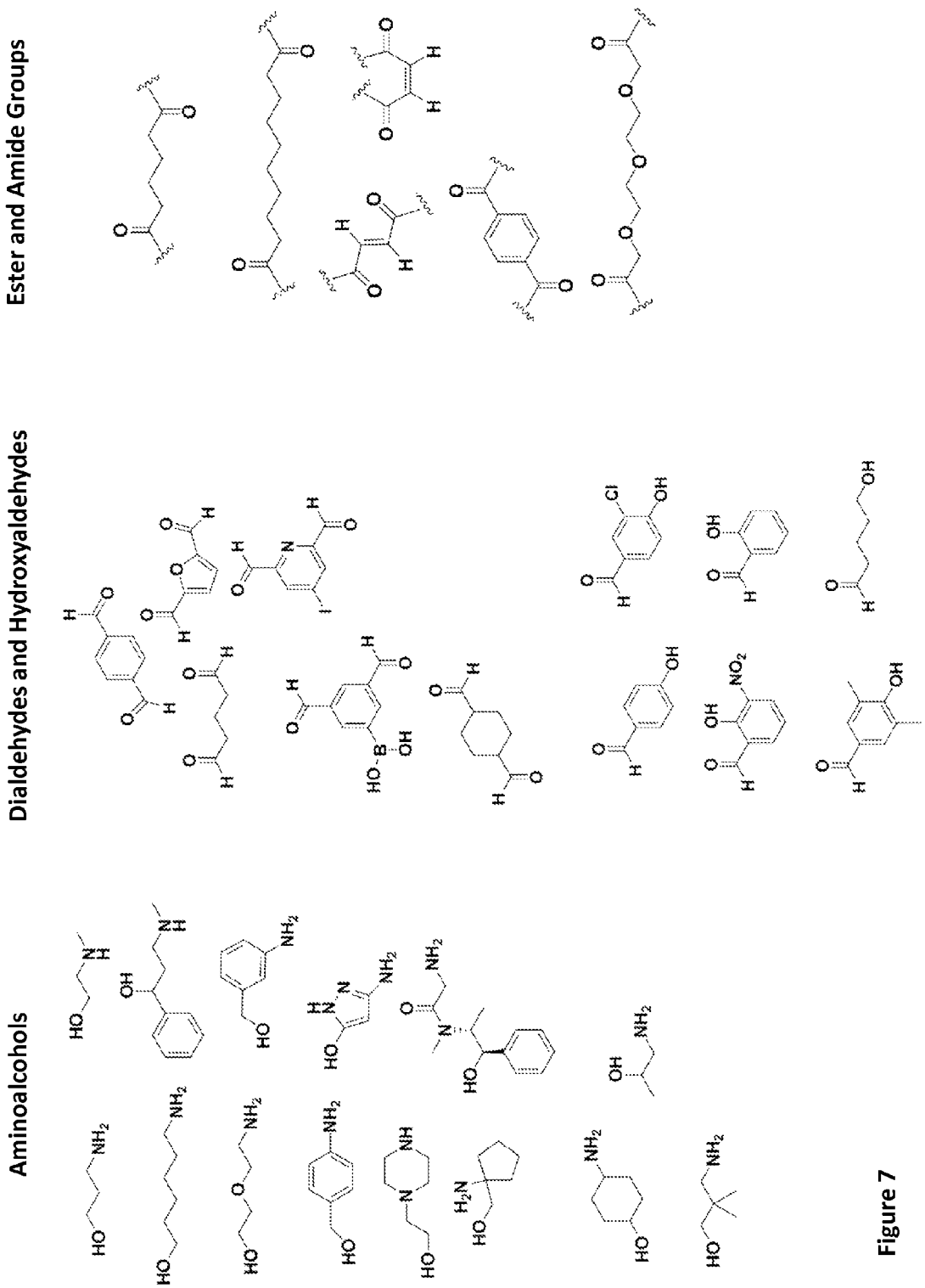
FIG. 7 depicts exemplary aminoalcohol and aldehyde starting materials.
Figure 8:
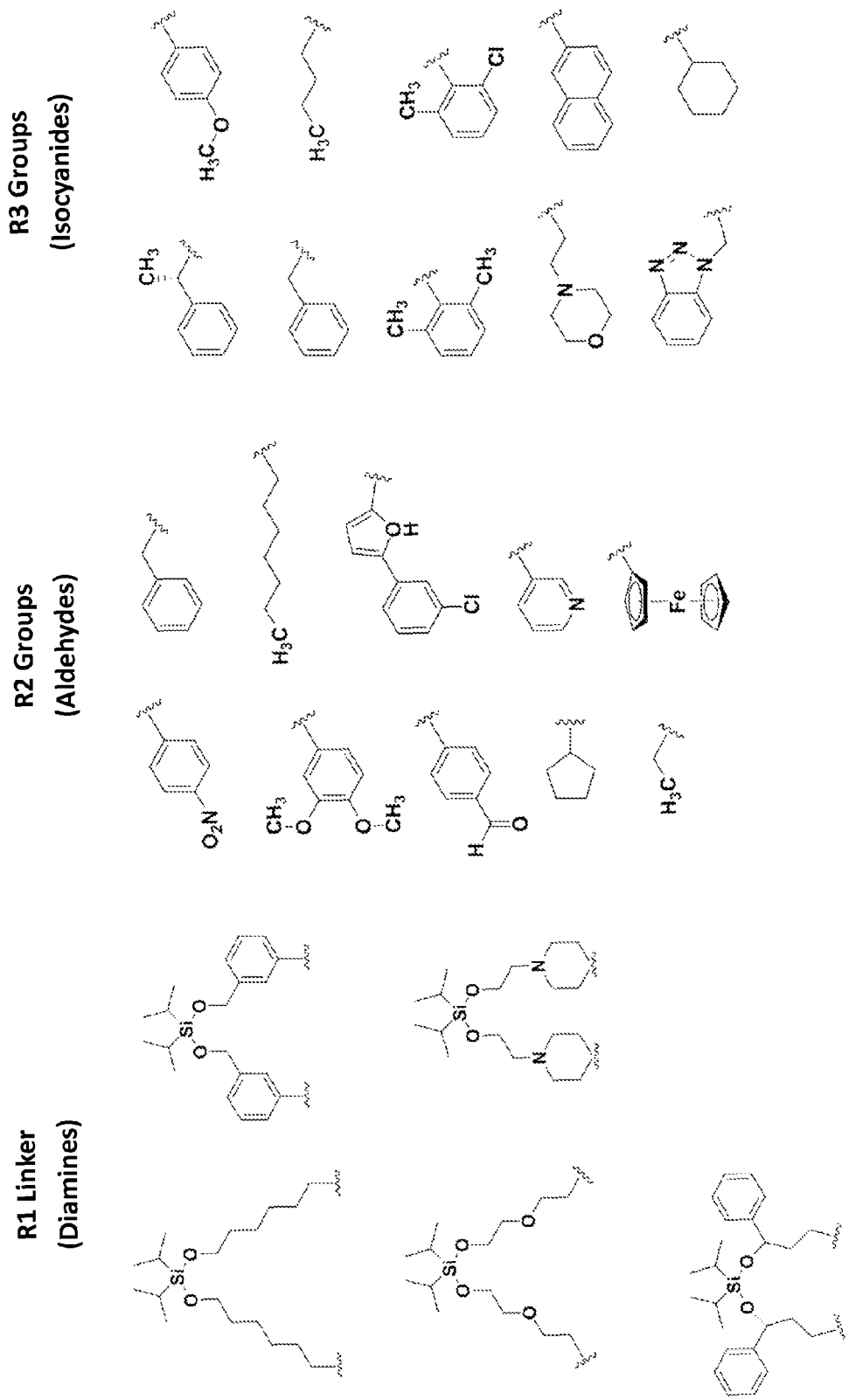
FIG. 8 depicts exemplary groups represented by $R_1$, $R_2$, and $R_3$.
Figure 9:
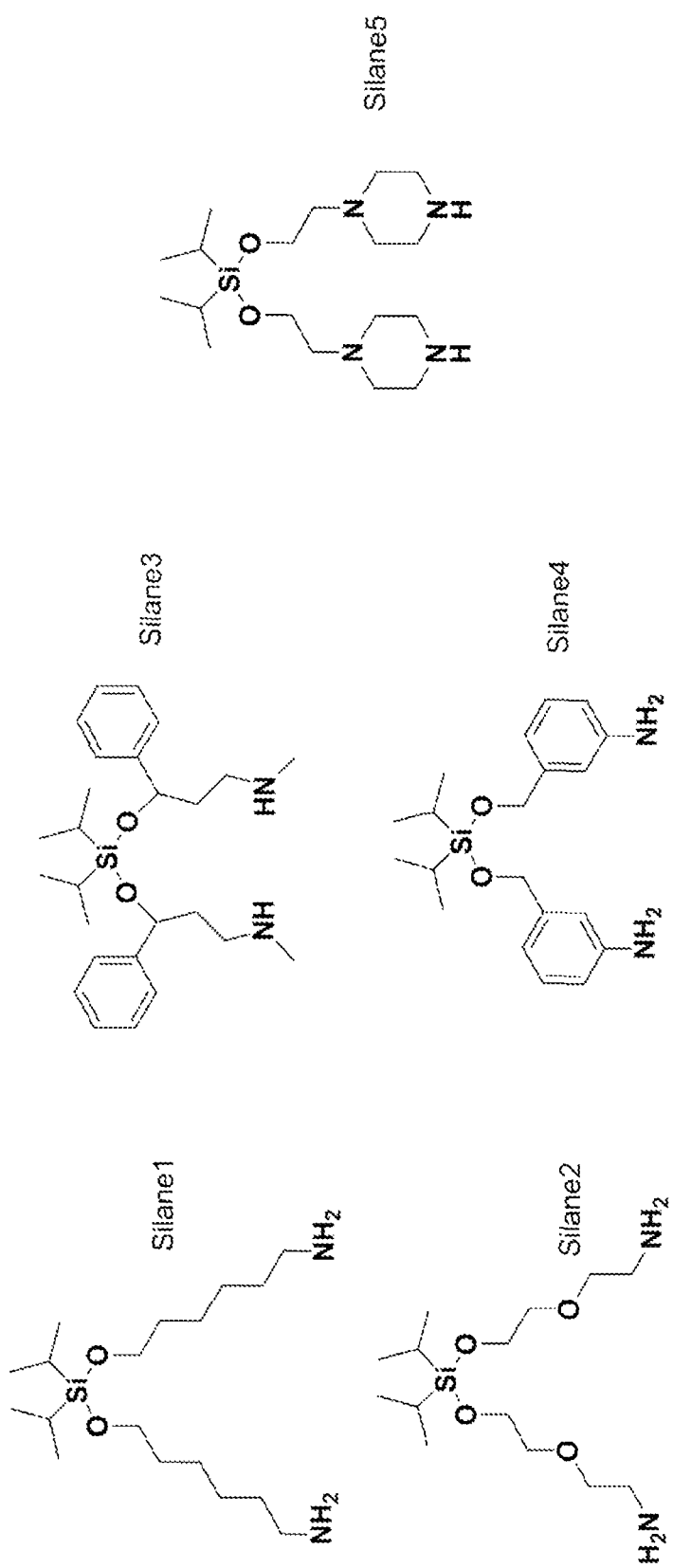
FIG. 9 depicts silanes 1 to 5.
Figure 10:
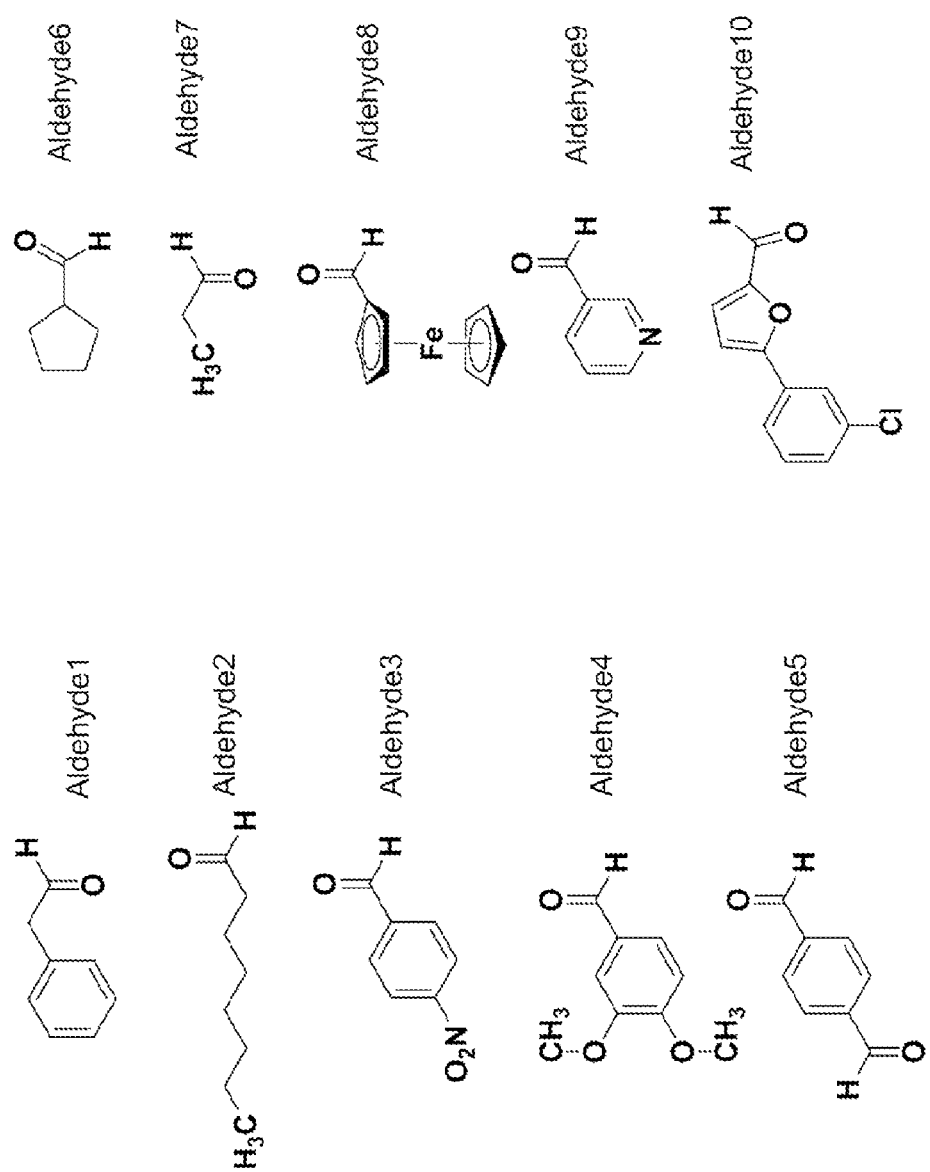
FIG. 10 depicts aldehydes 1 to 10.
Figure 11:
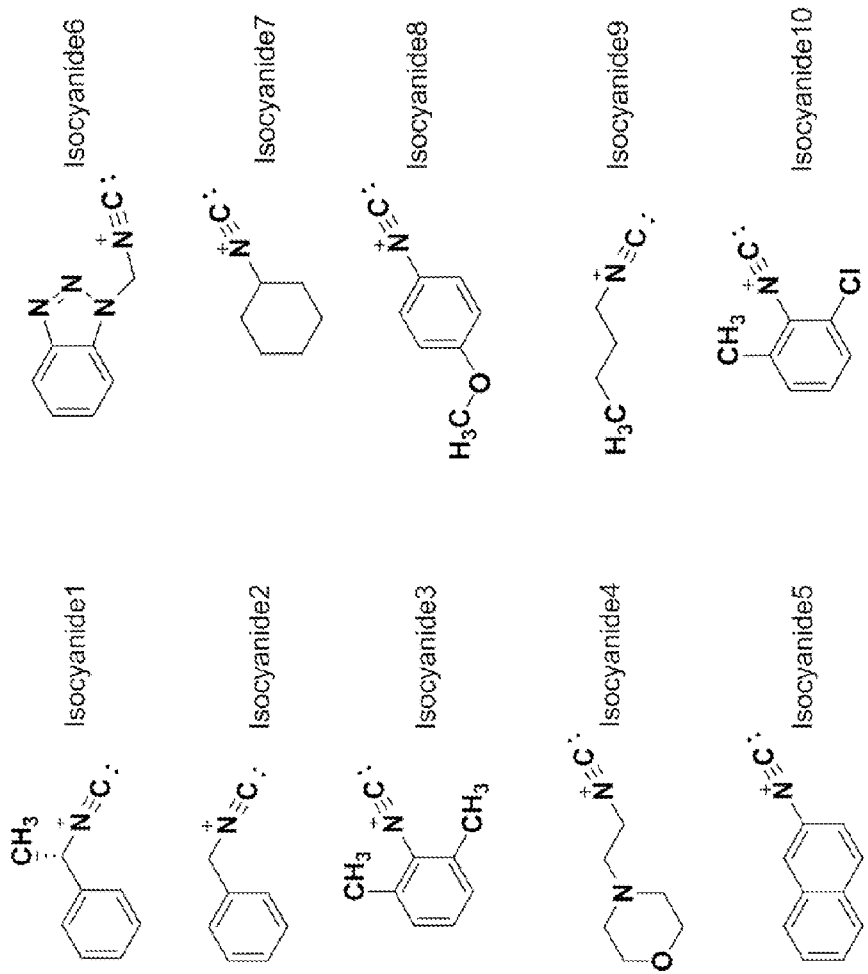
FIG. 11 depicts isocyanides 1 to 10.

The present invention provides novel α-aminoamidine polymers and drug delivery systems based on the use of such α-aminoamidine polymers. The system may be used in the pharmaceutical/drug delivery arts to deliver polynucleotides, proteins, small molecules, peptides, antigen, drugs, etc. to a patient, tissue, organ, cell, etc. These novel polymers may also be used as materials for coatings, additives, excipients, materials, plastics, and bioengineering, etc.

The α-aminoamidine polymers of the present invention provide for several different uses in the drug delivery art. The amine-containing portion of the α-aminoamidine polymers may be used to complex polynucleotides, thereby enhancing the delivery of polynucleotides to a cell and preventing their degradation. The α-aminoamidine polymers may also be used in the formation of picoparticles, nanoparticles, microparticles, liposomes, and micelles containing the agent to be delivered. Preferably, the α-aminoamidine polymers are biocompatible and biodegradable, and the formed particles are also biodegradable and biocompatible and may be used to provide controlled, sustained release of the agent to be delivered. These α-aminoamidines and their corresponding particles may also be responsive to pH changes given that the α-aminoamidine moiety or other amines of the polymer may be protonated at lower pH. The α-aminoamidines may also act as proton sponges in the delivery of an agent to a cell to cause endosome lysis.

α-Aminoamidine Polymers

The α-aminoamidine polymers of the present invention are α-aminoamidine polymers containing primary, secondary, tertiary, and/or quaternary amines, and salts thereof.

In certain embodiments, the α-aminoamidine polymers may be prepared by reacting an amine with one or more aldehydes and one or more isocyanides. As will be appreciated by one of skill in the art, the amine may be reacted with an excess of one or more aldehydes and one or more isocyanides to form a fully functionalized α-aminoamidine polymer. Alternatively, the α-aminoamidine may have fewer aldehyde-derived and/or isocyanide-derived tails than when fully functionalized.

In certain embodiments, the inventive α-aminoamidine polymers are relatively non-cytotoxic. In another embodiment, the inventive α-aminoamidine polymers are biocompatible and biodegradable. In certain embodiments, the α-aminoamidine polymers of the present invention have $pK_a$s in the range of approximately 5.5 to approximately 7.5, more preferably between approximately 6.0 and approximately 7.0. In another embodiment, the α-aminoamidine polymers may be designed to have a desired $pK_a$ between approximately 3.0 and approximately 9.0, or between approximately 5.0 and approximately 8.0. The inventive α-aminoamidine polymers are particularly attractive for drug delivery for several reasons: 1) they contain amino groups for interacting with DNA, RNA, other polynucleotides, and other negatively charged agents, for buffering the pH, for causing endosomolysis, for protecting the agent to be delivered, etc.; 2) they can be synthesized from commercially available starting materials; and/or 3) they are pH responsive and can be engineered with a desired $pK_a$.

In certain embodiments, the aldehyde is stereochemically pure (e.g., enantiomerically pure). In certain embodiments, the amine is stereochemically pure (e.g., enantiomerically pure). In certain embodiments, the isocyanide is stereochemically pure (e.g., enantiomerically pure).

In certain embodiments, the α-aminoamidine polymer of the present invention is of Formula (I):

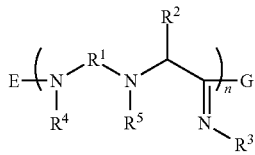
(I)

or a pharmaceutically acceptable salt or isomer thereof; wherein:

$R^1$ is a linking group comprising one or more combinations of substituted or unsubstituted, branched or unbranched, cyclic or acyclic $C_{1-20}$ aliphatic; substituted or unsubstituted, branched or unbranched, cyclic or acyclic $C_{1-20}$ heteroaliphatic; substituted or unsubstituted aryl; or substituted or unsubstituted heteroaryl; optionally interrupted by one or more groups independently selected from —O—, —S—, —OSi($R^7R^8$)O—, —Si$R^7R^8$—, and —N$R^{10}$—;

$R^2$ is hydrogen, substituted or unsubstituted, branched or unbranched, cyclic or acyclic $C_{1-20}$ aliphatic; substituted or unsubstituted, branched or unbranched cyclic or acyclic $C_{1-20}$ heteroaliphatic; substituted or unsubstituted aryl; or substituted or unsubstituted heteroaryl;

$R^3$ is substituted or unsubstituted, branched or unbranched, cyclic or acyclic $C_{1-20}$ aliphatic; substituted or unsubstituted, branched or unbranched cyclic or acyclic $C_{1-20}$ heteroaliphatic; substituted or unsubstituted aryl; or substituted or unsubstituted heteroaryl;

each instance of $R^4$, $R^5$, and $R^{10}$ is, independently, hydrogen, substituted or unsubstituted, branched or unbranched, cyclic or acyclic $C_{1-20}$ aliphatic; substituted or unsubstituted, branched or unbranched cyclic or acyclic $C_{1-20}$ heteroaliphatic; substituted or unsubstituted aryl; or substituted or unsubstituted heteroaryl, acyl, sulfonyl, or a nitrogen protecting group;

or $R^4$ and $R^5$ are joined to form a cyclic structure;
or $R^4$ and $R^1$ optionally form a cyclic structure;
or $R^5$ and $R^1$ optionally form a cyclic structure;

each of $R^7$ and $R^8$ is substituted or unsubstituted, branched or unbranched, cyclic or acyclic $C_{1-20}$ aliphatic; substituted or unsubstituted, branched or unbranched, cyclic or acyclic $C_{1-20}$ heteroaliphatic; substituted or unsubstituted aryl; or substituted or unsubstituted heteroaryl;

each E is independently, hydrogen or a group of formula $R^4$ or $R^5$;

G is

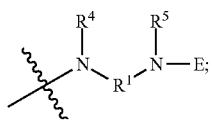

and n is an integer from 1 to 100, inclusive.

In certain embodiments, the α-aminoamidine polymer of the present invention is of Formula (II):

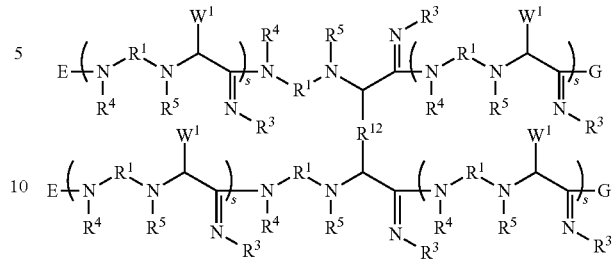
(II)

or a pharmaceutically acceptable salt or isomer thereof; wherein:

$W^1$ is $R^2$ or a group of formula:

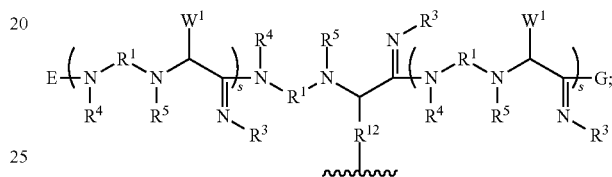

$R^1$ is a linking group comprising one or more combinations of substituted or unsubstituted, branched or unbranched, cyclic or acyclic $C_{1-20}$ aliphatic; substituted or unsubstituted, branched or unbranched, cyclic or acyclic $C_{1-20}$ heteroaliphatic; substituted or unsubstituted aryl; or substituted or unsubstituted heteroaryl; optionally interrupted by one or more groups independently selected from —O—, —S—, —OSi($R^7R^8$)O—, —Si$R^7R^8$—, and —N$R^{10}$—;

$R^2$ is hydrogen, substituted or unsubstituted, branched or unbranched, cyclic or acyclic $C_{1-20}$ aliphatic; substituted or unsubstituted, branched or unbranched cyclic or acyclic $C_{1-20}$ heteroaliphatic; substituted or unsubstituted aryl; or substituted or unsubstituted heteroaryl;

$R^3$ is substituted or unsubstituted, branched or unbranched, cyclic or acyclic $C_{1-20}$ aliphatic; substituted or unsubstituted, branched or unbranched cyclic or acyclic $C_{1-20}$ heteroaliphatic; substituted or unsubstituted aryl; or substituted or unsubstituted heteroaryl;

each instance of $R^4$, $R^5$, and $R^{10}$ is, independently, hydrogen, substituted or unsubstituted, branched or unbranched, cyclic or acyclic $C_{1-20}$ aliphatic; substituted or unsubstituted, branched or unbranched cyclic or acyclic $C_{1-20}$ heteroaliphatic; substituted or unsubstituted aryl; or substituted or unsubstituted heteroaryl, acyl, sulfonyl, or a nitrogen protecting group;

or $R^4$ and $R^5$ are joined to form a cyclic structure;
or $R^4$ and $R^1$ optionally form a cyclic structure;
or $R^5$ and $R^1$ optionally form a cyclic structure;

$R^{12}$ is a linking group comprising one or more combinations of substituted or unsubstituted, branched or unbranched, cyclic or acyclic $C_{2-20}$ aliphatic; substituted or unsubstituted, branched or unbranched, cyclic or acyclic $C_{1-20}$ heteroaliphatic; substituted or unsubstituted aryl; or substituted or unsubstituted heteroaryl; optionally interrupted by one or more groups independently selected from —O—, —S—, —OSi($R^7R^8$)O—, —Si$R^7R^8$—, and —N$R^{10}$—;

each of $R^7$ and $R^8$ is substituted or unsubstituted, branched or unbranched, cyclic or acyclic $C_{1-20}$ aliphatic;

substituted or unsubstituted, branched or unbranched, cyclic or acyclic $C_{1-20}$ heteroaliphatic; substituted or unsubstituted aryl; or substituted or unsubstituted heteroaryl;

each E is independently, hydrogen or a group of formula $R^4$ or $R^5$;

G is

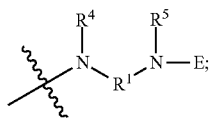

and each s is independently 0 or an integer from 1 to 100, inclusive.

In certain embodiments, the α-aminoamidine polymer of the present invention is of Formula (III):

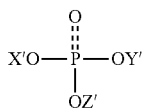

wherein each instance of X', Y', and Z' is, independently, a substituent group of formula:

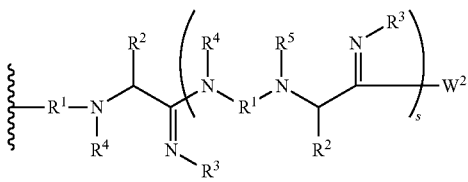

and pharmaceutically acceptable salts and isomers thereof; where $W^2$ is G or a group of formula:

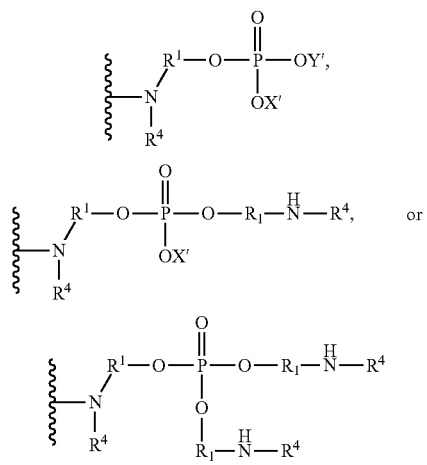

or polymers of Formula (III):

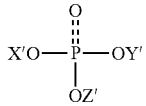

and pharmaceutically acceptable salts and isomers thereof; wherein each instance of X', Y', and Z' is, independently, a substituent group of formula:

wherein $W^3$ is $R^2$ or a group of formula:

$R^1$ is a linking group comprising one or more combinations of substituted or unsubstituted, branched or unbranched, cyclic or acyclic $C_{2-10}$ aliphatic; substituted or unsubstituted, branched or unbranched, cyclic or acyclic $C_{1-20}$ heteroaliphatic; substituted or unsubstituted aryl; or substituted or unsubstituted heteroaryl; optionally interrupted by one or more groups independently selected from —O—, —S—, —OSi($R^7R^8$)O—, —Si$R^7R^8$—, and —$NR^{10}$—;

$R^2$ is hydrogen, substituted or unsubstituted, branched or unbranched, cyclic or acyclic $C_{1-20}$ aliphatic; substituted or unsubstituted, branched or unbranched cyclic or acyclic $C_{1-20}$ heteroaliphatic; substituted or unsubstituted aryl; or substituted or unsubstituted heteroaryl;

$R^3$ is substituted or unsubstituted, branched or unbranched, cyclic or acyclic $C_{1-20}$ aliphatic; substituted or unsubstituted, branched or unbranched cyclic or acyclic $C_{1-20}$ heteroaliphatic; substituted or unsubstituted aryl; or substituted or unsubstituted heteroaryl;

each instance of $R^4$, $R^5$, and $R^{10}$ is, independently, hydrogen, substituted or unsubstituted, branched or unbranched, cyclic or acyclic $C_{1-20}$ aliphatic; substituted or unsubstituted, branched or unbranched cyclic or acyclic $C_{1-20}$ heteroaliphatic; substituted or unsubstituted aryl; or substituted or unsubstituted heteroaryl, acyl, sulfonyl, or a nitrogen protecting group;

or $R^4$ and $R^5$ are joined to form a cyclic structure;

or $R^4$ and $R^1$ optionally form a cyclic structure;

or $R^5$ and $R^1$ optionally form a cyclic structure;

each E is independently, hydrogen or a group of formula $R^4$ or $R^5$;

G is

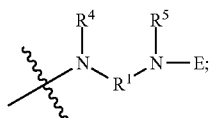

$R^{12}$ is a linking group comprising one or more combinations of substituted or unsubstituted, branched or unbranched, cyclic or acyclic $C_{2-20}$ aliphatic; substituted or unsubstituted, branched or unbranched, cyclic or acyclic $C_{1-20}$ heteroaliphatic; substituted or unsubstituted aryl; or substituted or unsubstituted heteroaryl; optionally interrupted by one or more groups independently selected from —O—, —S—, —OSi($R^7R^8$)O—, —Si$R^7R^8$—, and —N$R^{10}$—;

each of $R^7$ and $R^8$ is substituted or unsubstituted, branched or unbranched, cyclic or acyclic $C_{1-20}$ aliphatic; substituted or unsubstituted, branched or unbranched, cyclic or acyclic $C_{1-20}$ heteroaliphatic; substituted or unsubstituted aryl; or substituted or unsubstituted heteroaryl;

each s is independently 0 or an integer from 1 to 100, inclusive; and

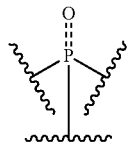

is either

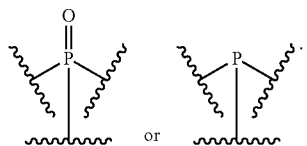

In certain embodiments, the α-aminoamidine polymer of the present invention is of Formula (III):

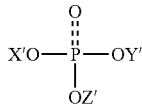

(III)

or a pharmaceutically acceptable salt or isomer thereof;

wherein each instance of X', Y', and Z' is, independently, a group of formula:

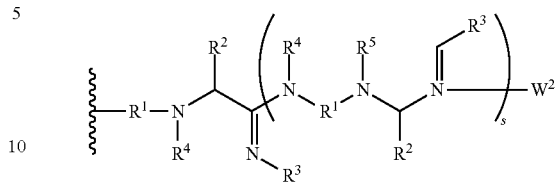

and pharmaceutically acceptable salts and isomers thereof; where $W^2$ is G or a group of formula:

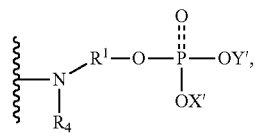

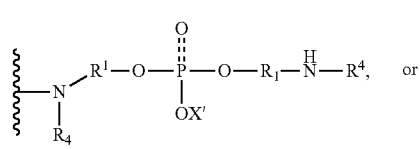

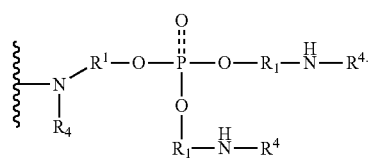

In certain embodiments, the α-aminoamidine polymer of the present invention is of Formula (III):

(III)

and pharmaceutically acceptable salts and isomers thereof; wherein each instance of X', Y', and Z' is, independently, a substituent group of formula:

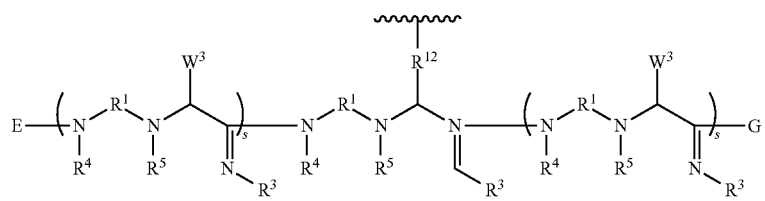

wherein $W^3$ is $R^2$ or a group of formula:

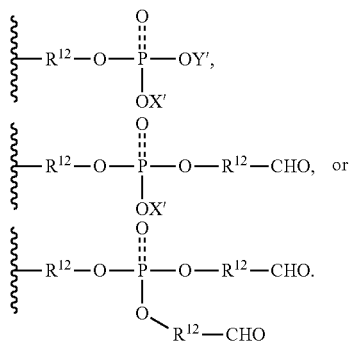

In certain embodiments, the α-aminoamidine polymer of the present invention is of Formula (IV):

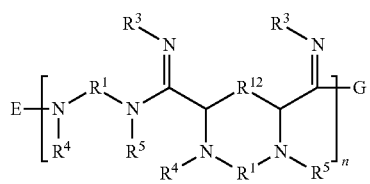

or a pharmaceutically acceptable salt or isomer thereof;
wherein:

$R^1$ is a linking group comprising one or more combinations of substituted or unsubstituted, branched or unbranched, cyclic or acyclic $C_{1-20}$ aliphatic; substituted or unsubstituted, branched or unbranched, cyclic or acyclic $C_{1-20}$ heteroaliphatic; substituted or unsubstituted aryl; or substituted or unsubstituted heteroaryl; optionally interrupted by one or more groups independently selected from —O—, —S—, —OSi($R^7R^8$)O—, —Si$R^7R^8$—, and —N$R^{10}$—;

$R^3$ is substituted or unsubstituted, branched or unbranched, cyclic or acyclic $C_{1-20}$ aliphatic; substituted or unsubstituted, branched or unbranched cyclic or acyclic $C_{1-20}$ heteroaliphatic; substituted or unsubstituted aryl; or substituted or unsubstituted heteroaryl;

each instance of $R^4$, $R^5$, and $R^{10}$ is, independently, hydrogen, substituted or unsubstituted, branched or unbranched, cyclic or acyclic $C_{1-20}$ aliphatic; substituted or unsubstituted, branched or unbranched cyclic or acyclic $C_{1-20}$ heteroaliphatic; substituted or unsubstituted aryl; or substituted or unsubstituted heteroaryl, acyl, sulfonyl, or a nitrogen protecting group;

or $R^4$ and $R^5$ are joined to form a cyclic structure;
or $R^4$ and $R^1$ optionally form a cyclic structure;
or $R^5$ and $R^1$ optionally form a cyclic structure;

each E is independently, hydrogen or a group of formula $R^4$ or $R^5$;

G is

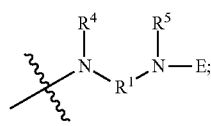

$R^{12}$ is a linking group comprising one or more combinations of substituted or unsubstituted, branched or unbranched, cyclic or acyclic $C_{2-20}$ aliphatic; substituted or unsubstituted, branched or unbranched, cyclic or acyclic $C_{1-20}$ heteroaliphatic; substituted or unsubstituted aryl; or substituted or unsubstituted heteroaryl; optionally interrupted by one or more groups independently selected from —O—, —S—, —OSi($R^7R^8$)O—, —Si$R^7R^8$—, and —N$R^{10}$—;

each of $R^7$ and $R^8$ is substituted or unsubstituted, branched or unbranched, cyclic or acyclic $C_{1-20}$ aliphatic; substituted or unsubstituted, branched or unbranched, cyclic or acyclic $C_{1-20}$ heteroaliphatic; substituted or unsubstituted aryl; or substituted or unsubstituted heteroaryl; and n is an integer from 1 to 100, inclusive.

In certain embodiments, $R^1$ is interrupted by one or more moieties selected from the group consisting of:

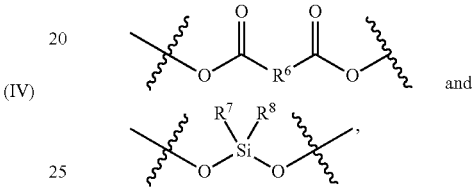

wherein $R^6$ is a linking group comprising one or more combinations of substituted or unsubstituted, branched or unbranched, cyclic or acyclic $C_{1-20}$ aliphatic; substituted or unsubstituted, branched or unbranched, cyclic or acyclic $C_{1-20}$ heteroaliphatic; substituted or unsubstituted aryl; or substituted or unsubstituted heteroaryl; optionally interrupted by one or more groups independently selected from —O—, —S—, —OSi($R^7R^8$)O—, —Si$R^7R^8$—, and —N$R^{10}$—, wherein $R^7$ and $R^8$ are as defined herein.

In certain embodiments, $R^1$ is a group of the formula:

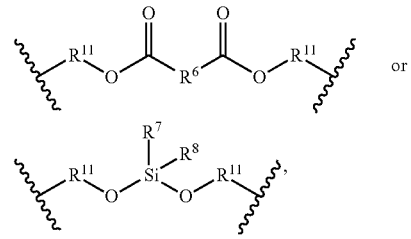

wherein $R^{11}$ is a linking group comprising one or more combinations of substituted or unsubstituted, branched or unbranched, cyclic or acyclic $C_{1-20}$ aliphatic; substituted or unsubstituted, branched or unbranched, cyclic or acyclic $C_{1-20}$ heteroaliphatic; substituted or unsubstituted aryl; or substituted or unsubstituted heteroaryl; optionally interrupted by one or more groups independently selected from —O—, —S—, —OSi($R^7R^8$)O—, —Si$R^7R^8$—, and —N$R^{10}$—, wherein $R^7$ and $R^8$ are as defined herein.

In certain embodiments, $R^6$ is unsubstituted, acyclic, branched or unbranched $C_{1-20}$ aliphatic. In certain embodiments, wherein $R^6$ is unsubstituted, acyclic, branched or unbranched $C_{1-6}$ alkyl. In certain embodiments, $R^6$ is substituted or unsubstituted, branched or unbranched alkyl. In certain embodiments, $R^6$ is substituted or unsubstituted, branched or unbranched alkenyl. In certain embodiments, $R^6$ is substituted or unsubstituted phenyl.

In certain embodiments, $R^6$ is selected from the group consisting of:

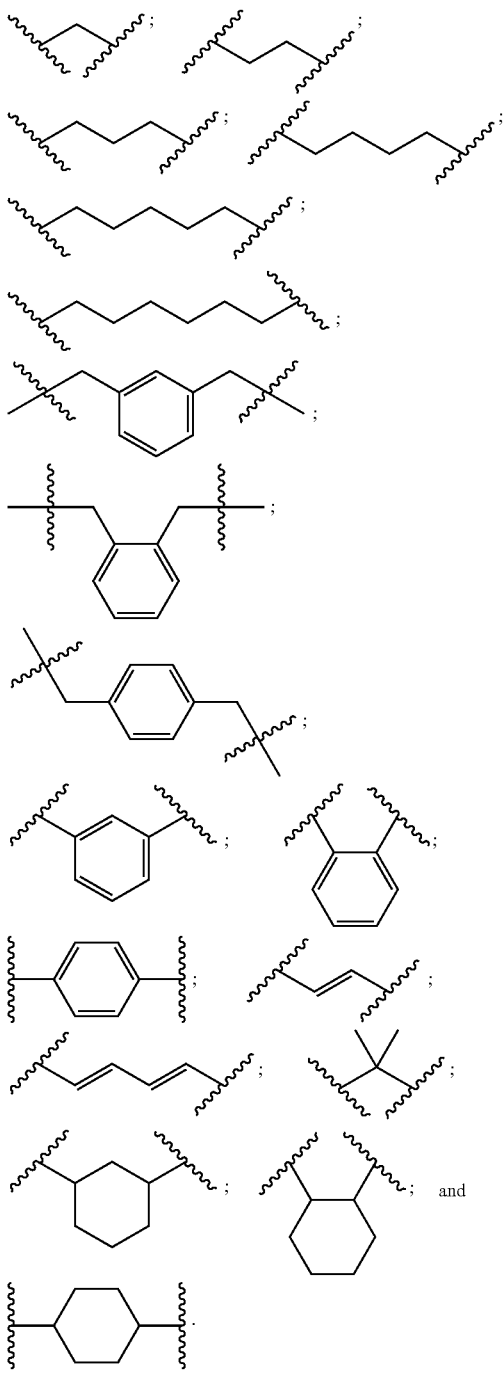

In certain embodiments, $R^{11}$ is a substituted or unsubstituted, branched or unbranched, cyclic or acyclic $C_{1-20}$ aliphatic; or a substituted or unsubstituted, branched or unbranched, cyclic or acyclic $C_{1-20}$ heteroaliphatic.

In certain embodiments, $R^{11}$ is a substituted or unsubstituted, branched or unbranched, cyclic or acyclic $C_{1-20}$ aliphatic interrupted by one or more heteroatoms independently selected from O, S, Si, and $NR^{10}$; or a substituted or unsubstituted, branched or unbranched, cyclic or acyclic $C_{1-20}$ heteroaliphatic interrupted by one or more heteroatoms independently selected from O, S, Si, and $NR^{10}$.

In certain embodiments, $R^{11}$ is interrupted by one or more moieties selected from the group consisting of

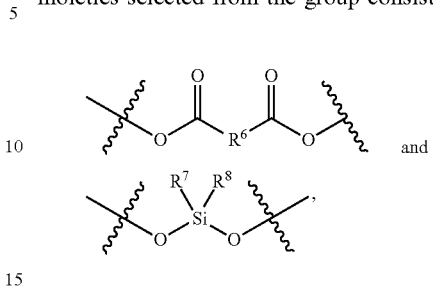

wherein $R^6$ is a substituted or unsubstituted, branched or unbranched, cyclic or acyclic $C_{1-20}$ aliphatic; or a substituted or unsubstituted, branched or unbranched, cyclic or acyclic $C_{1-20}$ heteroaliphatic; substituted or unsubstituted aryl; substituted or unsubstituted heteroaryl; optionally interrupted by one or more groups independently selected from —O—, —S—, —OSi($R^7R^8$)O—, —Si$R^7R^8$—, and —$NR^{10}$—, wherein $R^7$ and $R^8$ are as defined herein.

In certain embodiments, $R^1$ is substituted or unsubstituted, branched or unbranched $C_{1-20}$ aliphatic. In certain embodiments, $R^1$ is substituted or unsubstituted, branched or unbranched $C_{1-20}$ heteroaliphatic. In certain embodiments, $R^1$ is substituted or unsubstituted, branched or unbranched $C_{1-20}$ alkylene. In certain embodiments, $R^1$ is an unsubstituted, unbranched, and acyclic $C_{2-20}$ alkylene. In certain embodiments, $R^1$ is a substituted or unsubstituted, branched or unbranched, cyclic or acyclic $C_{2-20}$ alkylene, optionally interrupted by 1 or more —$NR^{10}$— groups.

In certain embodiments, $R^1$ is a substituted, unbranched, and acyclic $C_{2-10}$ alkylene, optionally interrupted, by 1 —O— atom.

In certain embodiments, $R^1$ is of the formula

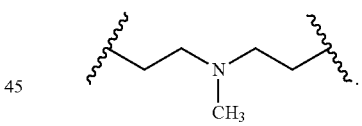

In certain embodiments, $R^1$ is a substituted or unsubstituted, branched or unbranched, cyclic or acyclic $C_{2-20}$ alkylene, optionally interrupted, by 1 or more —O— atoms.

In certain embodiments $R^1$ is an unsubstituted, unbranched, and acyclic $C_{2-10}$ alkylene, optionally interrupted by 1 or more —O— atoms.

In certain embodiments $R^1$ is an unsubstituted, unbranched, and acyclic $C_{2-10}$ alkylene, optionally interrupted by 2 —O— atoms.

In certain embodiments, $R^1$ is of the formula

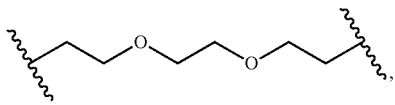 [SMILES: *CCOCCOCC*]

In certain embodiments, $R^1$ is of the formula

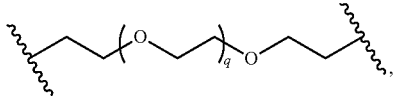

wherein q is an integer between 1 and 10, inclusive.

In certain embodiments, $R^1$ is a substituted or unsubstituted, branched or unbranched, cyclic or acyclic $C_{2-20}$ alkylene, optionally interrupted by 1 or more $—NR^{10}—$ groups.

In certain embodiments $R^1$ is an unsubstituted, unbranched, and acyclic $C_{2-10}$ alkylene, optionally interrupted by 1 or more $—NR^{10}—$ groups.

In certain embodiments $R^1$ is an unsubstituted, unbranched, and acyclic $C_{2-10}$ alkylene, optionally interrupted by 2 $—NR^{10}—$ groups.

In certain embodiments, $R^1$ is of the formula

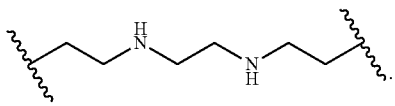 [SMILES: *CCNCCNCC*]

In certain embodiments, $R^1$ is of the formula

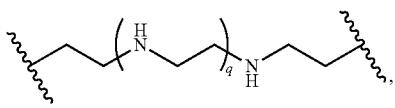

wherein q is an integer between 1 and 10, inclusive.

In certain embodiments, $R^1$ is selected from any one of the following formula:

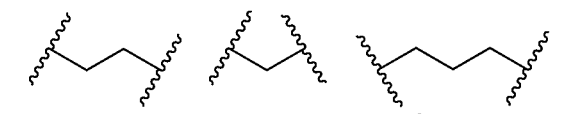
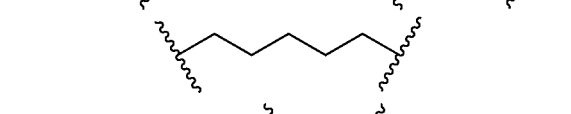
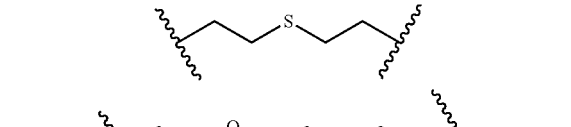
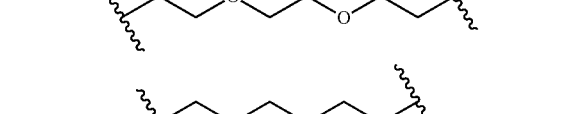
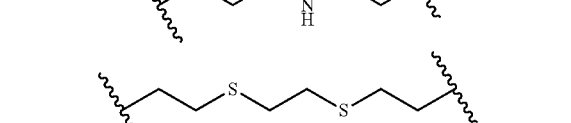

-continued

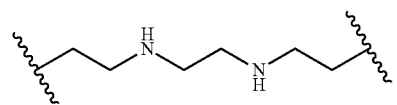
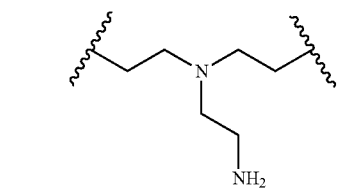
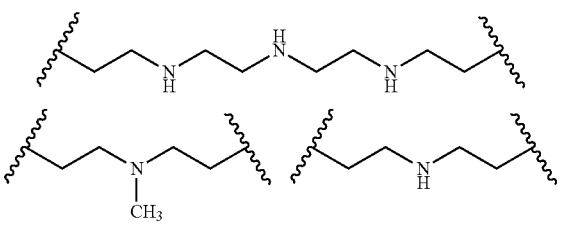
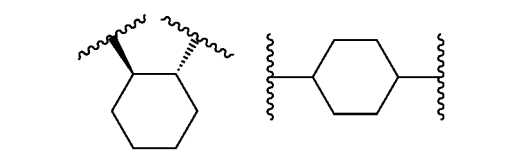
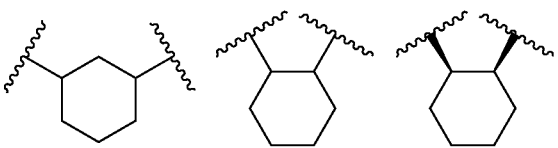
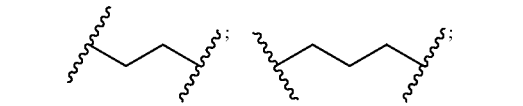
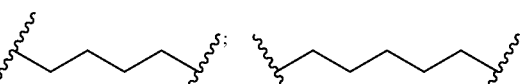
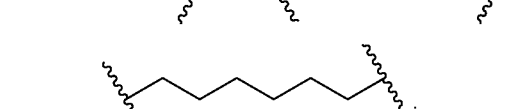
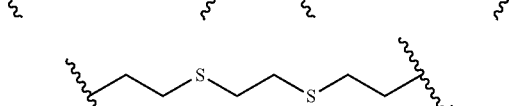
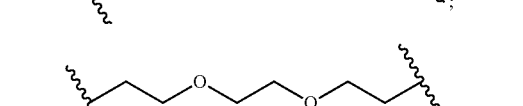
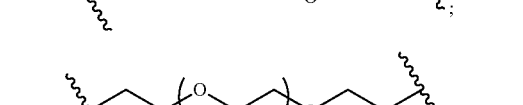
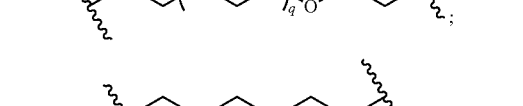
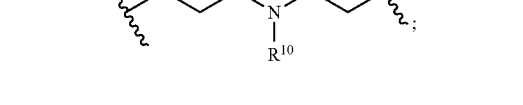

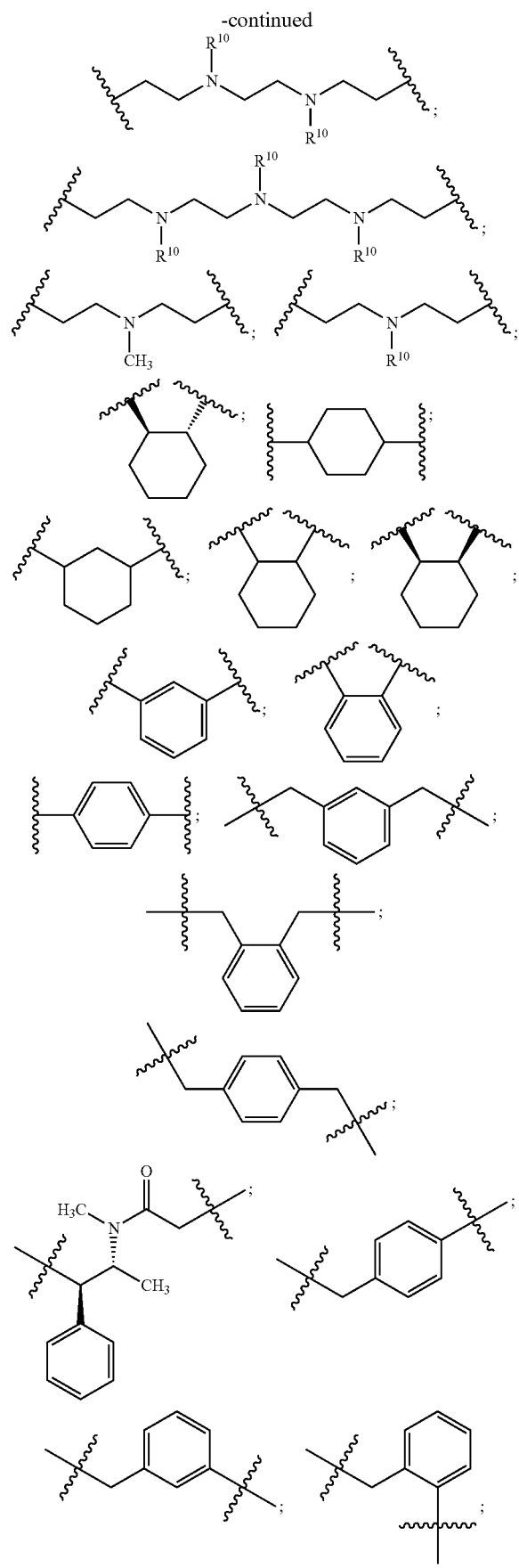
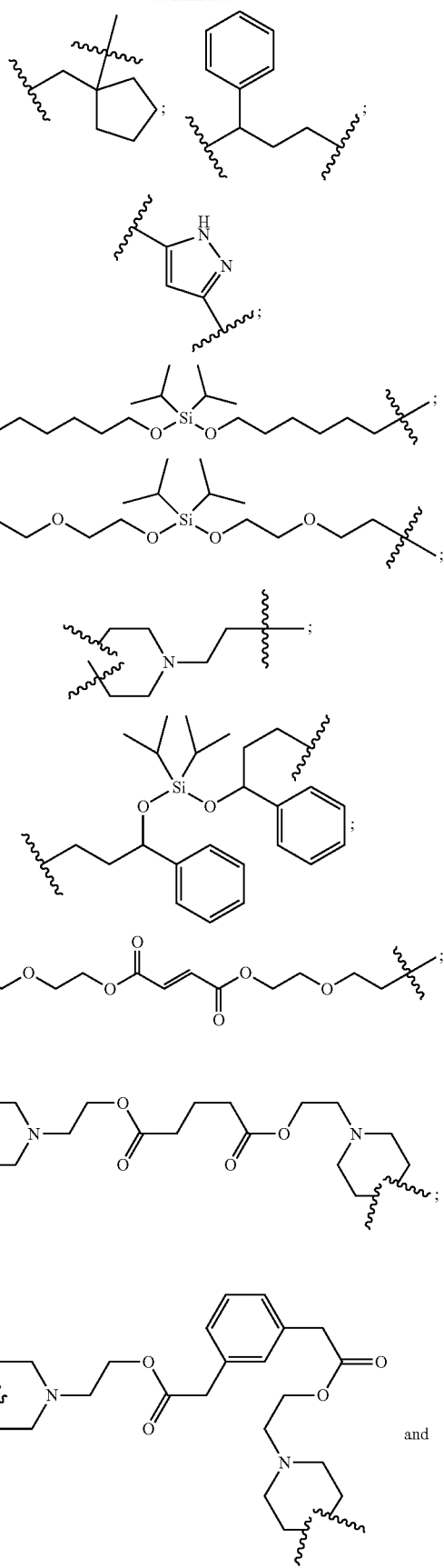

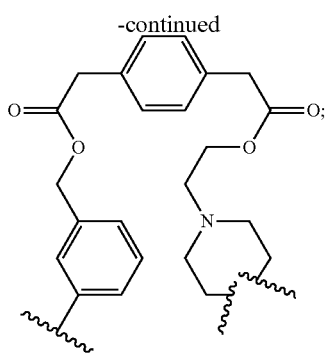

wherein q is an integer between 1 and 10, inclusive.

In certain embodiments, at least one instance of $R^2$ is hydrogen. In certain embodiments, each instance of $R^2$ is hydrogen.

In certain embodiments, $R^2$ is a substituted or unsubstituted, branched or unbranched, cyclic or acyclic $C_{1-20}$ aliphatic. In certain embodiments, $R^2$ is a substituted or unsubstituted, branched or unbranched cyclic or acyclic $C_{1-20}$ heteroaliphatic. In certain embodiments $R^2$ is a substituted or unsubstituted aryl. In certain embodiments, $R^2$ is a substituted or unsubstituted heteroaryl.

In certain embodiments, $R^2$ is substituted or unsubstituted $C_{1-20}$ alkyl. In certain embodiments, $R^2$ is selected from the following formula:

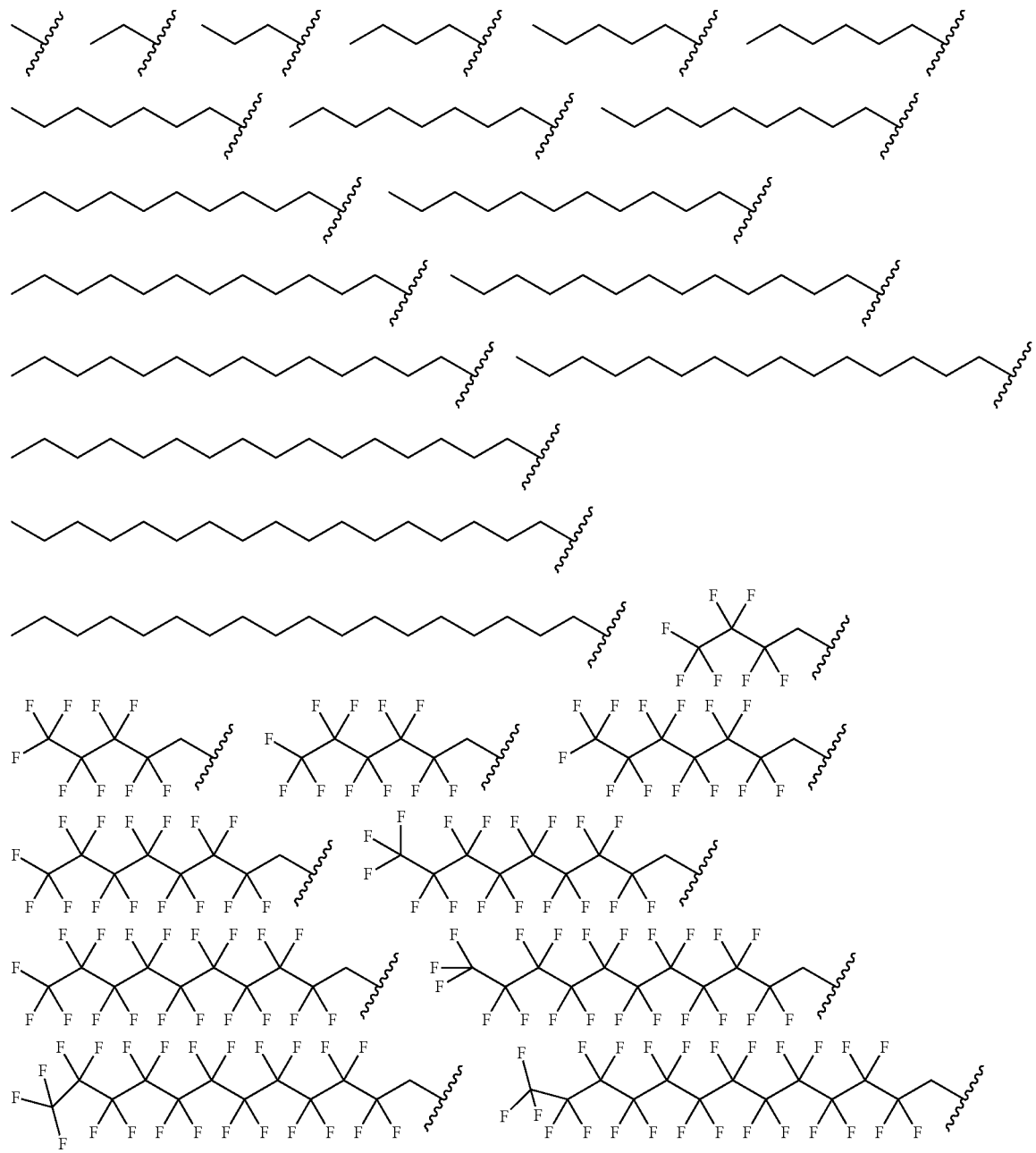

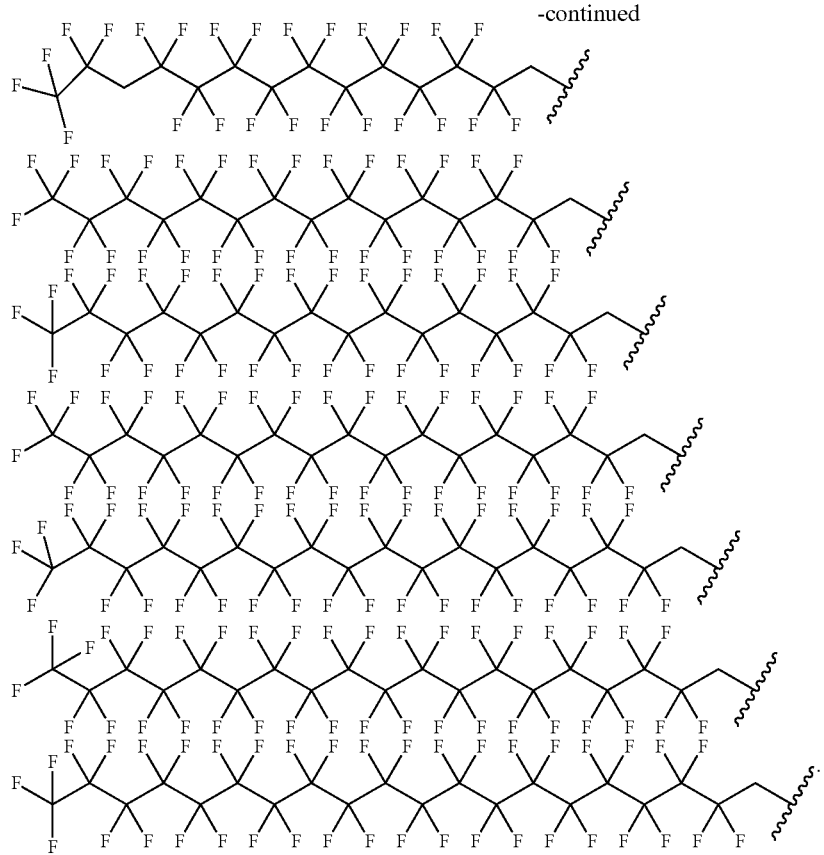
In certain embodiments, $R^2$ is substituted or unsubstituted $C_{2-20}$ alkenyl. In certain embodiments, $R^2$ is selected from the following formula:
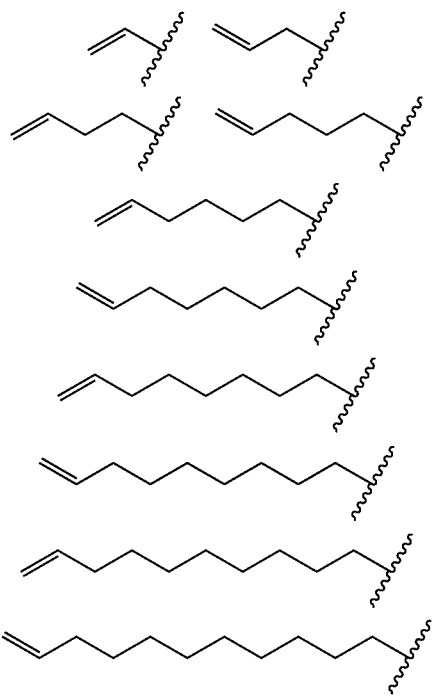
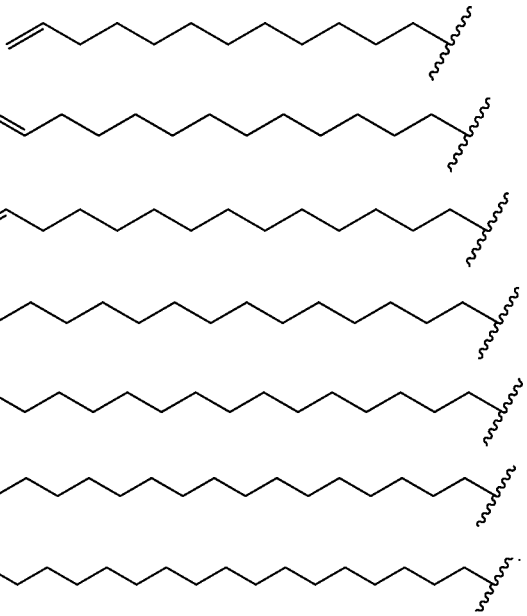
In certain embodiments, $R^2$ is substituted or unsubstituted $C_{1-20}$ heteroaliphatic. In certain embodiments, $R^2$ is selected from the following formula:

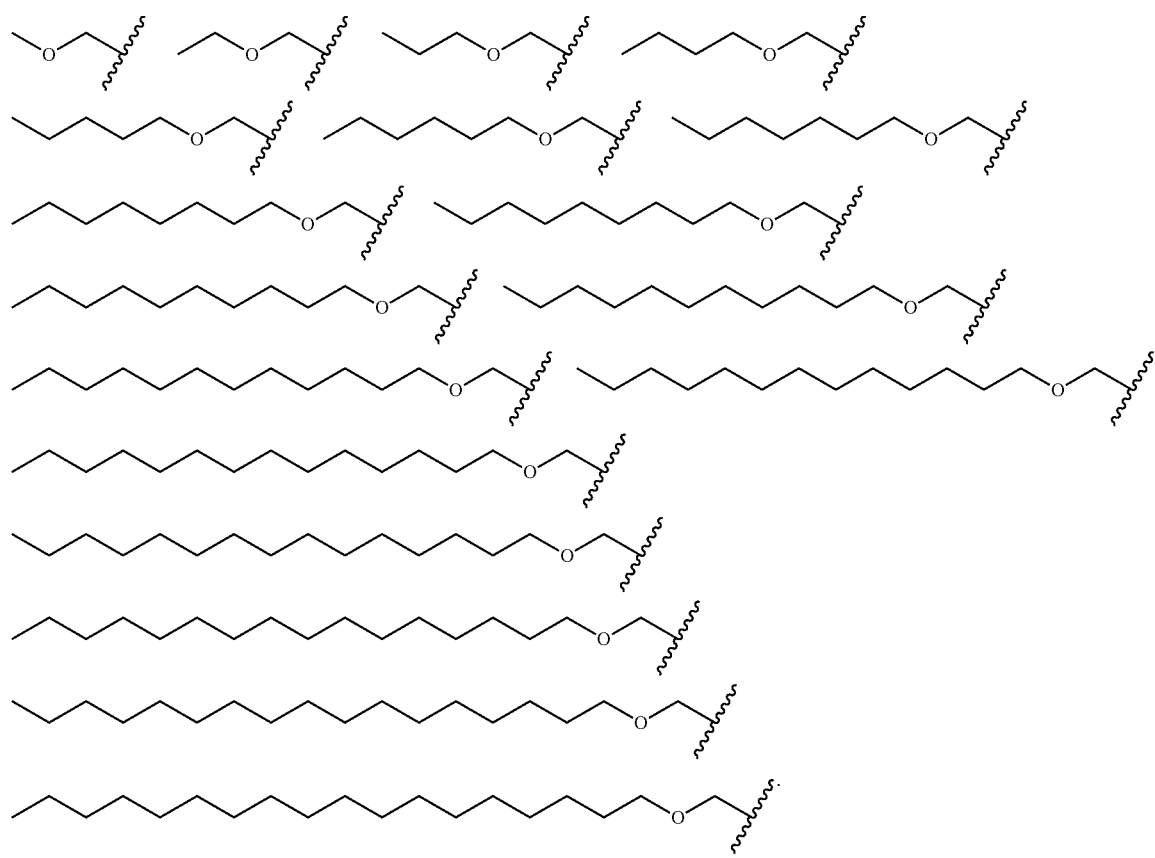
In certain embodiments, $R^2$ is a substituted or unsubstituted phenyl. In certain embodiments, $R^2$ is substituted or unsubstituted aralkyl, e.g., substituted or unsubstituted benzyl.
In certain embodiments, $R^2$ is selected from the group consisting of:
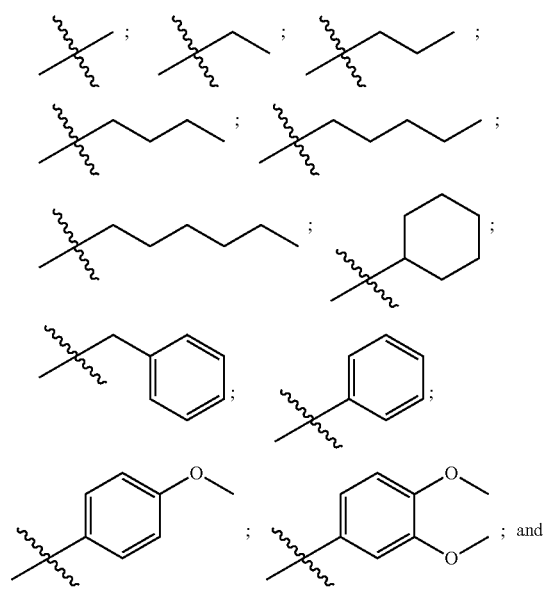
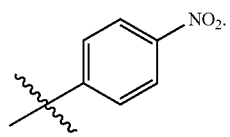
In certain embodiments, $R^2$ is selected from the group consisting of:
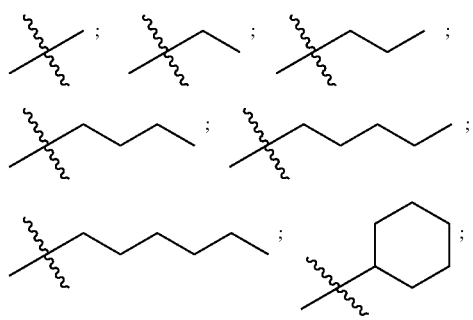

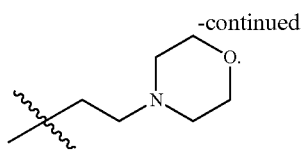

In certain embodiments, $R^3$ is a substituted or unsubstituted, branched or unbranched, cyclic or acyclic $C_{1-20}$ aliphatic. In certain embodiments, $R^3$ is a substituted or unsubstituted, branched or unbranched cyclic or acyclic $C_{1-20}$ heteroaliphatic. In certain embodiments $R^3$ is a substituted or unsubstituted aryl. In certain embodiments, $R^3$ is a substituted or unsubstituted heteroaryl.

In certain embodiments, $R^3$ is substituted or unsubstituted $C_{1-20}$ alkyl. In certain embodiments, $R^3$ is selected from the following formula:

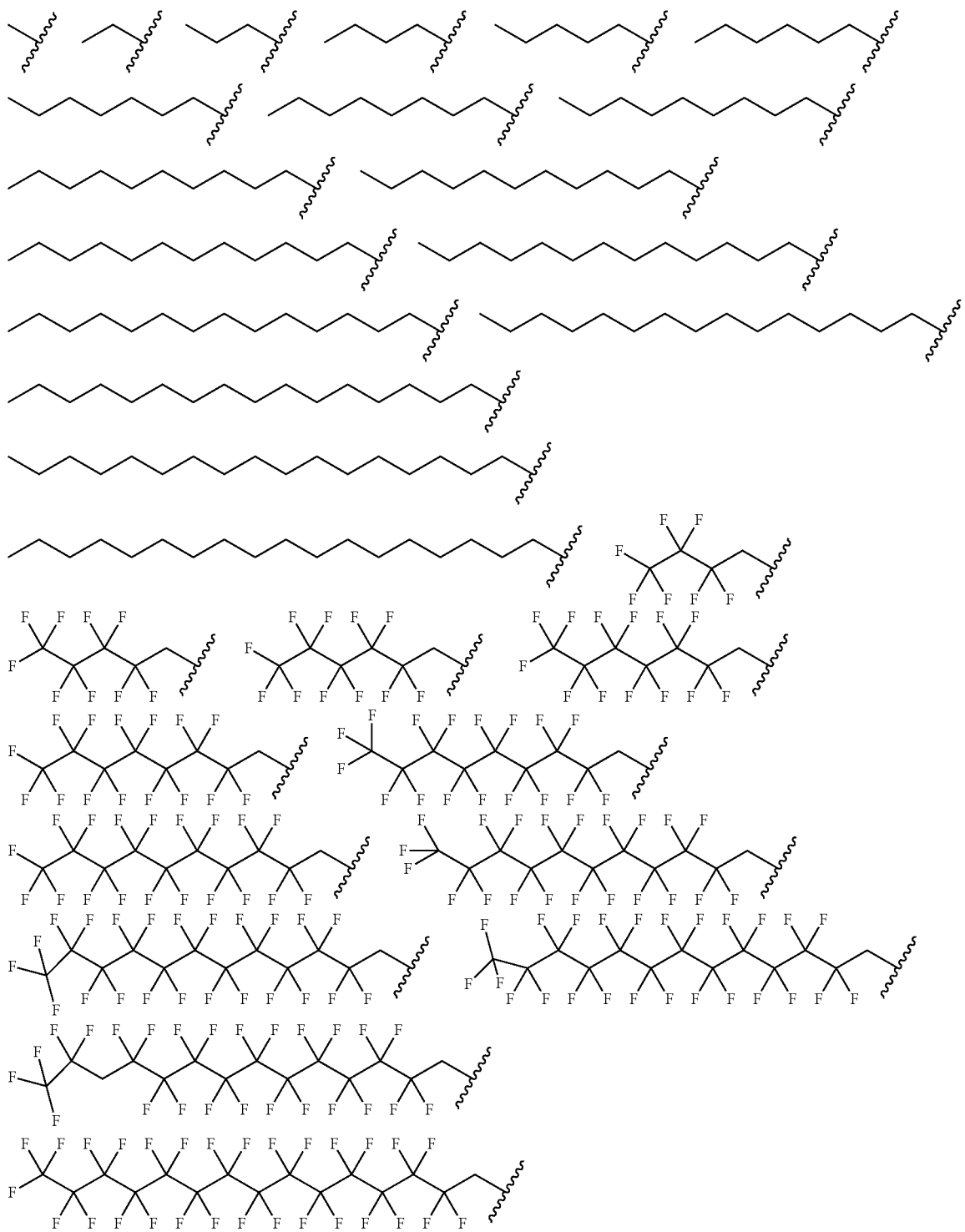

-continued
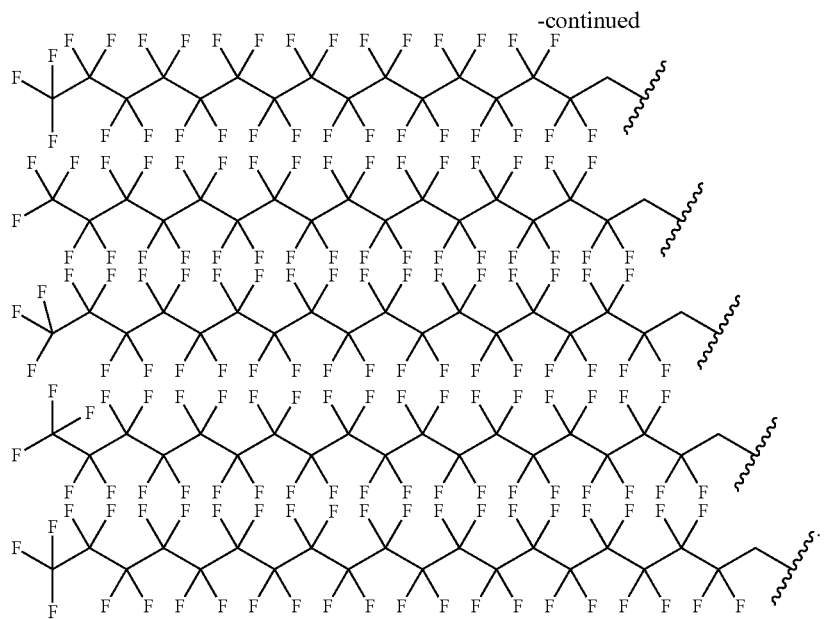
In certain embodiments, $R^3$ is substituted or unsubstituted $C_{2-20}$ alkenyl. In certain embodiments, $R^3$ is selected from the following formula:
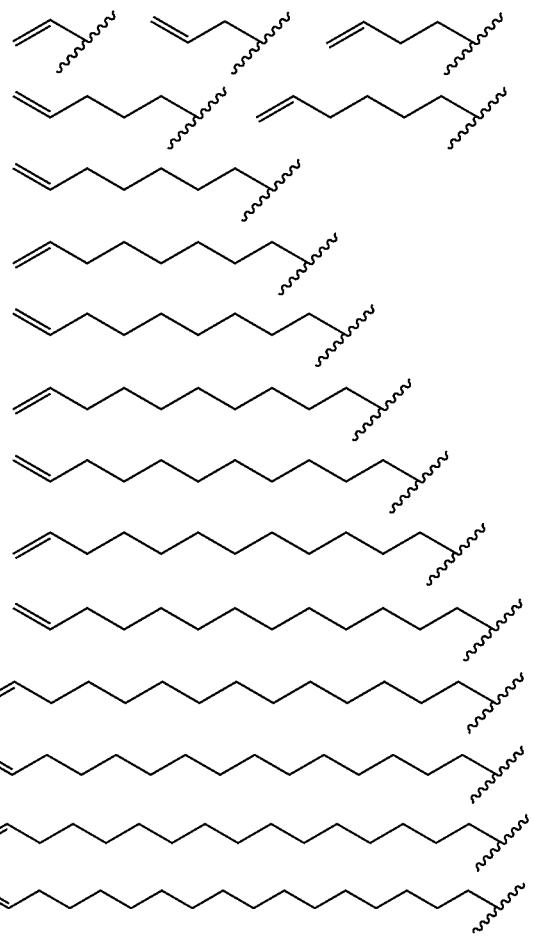
-continued
In certain embodiments, $R^3$ is substituted or unsubstituted $C_{1-20}$ heteroaliphatic. In certain embodiments, $R^3$ is selected from the following formula:
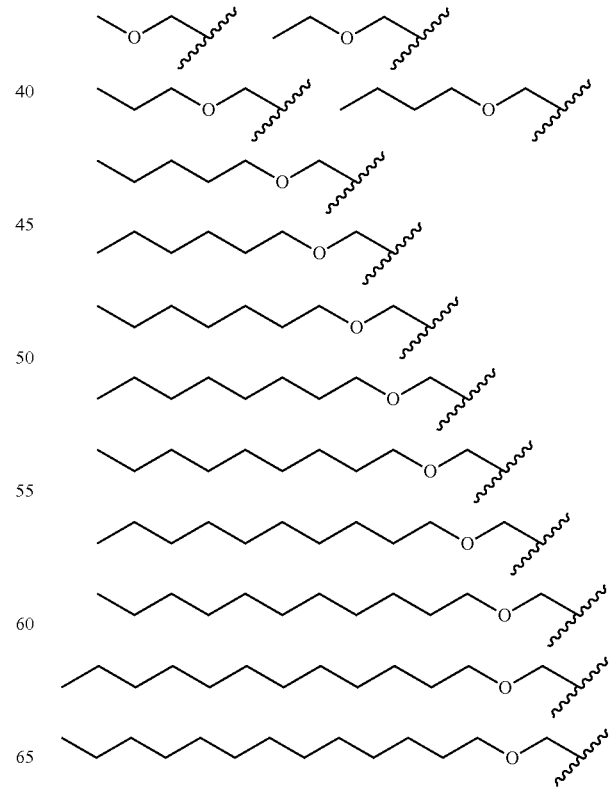

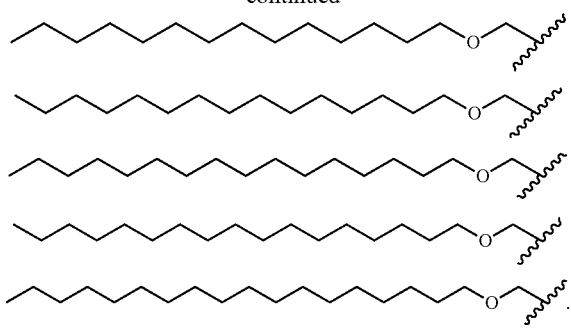

In certain embodiments, R³ is a substituted or unsubstituted phenyl. In certain embodiments, R³ is substituted or unsubstituted aralkyl, e.g., substituted or unsubstituted benzyl.

In certain embodiments, R³ is selected from the group consisting of:

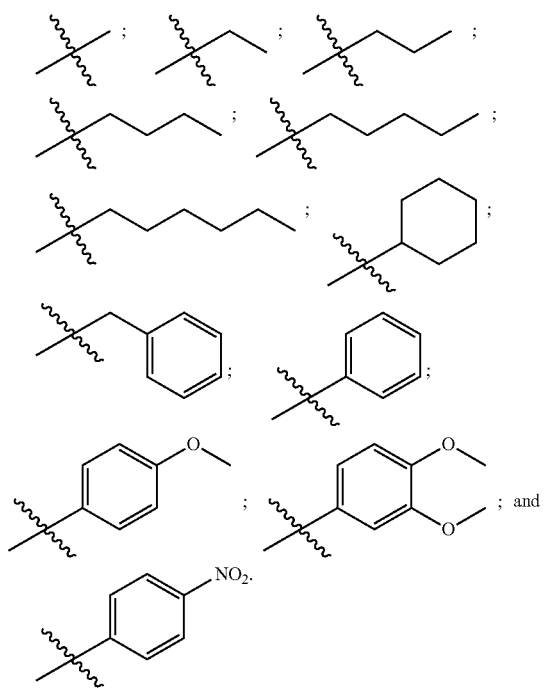

In certain embodiments, R³ is selected from the group consisting of:

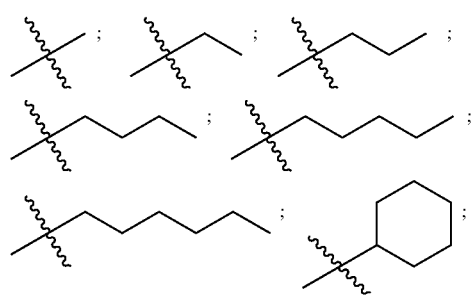

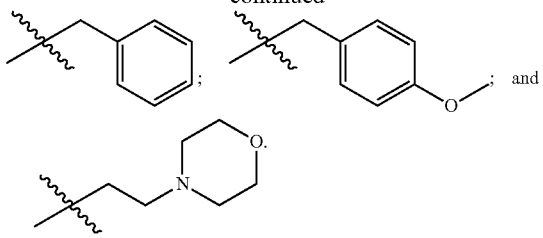

In certain embodiments, each of R⁴ and R⁵ is, independently, hydrogen, methyl, ethyl, propyl, or butyl. In certain embodiments, all R⁴ and R⁵ are hydrogen. In certain embodiments, all R⁴ and R⁵ are, independently, hydrogen or methyl.

In certain embodiments, R⁴ and R¹ together within each

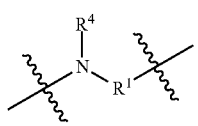

form a cyclic structure, e.g., such as a group of the formula:

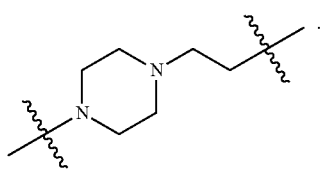 [SMILES: *CCN1CCN(*)CC1]

In certain embodiments, R⁵ and R¹ together within each

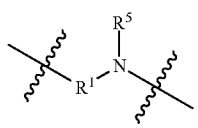

form a cyclic structure, e.g., such as a group of the formula:

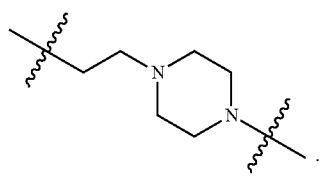 [SMILES: *CCN1CCN(*)CC1]

In certain embodiments, R⁴ and R⁵ together within each

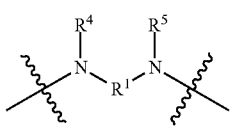

form a cyclic structure, e.g., such as a group of the formula:

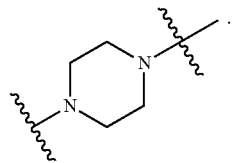 [SMILES: *N1CCN(*)CC1]

In certain embodiments, each of $R^7$ and $R^8$ is a substituted or unsubstituted, branched or unbranched, cyclic or acyclic $C_{1-20}$ alkyl, or a substituted or unsubstituted aryl. In certain embodiments, $R^7$ and $R^8$ are selected from the group consisting of methyl, ethyl, propyl, butyl, and phenyl.

In certain embodiments, $R^{10}$ is hydrogen or methyl.

In certain embodiments, $R^4$, $R^5$, and $R^{10}$ are, independently, selected from the group consisting of hydrogen, methyl, ethyl, n-propyl, isopropyl, cyclopropyl, —CH$_2$—cyclopropyl, vinyl, allyl, n-butyl, sec-butyl, isobutyl, tert-butyl, cyclobutyl, —CH$_2$-cyclobutyl, n-pentyl, sec-pentyl, isopentyl, tert-pentyl, cyclopentyl, —CH$_2$-cyclopentyl, n-hexyl, sec-hexyl, and cyclohexyl.

In certain embodiments, $R^{12}$ is a substituted or unsubstituted, branched or unbranched, cyclic or acyclic $C_{1-20}$ aliphatic; or a substituted or unsubstituted, branched or unbranched, cyclic or acyclic $C_{1-20}$ heteroaliphatic.

In certain embodiments, $R^{12}$ is a substituted or unsubstituted, branched or unbranched, cyclic or acyclic $C_{1-20}$ aliphatic interrupted by one or more groups independently selected from —O—, —S—, —OSi($R^7R^8$)O—, —SiR$^7$R$^8$—, and —NR$^{10}$—, wherein $R^7$ and $R^8$ are as defined herein.

In certain embodiments, $R^{12}$ is interrupted by one or more moieties selected from the group consisting of

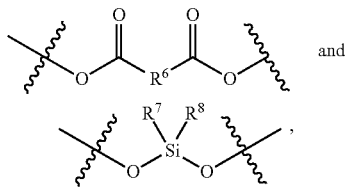
and wherein $R^6$ is a substituted or unsubstituted, branched or unbranched, cyclic or acyclic $C_{1-20}$ aliphatic; or a substituted or unsubstituted, branched or unbranched, cyclic or acyclic $C_{1-20}$ heteroaliphatic; substituted or unsubstituted aryl; substituted or unsubstituted heteroaryl; optionally interrupted by one or more groups independently selected from —O—, —S—, —OSi($R^7R^8$)O—, —SiR$^7$R$^8$—, and —NR$^{10}$—, wherein $R^7$ and $R^8$ are as defined herein.

In certain embodiments, $R^{12}$ is selected from the group consisting of:

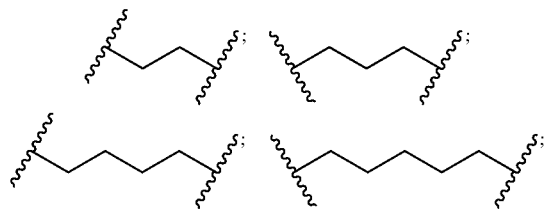

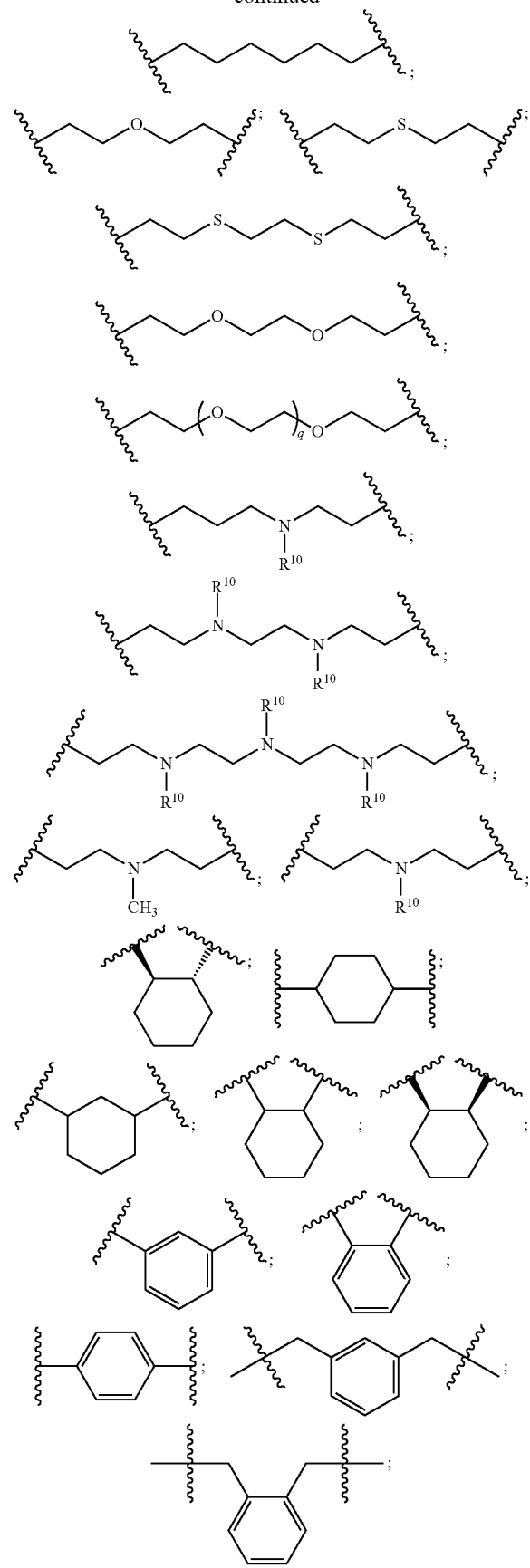

-continued
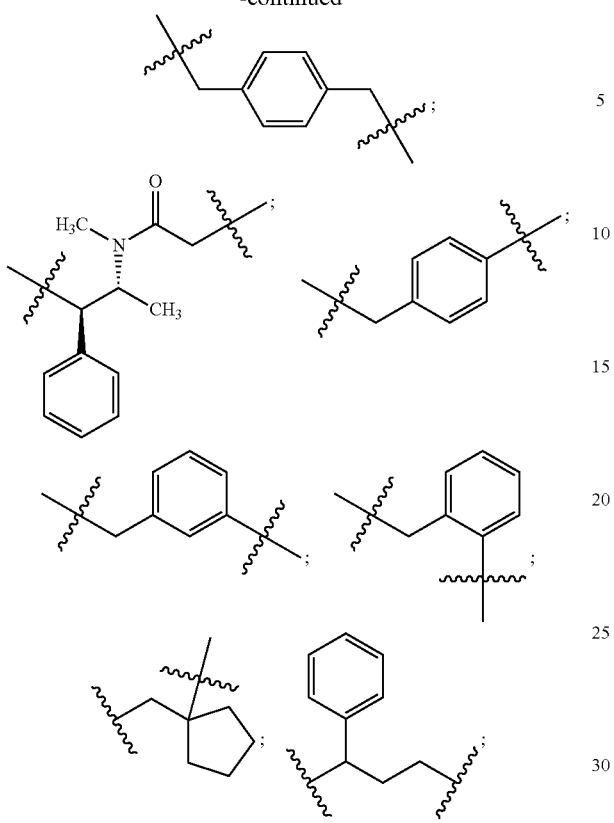
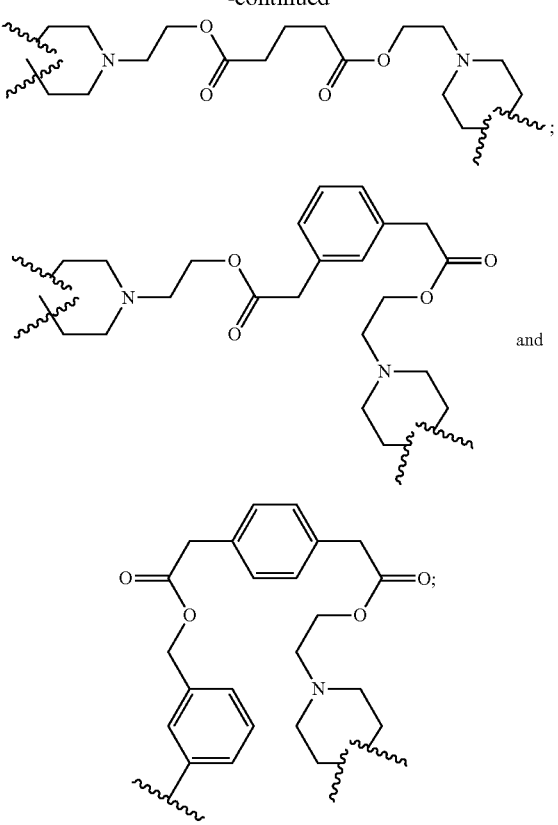
wherein q is an integer between 1 and 10, inclusive.
In certain embodiments,
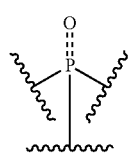
is
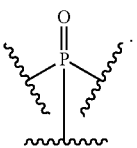
In certain embodiments,
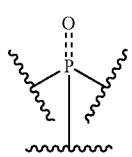
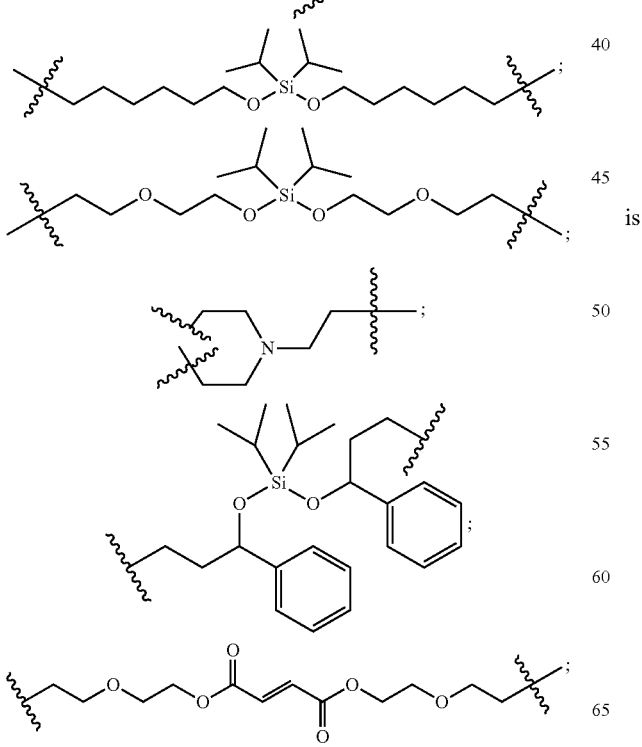

is

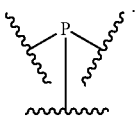

In certain embodiments, n is 1. In certain embodiments, n is 2. In certain embodiments, n is 3. In certain embodiments, n is 4. In certain embodiments, n is 5. In certain embodiments, n is 6. In certain embodiments, n is 7. In certain embodiments, n is 8. In certain embodiments, n is 9. In certain embodiments, n is 10.

In certain embodiments, q is 1. In certain embodiments, q is 2. In certain embodiments, q is 3. In certain embodiments, q is 4. In certain embodiments, q is 5. In certain embodiments, q is 6. In certain embodiments, q is 7. In certain embodiments, q is 8. In certain embodiments, q is 9. In certain embodiments, q is 10.

In certain embodiments, s is 0. In certain embodiments, s is 1. In certain embodiments, s is 2. In certain embodiments, s is 3. In certain embodiments, s is 4. In certain embodiments, s is 5. In certain embodiments, s is 6. In certain embodiments, s is 7. In certain embodiments, s is 8. In certain embodiments, s is 9. In certain embodiments, s is 10.

Figure 12A:
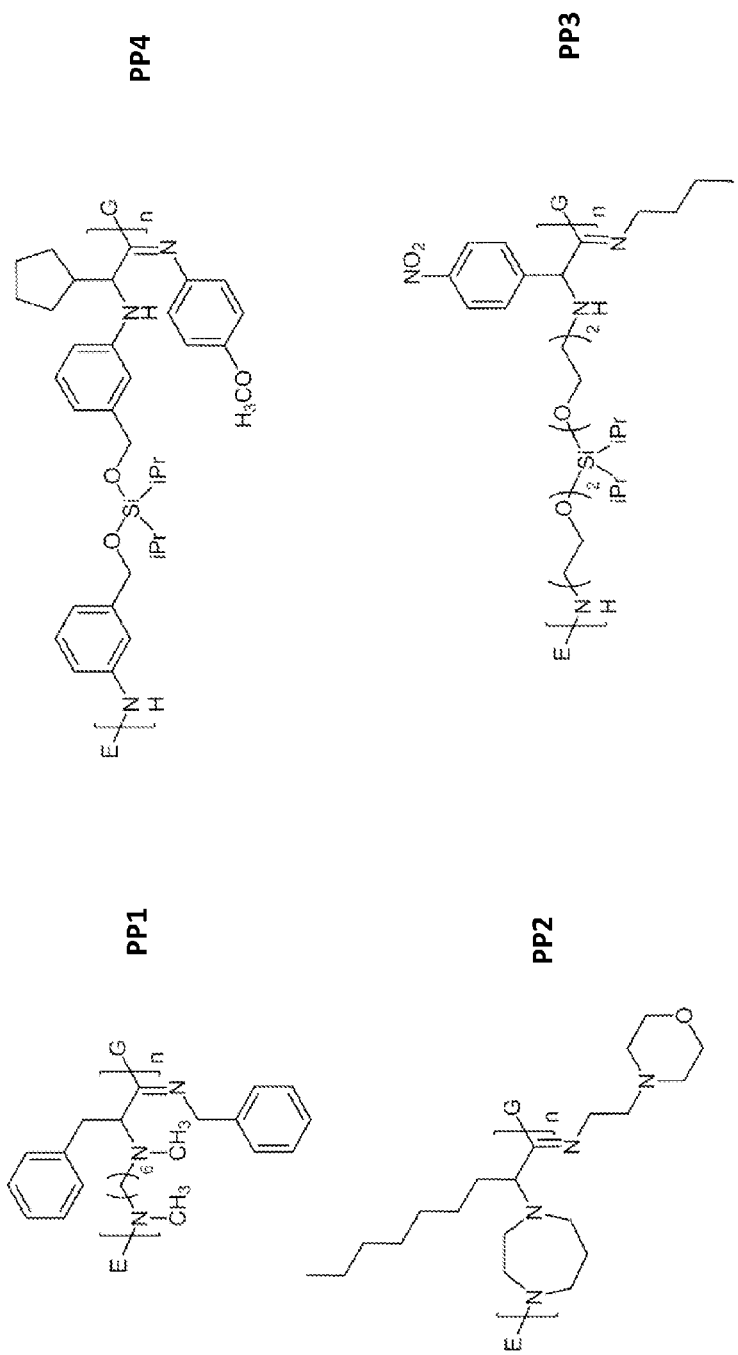
FIGS. 12A-12Z depict exemplary polymers of the present invention. The percentage of silencing in HeLa cell culture that is observed is listed for certain polymers.
Figure 12B:
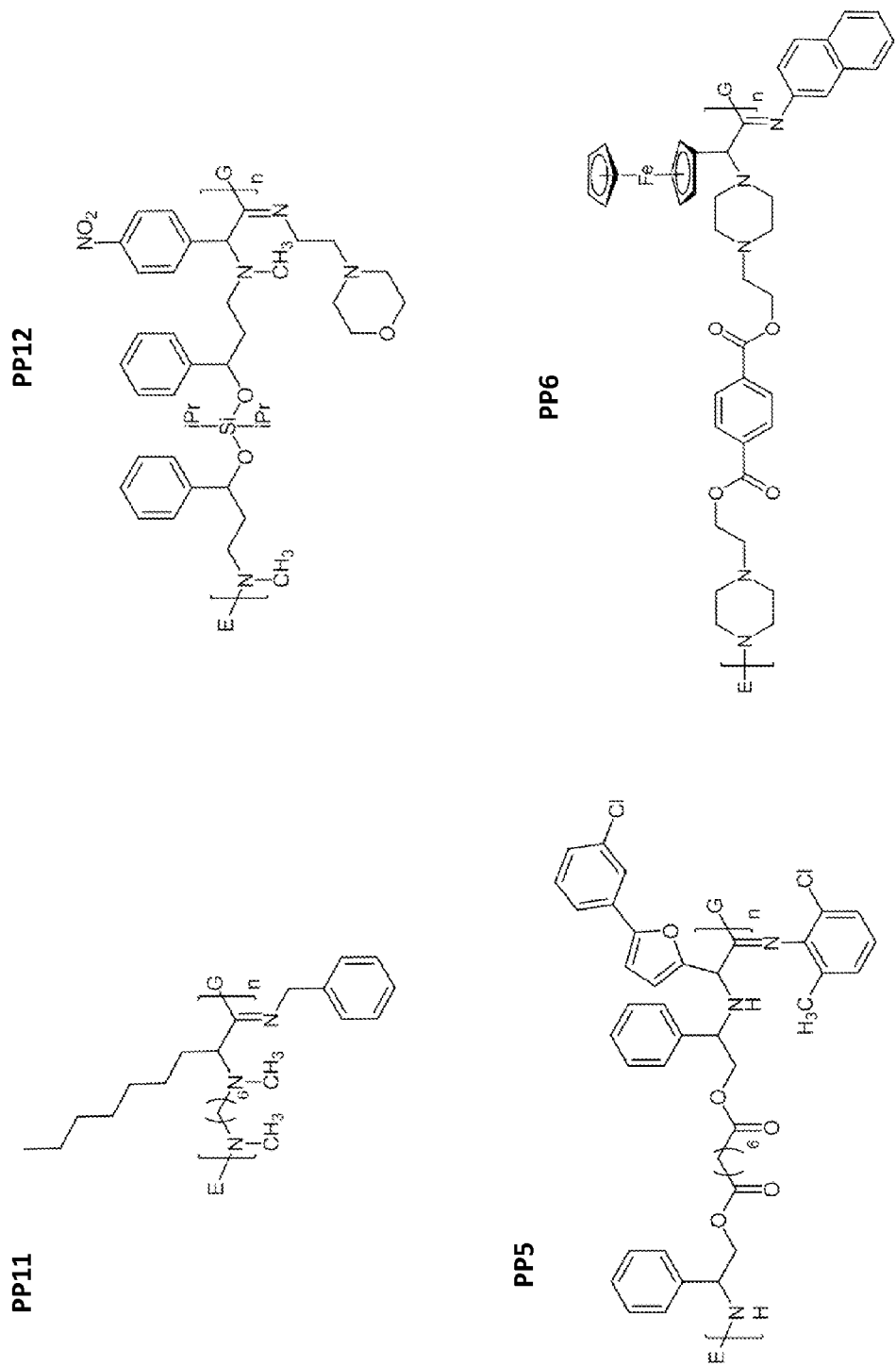
Figure 12C:
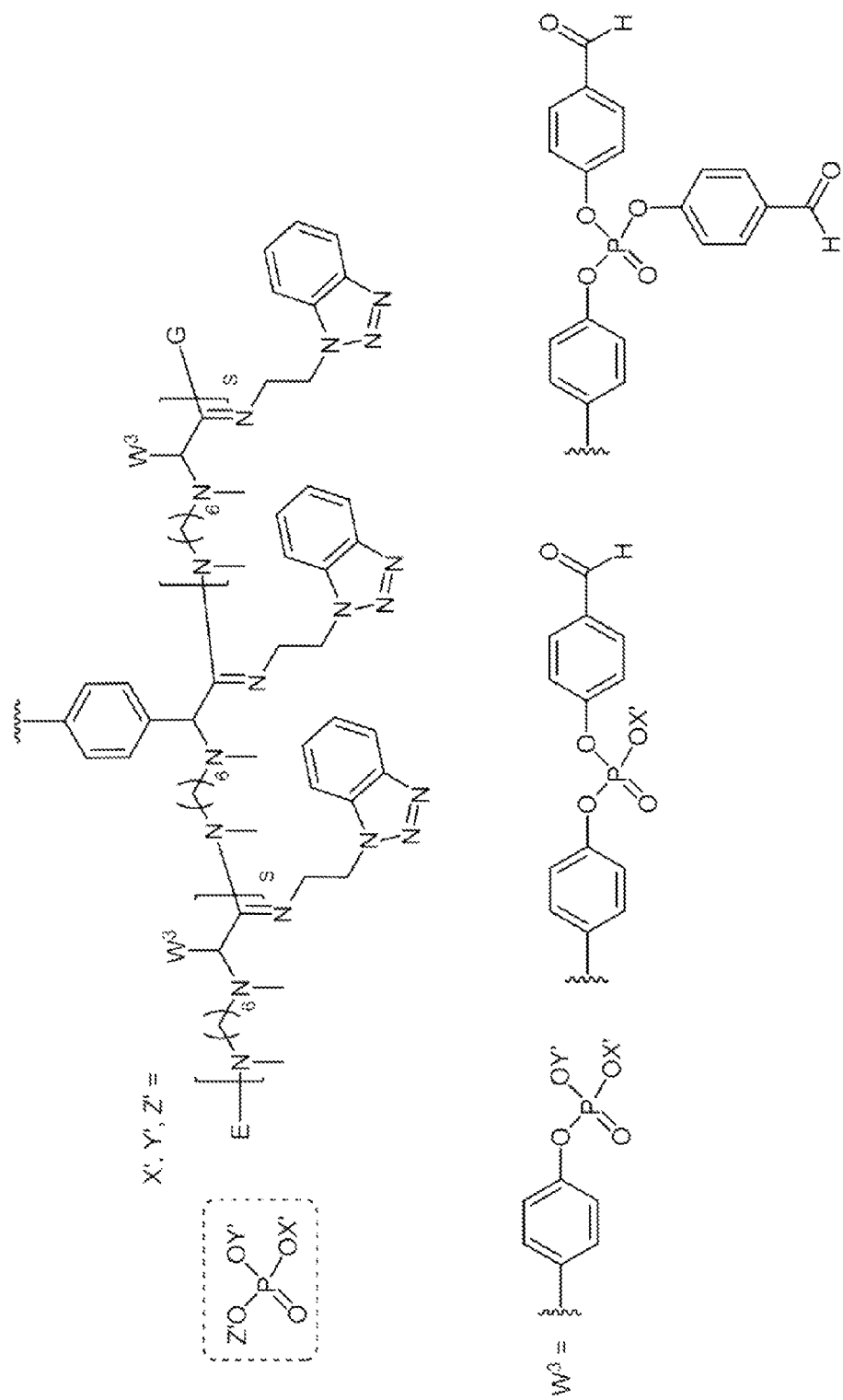
Figure 12D:
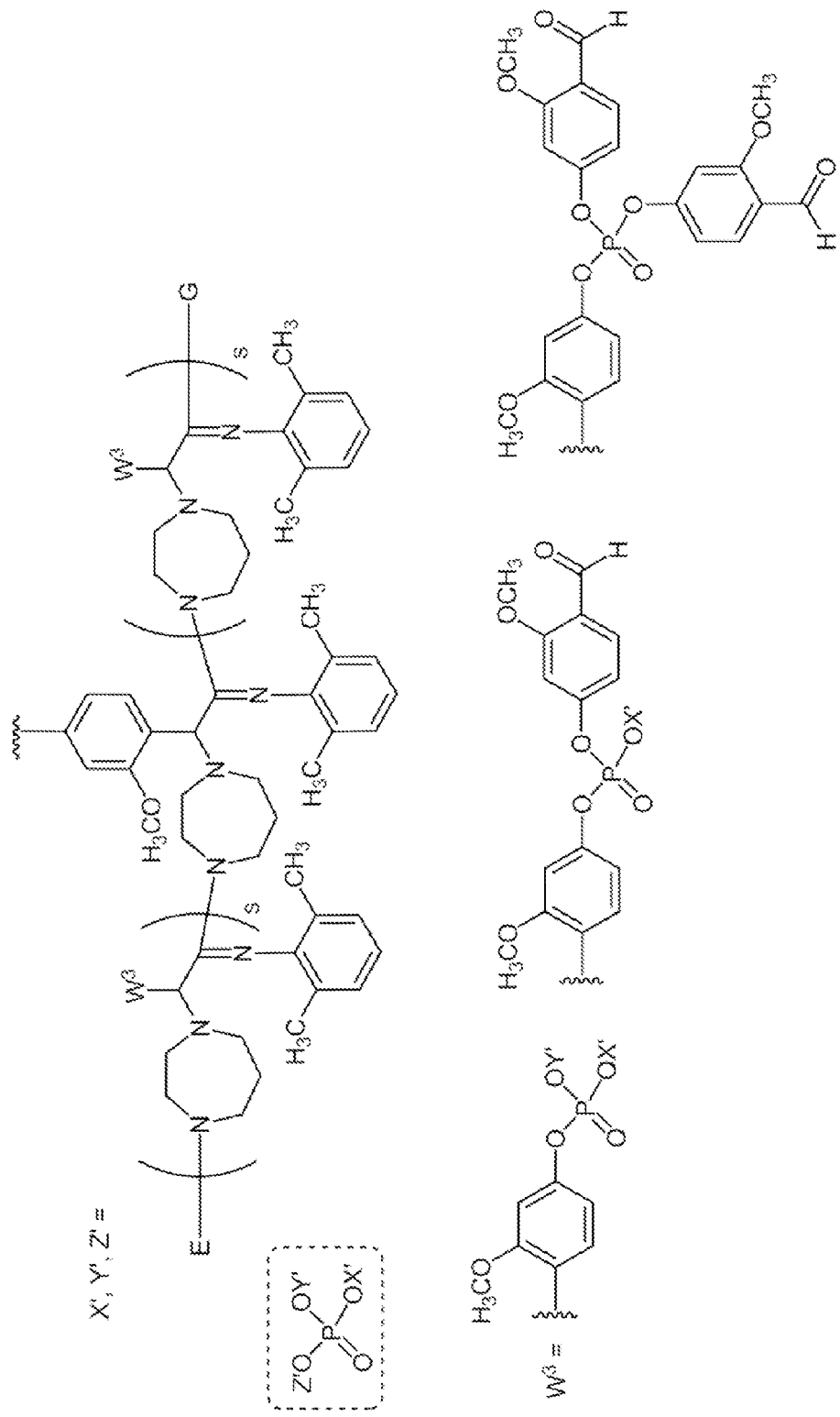
Figure 12E:
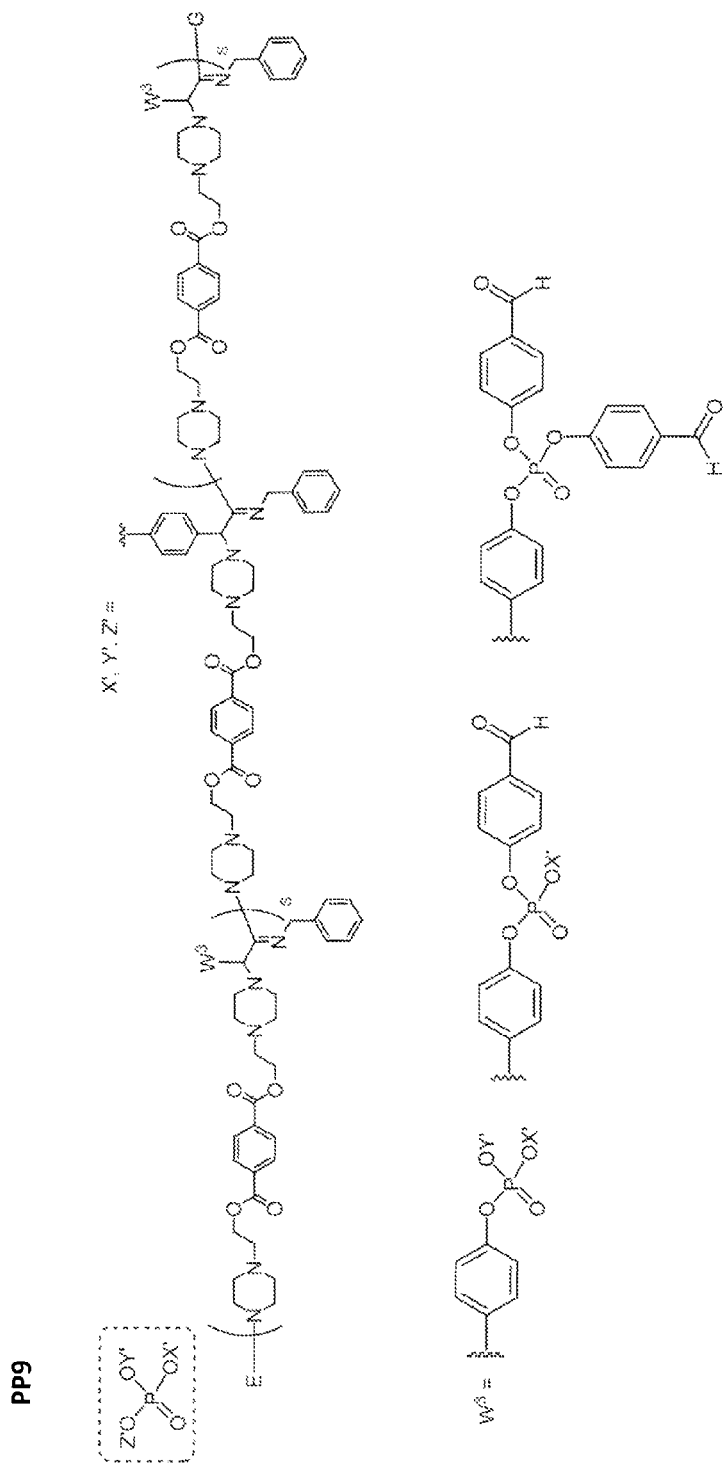
Figure 12F:
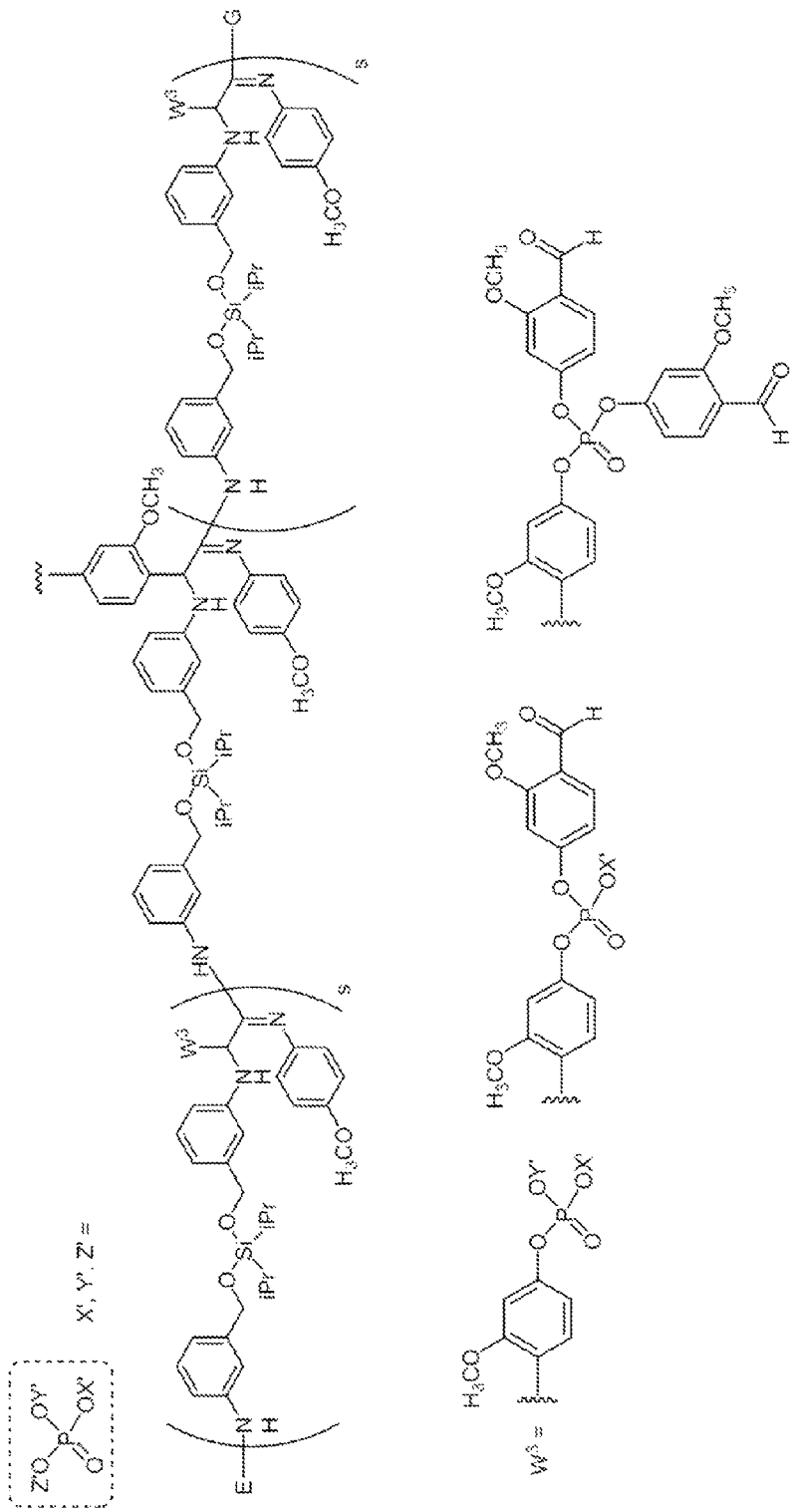
Figure 12G:
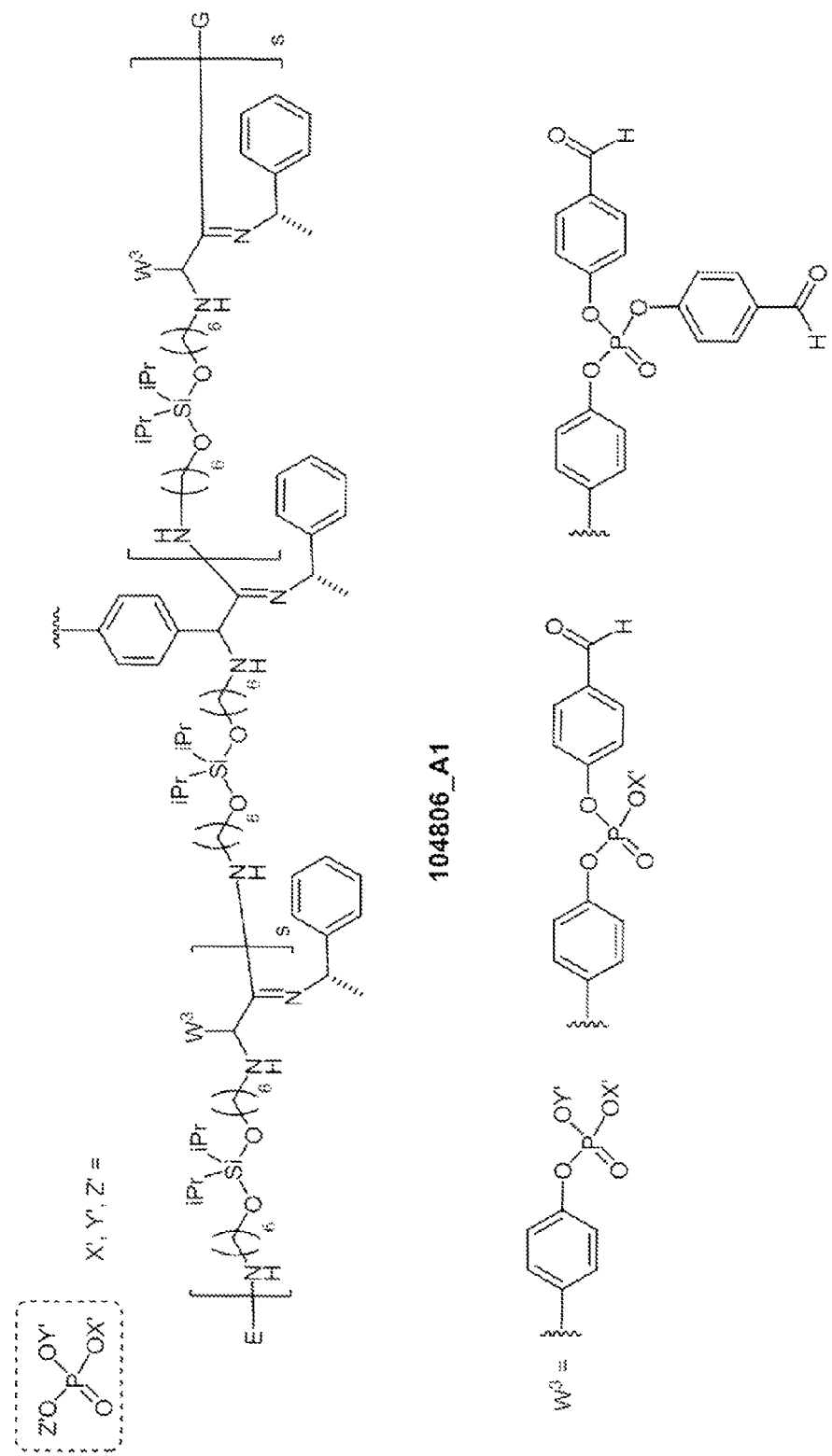
Figure 12H:
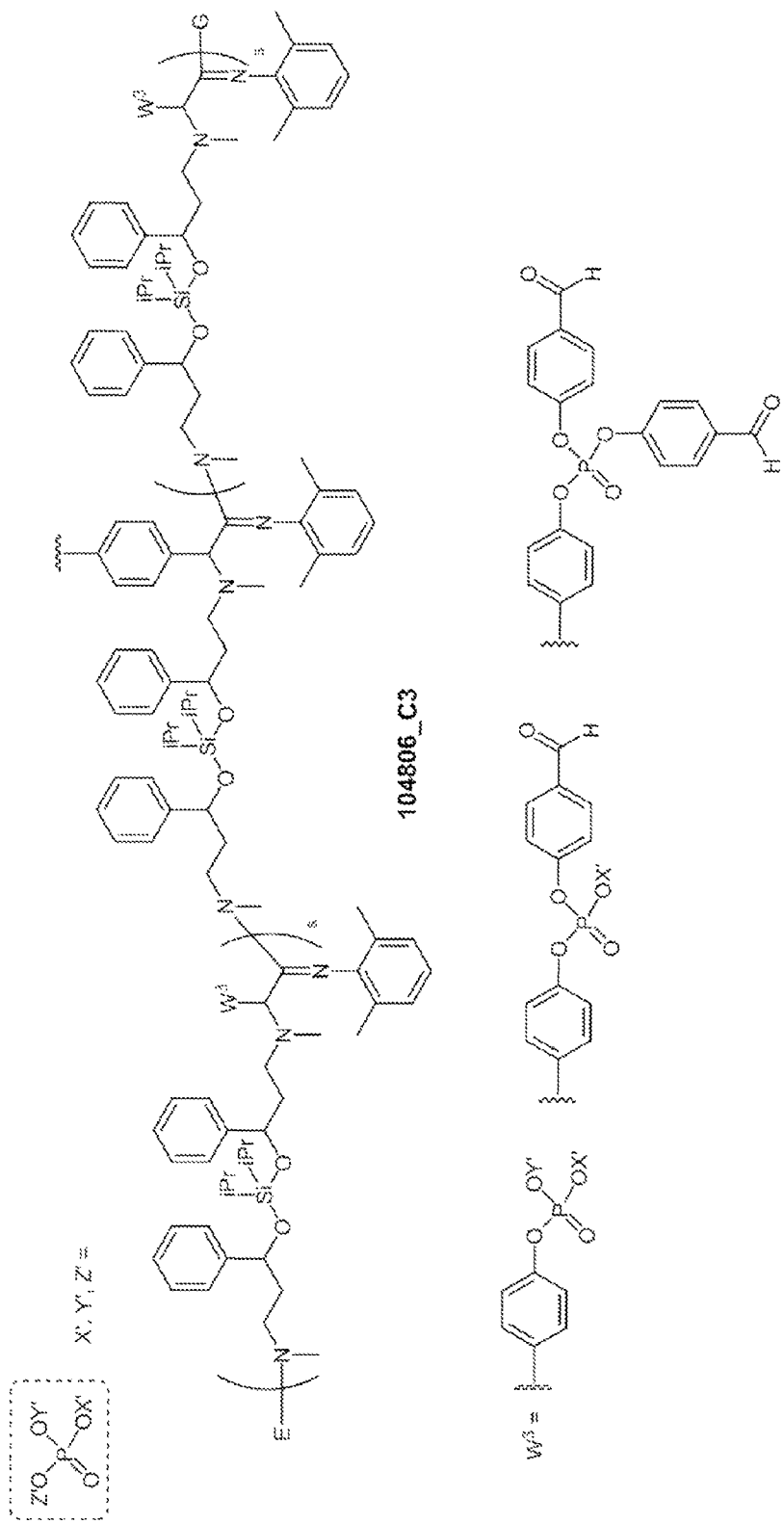
Figure 12I:
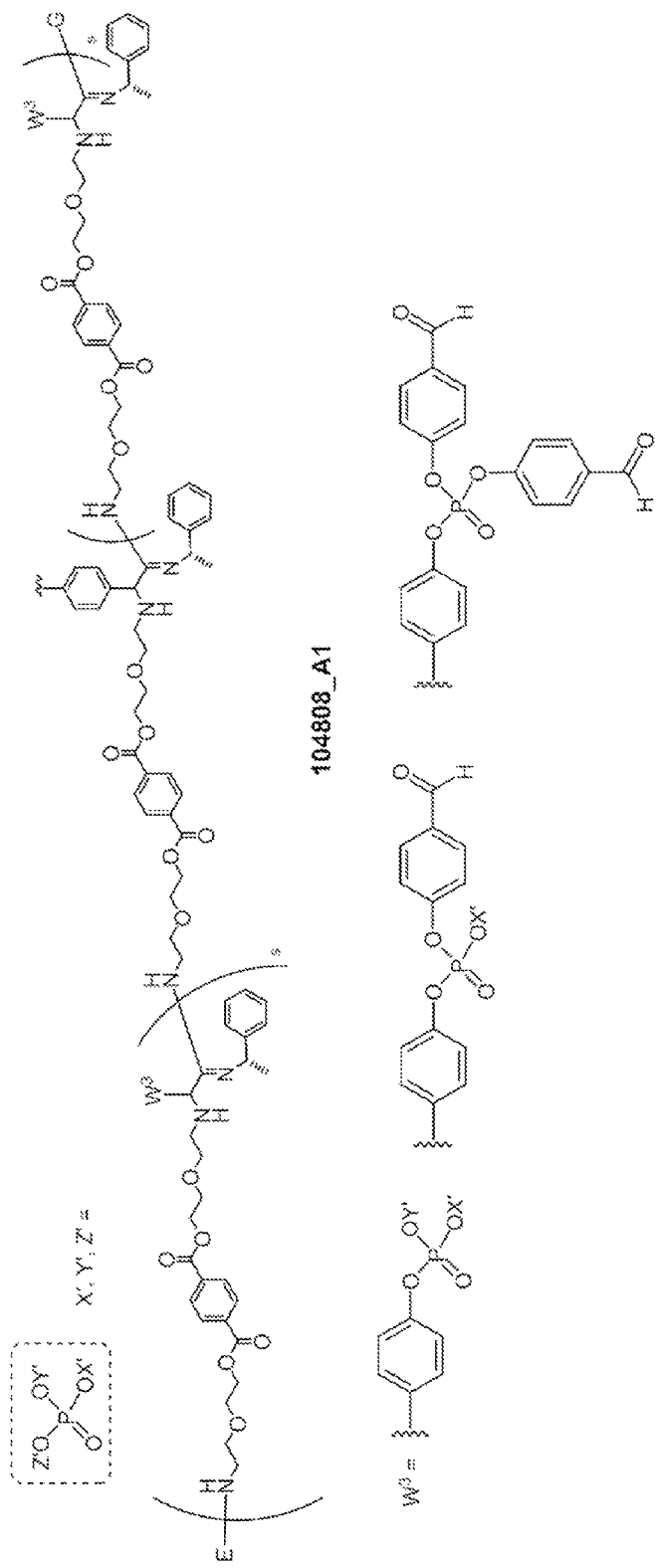
Figure 12J:
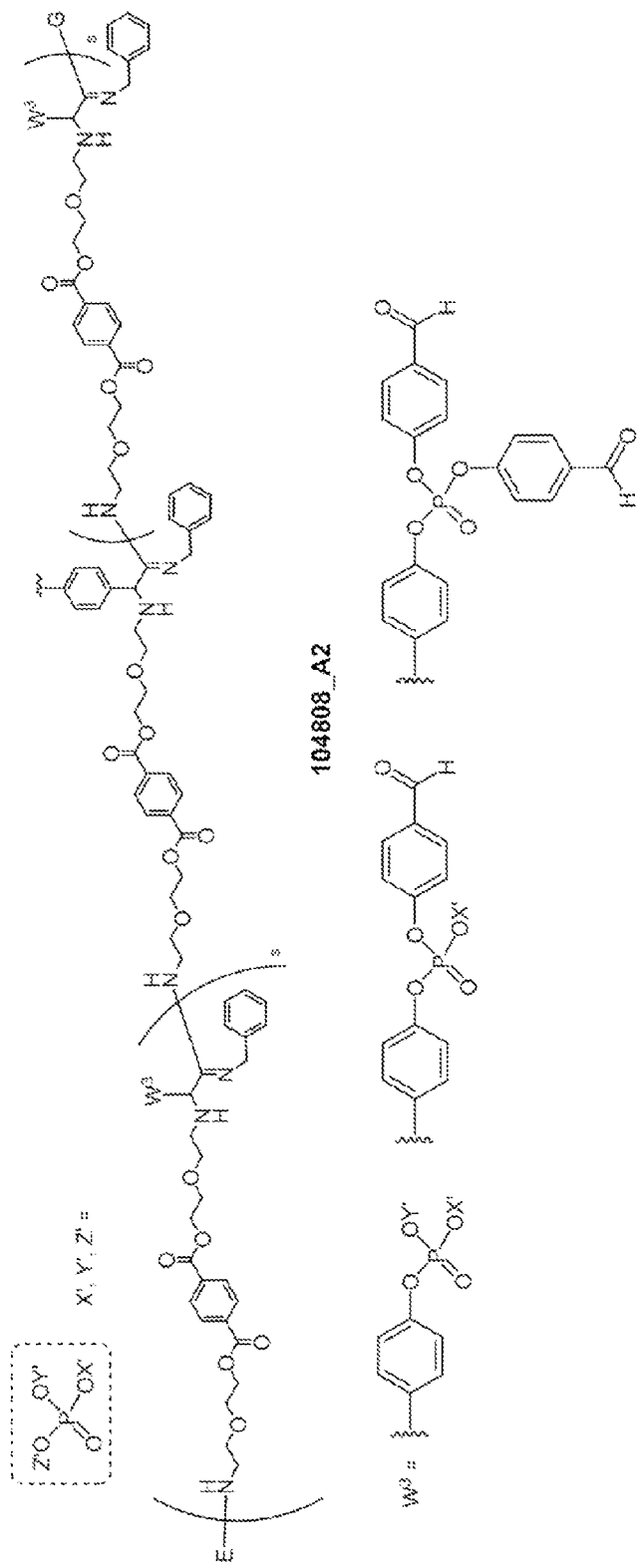
Figure 12K:
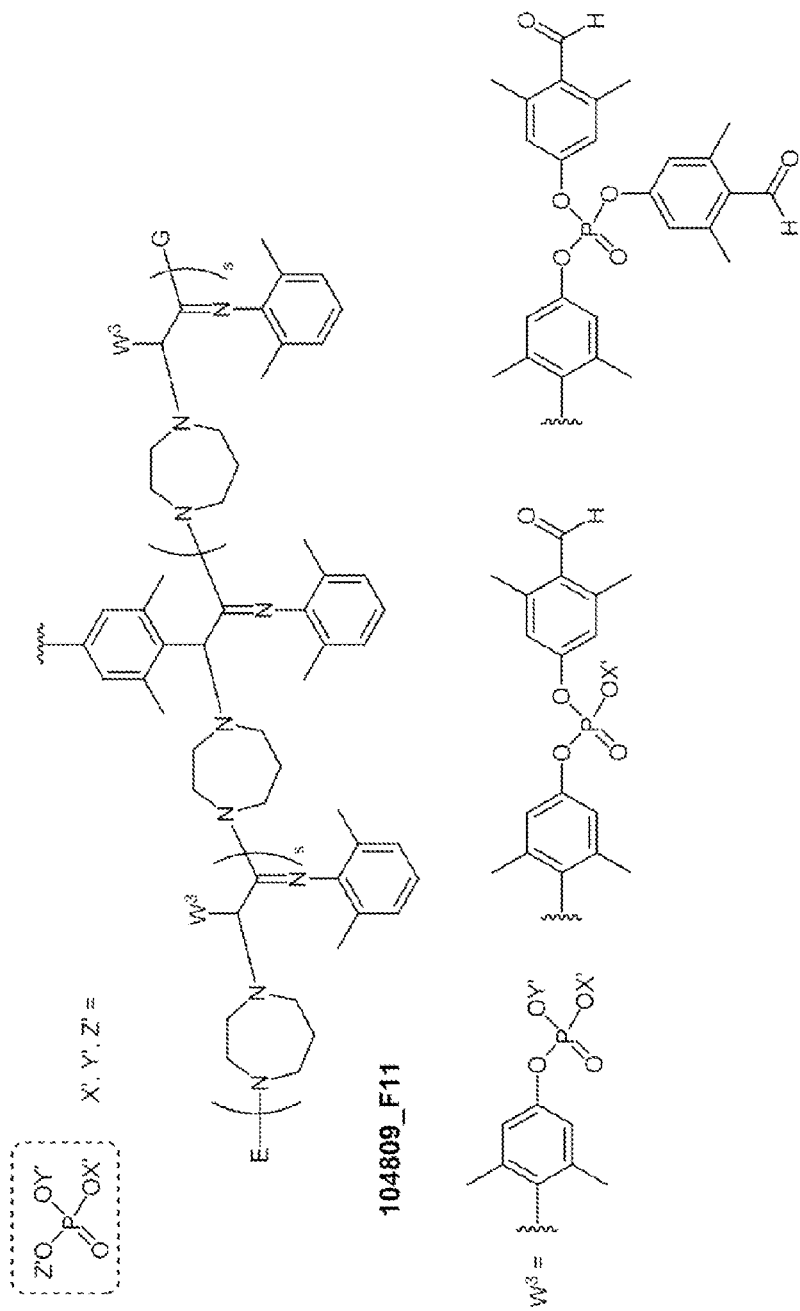
Figure 12L:
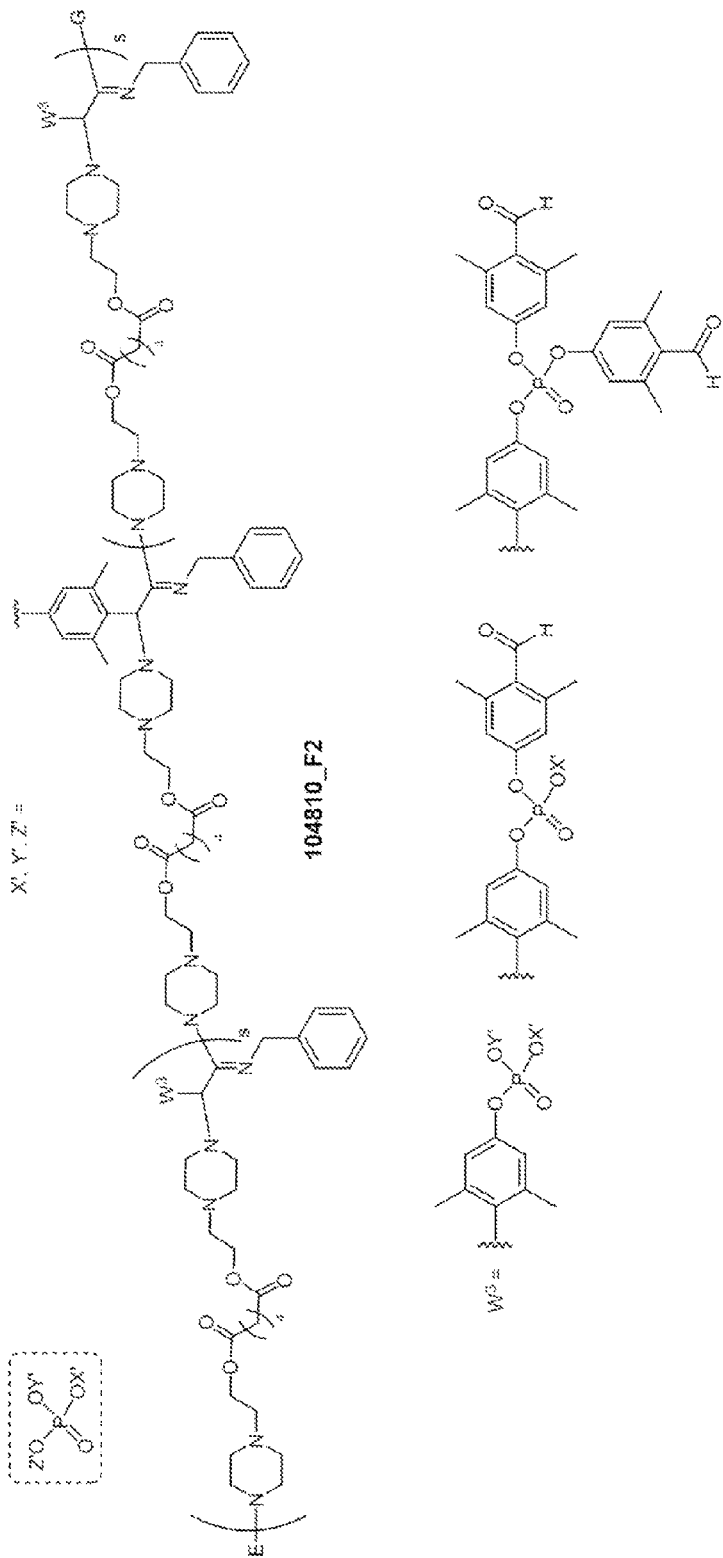
Figure 12M:
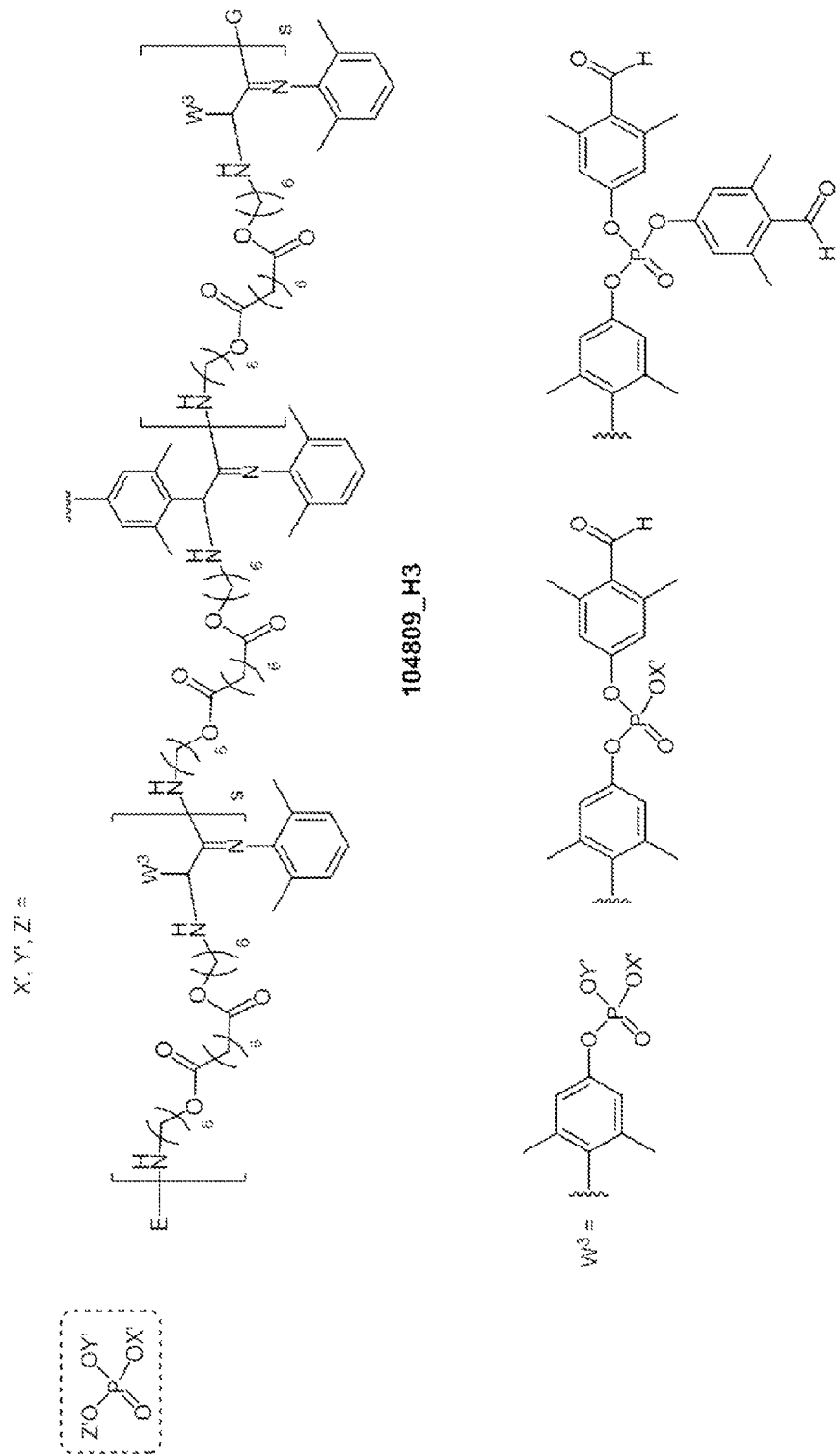
Figure 12N:
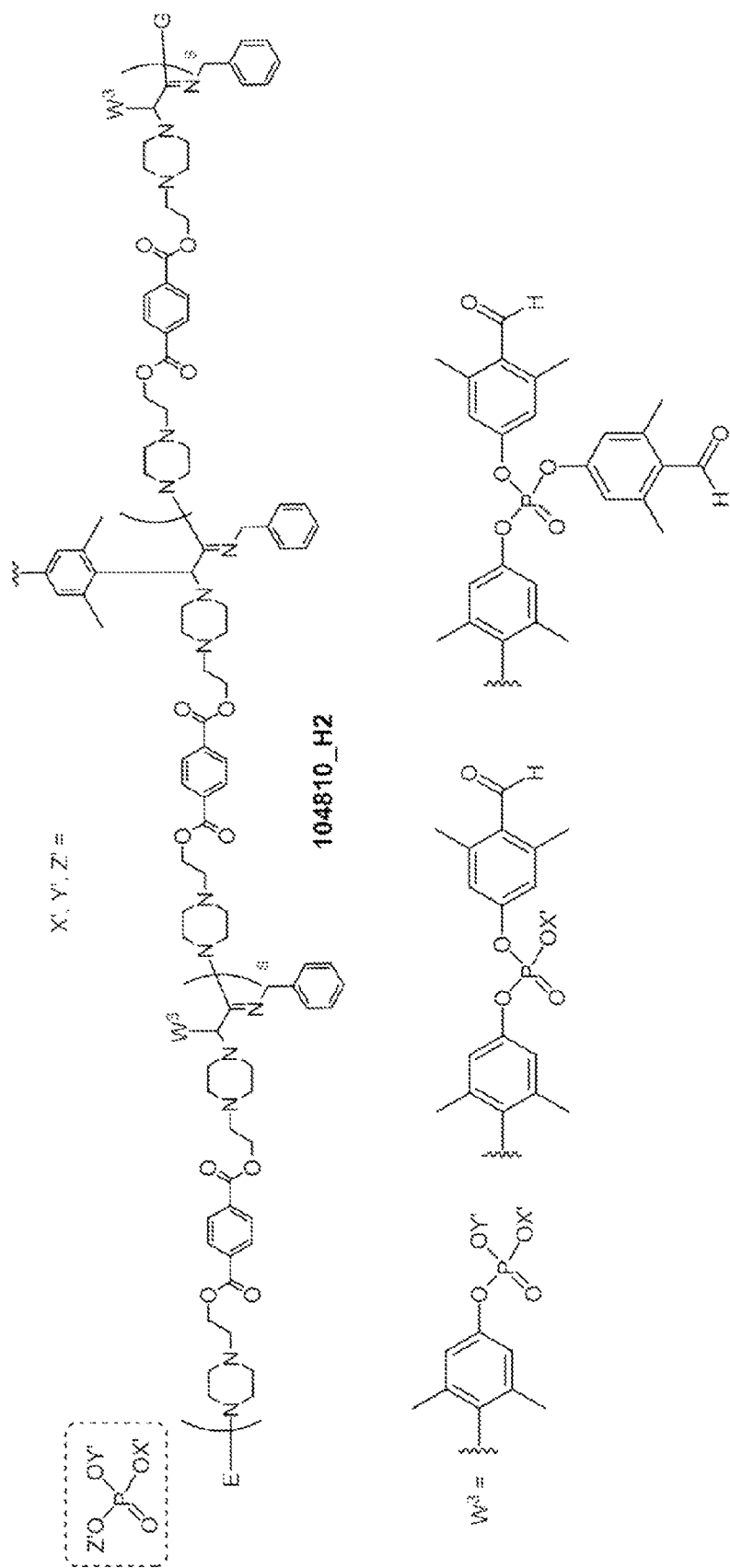
Figure 12O:
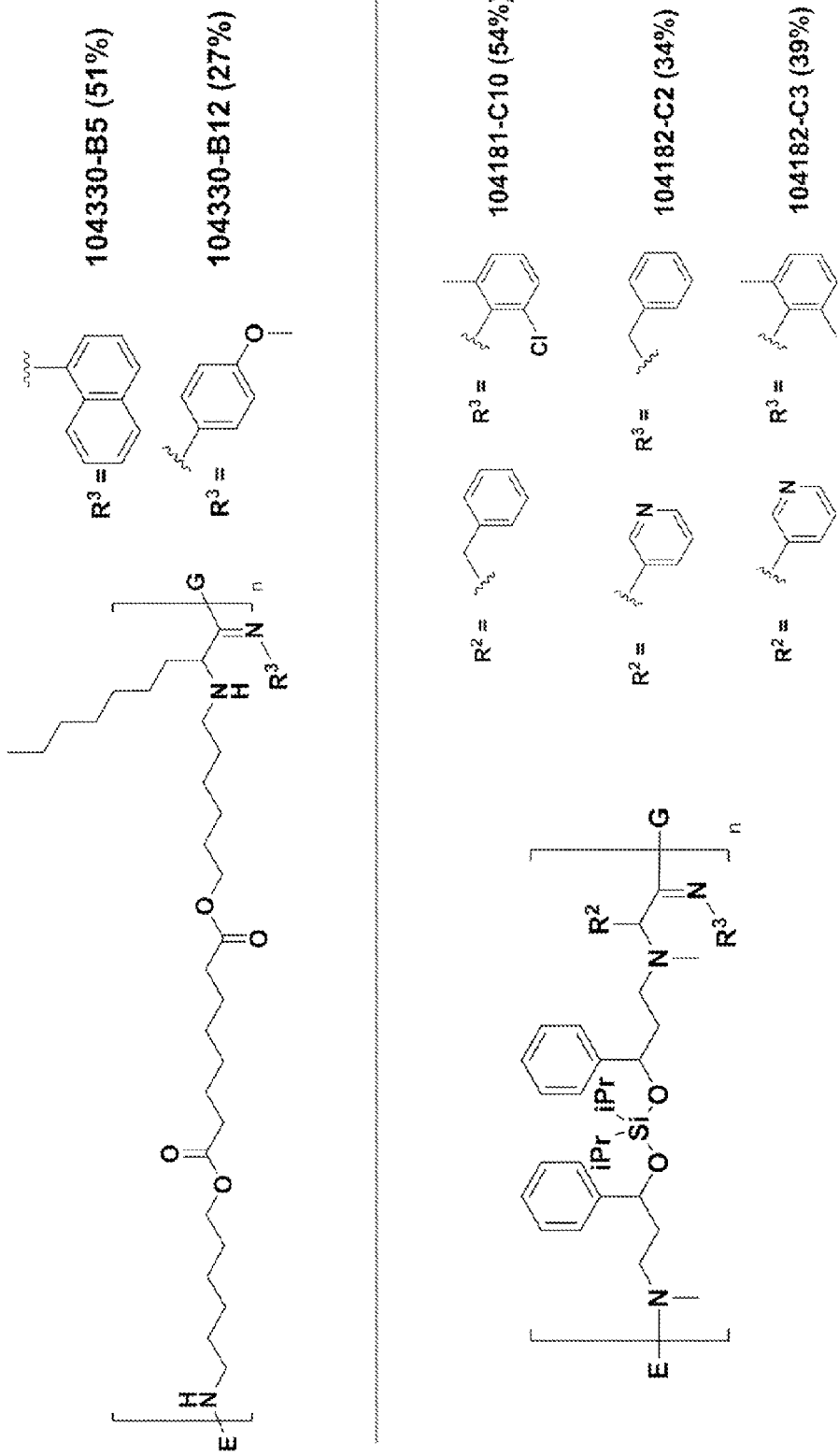
Figure 12P:
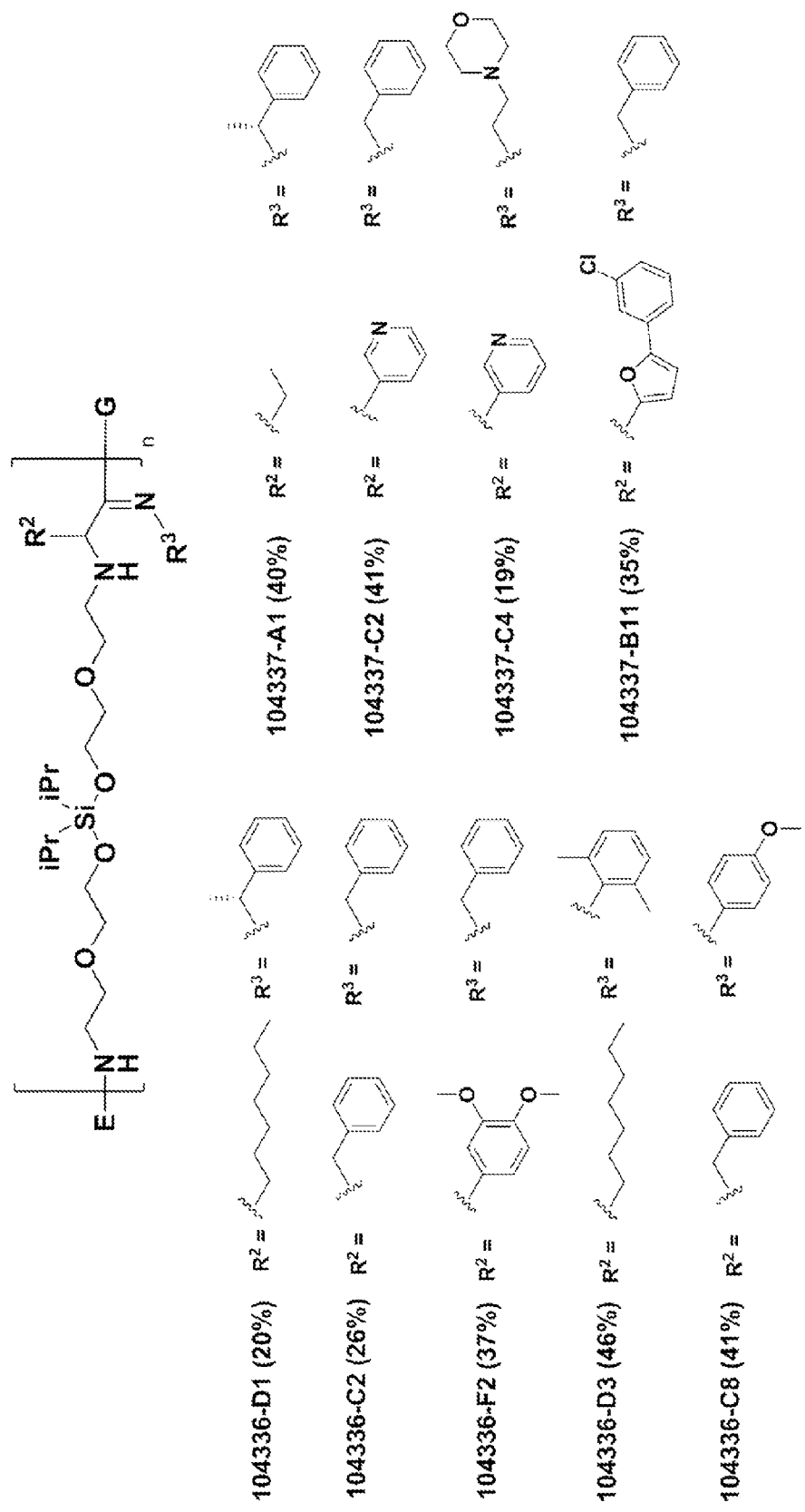
Figure 12Q:
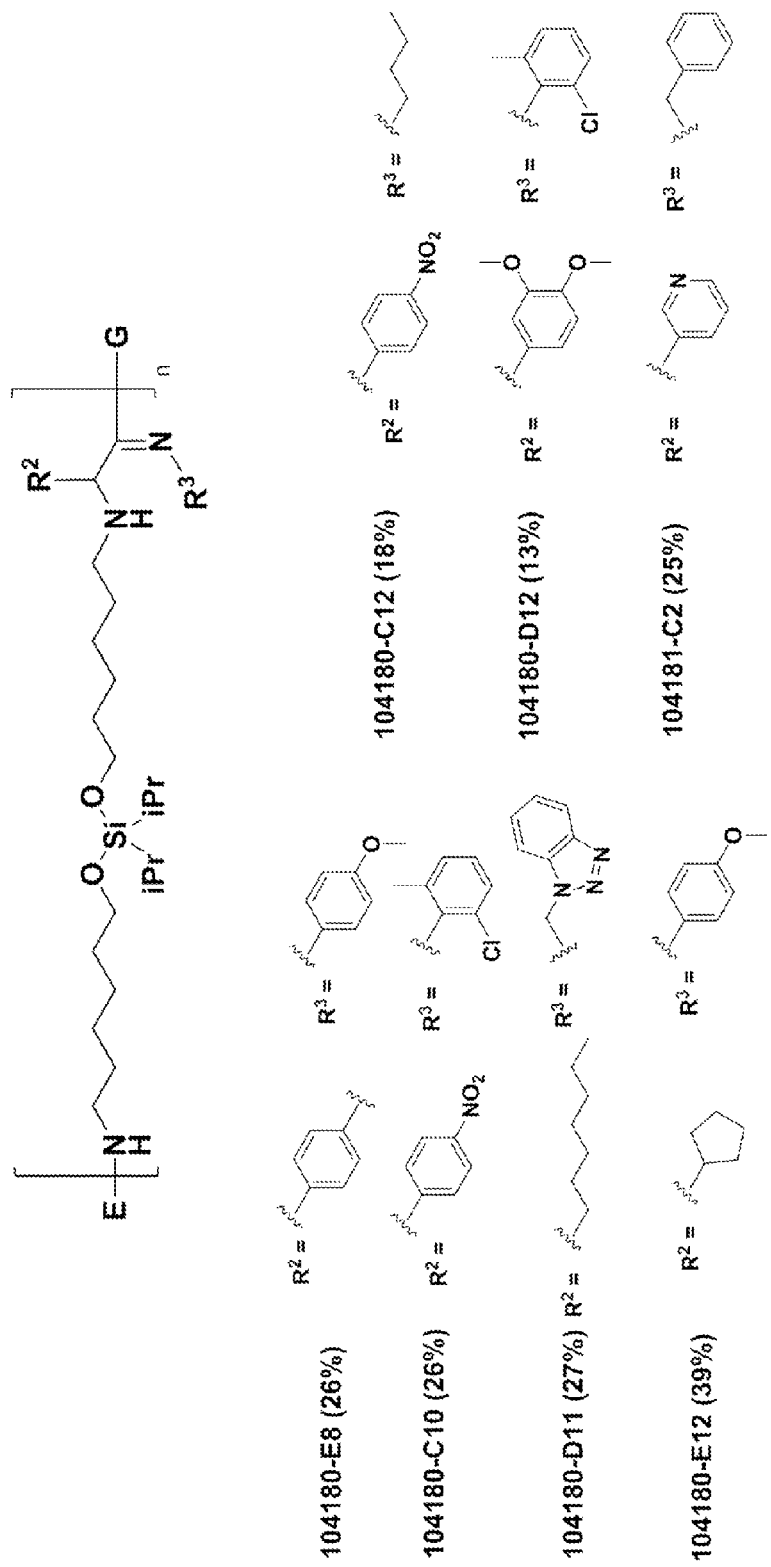
Figure 12R:
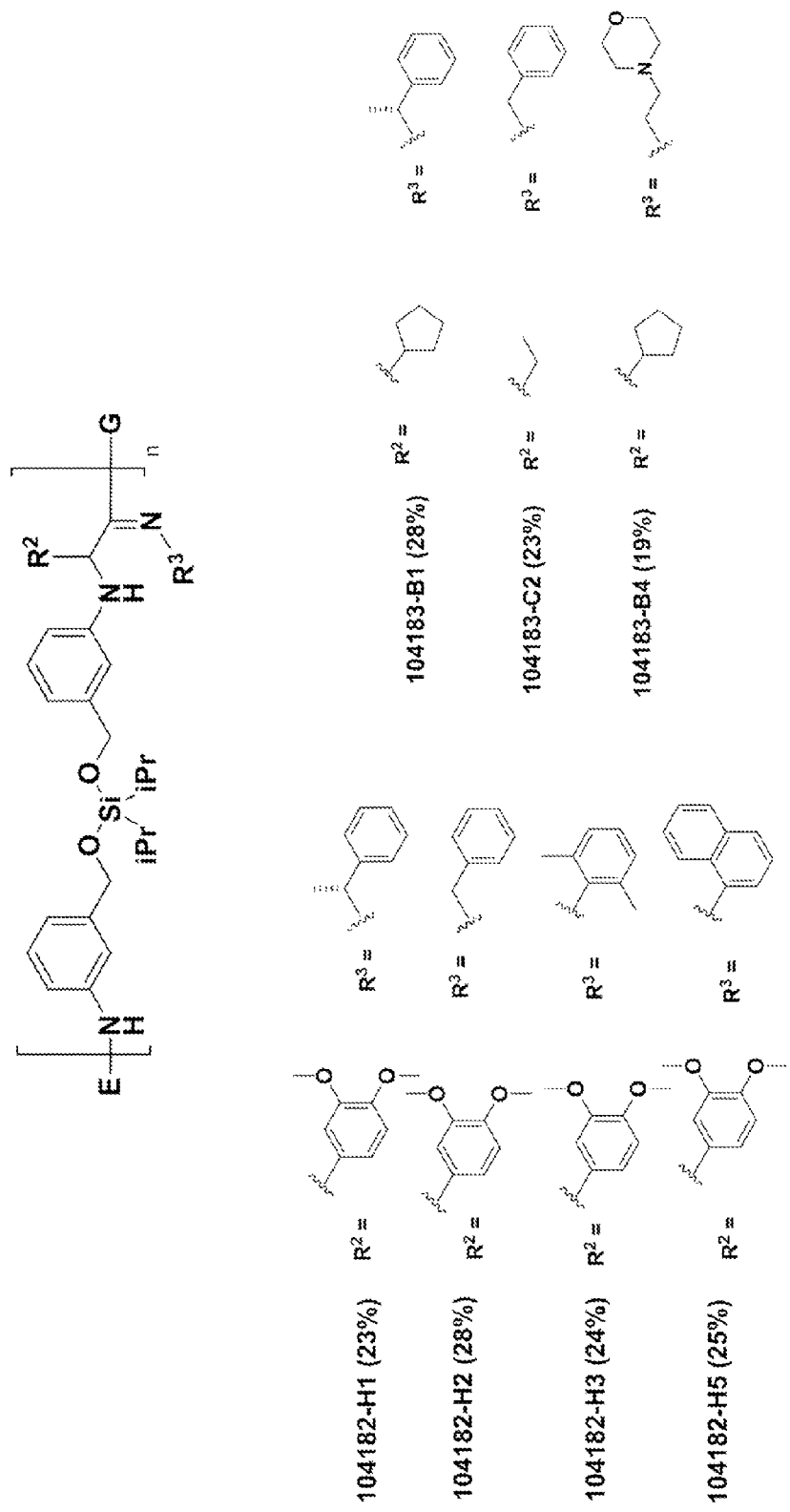
Figure 12S:
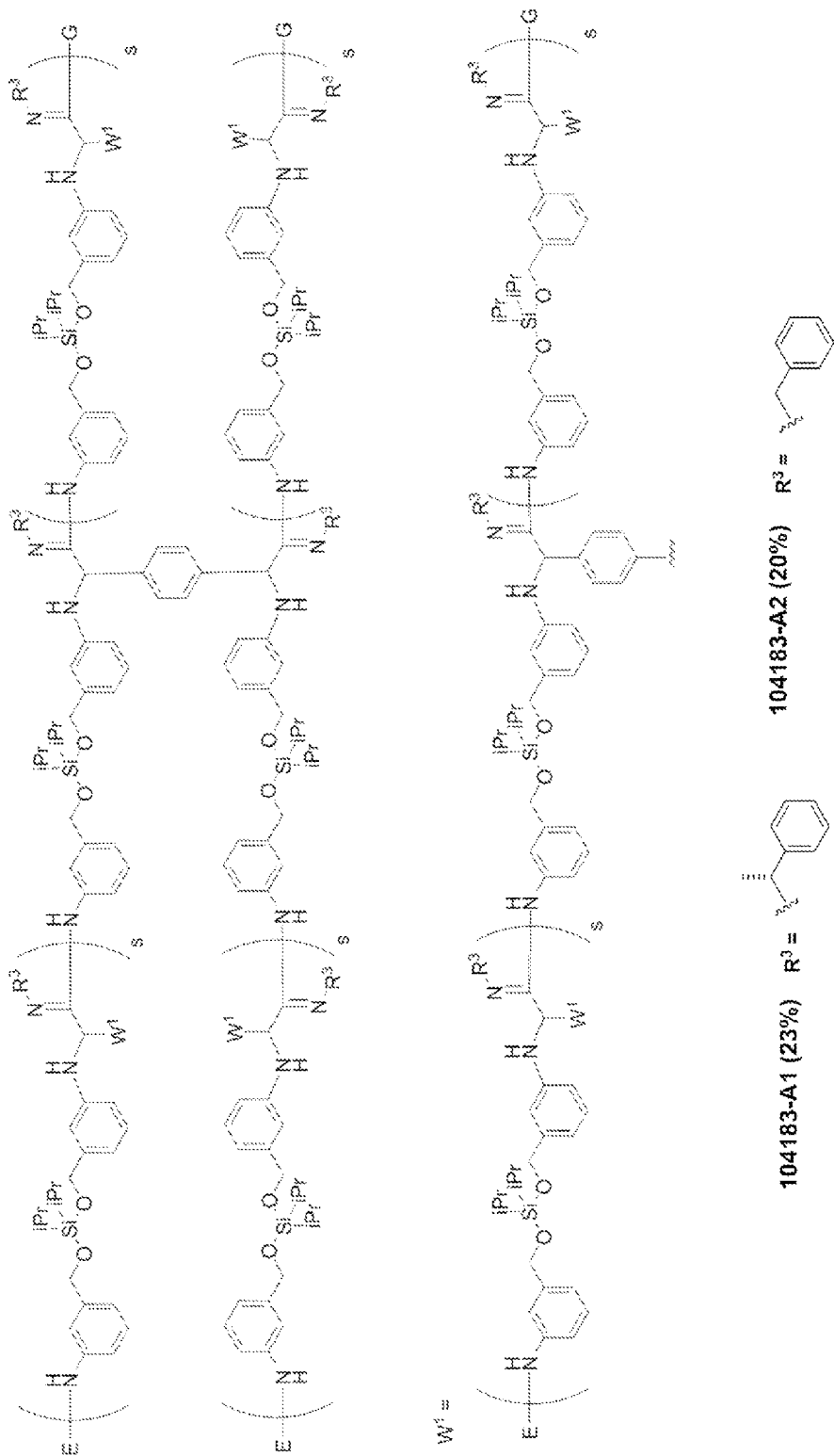
Figure 12T:
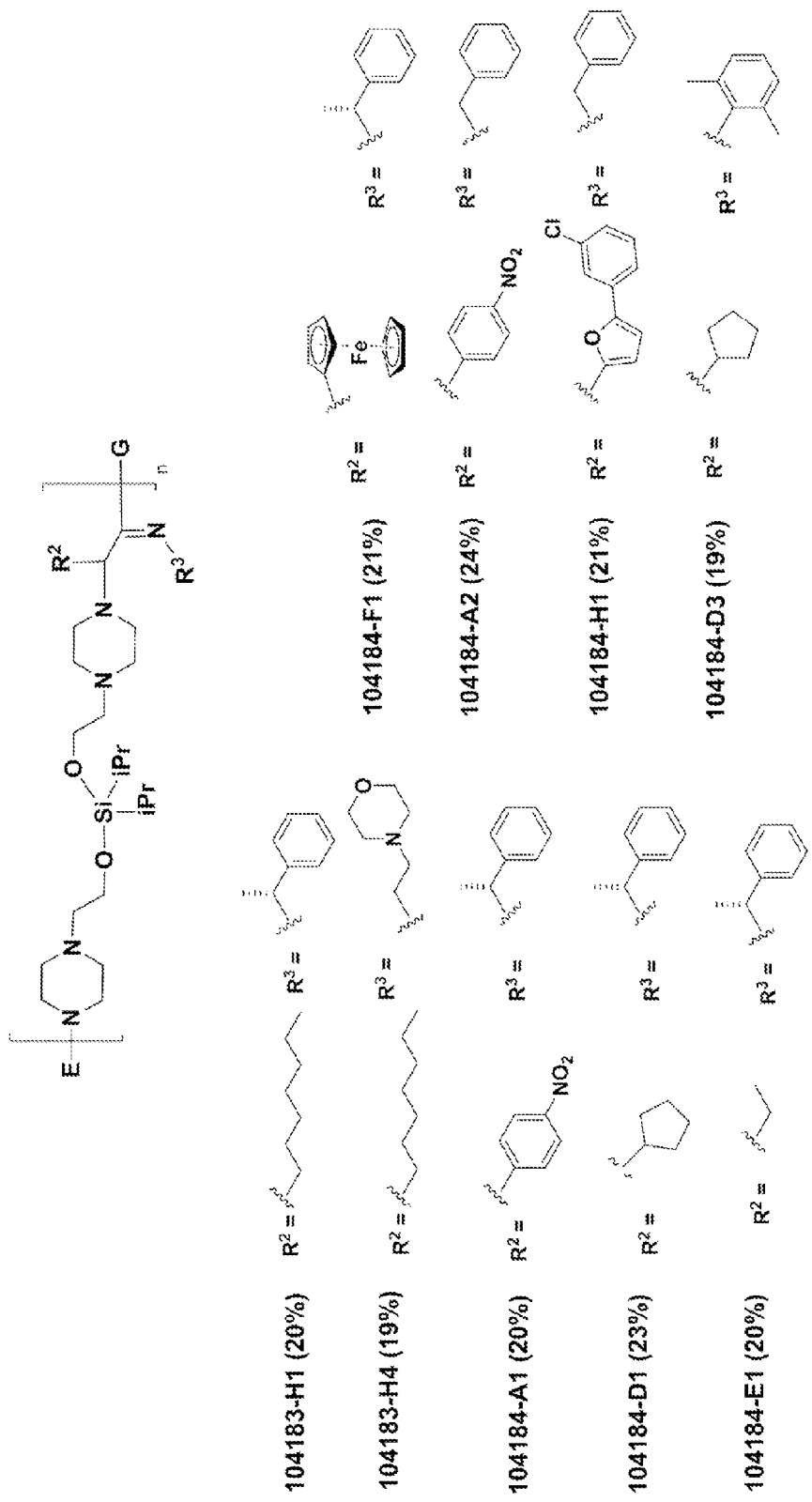
Figure 12U:
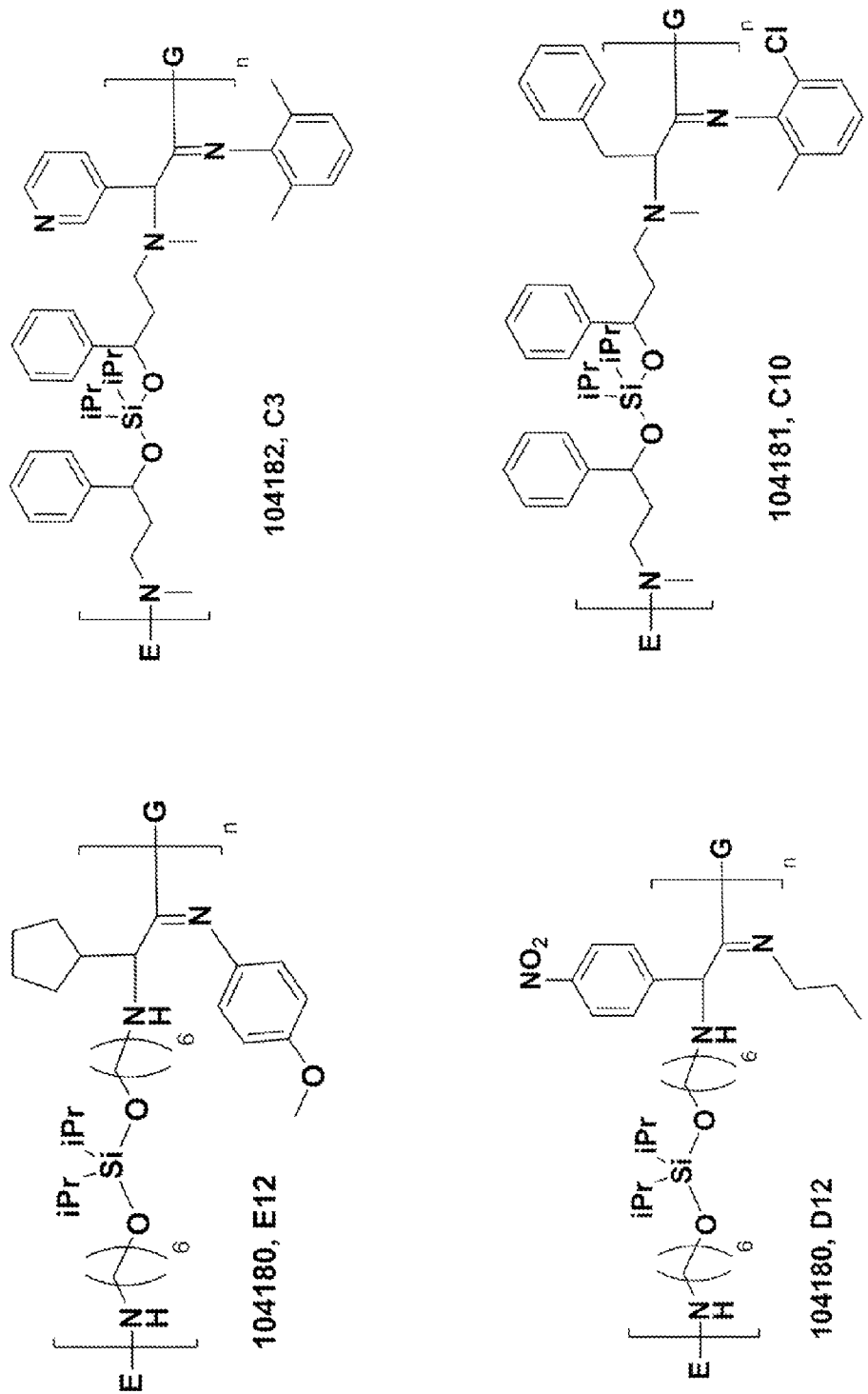
Figure 12V:
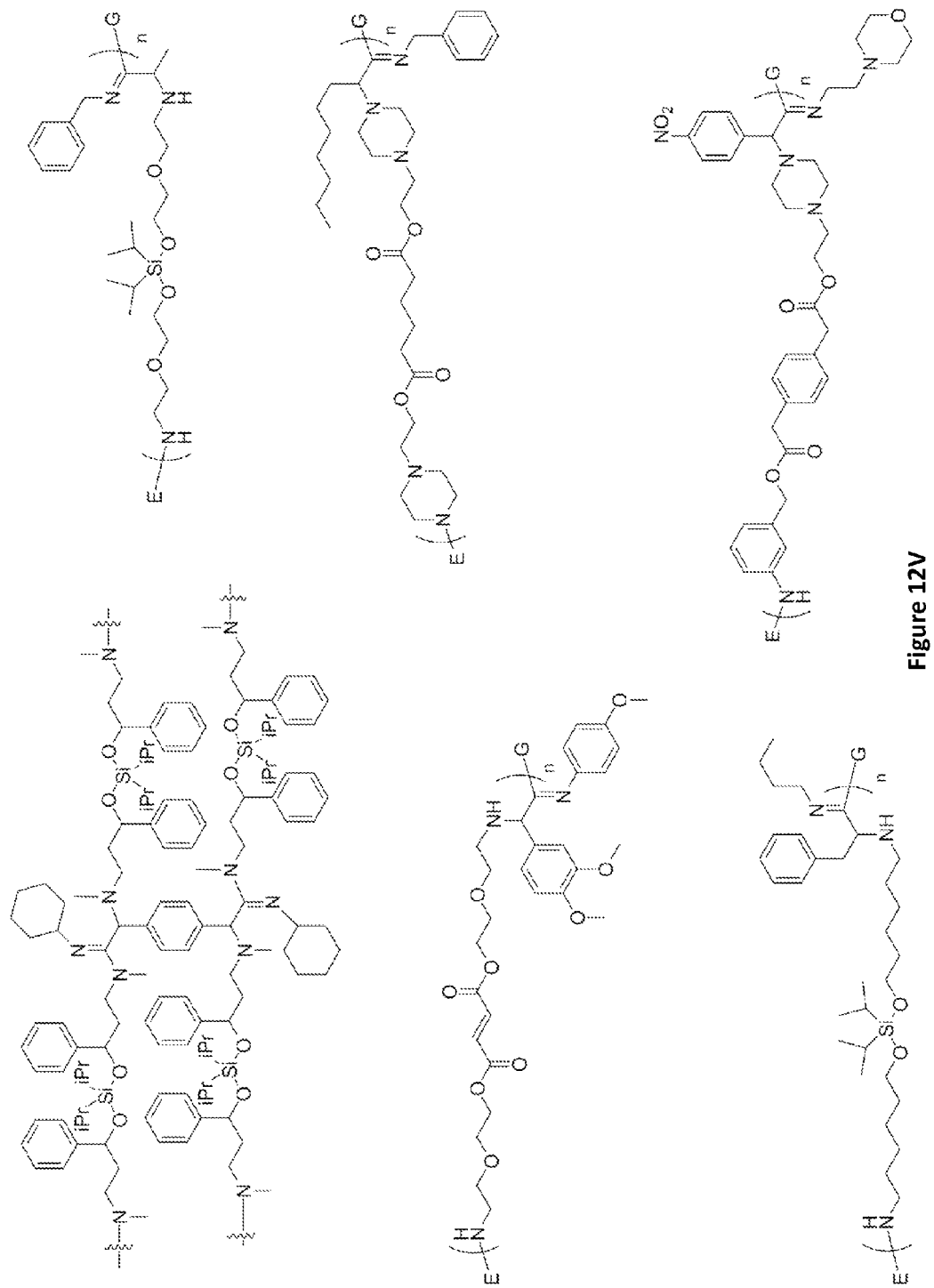
Figure 12W:
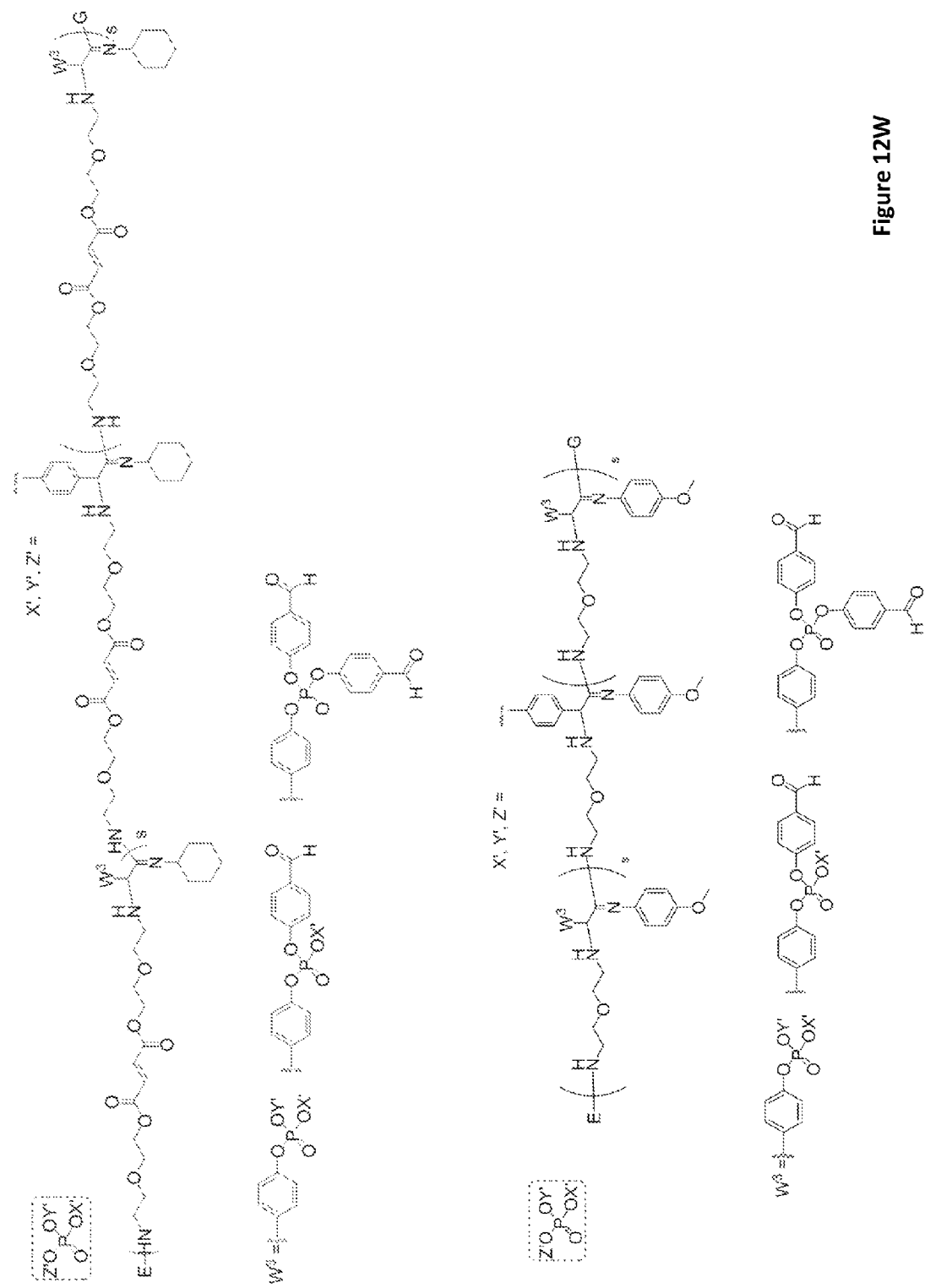
Figure 12X:
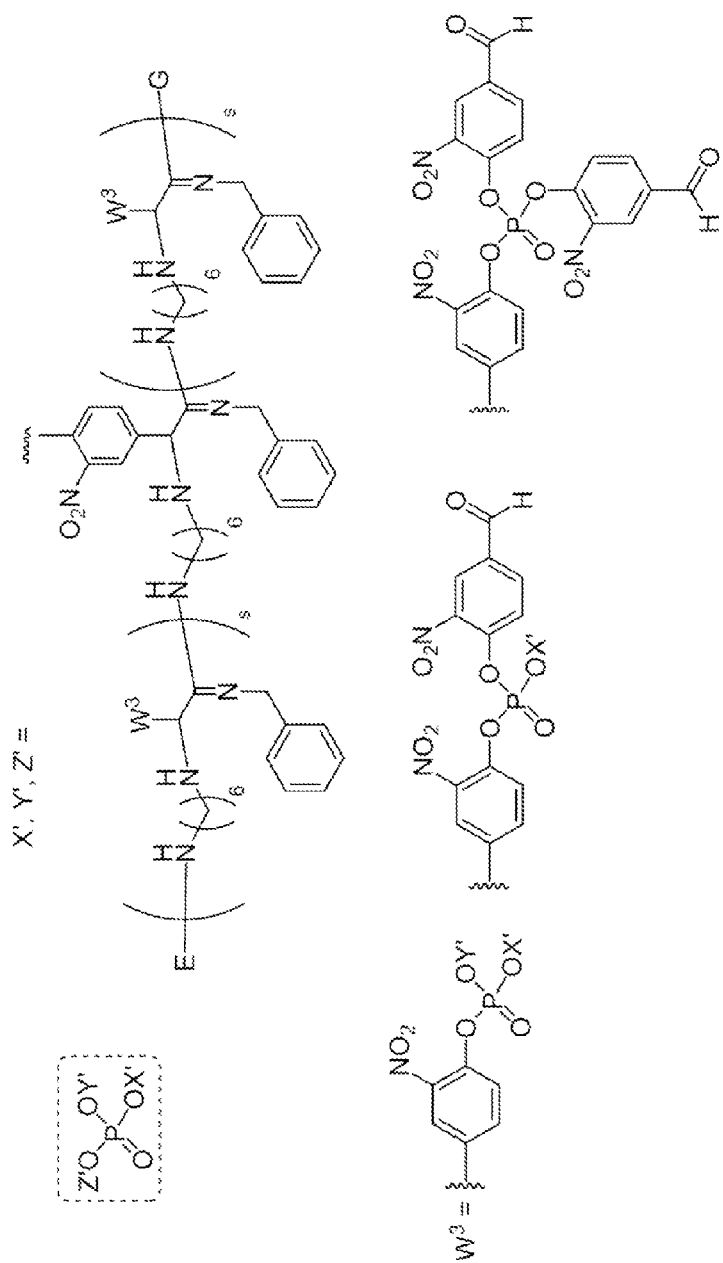
Figure 12Y:
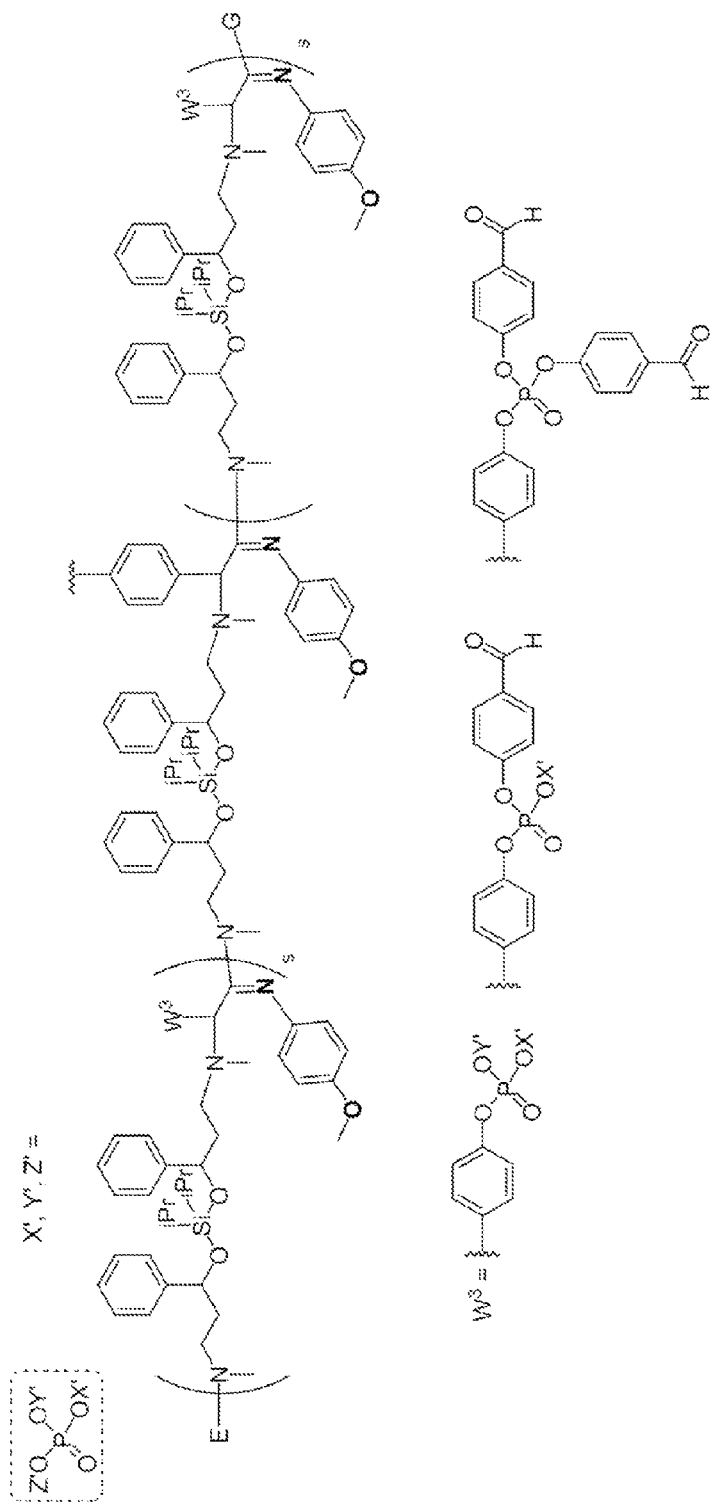
Figure 12Z:
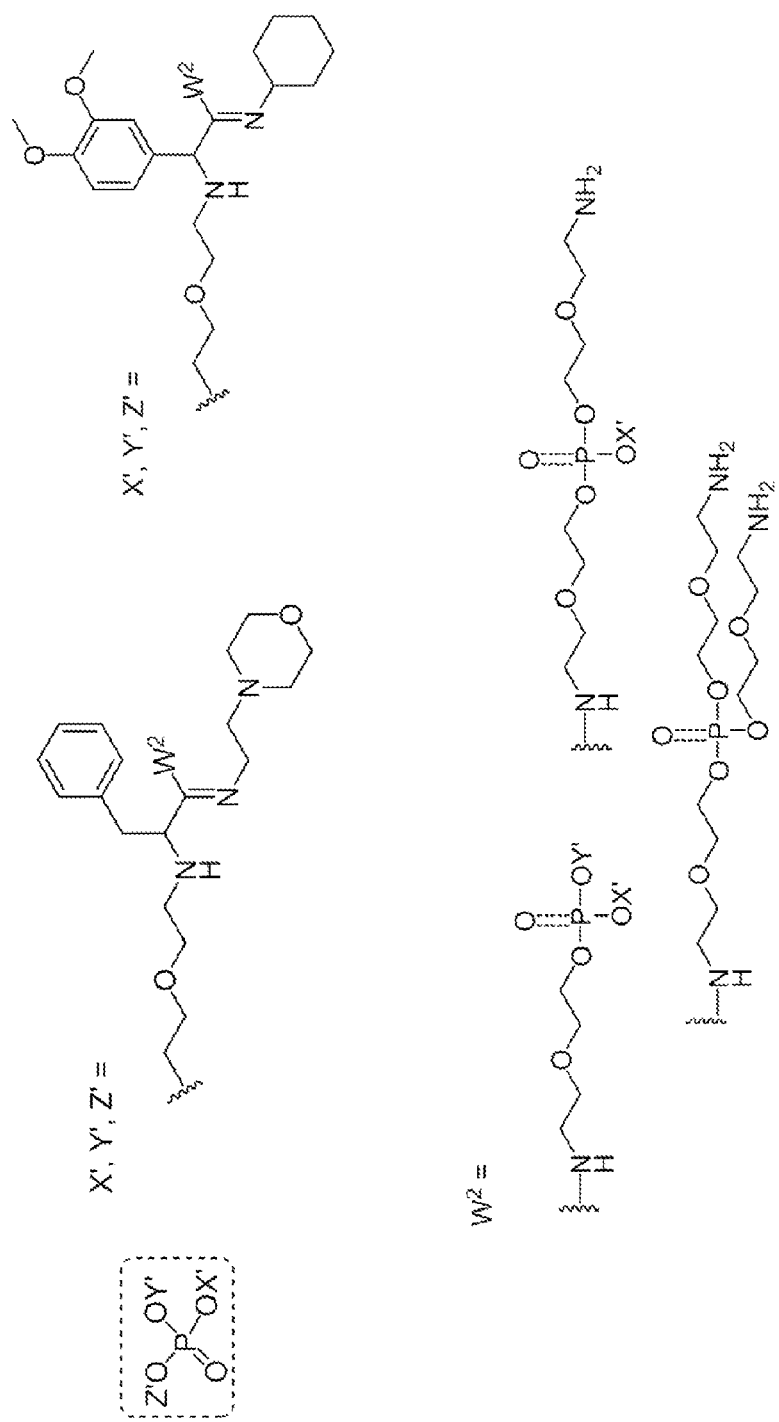
Figure 18:
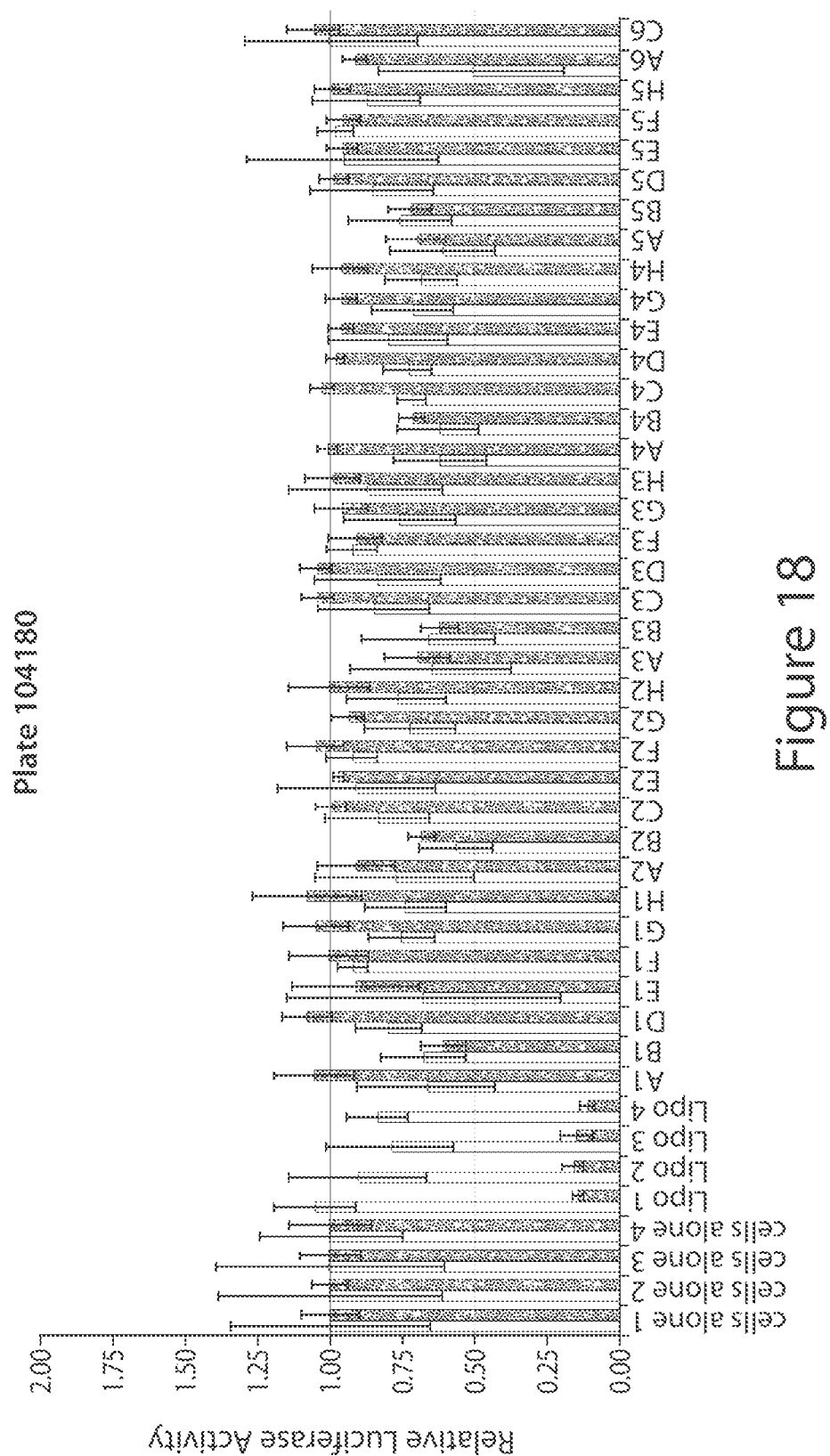
FIGS. 18 to 22 depict the results of the gene silencing via the delivery of siRNA.
Figure 18:
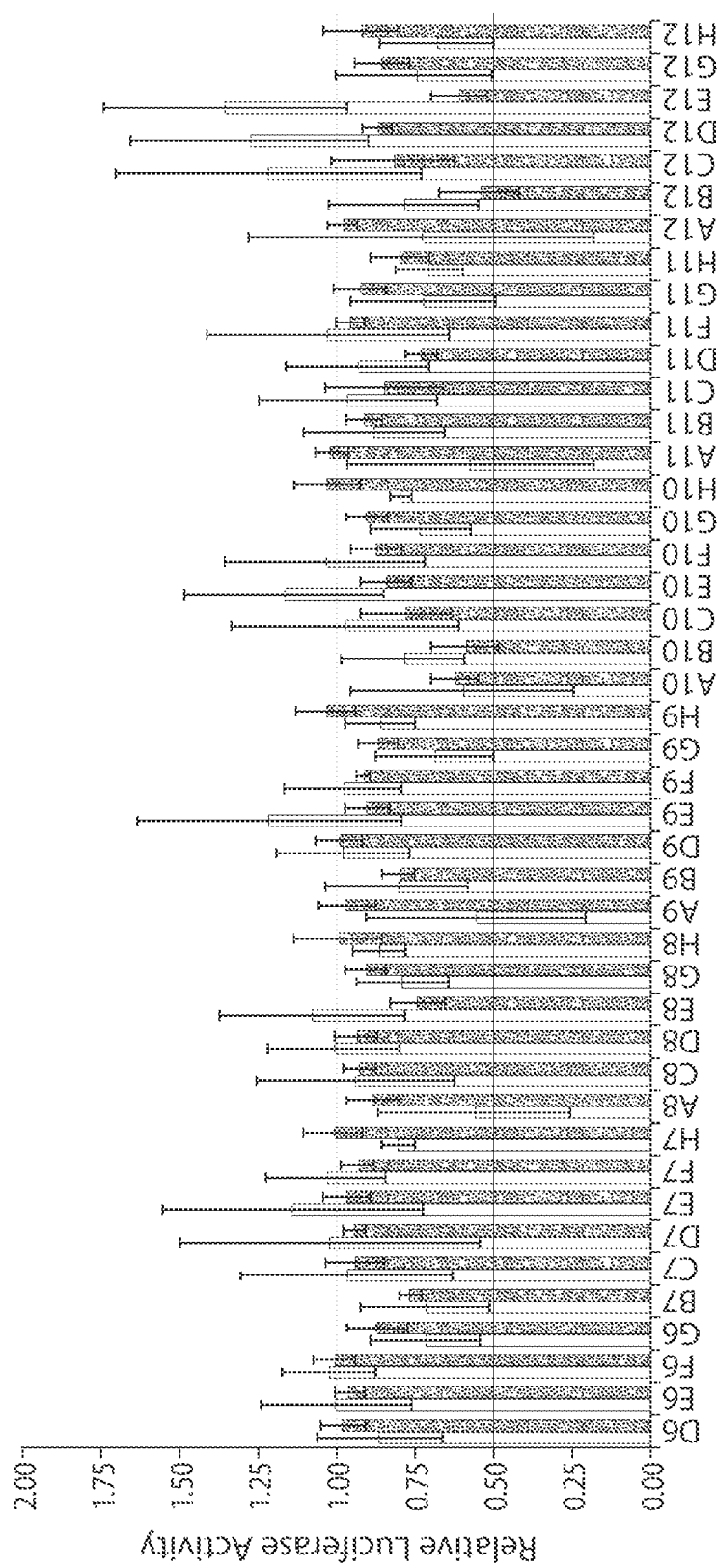
Figure 19:
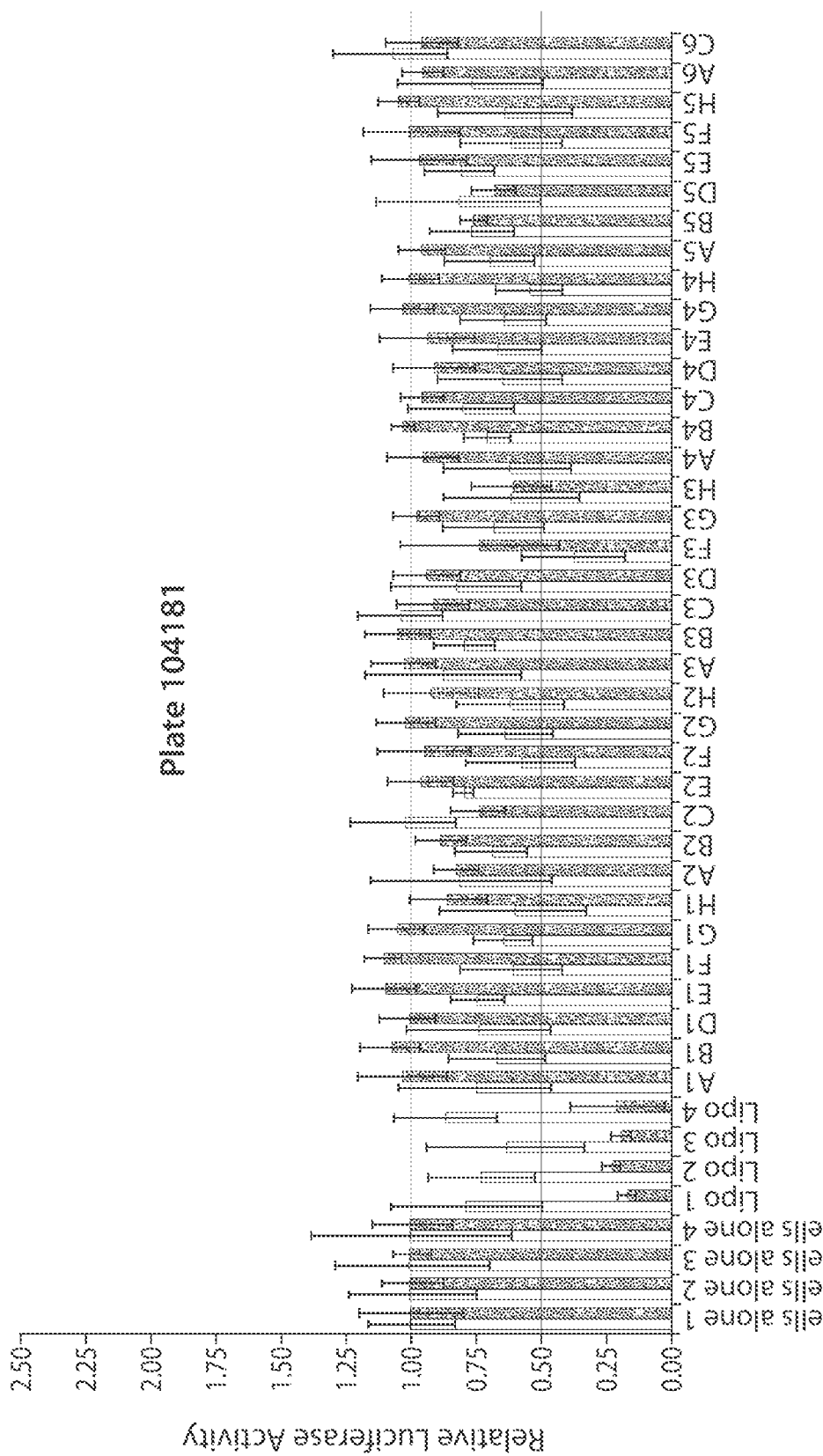
Figure 19:
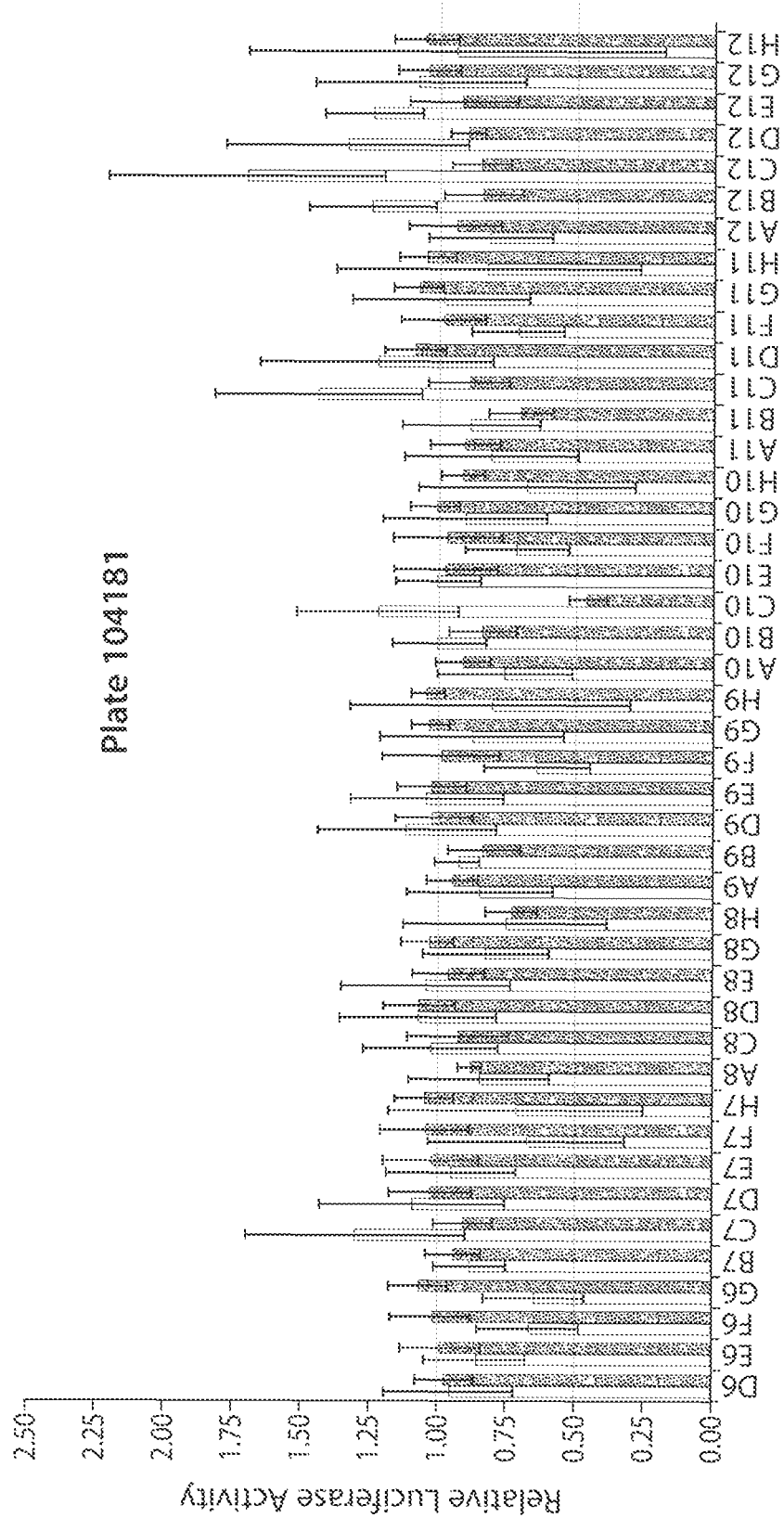
Figure 20:
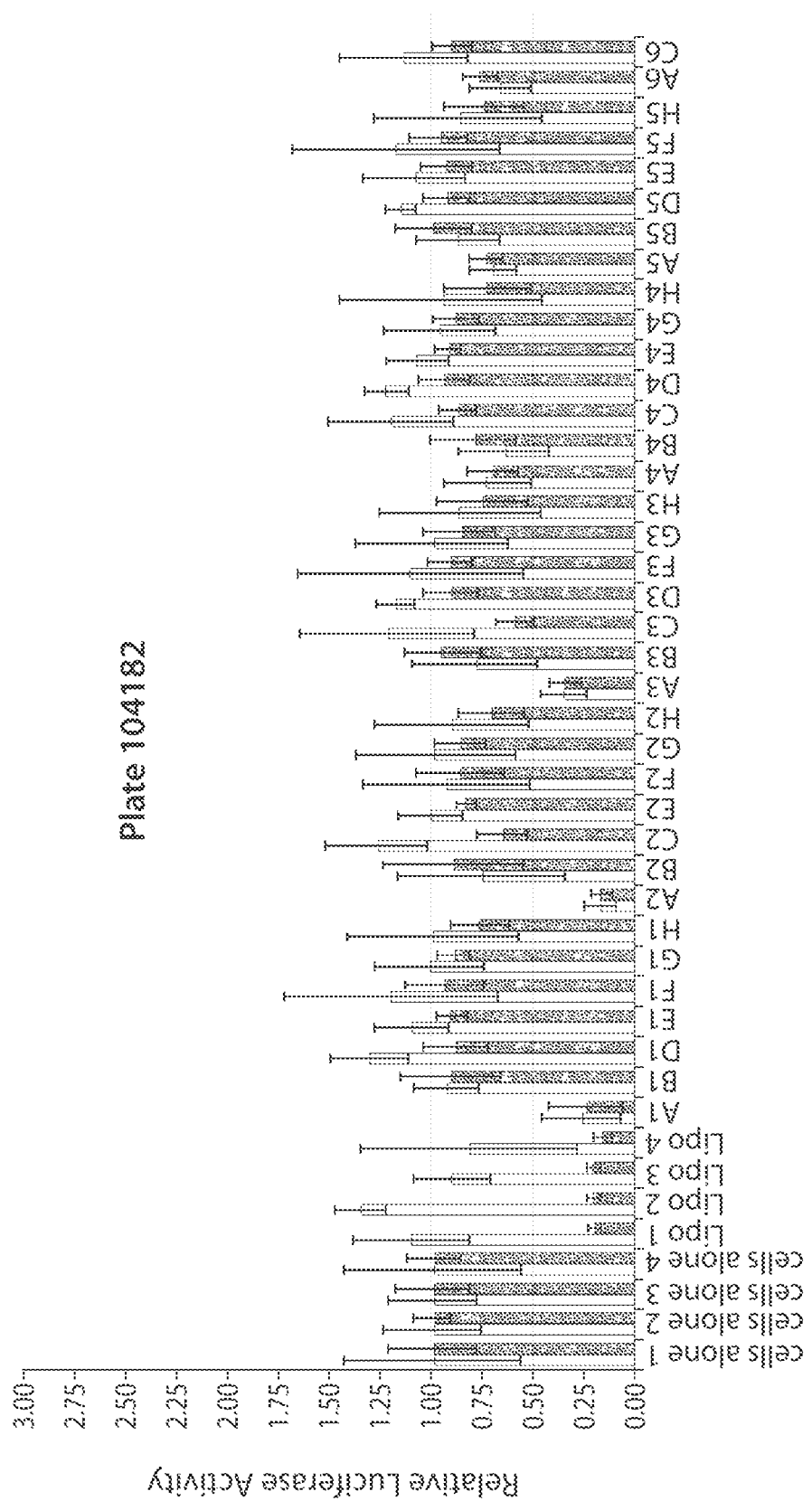
Figure 20:
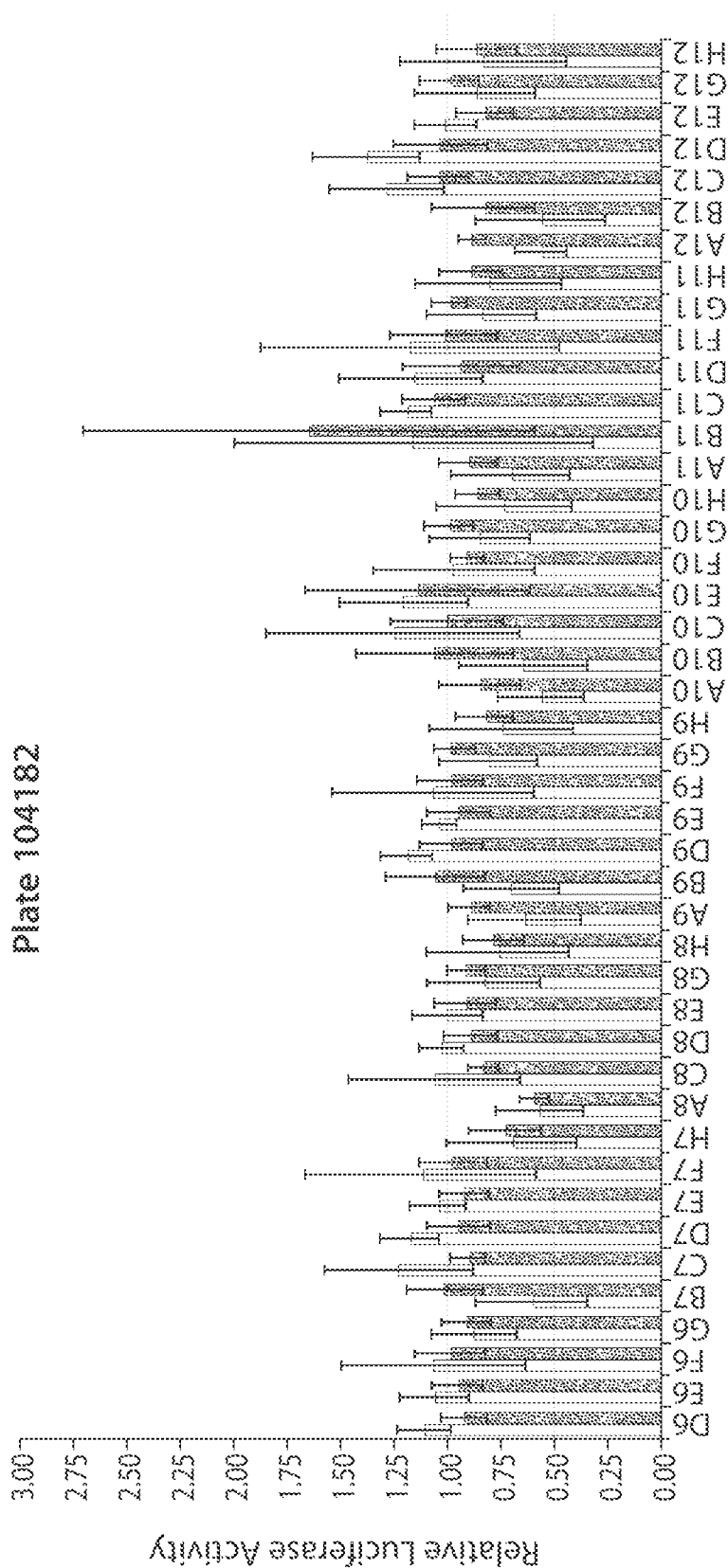
Figure 21:
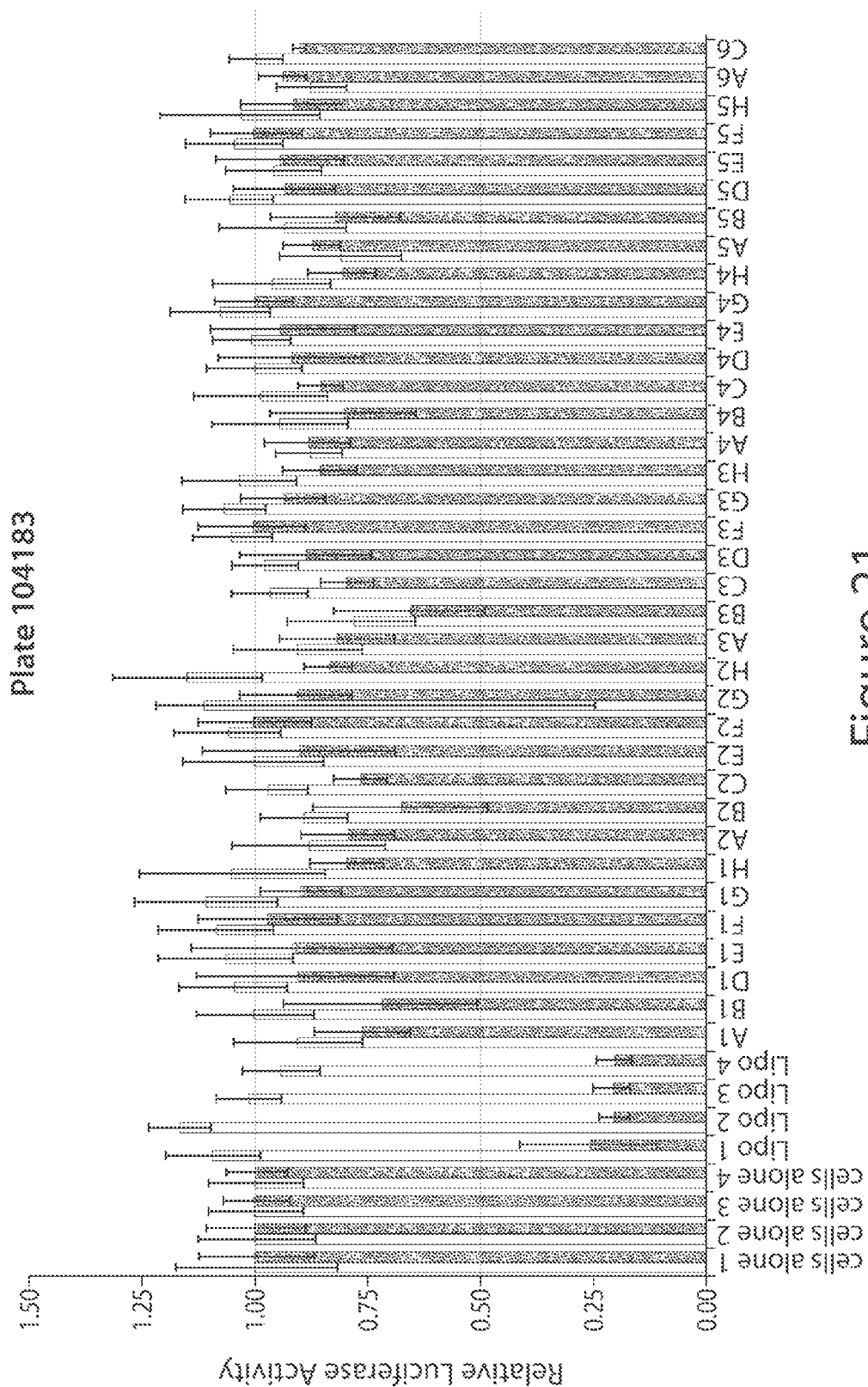
Figure 21:
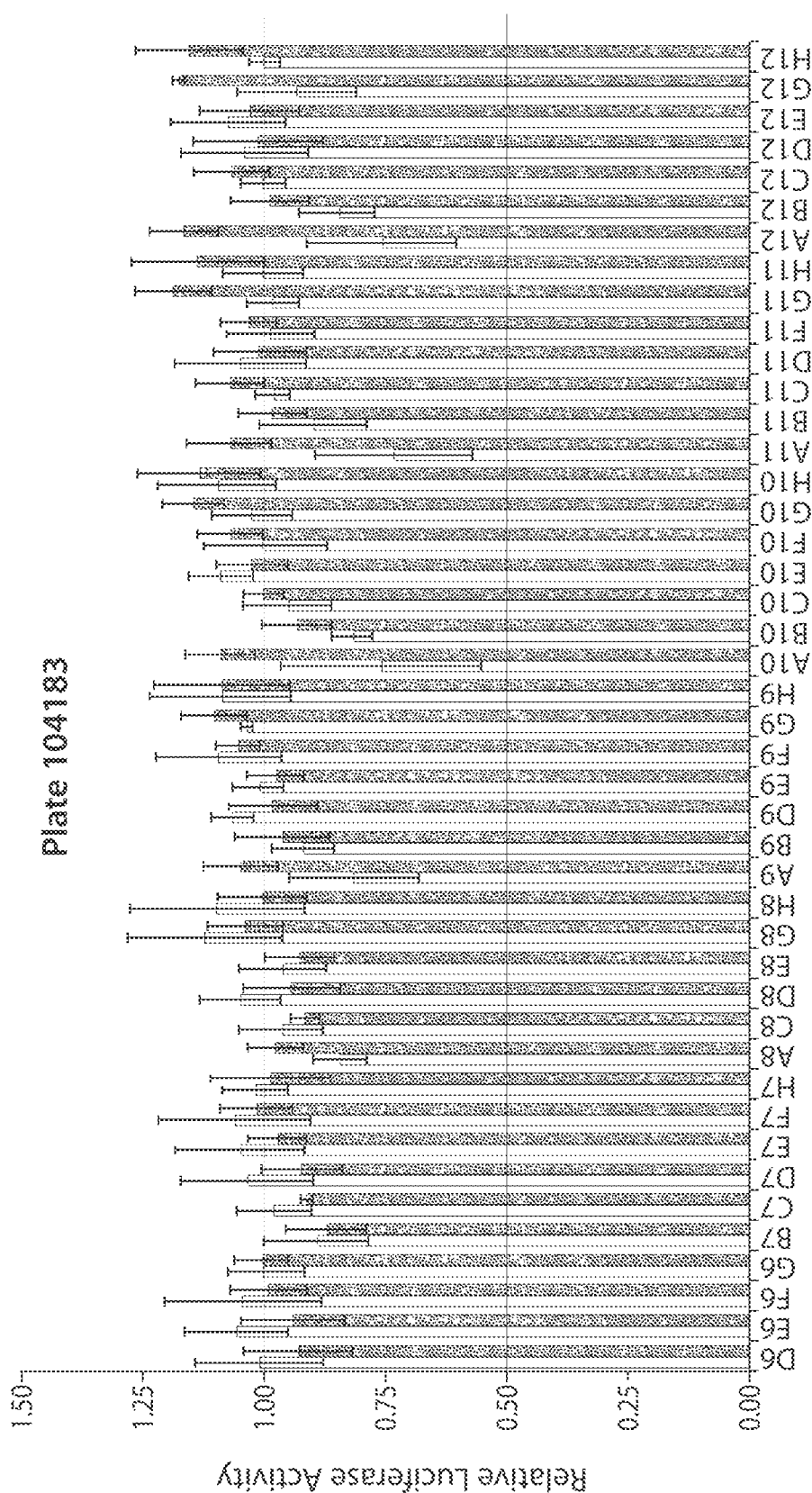
Figure 22:
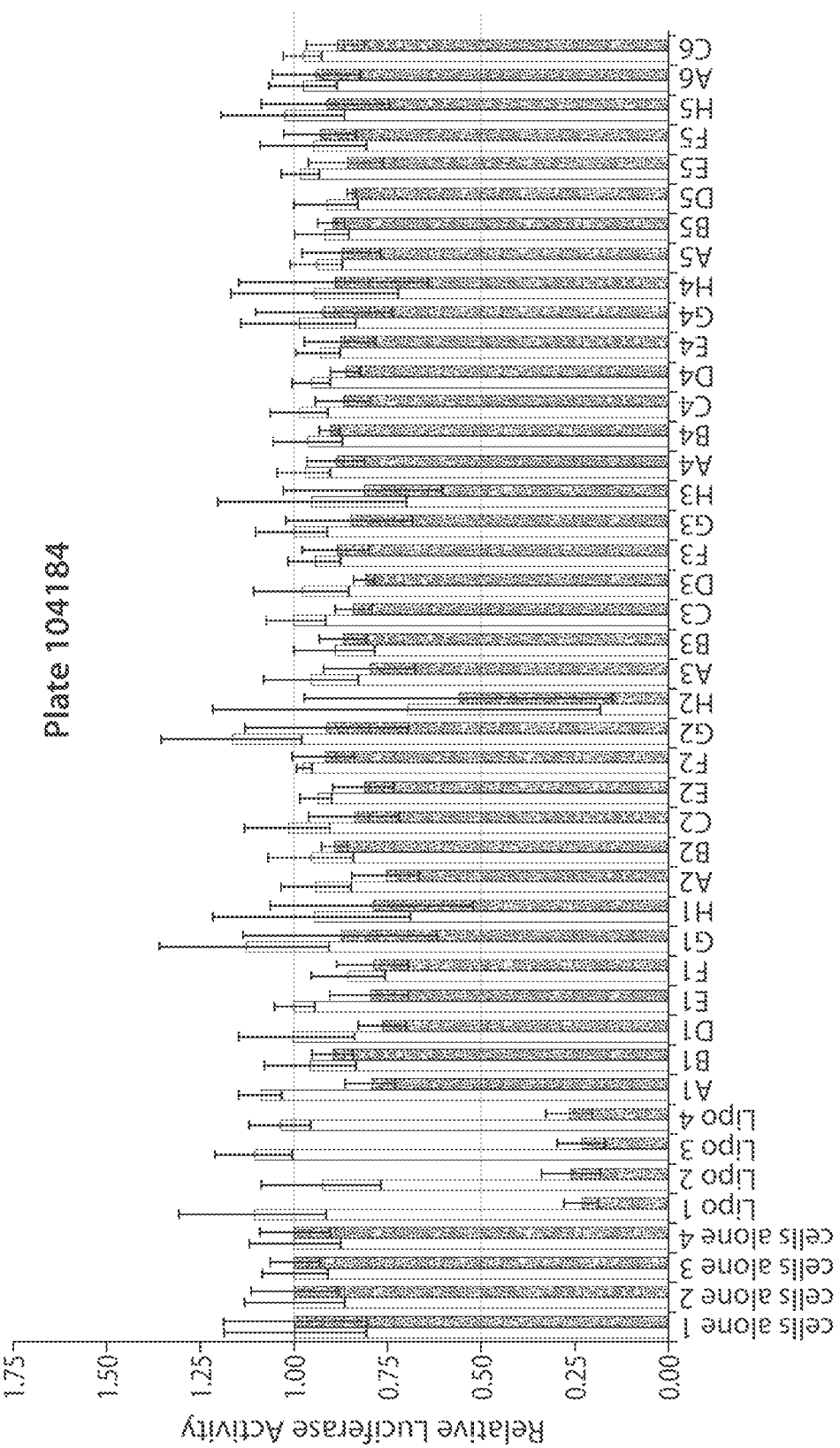
Figure 22:
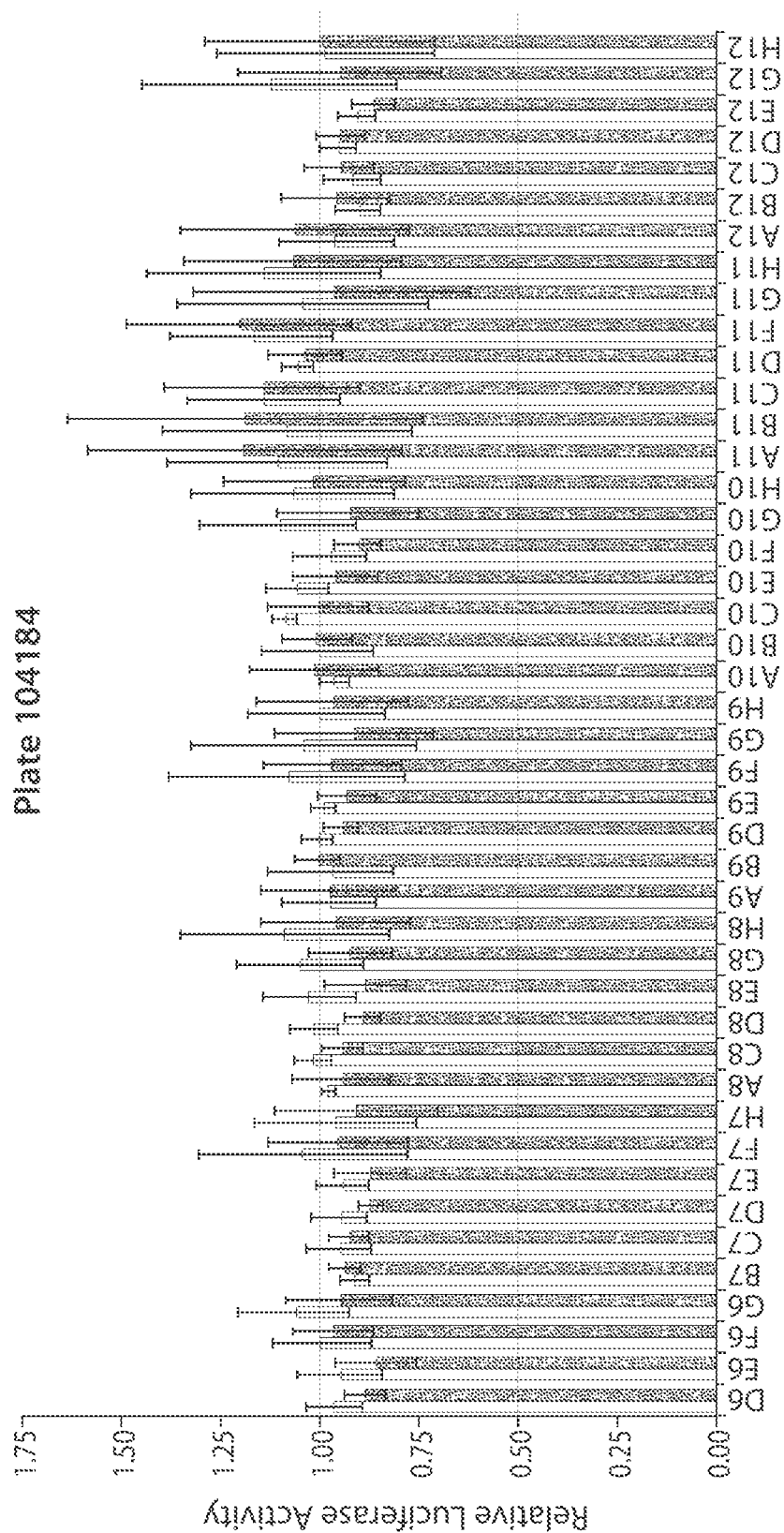
Figure 23A:
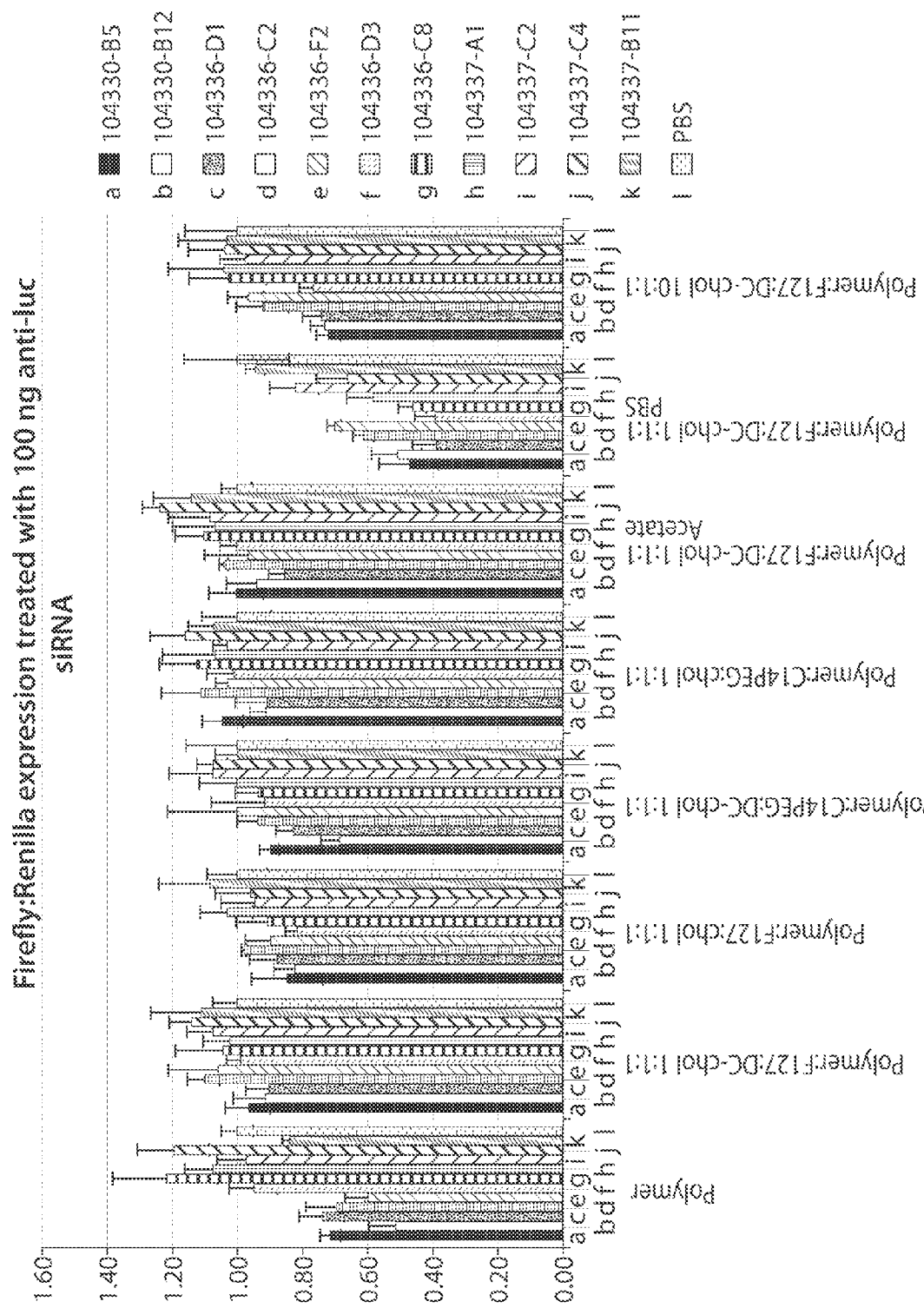
FIGS. 23A-23B depict the results of Firefly:Renilla expression treatment via the delivery of 100 ng anti-luc siRNA.
Figure 23B:
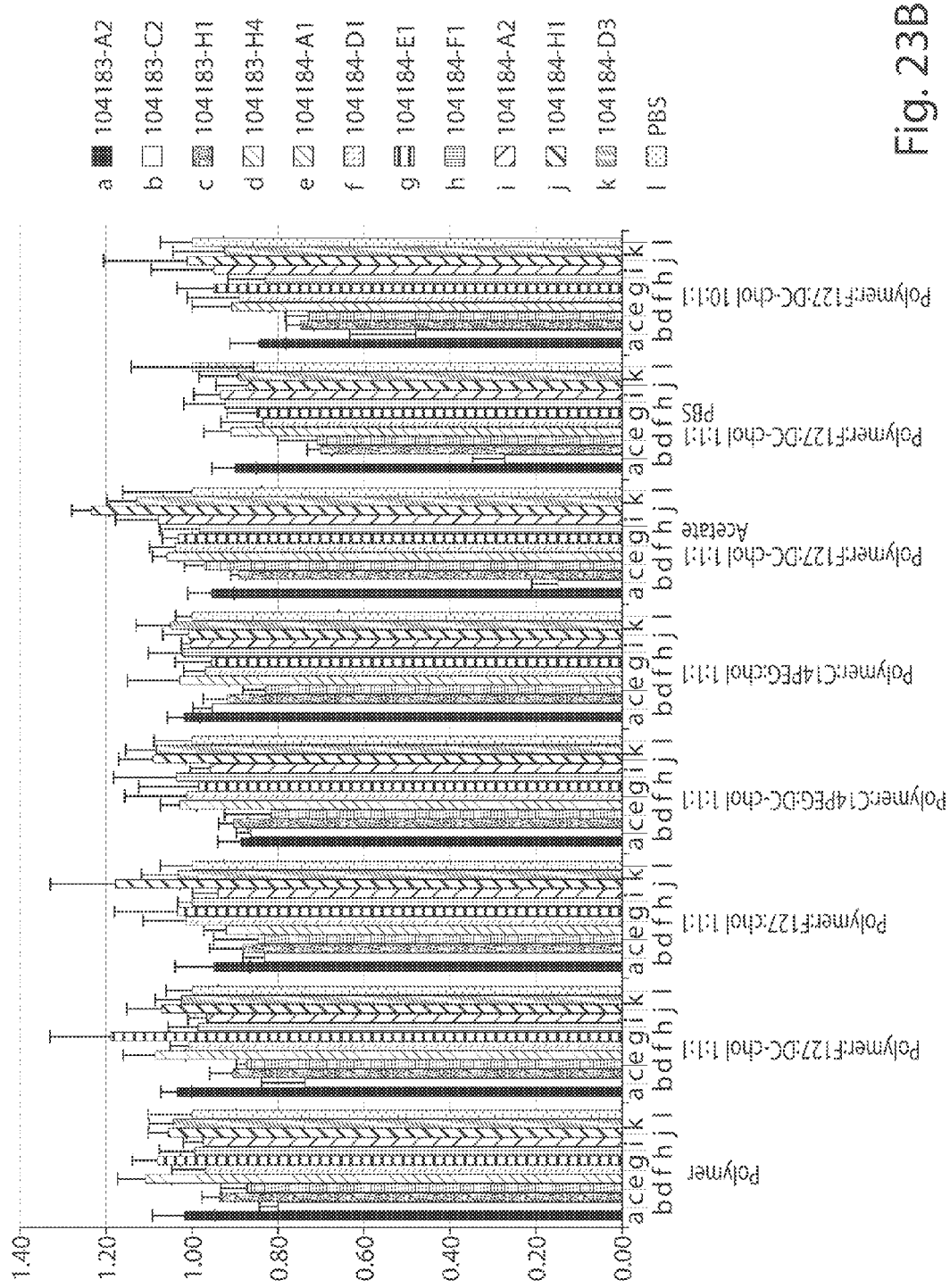
Figure 24:
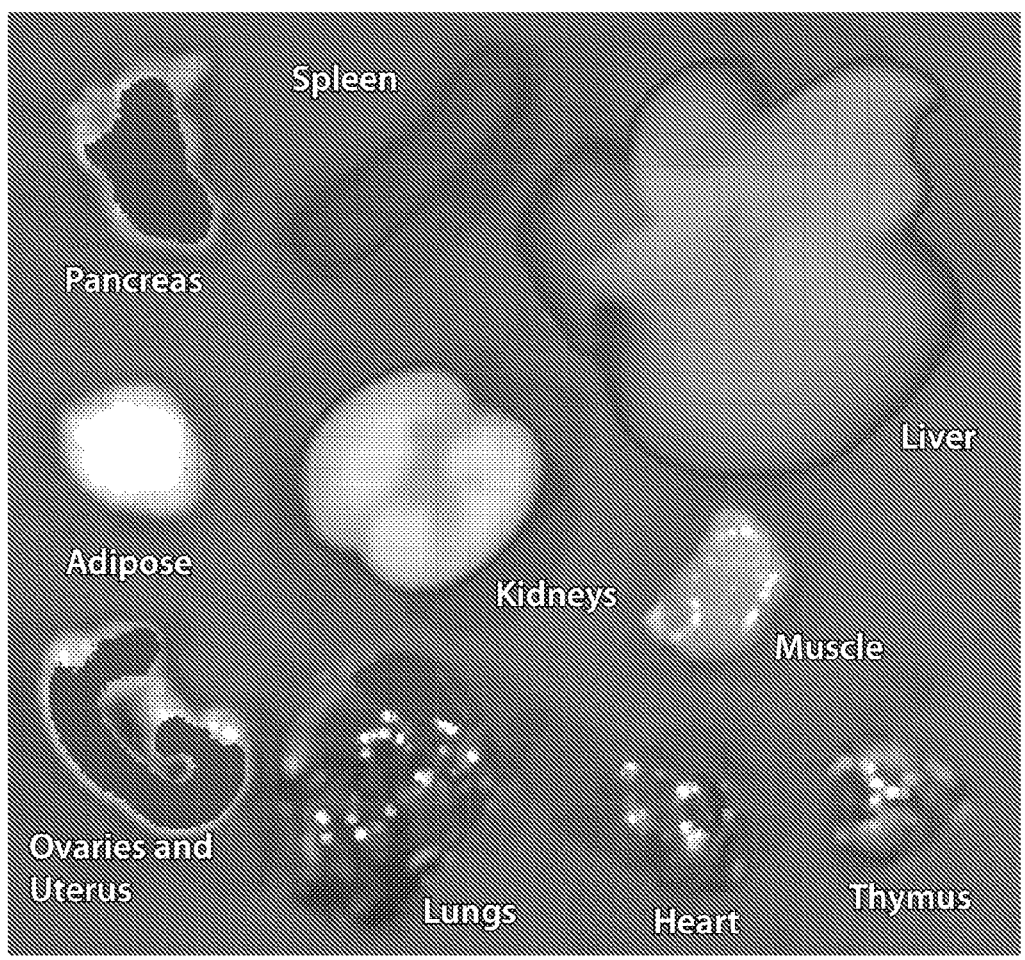
FIG. 24 depicts the mouse organ distribution of nanoparticles made using formulation VNP001 with fluorescently labeled siRNA. Organs were harvested and images collected 1 hour after tail vein injection. Significant fluorescence was observed in the liver.
Figure 25:
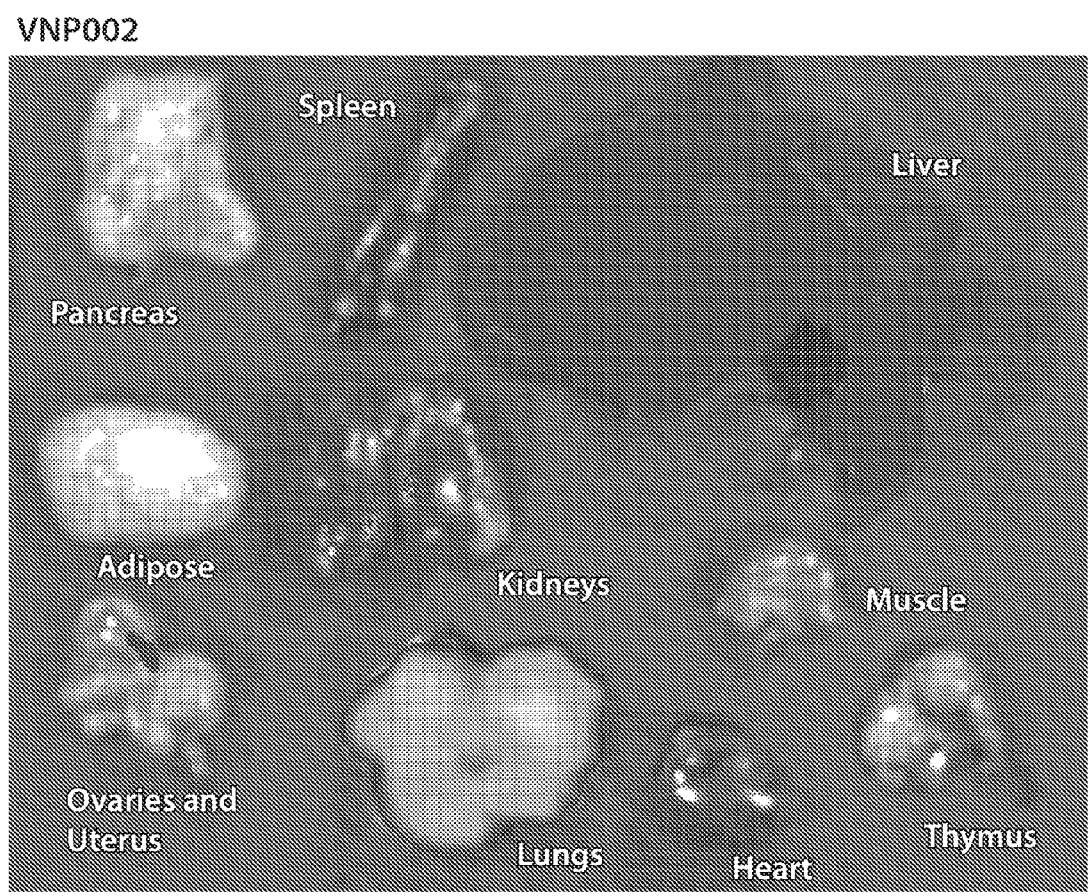
FIG. 25 depicts the mouse organ distribution of nanoparticles made using formulation VNP002 with fluorescently labeled siRNA. Organs were harvested and images collected 1 hour after tail vein injection. Significant fluorescence was observed in the lung.
Figure 26:
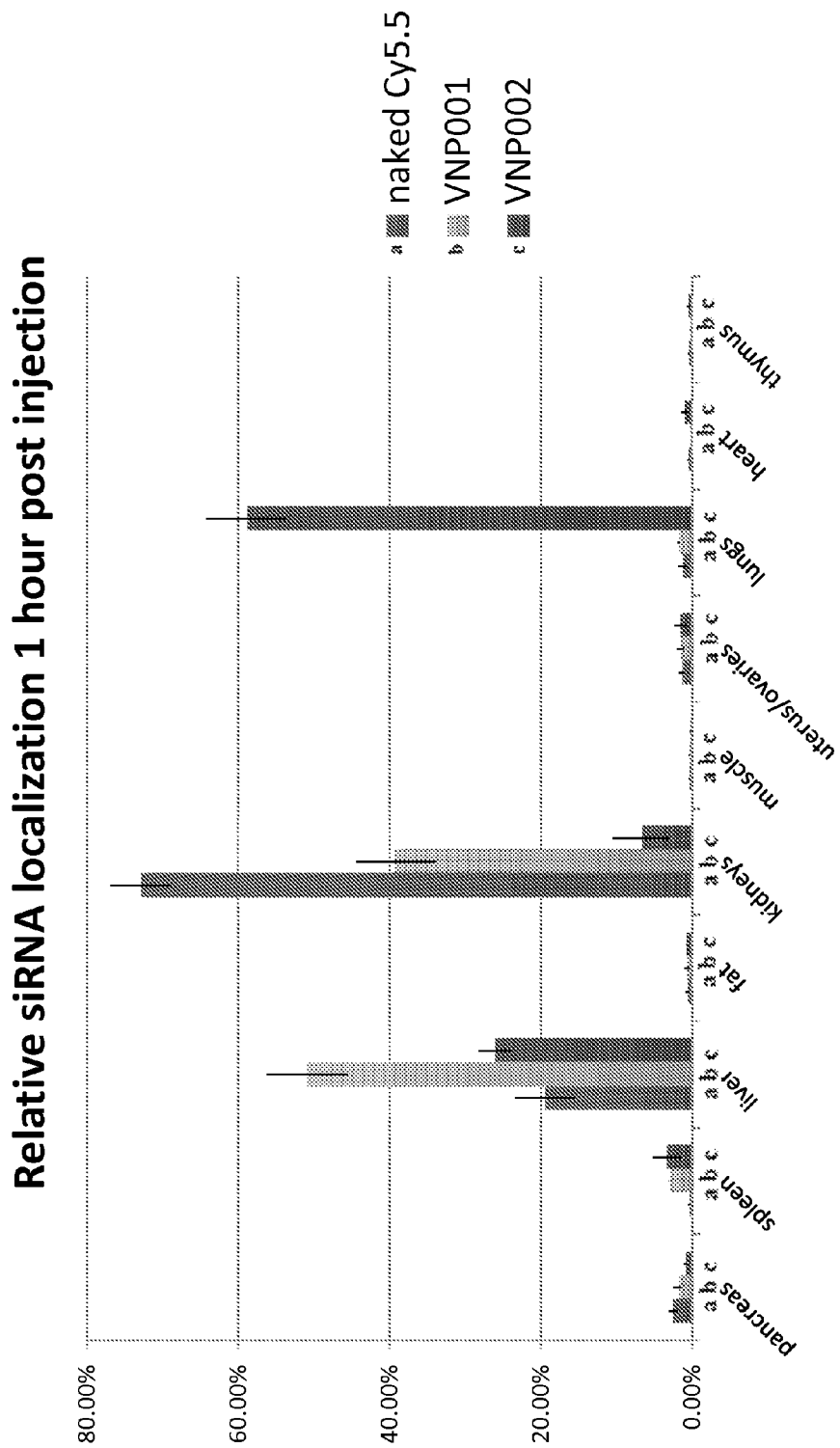
FIG. 26 depicts relative siRNA localization 1 hour post injection in: 'naked' Cy5.5 (control) and VNP001 and VNP002 formulations (see Tables 1-3).
Figure 27:
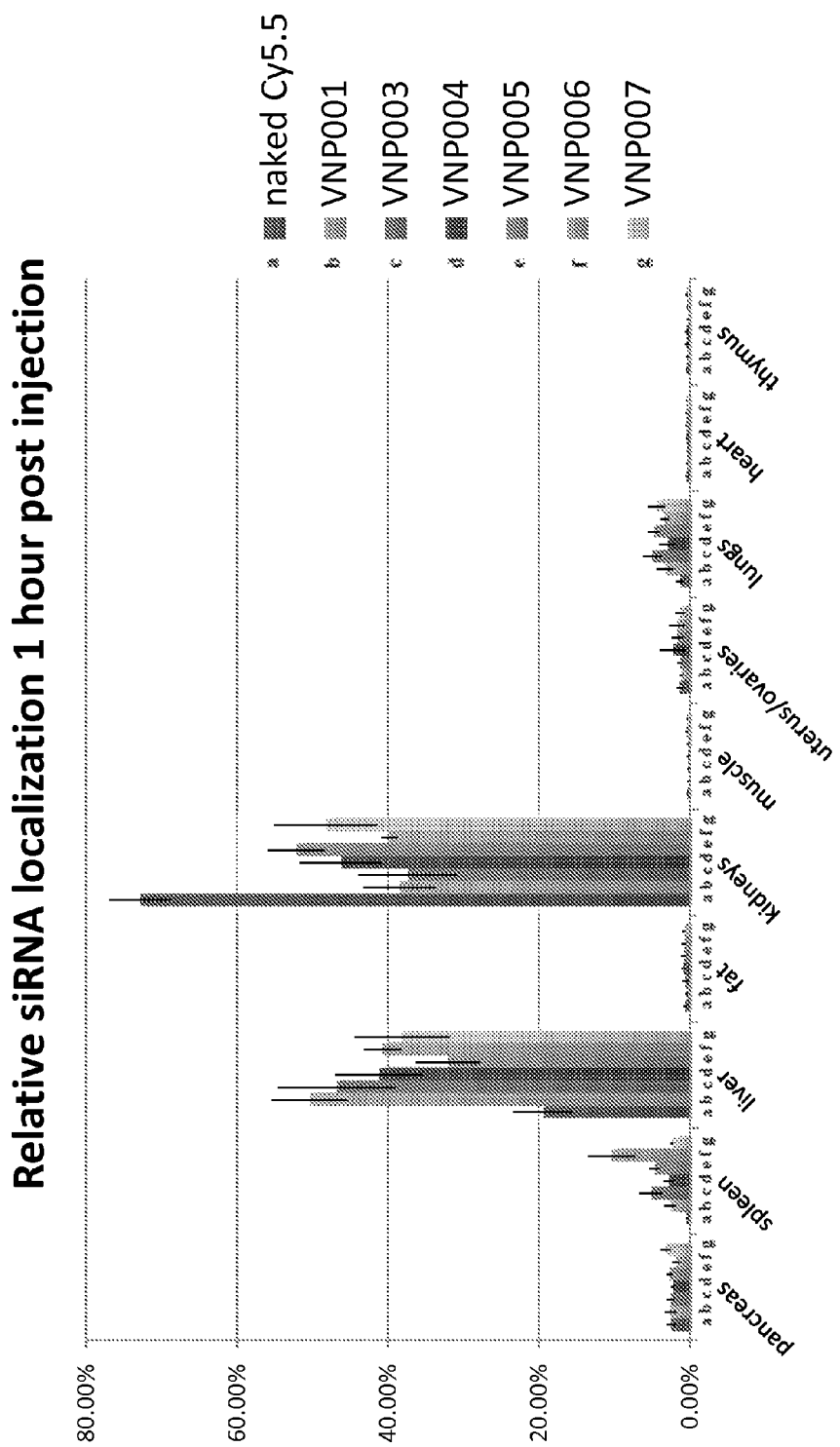
FIG. 27 depicts relative siRNA localization 1 hour post injection in: 'naked' Cy5.5 (control) and VNP001, VNP003, VNP004, VNP005, VNP006 and VNP007 formulations (see Tables 1-3).
Figure 28:
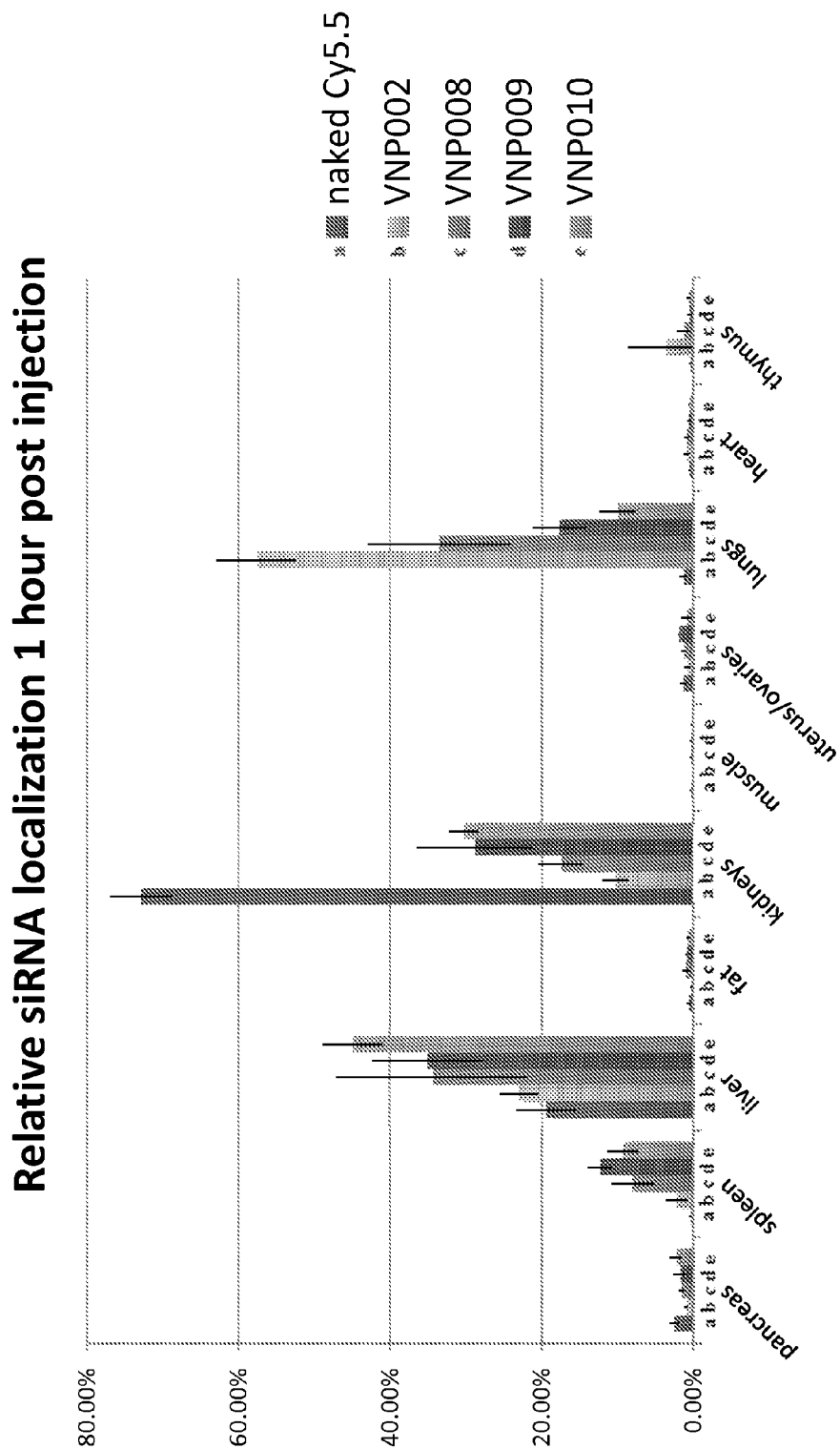
FIG. 28 depicts relative siRNA localization 1 hour post injection in: 'naked' Cy5.5 (control) and VNP002, VNP008, VNP009 and VNP010 formulations (see Tables 1-3).
Figure 29:
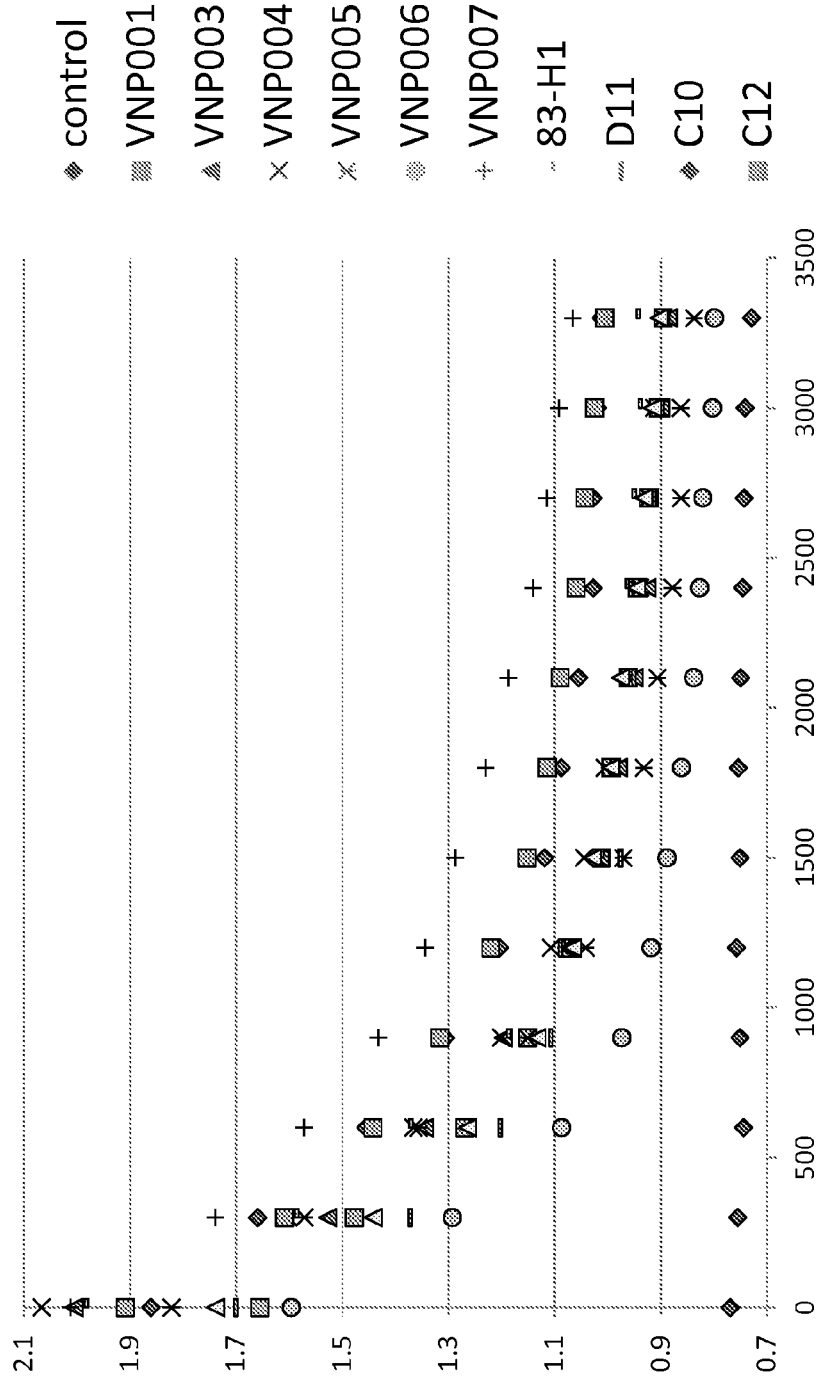
FIG. 29 depicts the serum stability of multiple α-aminoamidine polymers formulated at a 30:30:30:1 weight ratio of polymer:F127:DCchol:siRNA. Fluorescence as a result of FRET within the nanoparticles decreases over time as particles slowly dissociate in 50% mouse serum (a physiological serum level).
Figure 30:
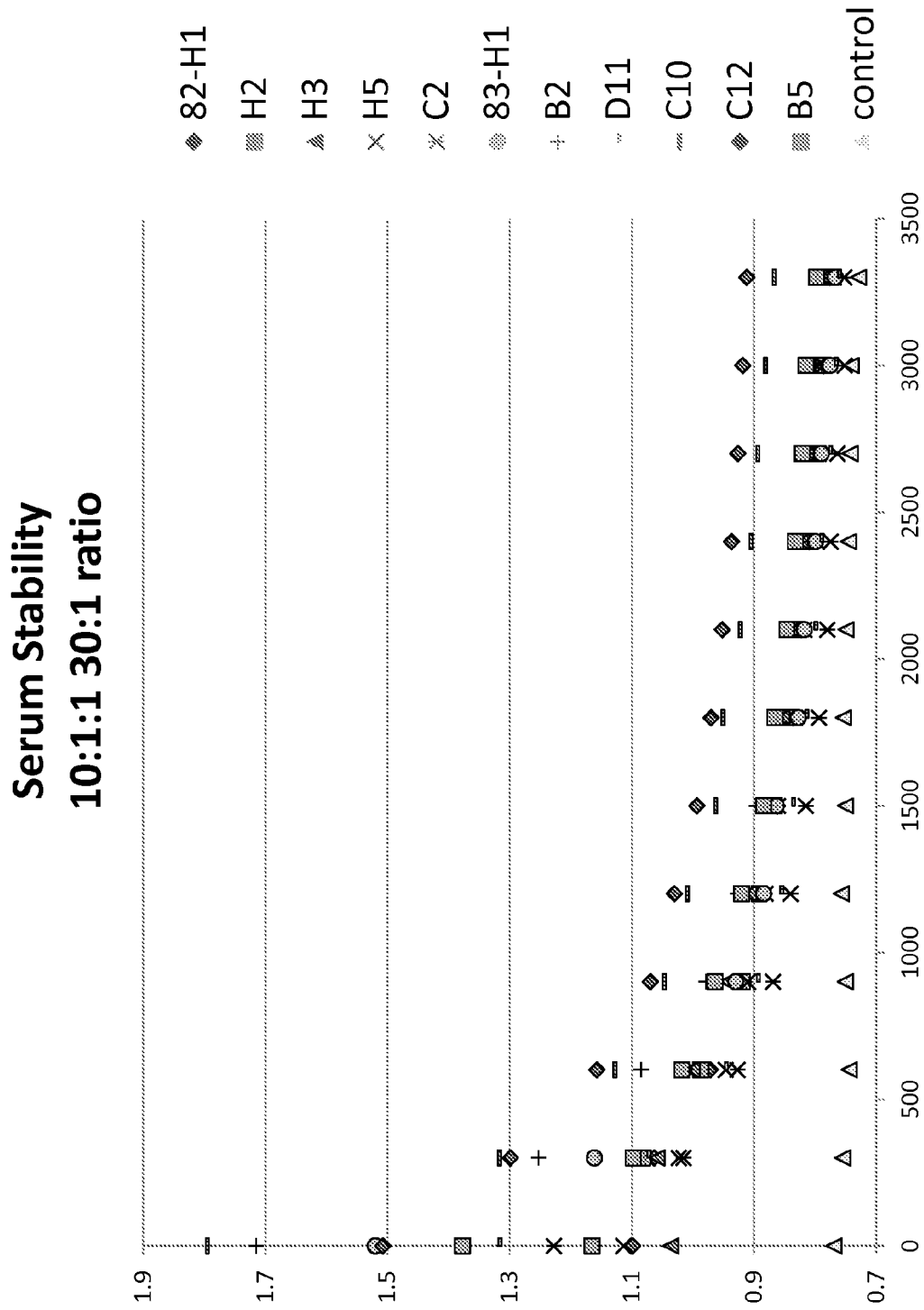
FIG. 30 depicts the serum stability of multiple α-aminoamidine polymers formulated at a 30:3:3:1 weight ratio of polymer:F127:DCchol:siRNA. Fluorescence as a result of FRET within the nanoparticles decreases over time as particles slowly dissociate in 50% mouse serum (a physiological serum level).
Figure 31:
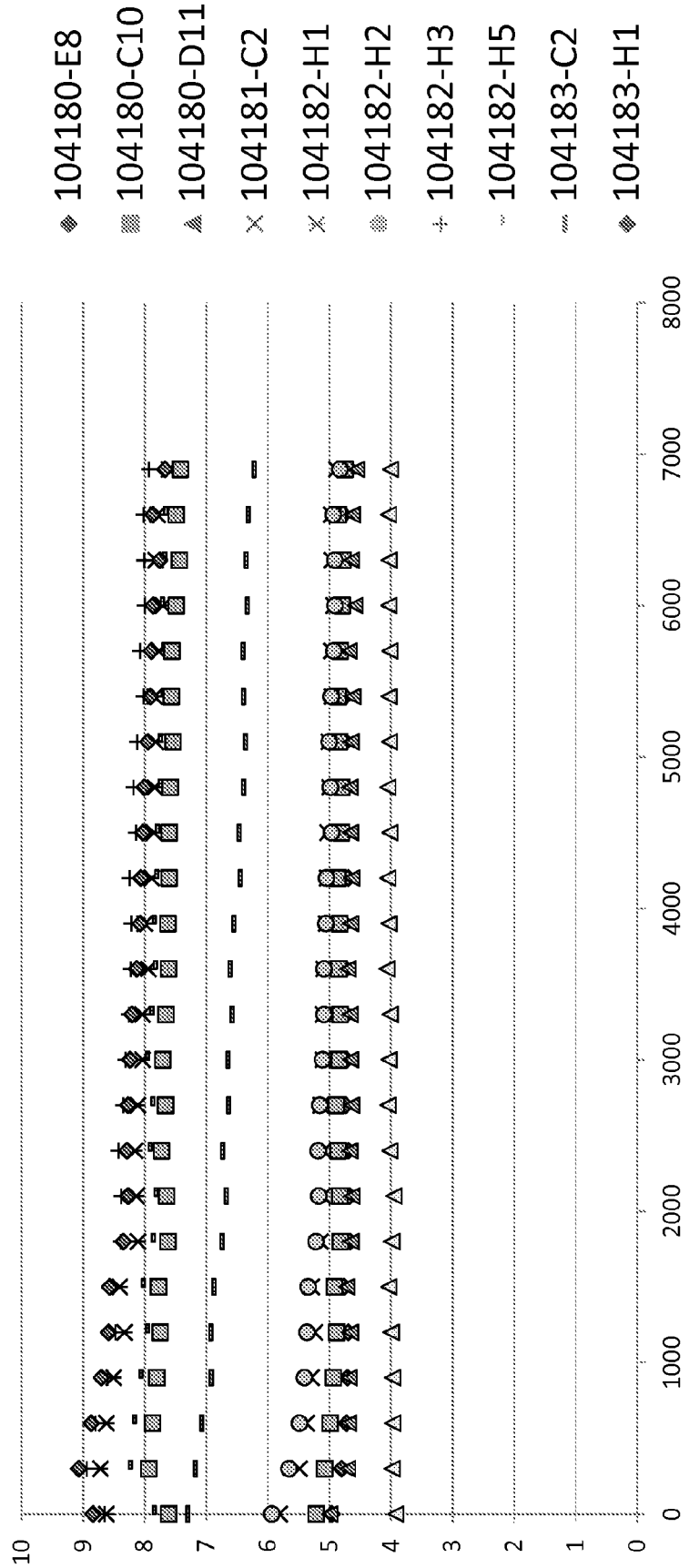
FIG. 31 depicts the serum stability of multiple α-aminoamidine polymers formulated at a 30:30:30:1 weight ratio of polymer:F127:DCchol:siRNA in a $CaCl_2$ solution. Fluorescence as a result of FRET within the nanoparticles is fairly stable, with decreases over time as particles slowly dissociate in 50% mouse serum (a physiological serum level).
Figure 32:
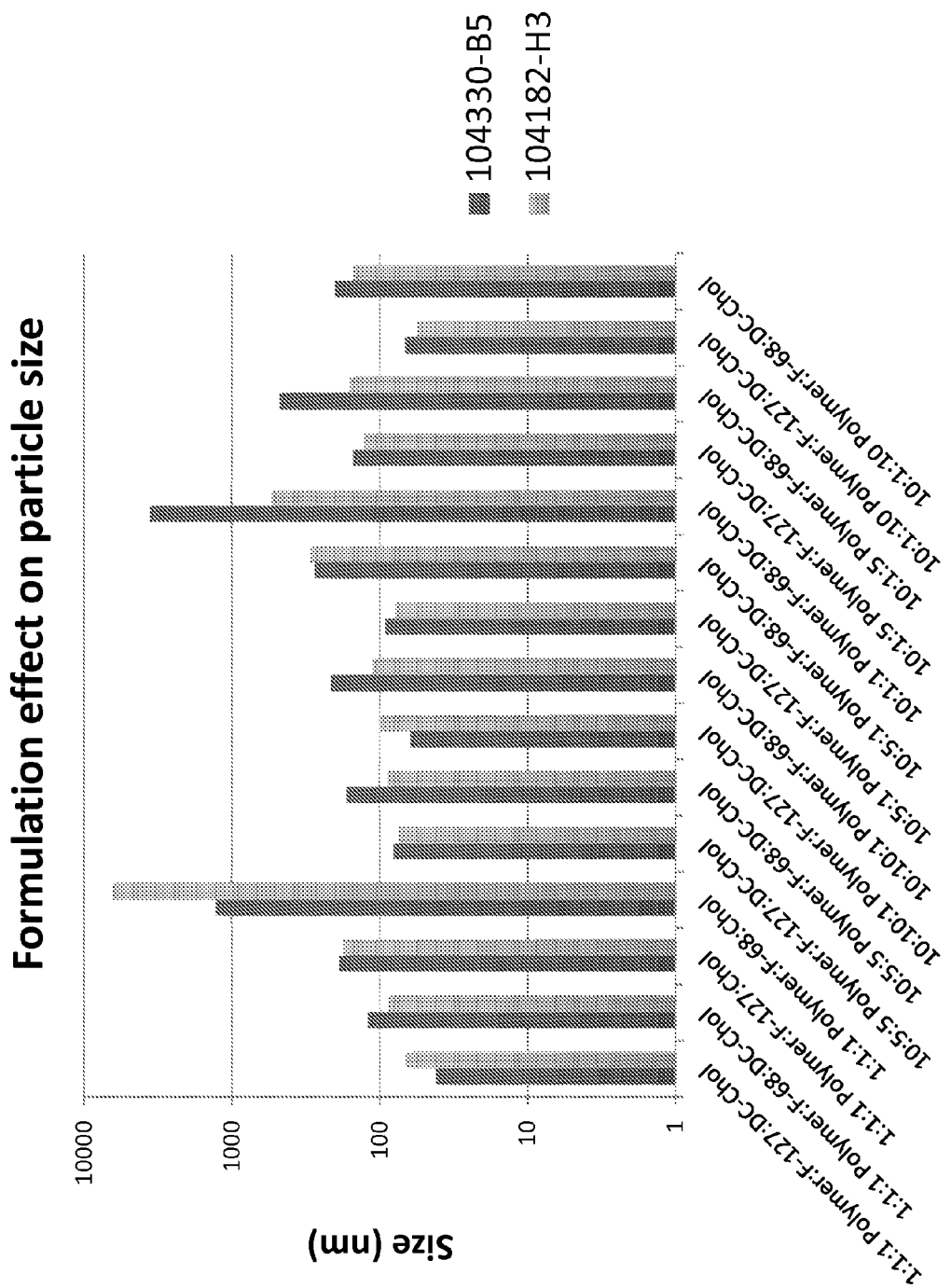
FIG. 32 depicts the formulation effect on particle size. Multiple weight ratios of polymer:F127:DCchol were tested at a 10:1 weight ratio of polymer:siRNA and their particle sizes measured by dynamic light scattering.
Figure 33:
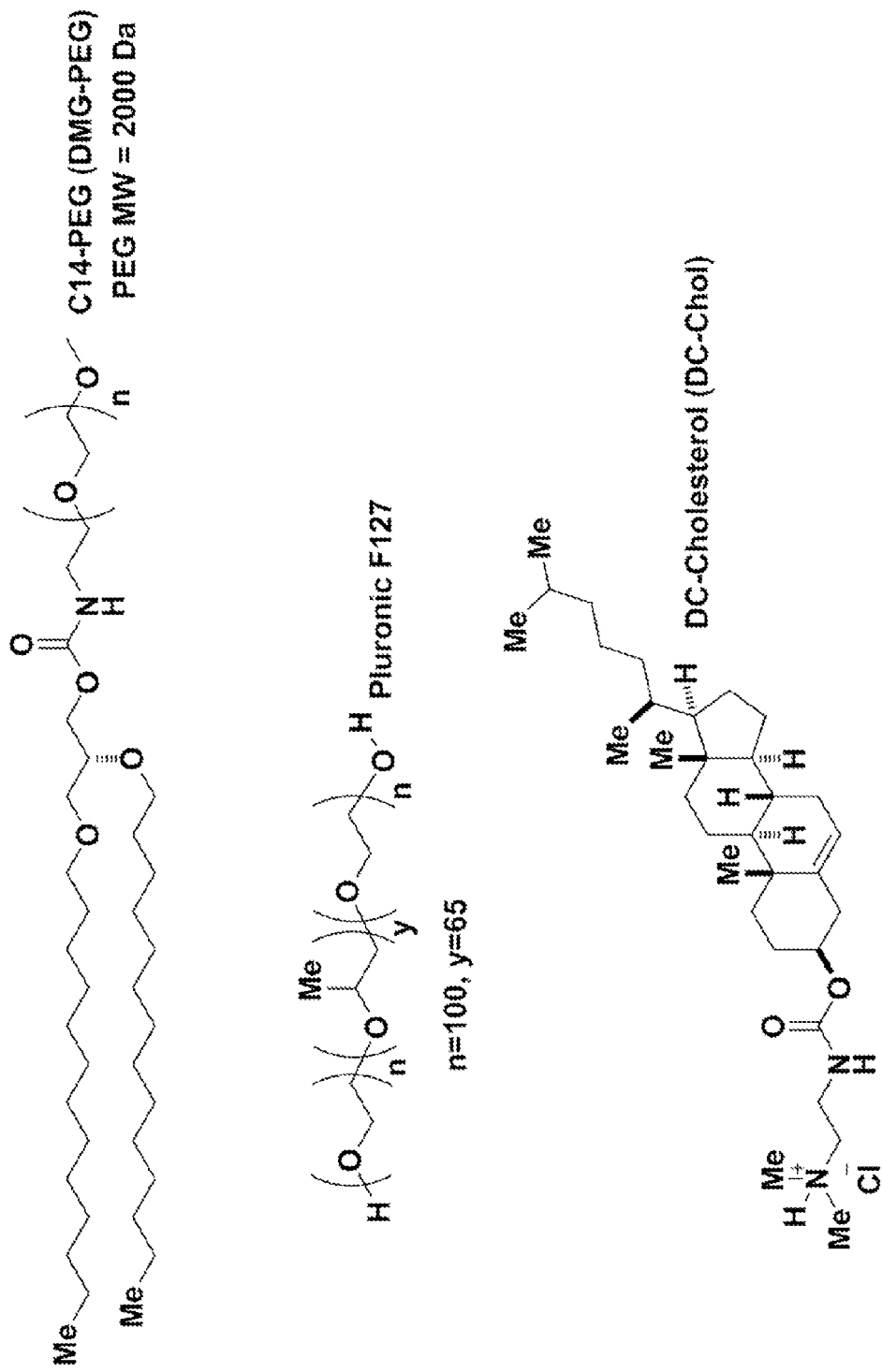
FIG. 33 depicts the structures of C14PEG (DMG-PEG), Pluronic F127 and DC-Cholesterol (DC-Chol used in the formulations.
Figure 34:
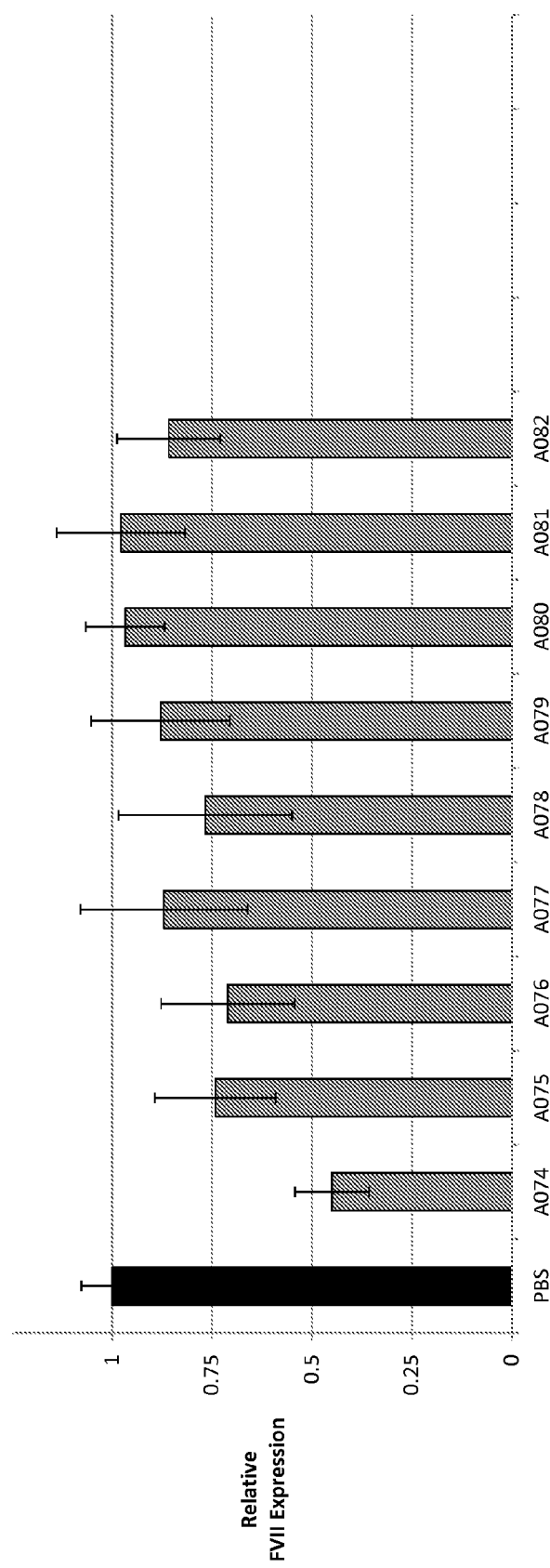
FIG. 34 depicts siRNA-mediated knockdown of protein factor VII in mice. Formulations A074 to A082 (see Tables 4-6) were administered via tail vein injection and factor VII levels were measured two days after injection from blood collected from injected mice. Percent factor VII expression (degree of protein knockdown) was determined by comparing protein levels from experimental samples to PBS injected mice. Depending on formulation, administered siRNA doses were 1, 2, or 4 mg/kg.

Polymers specifically contemplated by the present invention and encompassed by Formula (I), (II), (III), and (IV) are depicted in the FIGS. 12A-12Z.

Synthesis of α-Aminoamidine Polymers

The inventive α-aminoamidine polymers may be prepared by any method known in the art. Preferably the α-aminoamidine polymers are prepared from commercially available starting materials, such as amines, aldehydes, and isocyanides. In another embodiment, the α-aminoamidine polymers are prepared from easily and/or inexpensively prepared starting materials. As would be appreciated by one of skill in the art, the inventive α-aminoamidine polymers can be prepared by total synthesis starting from commercially available starting materials. A particular α-aminoamidine polymer may be the desired final product of the synthesis, or a mixture of α-aminoamidine polymers, regioisomers, and/or stereoisomers may be the desired final product.

In certain embodiments, one equivalent of an amine is reacted with one equivalent of an aldehyde-terminated polymer and one equivalent of an isocyanide-terminated polymer. In certain embodiments, one equivalent of an amine is reacted with one, two, three, four, five, six, or more equivalents of an aldehyde-terminated polymer and/or an isocyanide-terminated polymer. In certain embodiments, the amount of aldehyde-terminated polymer and/or isocyanide-terminated polymer is limiting to prevent the functionalization of all amino groups. The resulting α-aminoamidine or α-aminoamidine composition in these instances contain secondary amino groups and/or primary amino groups. α-Aminoamidine polymers having secondary amines are particularly useful in certain instances. In certain embodiments, amine-containing α-aminoamidine polymers that have not been fully functionalized are further reacted with another electrophile (e.g., aldehyde, isocyanide, terminal epoxide, alkyl halide, etc.). Such further functionalization of the amines of the α-aminoamidine polymer results in α-aminoamidine polymers with different tails. One, two, three, four, five, or more tails may be different from the other tails of the α-aminoamidine polymers.

In certain embodiments, the one or more aldehydes are stereochemically pure (e.g., enantiomerically pure). In certain embodiments, the one or more amines are stereochemically pure (e.g., enantiomerically pure). In certain embodiments, the one or more isocyanides are stereochemically pure (e.g., enantiomerically pure). The α-aminoamidine polymers of the invention can have an enantiomeric excess or a diastereomeric excess up to and including 2%, 5%, 10%, 15%, 20%, 25%, 30%, 35%, 40%, 45%, 50%, 55%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, 99%, 99.5%, or 100%.

Any amine containing between two, three, four, five, and six amine functionalities is useful in preparing inventive α-aminoamidine polymers. Bis(primary amine) is particularly useful in this invention. The bis(primary amine) includes, but is not limited to, ethylenediamine, 1,3 diaminopropane, 1,4 diamino butane, 1,5 diaminopentane, 1,6 diaminohexane, 2,2 (ethylenedioxy)bis(ethylamine). The amine may be a bis(secondary amine). Secondary amines useful in this invention include, but are not limited to, dipropylamine and methylpentylamine. The amine may include both primary and secondary amines including, but not limited to, (2-aminoethyl) ethanolamine, diethylenetriamine and triethylenetetramine. Preferably, the amine is commercially available. In certain embodiments, the amine is stereochemically pure (e.g., enantiomerically pure).

In one aspect, provided is a method of preparing a polymer of Formula (I), the method comprising the step of reacting one or more equivalents of an amine of one of the formula:

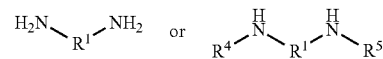

with an isocyanide of one of the formula:

and with an aldehyde of one of the formula:

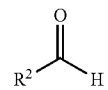

and, optionally, with an electrophile of one of the formula $R^4$-LG and/or $R^5$-LG wherein LG is a leaving group; to form a polymer of one of Formula (I) as defined herein.

In another aspect, provided is a method of preparing a polymer of Formula (II), the method comprising the step of reacting one or more equivalents of an amine of one of the formula:

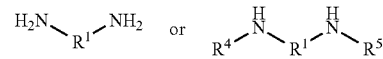

with an isocyanide of one of the formula:

and with an aldehyde of one of the formula:

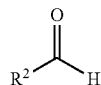

and with an aldehyde of one of the formula:

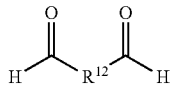

and, optionally, with an electrophile of one of the formula $R^4$-LG and/or $R^5$-LG wherein LG is a leaving group; to form a polymer of Formula (II), or a pharmaceutically acceptable salt or isomer thereof, as defined herein.

In another aspect, provided is a method of preparing a polymer of Formula (III), the method comprising the step of reacting one or more equivalents of an amine of one of the formula:

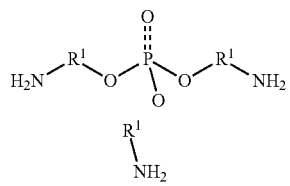

with an amine of one of the formula:

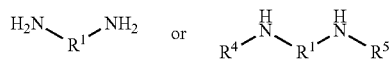

with an isocyanide of one of the formula:

and with an aldehyde of one of the formula:

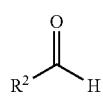

and, optionally, with an electrophile of one of the formula $R^4$-LG and/or $R^5$-LG, wherein LG is a leaving group to form a polymer of Formula (II), or a pharmaceutically acceptable salt or isomer thereof, as defined herein, wherein each X', Y', and Z' is, independently, a substituent of the formula:

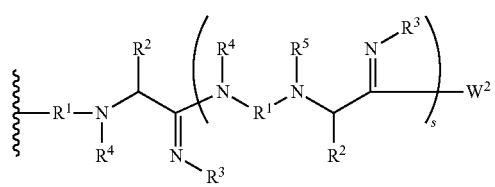

where $W^2$ is G or a group of formula:

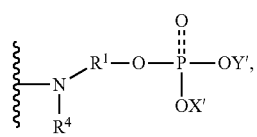

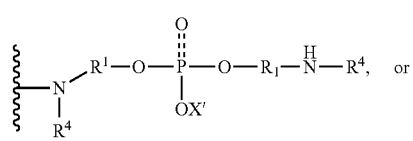

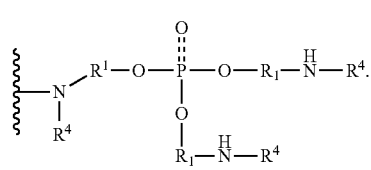

In another aspect, provided is a method of preparing a polymer of Formula (III), the method comprising the step of reacting one or more equivalents of an amine of one of the formula:

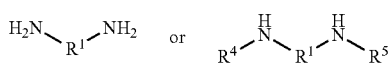

with an isocyanide of one of the formula:

and with an aldehyde of one of the formula:

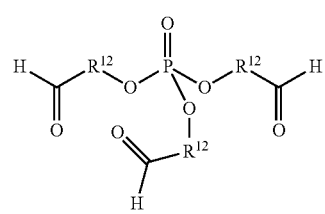

and, optionally, with an electrophile of one of the formula $R^4$-LG and/or $R^5$-LG wherein LG is a leaving group, to form a polymer of Formula (II), or a pharmaceutically acceptable salt or isomer thereof, as defined herein, wherein each X', Y', and Z' is, independently, a substituent of the formula:

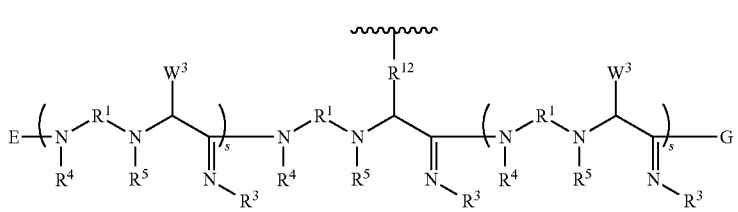

wherein $W^3$ is $R^2$ or a group of formula:

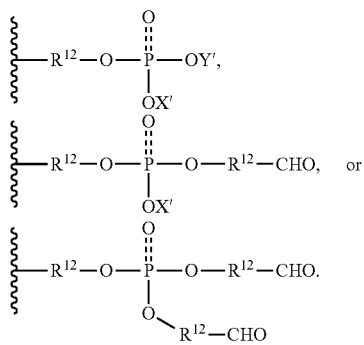

In another aspect, provided is a method of preparing a polymer of Formula (IV), the method comprising the step of reacting one or more equivalents of an amine of one of the formula:

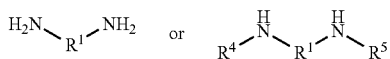

with an isocyanide-containing polymer of one of the formula:

and with a aldehyde of one of the formula:

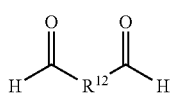

and, optionally, with an electrophile of one of the formula $R^4$-LG and/or $R^5$-LG wherein LG is a leaving group to form a polymer of one of formula:

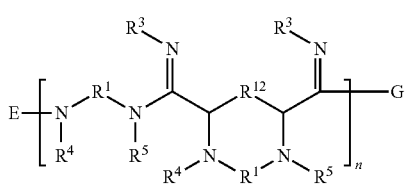

or pharmaceutically acceptable salt or isomer thereof.

In certain embodiments, the polymers are prepared from amines of formula

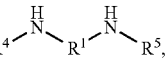

wherein $R^1$, $R^4$, and $R^5$ are described herein.

In certain embodiments, the polymers are prepared from amines of formula

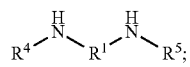

wherein $R^1$ is a substituted or unsubstituted, branched or unbranched, cyclic or acyclic $C_{2-20}$ aliphatic; optionally interrupted by one or more heteroatoms independently selected from O, S, Si, and $NR^{10}$; wherein each $R^4$ and $R^5$ is, independently, hydrogen or a $C_1$-$C_6$ alkyl, and each $R^{10}$ is, independently, hydrogen or a $C_{1-6}$ alkyl.

In certain embodiments, the polymers are prepared from amines of formula:

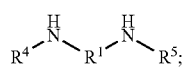

wherein $R^1$ is a substituted or unsubstituted, branched or unbranched, cyclic or acyclic $C_{1-20}$ heteroaliphatic; optionally interrupted by one or more groups independently selected from —O—, —S—, —OSi($R^7R^8$)O—, —Si$R^7R^8$—, and —$NR^{10}$—; wherein each $R^4$ and $R^5$ is, independently, hydrogen or a $C_1$-$C_6$ alkyl, and each $R^{10}$ is, independently, hydrogen or a $C_{1-6}$ alkyl.

In certain embodiments, the polymers are prepared from amines of formula:

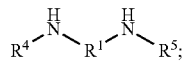

wherein $R^1$ is a substituted or unsubstituted aryl; optionally interrupted by one or more groups independently selected from —O—, —S—, —OSi($R^7R^8$)O—, —Si$R^7R^8$—, and —$NR^{10}$—; wherein each $R^4$ and $R^5$ is, independently, hydrogen or a $C_1$-$C_6$ alkyl, and each $R^{10}$ is, independently, hydrogen or a $C_{1-6}$ alkyl.

In certain embodiments, the polymers are prepared from amines of formula

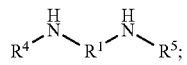

wherein $R^1$ is a unsubstituted heteroaryl; optionally interrupted by one or more groups independently selected from —O—, —S—, —OSi($R^7R^8$)O—, —Si$R^7R^8$—, and —N$R^{10}$—; wherein each $R^4$ and $R^5$ is, independently, hydrogen or a $C_1$-$C_6$ alkyl, and each $R^{10}$ is, independently, hydrogen or a $C_{1-6}$ alkyl.

In certain embodiments, the amine of the formula $$H_2N\underset{R^1}{\diagdown}NH_2$$

is an amine of the formula $$H_2N\diagdown R^{11}\diagdown O\diagdown \underset{R^7\ R^8}{Si}\diagdown O\diagdown R^{11}\diagdown NH_2,$$

wherein $R^1$, $R^7$, $R^8$, and $R^{11}$ are described herein.

In certain embodiments, the amine of the formula $$H_2N\diagdown R^{11}\diagdown O\diagdown \underset{R^7\ R^8}{Si}\diagdown O\diagdown R^{11}\diagdown NH_2$$

is prepared by the reaction of a compound of the formula $$X\diagdown \underset{R^7\ R^8}{Si}\diagdown X,$$

(i.e. di-t-butylsilyldichloride or di-t-butylsilyldibromide), with two equivalents of an aminoalcohol of the formula $$H_2N\diagdown R^{11}\diagdown OH,$$

wherein X is a leaving group, $R^7$, $R^8$, and $R^{11}$ are defined herein.

In some embodiments the aminoalcohol of the formula $$H_2N\diagdown R^{11}\diagdown OH$$

is selected from the group consisting of:

[chemical structures of aminoalcohols]

-continued

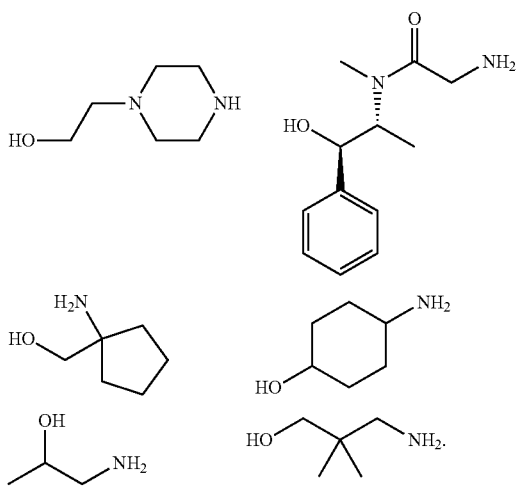

In certain embodiments, the amine of the formula

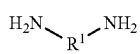

is an amine of the formula

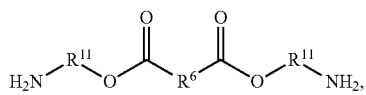

wherein $R^1$, $R^6$, and $R^{11}$ are described herein.

In certain embodiments, the amine of the formula

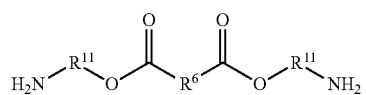

is prepared by the deprotection of the protected amine of the formula

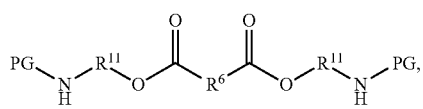

wherein PG is an amino protecting group and $R^6$ and $R^{11}$ are described herein.

In certain embodiments, the amine of the formula

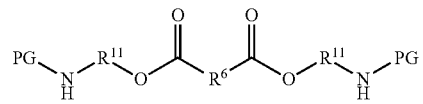

is prepared from the reaction of a compound of the formula

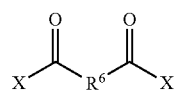

with two equivalents of a protected amino alcohol of the formula

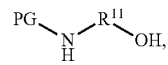

wherein PG is a protecting group, X is a leaving group, and $R^{11}$ is defined herein.

In certain embodiments, the protected aminoalcohol of the formula

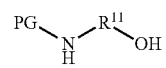

is prepared by the protection of the aminoalcohol of the formula

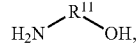

wherein PG is a protecting group and $R^{11}$ is defined herein.

In some embodiments the aminoalcohol of the formula

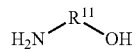

is selected from the group consisting of:

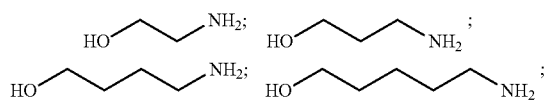
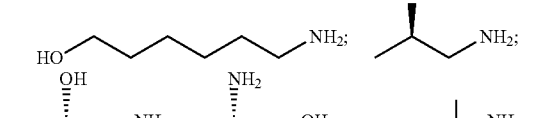
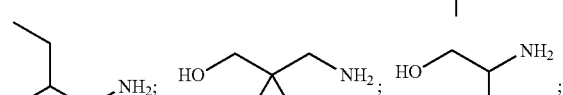
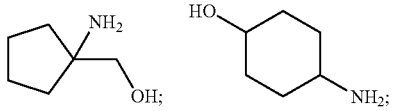

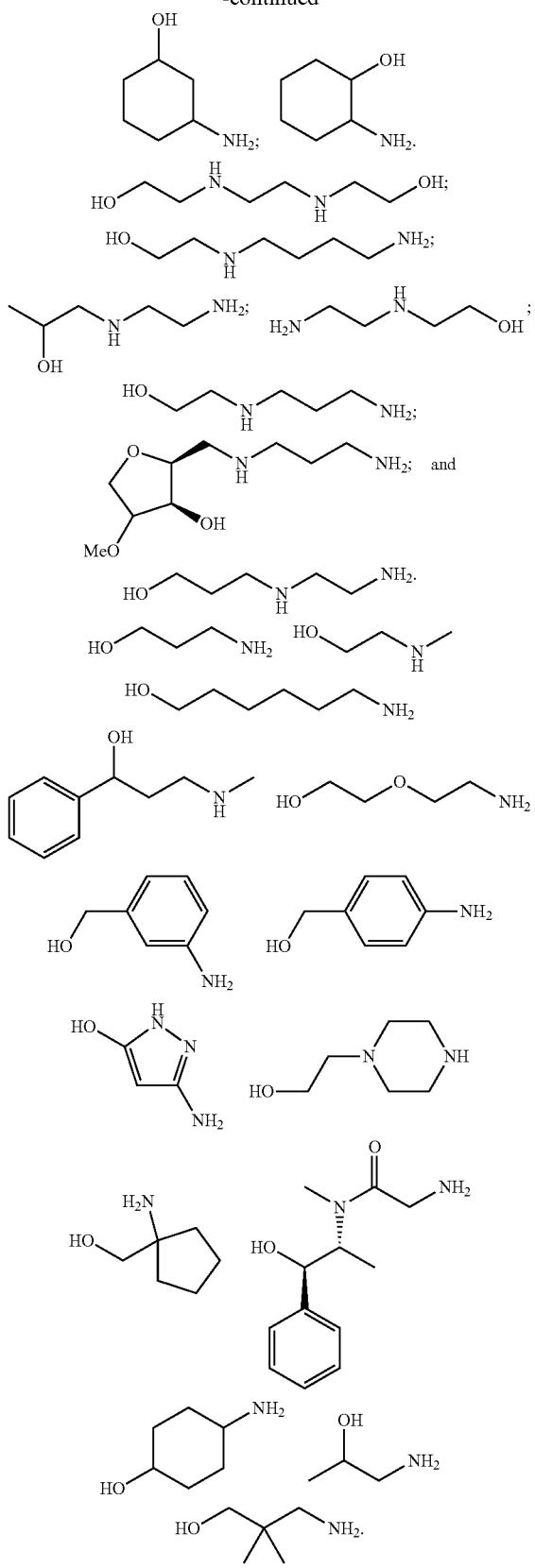

In certain embodiments, α-aminoamidine polymers are prepared from an amine of the formula

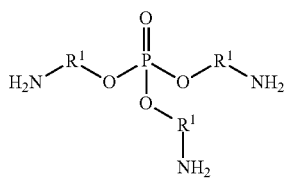

wherein $R^1$ is described herein.

In certain embodiments, the amine of the formula

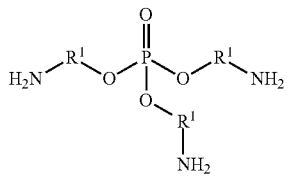

is prepared by the deprotection of the protected amine of the formula

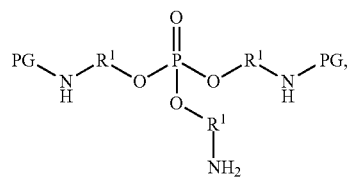

wherein PG is a protecting group and $R^1$ is described herein.

In certain embodiments, the amine of the formula

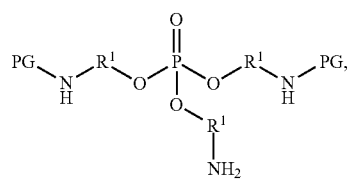

is prepared from the reaction of a compound of the formula

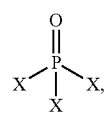

(i.e. phosphorous pentoxide, phosphorous oxychloride, or phosphorous oxybromide), with three equivalents of a protected aminoalcohol of the formula

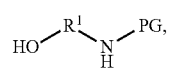

wherein PG is a protecting group, X is a leaving group, and $R^{11}$ is defined herein.

In certain embodiments, the protected aminoalcohol of the formula

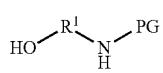

is prepared by the protection of the aminoalcohol of the formula

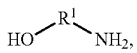

wherein PG is a protecting group and $R^1$ is defined herein.

In certain embodiments, the amine of the formula

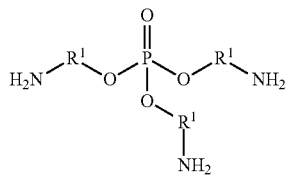

is prepared directly from the reaction of a compound of the formula

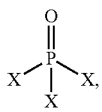

(i.e. phosphorous pentoxide, phosphorous oxychloride, or phosphorous oxybromide), with three equivalents of an aminoalcohol of the formula

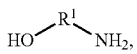

wherein X is a leaving group and $R^1$ is defined herein.

In some embodiments the aminoalcohol of the formula

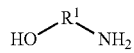

is selected from the group consisting of:

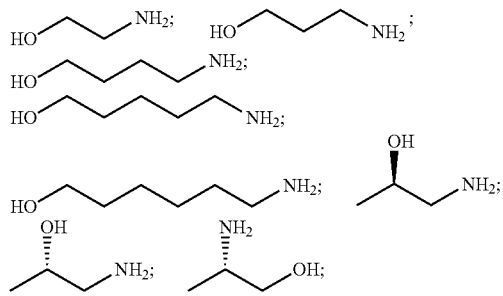

-continued

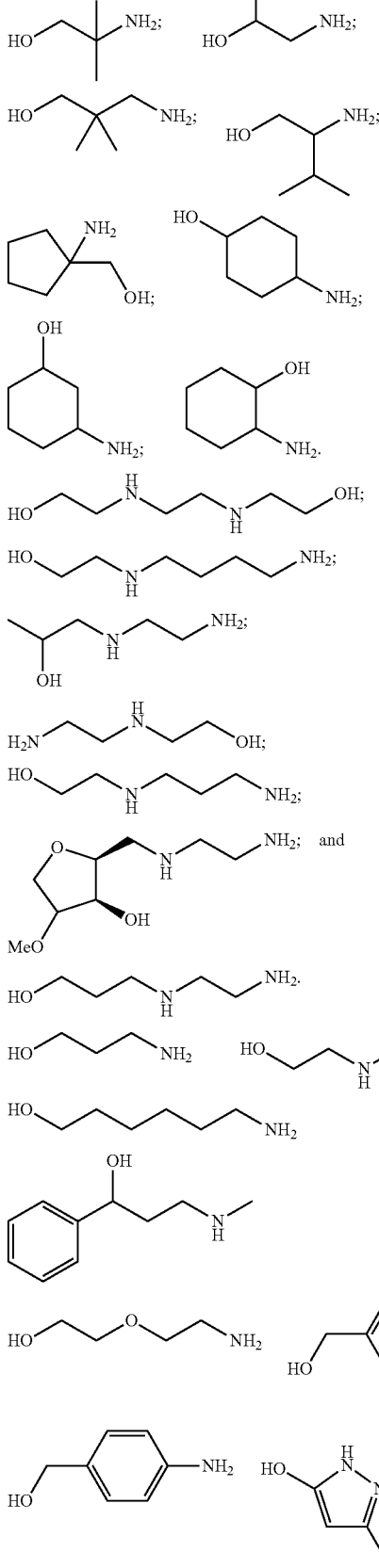

-continued

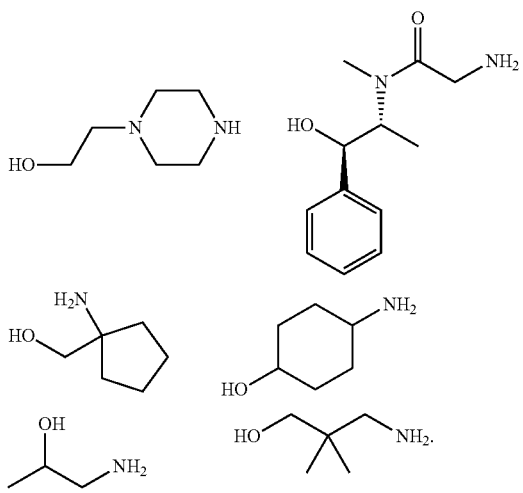

In certain embodiments, α-aminoamidine polymers are prepared from an amine of the formula

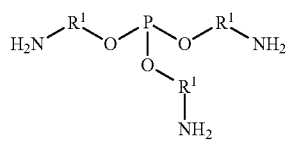

wherein R¹ is as described herein.

In certain embodiments, the amine of the formula

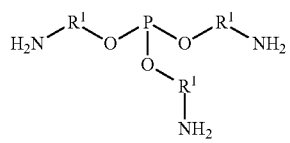

is prepared by the deprotection of the protected amine of the formula

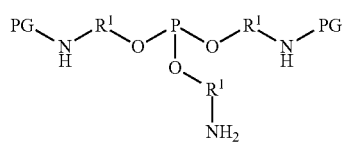

wherein PG is a protecting group and R¹ is described herein.

In certain embodiments, the amine of the formula

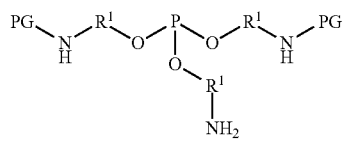

is prepared from the reaction of a compound of the formula

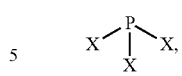

(i.e. phosphorpous trichloride or phosphorpous tribromide), with three equivalents of a protected aminoalcohol of the formula

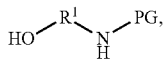

wherein PG is a protecting group, X is a leaving group, and R¹ is defined herein.

In certain embodiments, the protected aminoalcohol of the formula

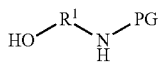

is prepared by the protection of the aminoalcohol of the formula

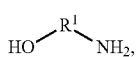

wherein PG is a protecting group and R¹ is defined herein.

In certain embodiments, the amine of the formula

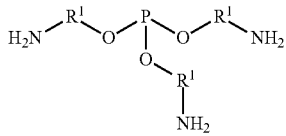

is prepared directly from the reaction of a compound of the formula

(i.e. phosphorpous trichloride or phosphorpous tribromide), with three equivalents of an aminoalcohol of the formula

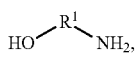

wherein X is a leaving group and R¹ is defined herein.

In some embodiments the aminoalcohol of the formula

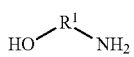

is selected from the group consisting of:
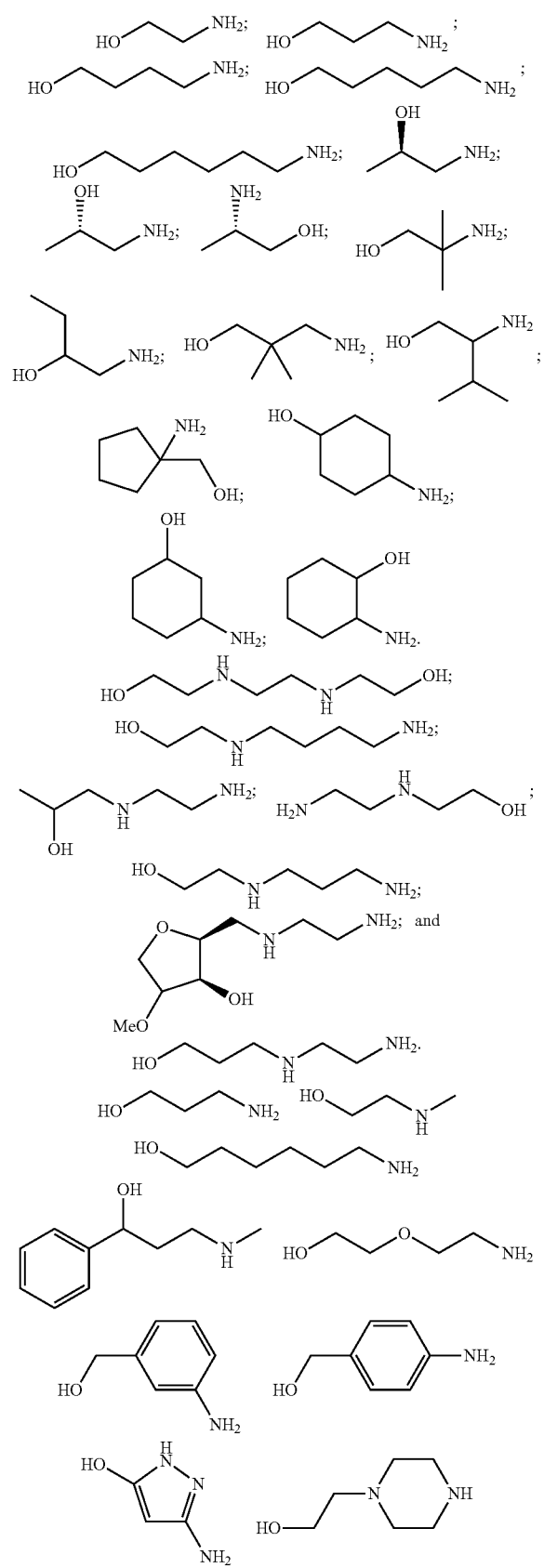
In certain embodiments, the amine used in the synthesis of the α-aminoamidine polymer is a bis(primary amine) or tris(primary amine) of the formula:

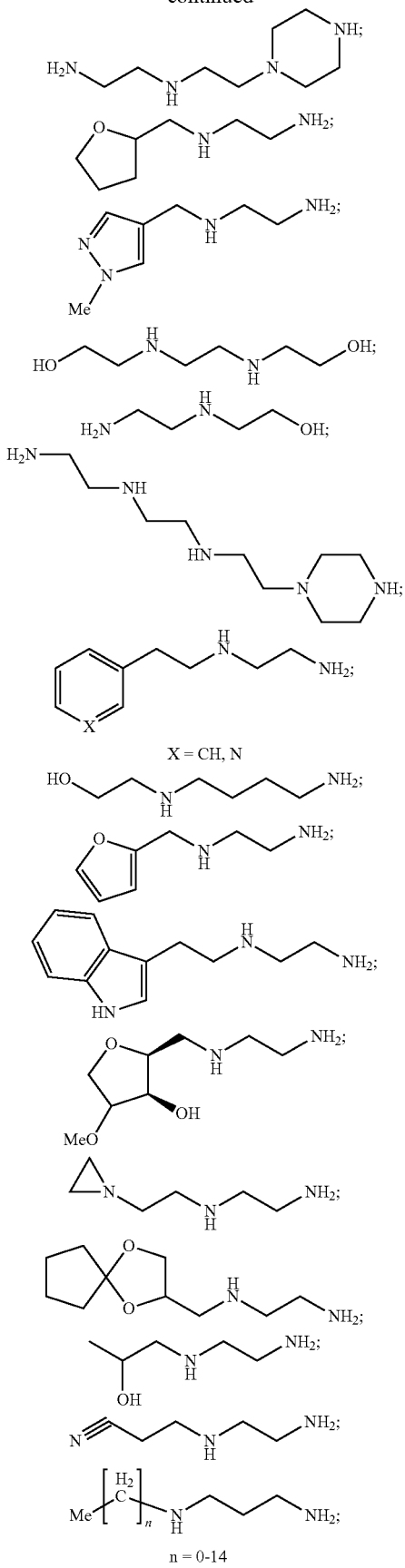
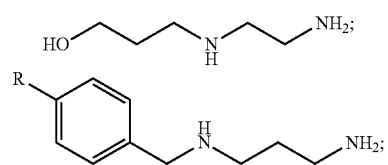
X = CH, N
R = H, F, CH₃, OMe
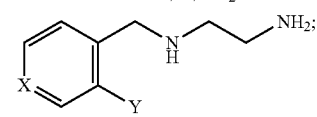
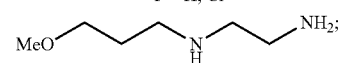
R = OMe, H, NO₂
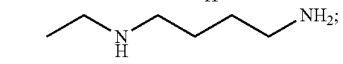
X = CH, N
Y = H, Cl
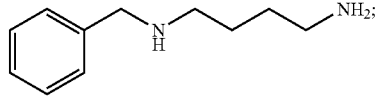
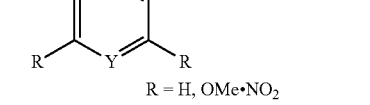
R = H, OMe•NO₂
Y = CH, N
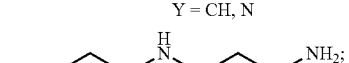
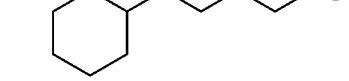
R = Me, Br, Cl, F₃C, H
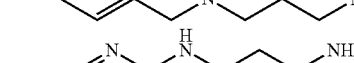
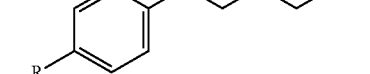
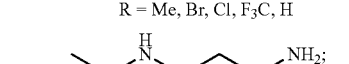 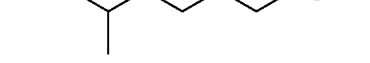
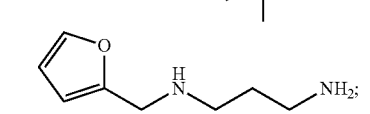

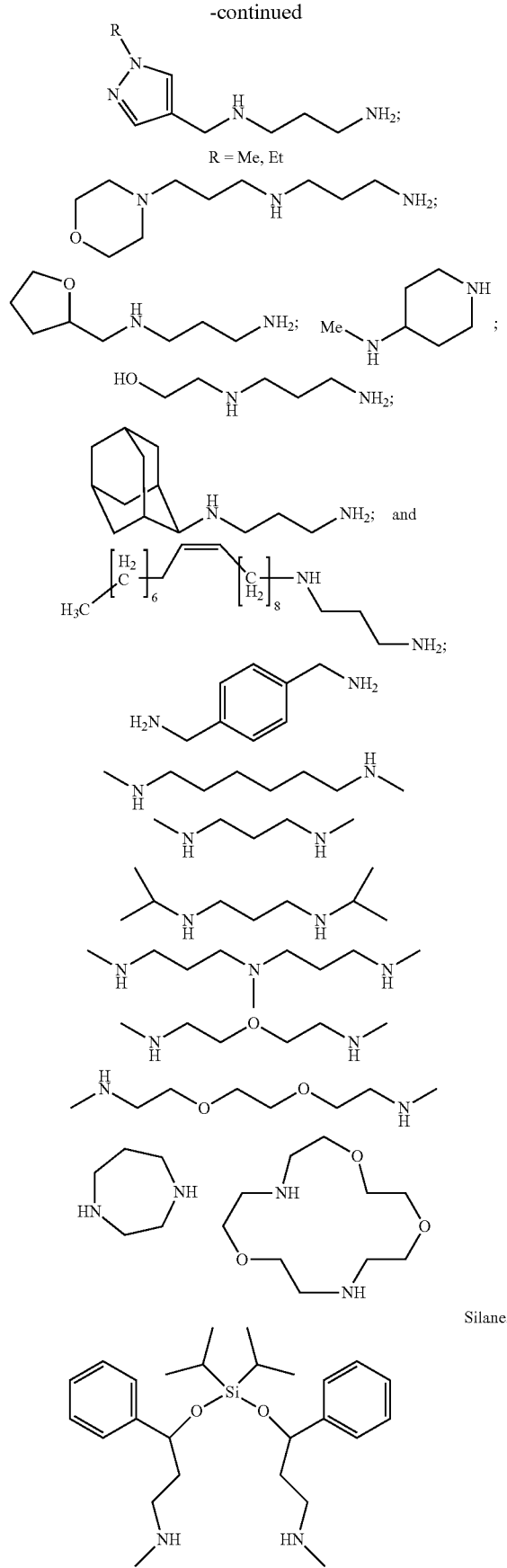

Aldehydes that are useful in the present invention can be racemic or stereoisomers thereof, all of varying chain lengths and feature unique functional groups having varying degrees of saturation. In certain embodiments, the aldehyde is stereochemically pure (e.g., enantiomerically pure). In certain embodiments, the aldehyde contains one or more chiral centers.

In certain embodiments, the aldehyde used in the synthesis of the α-aminoamidine polymer is of the formula:

-continued
Aldehyde1
Aldehyde2
Aldehyde3
Aldehyde4
Aldehyde5
Aldehyde6
Aldehyde7
Aldehyde8
Aldehyde9
Aldehyde10
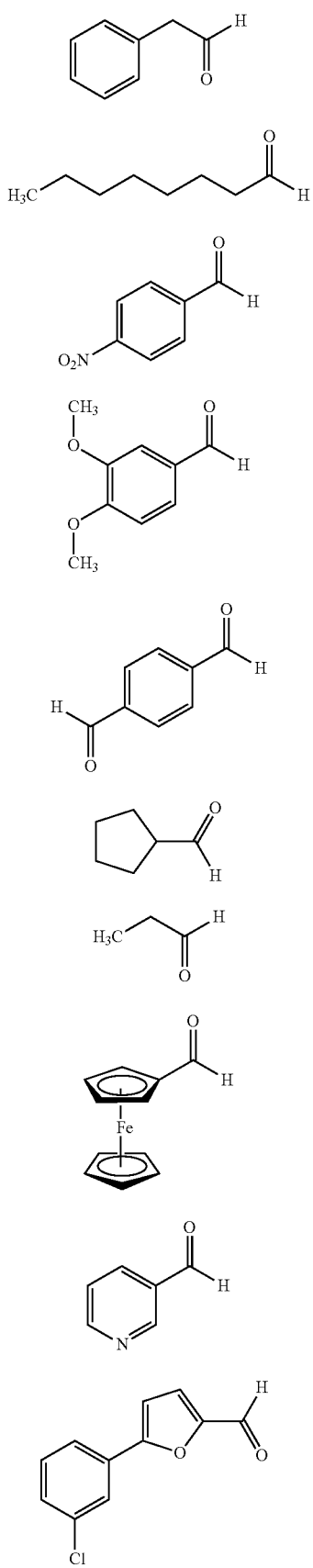
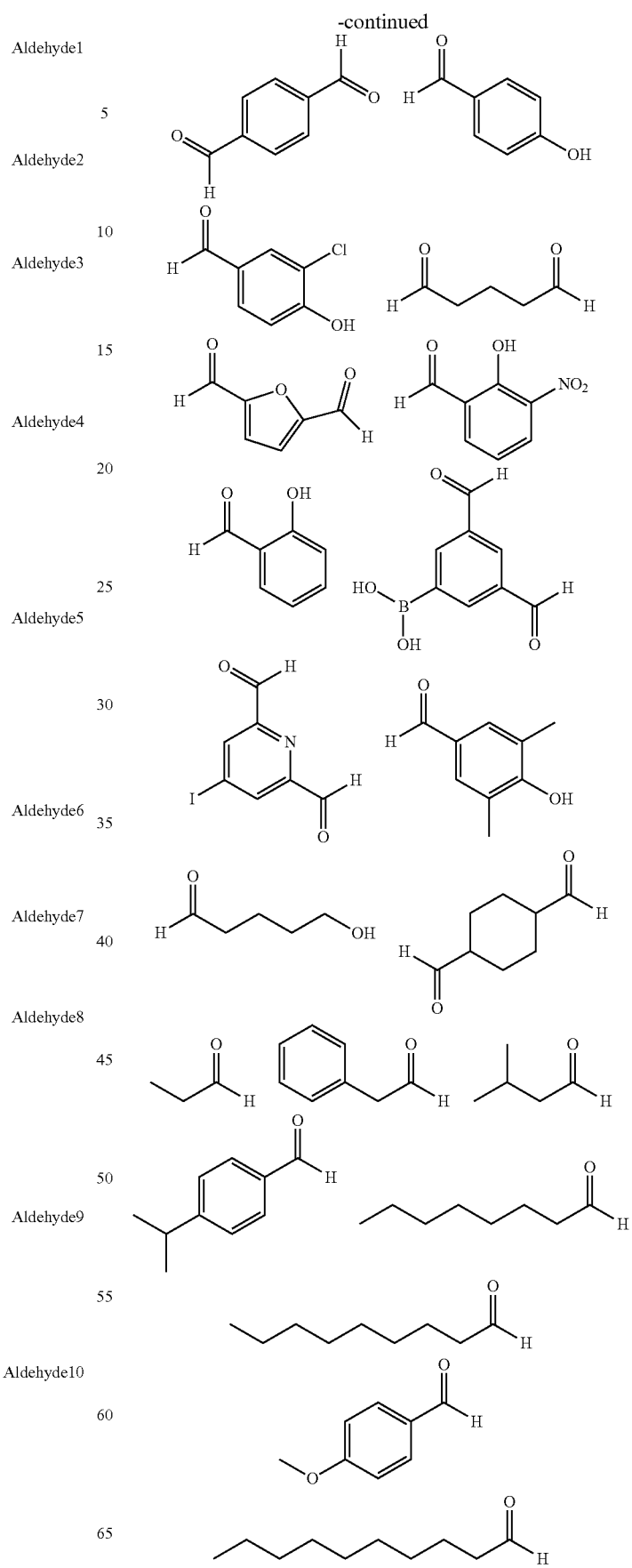

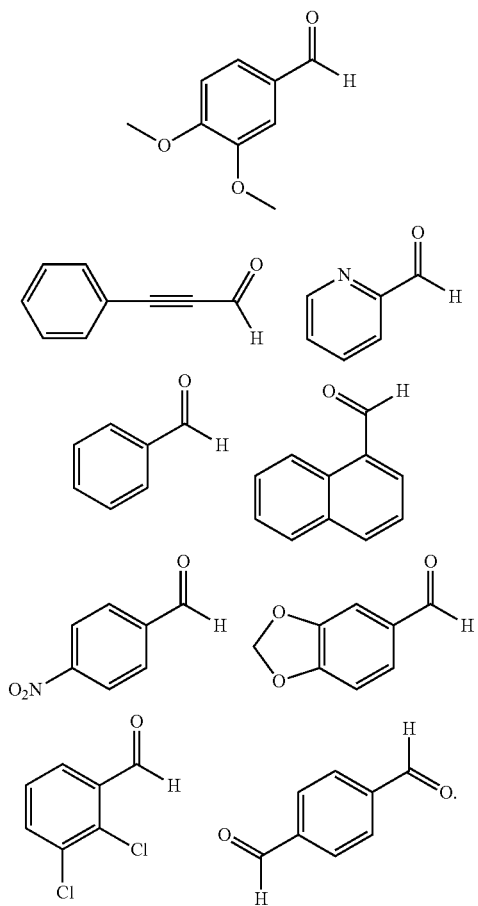

Isocyanides that are useful in the present invention can be racemic or stereoisomers thereof, all of varying chain lengths and feature unique functional groups having varying degrees of saturation. In certain embodiments, the isocyanide is stereochemically pure (e.g., enantiomerically pure). In certain embodiments, the isocyanide contains one or more chiral centers.

In certain embodiments, the isocyanide used in the synthesis of the α-aminoamidine polymer is of the formula:

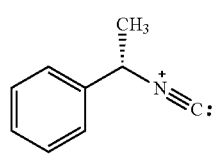

Isocyanide1

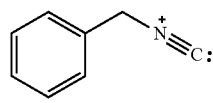

Isocyanide2

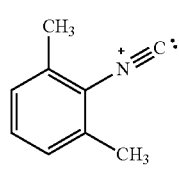

Isocyanide3

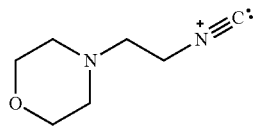

Isocyanide4

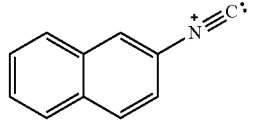

Isocyanide5

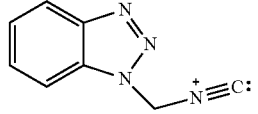

Isocyanide6

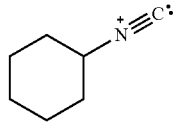

Isocyanide7

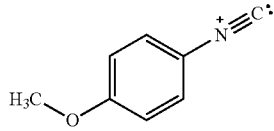

Isocyanide8

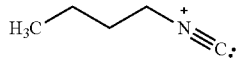

Isocyanide9

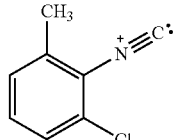

Isocyanide10

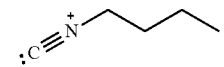

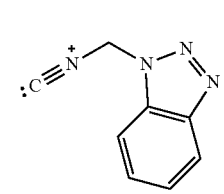

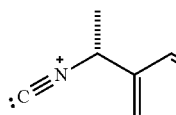

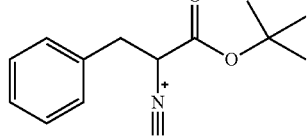

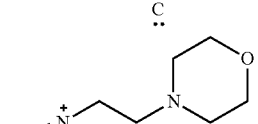

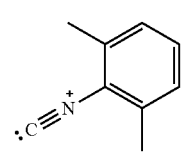

-continued

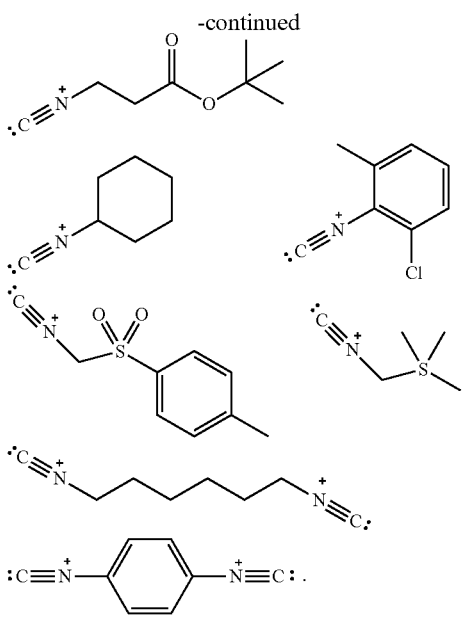

In certain embodiments, the reaction is performed neat without the use of a solvent. In other embodiments, a solvent is used for the reaction. All or one of the starting amine, aldehyde, or isocyanide is dissolved in an organic solvent (e.g., THF, $CH_2Cl_2$, MeOH, EtOH, $CHCl_3$, hexanes, toluene, benzene, $CCl_4$, glyme, diethyl ether, etc.). The resulting solutions are combined, and the reaction mixture is heated to yield the desired α-aminoamidine polymer. In certain embodiments, the reaction mixture is heated to a temperature ranging from 25° C. to 100° C., preferably at approximately 90° C. The reaction may also be catalyzed. For example, the reaction may be catalyzed by the addition of an acid, base, or metal (e.g., Lewis acid). The reagents may be allowed to react for hours, days, or weeks. Preferably, the reaction is allowed to proceed from overnight (e.g., 8-12 hours) to 7 days. In certain embodiments, the reaction is allowed to proceed for 1-7 days. In certain embodiments, the reactions were run from about 1 to about 3 days. The resulting composition may be used with or without purification. In certain embodiments, the α-aminoamidines are subsequently subjected to an acylation step. In certain embodiments, the α-aminoamidines are subsequently subjected to an alkylation step (e.g., reaction with methyl iodide, $R^4$-LG, or $R^5$-LG) to form quaternary amine salts. Optionally, various salt forms of the α-aminoamidines may be prepared. In certain embodiments, the salts are pharmaceutically acceptable salts.

The synthesized α-aminoamidine polymers may be purified by any technique known in the art including, but not limited to, precipitation, crystallization, chromatography, distillation, etc. In certain embodiments, the α-aminoamidine polymer is purified through repeated precipitations in organic solvent (e.g., diethyl ether, hexane, etc.). In certain embodiments, the α-aminoamidine polymer is isolated as a salt. The α-aminoamidine polymer is reacted with an acid (e.g., an organic acid or inorganic acid) to form the corresponding salt. In certain embodiments, the tertiary amine is alkylated to form a quaternary ammonium salt of the α-aminoamidine polymer. The tertiary amines may be alkylated with any alkylating agent, for example, such as alkyl halides (i.e. methyl iodide) to from the quaternary amino groups. The anion associated with the quaternary amine may be any organic or inorganic anion. Preferably, the anion is a pharmaceutically acceptable anion.

In certain embodiments, the reaction mixture results in a mixture of isomers with varying numbers and positions of tails. Such mixtures of products or polymers may be used as is, or a single isomer, or polymer, may be purified from the reaction mixture. When an amine is not exhaustively alkylated, the resulting primary, secondary, or tertiary amines may be further reacted with another α-aminoamidine polymer, one or more aldehydes, one or more isocyanides, or other electrophile. The resulting α-aminoamidine polymer may then be optionally purified.

In certain embodiments, a desired α-aminoamidine polymer is prepared by traditional total synthesis. In certain embodiments, a commercially available amine is the starting material. One or more amino groups of the amine are optionally protected. The unprotected amino groups are reacted with one or more aldehydes and/or one or more isocyanides. The product is optionally purified. Protecting groups are removed, and the free amino groups are optionally reacted with another α-aminoamidine polymer, one or more aldehydes, one or more isocyanides, or other electrophile. Such a sequence may be repeated depending on the desired complexity of the inventive product being prepared. The final product may then be optionally purified.

In one embodiment, a library of different α-aminoamidine polymers is prepared in parallel. Different amine, aldehydes, and/or isocyanides are added to each vial in a set of vials or to each well of a multi-well plate used to prepare the library. The array of reaction mixtures is incubated at a temperature and length of time sufficient to allow formation of the library of α-aminoamidine polymers to occur. In one embodiment, the vials are incubated at approximately 90° C. overnight. In certain embodiments, the vials are incubated from 1 to 7 days at approximately 90° C. In certain embodiments, the vials are incubated from 3 to 4 days at approximately 90° C. In certain embodiments, the vials are incubated from 1 to 2 days at approximately 90° C. The α-aminoamidine polymers may then be isolated and purified using techniques known in the art. The α-aminoamidine polymers may then be screened using high-throughput techniques to identify α-aminoamidine polymers with a desired characteristic (e.g., solubility in water, solubility at different pH, ability to bind polynucleotides, ability to bind heparin, ability to bind small molecules, ability to bind protein, ability to form microparticles, ability to increase tranfection efficiency, etc.). In certain embodiments the α-aminoamidine polymers may be screened for properties or characteristics useful in gene therapy (e.g., ability to bind polynucleotides, increase in transfection efficiency).

Particles, Micelles, and Liposomes

The α-aminoamidine polymers of the present invention may also be used to form drug delivery devices. The inventive α-aminoamidine polymers may be used to encapsulate agents including polynucleotides, small molecules, proteins, peptides, metals, organometallic complexes, etc. The inventive α-aminoamidine polymers have several properties that make them particularly suitable in the preparation of drug delivery devices. These include: 1) the ability of the polymer to complex and "protect" labile agents; 2) the ability to buffer the pH in the endosome; 3) the ability to act as a "proton sponge" and cause endosomolysis; and 4) the ability to neutralize the charge on negatively charged agents. In certain embodiments, the α-aminoamidine polymers are used to form particles containing the agent to be delivered. These particles may include other materials such as nucleic acids, peptides, proteins, carbohydrates, synthetic polymers (e.g., PEG, PLGA), and natural polymers.

In certain embodiments, the diameter of the particles range from between 1 micrometer to 1,000 micrometers. In certain embodiments, the diameter of the particles range from between from 1 micrometer to 100 micrometers. In certain embodiments, the diameter of the particles range from between from 1 micrometer to 10 micrometers. In certain embodiments, the diameter of the particles range from between from 10 micrometer to 100 micrometers. In certain embodiments, the diameter of the particles range from between from 100 micrometer to 1,000 micrometers. In certain embodiments, the particles range from 1-5 micrometers. In certain embodiments, the diameter of the particles range from between 1 nm to 1,000 nm. In certain embodiments, the diameter of the particles range from between from 1 nm to 100 nm. In certain embodiments, the diameter of the particles range from between from 1 nm to 10 nm. In certain embodiments, the diameter of the particles range from between from 10 nm to 100 nm. In certain embodiments, the diameter of the particles range from between from 100 nm to 1,000 nm. In certain embodiments, the particles range from 1-5 nm. In certain embodiments, the diameter of the particles range from between 1 pm to 1,000 pm. In certain embodiments, the diameter of the particles range from between from 1 pm to 100 pm. In certain embodiments, the diameter of the particles range from between from 1 pm to 10 pm. In certain embodiments, the diameter of the particles range from between from 10 pm to 100 pm. In certain embodiments, the diameter of the particles range from between from 100 pm to 1,000 pm. In certain embodiments, the particles range from 1-5 pm.

The inventive particles may be prepared using any method known in this art. These include, but are not limited to, spray drying, single and double emulsion solvent evaporation, solvent extraction, phase separation, simple and complex coacervation, and other methods well known to those of ordinary skill in the art. In certain embodiments, methods of preparing the particles are the double emulsion process and spray drying. The conditions used in preparing the particles may be altered to yield particles of a desired size or property (e.g., hydrophobicity, hydrophilicity, external morphology, "stickiness," charge, shape, etc.). The method of preparing the particle and the conditions (e.g., solvent, temperature, concentration, air flow rate, etc.) used may also depend on the agent being encapsulated and/or the composition of the matrix.

Methods developed for making particles for delivery of encapsulated agents are described in the literature (for example, please see Doubrow, M., Ed., "Microcapsules and Nanoparticles in Medicine and Pharmacy," CRC Press, Boca Raton, 1992; Mathiowitz and Langer, *J. Controlled Release* 5:13-22, 1987; Mathiowitz et al. *Reactive Polymers* 6:275-283, 1987; Mathiowitz et al. *J. Appl. Polymer Sci.* 35:755-774, 1988; each of which is incorporated herein by reference).

If the particles prepared by any of the above methods have a size range outside of the desired range, the particles can be sized, for example, using a sieve. The particle may also be coated. In certain embodiments, the particles are coated with a targeting agent. In other embodiments, the particles are coated to achieve desirable surface properties (e.g., a particular charge).

The α-aminoamidine polymers of the invention may also be used to prepare micelles or liposomes. Many techniques for preparing micelles and liposomes are known in the art, and any method may be used with the inventive α-aminoamidine polymers to make micelles and liposomes. In addition, any agent including polynucleotides, small molecules, proteins, peptides, metals, organometallic polymers, etc. may be included in a micelle or liposome. Micelles and liposomes are particularly useful in delivering hydrophobic agents such as hydrophobic small molecules. When the micelle or liposome is complexed with (e.g., encapsulates or covers) a polynucleotide it is referred to as a "lipoplex." Many techniques for preparing micelle and liposomes are known in the art, and any such method may be used with an APPL to make micelles and liposomes.

In certain embodiments, polyplexes (α-aminoamidine polymer nucleic acid particles) are formed through spontaneous assembly. In other embodiments, liposomes are formed when thin lipid films or lipid cakes are hydrated and stacks of lipid crystalline bilayers become fluid and swell. The hydrated lipid sheets detach during agitation and self-close to form large, multilamellar vesicles (LMV). This prevents interaction of water with the hydrocarbon core of the bilayers at the edges. Once these particles have formed, reducing the size of the particle can be modified through input of sonic energy (sonication) or mechanical energy (extrusion). The preparation of polyplexes involves preparing the α-aminoamidine polymers for hydration, hydrating the α-aminoamidine polymers with agitation, and sizing the particles to achieve a homogenous distribution of particles. α-Aminoamidine polymers are first dissolved in an organic solvent to assure a homogeneous mixture of α-aminoamidine polymers. Added to the polymer mixture is a solution of polynucleotide under fast-mixing conditions along with any other formulation additives (PEG, cholesterol, etc.). Particles are then sized and can be extruded to obtain a homogenous particle distribution anywhere between 100-500 nm. In certain embodiments, the polynucleotide is an RNA molecule (e.g., an RNAi molecule). In other embodiments, the polynucleotide is a DNA molecule. In certain embodiments, the amount of α-aminoamidine polymer in the particle ranges from 30-80 mol %, preferably 40-70 mol %, more preferably 60-99 mol %. These particles may be prepared using any method known in the art. In certain embodiments the particles are prepared by particle extrusion.

Certain α-aminoamidine polymers can spontaneously self assemble around certain molecules, such as DNA and RNA, to form particles, liposomes, or micelles. In some embodiments, the application is the delivery of polynucleotides. Use of these α-aminoamidine polymers allows for simple assembly of particles without the need for additional steps or devices such as an extruder.

The following scientific papers described other methods for preparing liposomes and micelles: Narang et al. "*Cationic Lipids with Increased DNA Binding Affinity for Non-viral Gene Transfer in Dividing and Nondividing Cells*" *Bioconjugate Chem.* 16:156-68, 2005; Hofland et al. "Formation of stable cationic lipid/DNA complexes for gene transfer" *Proc. Natl. Acad. Sci. USA* 93:7305-7309, July 1996; Byk et al. "Synthesis, Activity, and Structure-Activity Relationship Studies of Novel Cationic Lipids for DNA Transfer" *J. Med. Chem.* 41(2):224-235, 1998; Wu et al. "Cationic Lipid Polymerization as a Novel Approach for Constructing New DNA Delivery Agents" *Bioconjugate Chem.* 12:251-57, 2001; Lukyanov et al. "Micelles from lipid derivatives of water-soluble polymers as delivery systems for poorly soluble drugs" *Advanced Drug Delivery Reviews* 56:1273-1289, 2004; Tranchant et al. "Physico-chemical optimisation of plasmid delivery by cationic lipids" *J. Gene Med.* 6:S24-S35, 2004; van Balen et al.

"Liposome/Water Lipophilicity: Methods, Information Content, and Pharmaceutical Applications" *Medicinal Research Rev.* 24(3):299-324, 2004; each of which is incorporated herein by reference.

The particle, micelle, or liposome may include various components which may serve to enhance the stability of particle, micelle, or liposome. Thus, in certain embodiments, the particle, micelle, or liposome further comprises a stabilizing agent. Stabilizing agents include detergents, wetting agents, and emulsifiers, all of which are well known in the art. See, e.g., US 2009/0191244, U.S. Pat. Nos. 7,105,151, and 6,315,981. The concentration of each of the various stabilizing agents can vary and optional concentrations can be determined via routine methodology. Examples of stabilizing agents include, but are not limited to, poloxamers, polyethylene glycol, nonionic polyoxyethylene surfactant, mannitol, cholesterol, and lecithin.

In some embodiments, the stabilizing agent is a poloxamer. Poloxamers are nonionic triblock copolymers composed of a central hydrophobic chain of polyoxypropylene (also known as poly(propylene oxide)) flanked by two hydrophilic chains of polyoxyethylene (also known as poly (ethylene oxide)). Examples of poloxamers include, but are not limited to, the PLURONIC™ family of block copolymers including PLURONIC® F68, PLURONIC® F108, PLURONIC® F127, PLURONIC® F38, PLURONIC® F68, PLURONIC® F77, PLURONIC® F87, PLURONIC® F88, PLURONIC® F98, PLURONIC® L10, PLURONIC® L101, PLURONIC® L121, PLURONIC® L31, PLURONIC® L35, PLURONIC® L43, PLURONIC® L44, PLURONIC® L61, PLURONIC® L62, PLURONIC® L64, PLURONIC® L81, PLURONIC® L92, PLURONIC® N3, PLURONIC® P103, PLURONIC® P104, PLURONIC® P105, PLURONIC® P123, PLURONIC® P65, PLURONIC® P84, and PLURONIC® P85

In certain embodiments, the stabilizing agent is an emulsifying agent. Exemplary emulsifying agents include, but are not limited to, a polyethylene glycol (PEG) polymer (e.g., PEG, a PEGylated lipid), a polypropylene glycol polymer, a polyvinyl alcohol polymer, a poly-N-vinyl pyrrolidone polymer and copolymers thereof, poloxamer nonionic surfactants (e.g., Pluronic F127), neutral water-soluble polysaccharides (e.g., dextran, Ficoll, celluloses), non-cationic poly (meth)acrylates, non-cationic polyacrylates, such as poly (meth)acrylic acid, and esters amide and hydroxyalkyl amides thereof, steroids such as cholesterol and cholesterol analogs (e.g., 3β-[N—(N',N'-dimethylaminoethane)-carbamoyl]cholesterol hydrochloride (DC-cholesterol)), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F68, Poloxamer 188, cetrimonium bromide, cetylpyridinium chloride, benzalkonium chloride, docusate sodium, etc. and/or combinations thereof.

In certain embodiments, the emulsifying agent is a polyethylene glycol (PEG) polymer, such as a PEGylated lipid. Exemplary PEGylated lipids include, but are not limited to, PEG-stearate, 1,2-Distearoyl-sn-glycero-3-Phosphoethanolamine-N-[Methoxy(Polyethylene glycol)-1000], 1,2-Distearoyl-sn-glycero-3-Phosphoethanolamine-N-[Methoxy(Polyethylene glycol)-2000], 1,2-Distearoyl-sn-glycero-3-Phosphoethanolamine-N-[Methoxy(Polyethylene glycol)-5000], and 2-Dimyristoyl-sn-glycerol methoxypolyethylene Glycol (DMG-PEG).

In certain embodiments, the particle, micelle, or liposome includes one or more polyethylene glycol (PEG) polymers (e.g., DMG-PEG) and/or a cholesterol or cholesterol analogs (e.g, DC-cholesterol), and/or poloxamers (e.g., PLURONIC® F127).

The particle, micelle, or liposome may also include one or more amino acids as a component of the particle. Such amino acid additives, in certain embodiments, serve to adjust the $pK_a$ of the particle. Exemplary amino acids include, without limitation, natural alpha-amino acids such as D- and L-isomers of the 20 common naturally occurring alpha-amino acids found in peptides (e.g., A, R, N, C, D, Q, E, G, H, I, L, K, M, F, P, S, T, W, Y, V), unnatural alpha-amino acids, natural beta-amino acids (e.g., beta-alanine), and unnnatural beta-amino acids. Exemplary unnatural amino acids include, but are not limited to, 4-hydroxyproline, desmosine, gamma-aminobutyric acid, beta-cyanoalanine, norvaline, 4-(E)-butenyl-4(R)-methyl-N-methyl-L-threonine, N-methyl-L-leucine, 1-aminocyclopropanecarboxylic acid, 1-amino-2-phenyl-cyclopropanecarboxylic acid, 1-aminocyclobutanecarboxylic acid, 4-aminocyclopentenecarboxylic acid, 3-aminocyclohexanecarboxylic acid, 4-piperidylacetic acid, 4-amino-1-methylpyrrole-2-carboxylic acid, 2,4-diaminobutyric acid, 2,3-diaminopropionic acid, 2,4-diaminobutyric acid, 2-aminoheptanedioic acid, 4-(aminomethyl)benzoic acid, 4-aminobenzoic acid, ortho-, meta- and para-substituted phenylalanines (e.g., substituted with —C(=O)$C_6H_5$; —CF$_3$; —CN; -halo; —NO$_2$; CH$_3$), disubstituted phenylalanines, substituted tyrosines (e.g., further substituted with —C(=O)$C_6H_5$; —CF$_3$; —CN; -halo; —NO$_2$; CH$_3$), and statine. Additionally, the amino acids may be derivatized to include amino acid residues that are hydroxylated, phosphorylated, sulfonated, acylated, and/or glycosylated. In certain embodiments, the amino acid is histidine (H).

Agents

The agents to be delivered by the system of the present invention may be therapeutic, diagnostic, or prophylactic agents. Any chemical polymer to be administered to an individual may be delivered using the inventive complexes, picoparticles, nanoparticles, microparticles, micelles, or liposomes. The agent may be a small molecule, organometallic polymer, nucleic acid, protein, peptide, a polynucleotide, a metal, an isotopically labeled chemical polymer, drug, vaccine, immunological agent, targeting agent, etc. In certain embodiments of the present invention, the agent to be delivered may be a mixture of agents.

In certain embodiments, the agents are organic polymers with pharmaceutical activity. In another embodiment of the invention, the agent is a clinically used drug. In certain embodiments, the drug is an antibiotic, anti-viral agent, anesthetic, steroidal agent, anti-inflammatory agent, anti-neoplastic agent, antigen, vaccine, antibody, decongestant, antihypertensive, sedative, birth control agent, progestational agent, anti-cholinergic, analgesic, anti-depressant, anti-psychotic, β-adrenergic blocking agent, diuretic, cardiovascular active agent, vasoactive agent, non-steroidal anti-inflammatory agent, nutritional agent, etc.

Diagnostic agents include gases; metals; commercially available imaging agents used in positron emissions tomography (PET), computer assisted tomography (CAT), single photon emission computerized tomography, x-ray, fluoroscopy, and magnetic resonance imaging (MRI); and contrast agents. Examples of suitable materials for use as contrast agents in MRI include gadolinium chelates, as well as iron, magnesium, manganese, copper, and chromium. Examples of materials useful for CAT and x-ray imaging include iodine-based materials.

Prophylactic agents include, but are not limited to, antibiotics, nutritional supplements, and vaccines. Vaccines may comprise isolated proteins or peptides, inactivated organisms and viruses, dead organisms and viruses, genetically altered organisms or viruses, and cell extracts. Prophylactic agents may be combined with interleukins, interferon, cytokines, and adjuvants such as cholera toxin, alum, Freund's adjuvant, etc. Prophylactic agents include antigens of such bacterial organisms as *Streptococccus pneumoniae, Haemophilus influenzae, Staphylococcus aureus, Streptococcus pyrogenes, Corynebacterium diphtheriae, Listeria monocytogenes, Bacillus anthracis, Clostridium tetani, Clostridium botulinum, Clostridium perfringens, Neisseria meningitidis, Neisseria gonorrhoeae, Streptococcus mutans, Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptospirosis interrogans, Borrelia burgdorferi, Camphylobacter jejuni,* and the like; antigens of such viruses as smallpox, influenza A and B, respiratory syncytial virus, parainfluenza, measles, HIV, varicella-zoster, herpes simplex 1 and 2, cytomegalovirus, Epstein-Ban virus, rotavirus, rhinovirus, adenovirus, papillomavirus, poliovirus, mumps, rabies, *rubella,* coxsackieviruses, equine encephalitis, Japanese encephalitis, yellow fever, Rift Valley fever, hepatitis A, B, C, D, and E virus, and the like; antigens of fungal, protozoan, and parasitic organisms such as *Cryptococcus neoformans, Histoplasma capsulatum, Candida albicans, Candida tropicalis, Nocardia asteroides, Rickettsia rickettsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis, Schistosoma mansoni,* and the like. These antigens may be in the form of whole killed organisms, peptides, proteins, glycoproteins, carbohydrates, or combinations thereof.

The inventive complexes, liposomes, micelles, microparticles, picoparticles, and nanoparticles may be modified to include targeting agents since it is often desirable to target a particular cell, collection of cells, or tissue. A variety of targeting agents that direct pharmaceutical compositions to particular cells are known in the art (see, for example, Cotten et al. *Methods Enzym.* 217:618, 1993; incorporated herein by reference). The targeting agents may be included throughout the particle or may be only on the surface. The targeting agent may be a protein, peptide, carbohydrate, glycoprotein, lipid, small molecule, nucleic acids, etc. The targeting agent may be used to target specific cells or tissues or may be used to promote endocytosis or phagocytosis of the particle. Examples of targeting agents include, but are not limited to, antibodies, fragments of antibodies, low-density lipoproteins (LDLs), transferrin, asialycoproteins, gp120 envelope protein of the human immunodeficiency virus (HIV), carbohydrates, receptor ligands, sialic acid, aptamers etc. If the targeting agent is included throughout the particle, the targeting agent may be included in the mixture that is used to form the particles. If the targeting agent is only on the surface, the targeting agent may be associated with (i.e., by covalent, hydrophobic, hydrogen bonding, van der Waals, or other interactions) the formed particles using standard chemical techniques.

Polynucleotide Complexes

The ability of cationic polymers to interact with negatively charged polynucleotides through electrostatic interactions is well known. Cationic lipids have been prepared and studied for their ability to complex and transfect polynucleotides. The interaction of the lipid with the polynucleotide is thought to at least partially prevent the degradation of the polynucleotide. By neutralizing the charge on the backbone of the polynucleotide, the neutral or slightly-positively-charged complex is also able to more easily pass through the hydrophobic membranes (e.g., cytoplasmic, lysosomal, endosomal, nuclear) of the cell. In certain embodiments, the complex is slightly positively charged. In certain embodiments, the complex has a positive $\zeta$-potential, more preferably the $\zeta$-potential is between 0 and +30.

In one aspect, provided is a method of delivering a polynucleotide to a biological cell, comprising providing a composition comprising a polymer of Formula (I), (II), (III), or (IV), or a pharmaceutically acceptable salt or isomer thereof, and a polynucleotide; and exposing the composition to the biological cell under conditions sufficient to facilitate delivery of the polynucleotide into the interior of the biological cell. In certain embodiments, the method is an in vivo method. In certain embodiments, the method is an in vitro method.

The α-aminoamidine polymers of the present invention possess tertiary amines. Although these amines are hindered, they are available to interact with a polynucleotide (e.g., DNA, RNA, synthetic analogs of DNA and/or RNA, DNA/RNA hydrids, etc.). Polynucleotides or derivatives thereof are contacted with the inventive α-aminoamidine polymers under conditions suitable to form polynucleotide/α-aminoamidine complexes. The α-aminoamidine is preferably at least partially protonated so as to form a complex with the negatively charged polynucleotide. In certain embodiments, the polynucleotide/α-aminoamidine complexes form particles that are useful in the delivery of polynucleotides to cells. In certain embodiments, multiple α-aminoamidine polymers may be associated with a polynucleotide molecule. The complex may include 1-5 α-aminoamidine polymers, 1-10 α-aminoamidine polymers, 1-25 α-aminoamidine polymers, 1-50 α-aminoamidine polymers, 1-100 α-aminoamidine polymers, 1-1000 α-aminoamidine polymers, 10-1000 α-aminoamidine polymers, or 100-10,000 α-aminoamidine polymers.

In certain embodiments, the complex may form a particle. In certain embodiments, the diameter of the particles ranges from 10-500 micrometers. In certain embodiments, the diameter of the particles ranges from 10-1200 micrometers. In certain embodiments, the diameter of the particles ranges from 50-150 micrometers. In certain embodiments, the diameter of the particles ranges from 10-500 nm, more preferably the diameter of the particles ranges from 10-1200 nm, and most preferably from 50-150 nm. The particles may be associated with a targeting agent as described below. In certain embodiments, the diameter of the particles ranges from 10-500 pm, more preferably the diameter of the particles ranges from 10-1200 pm, and most preferably from 50-150 pm. The particles may be associated with a targeting agent as described below.

The polynucleotide to be complexed, encapsulated by the inventive α-aminoamidine polymers, or included in a composition with the inventive α-aminoamidine polymers may be any nucleic acid including, but not limited to, RNA and DNA. In certain embodiments, the polynucleotide is DNA. In certain embodiments, the polynucleotide is RNA.

In certain embodiments, the polynucleotide is an RNA that carries out RNA interference (RNAi). The phenomenon of RNAi is discussed in greater detail, for example, in the following references, each of which is incorporated herein by reference: Elbashir et al., 2001, *Genes Dev.*, 15:188; Fire et al., 1998, *Nature*, 391:806; Tabara et al., 1999, *Cell*, 99:123; Hammond et al., *Nature*, 2000, 404:293; Zamore et al., 2000, *Cell*, 101:25; Chakraborty, 2007, *Curr. Drug Targets*, 8:469; and Morris and Rossi, 2006, *Gene Ther.*, 13:553. In certain embodiments, the RNA is able to interfere with the expression of a specific gene in the biological cell.

In certain embodiments, the polynucleotide is a dsRNA (double-stranded RNA).

In certain embodiments, the polynucleotide is an siRNA (short interfering RNA).

In certain embodiments, the polynucleotide is an shRNA (short hairpin RNA).

In certain embodiments, the polynucleotide is an miRNA (micro RNA). micro RNAs (miRNAs) are genomically encoded non-coding RNAs of about 21-23 nucleotides in length that help regulate gene expression, particularly during development (see, e.g., Bartel, 2004, *Cell*, 116:281; Novina and Sharp, 2004, *Nature*, 430:161; and U.S. Patent Publication 2005/0059005; also reviewed in Wang and Li, 2007, *Front. Biosci.*, 12:3975; and Zhao, 2007, *Trends Biochem. Sci.*, 32:189; each of which are incorporated herein by reference).

In certain embodiments, the polynucleotide is an antisense RNA.

In some embodiments, a dsRNA, siRNA, shRNA, miRNA and/or antisense RNA can be designed and/or predicted using one or more of a large number of available algorithms. To give but a few examples, the following resources can be utilized to design and/or predict dsRNA, siRNA, shRNA, and/or miRNA: algorithms found at Alnylam Online, Dharmacon Online, OligoEngine Online, Molecula Online, Ambion Online, BioPredsi Online, RNAi Web Online, Chang Bioscience Online, Invitrogen Online, LentiWeb Online GenScript Online, Protocol Online; Reynolds et al., 2004, *Nat. Biotechnol.*, 22:326; Naito et al., 2006, *Nucleic Acids Res.*, 34:W448; Li et al., 2007, *RNA*, 13:1765; Yiu et al., 2005, *Bioinformatics*, 21:144; and Jia et al., 2006, *BMC Bioinformatics*, 7: 271; each of which is incorporated herein by reference).

The polynucleotides may be of any size or sequence, and they may be single- or double-stranded. In certain embodiments, the polynucleotide is greater than 100 base pairs long. In certain embodiments, the polynucleotide is greater than 1000 base pairs long and may be greater than 10,000 base pairs long. The polynucleotide is optionally purified and substantially pure. Preferably, the polynucleotide is greater than 50% pure, more preferably greater than 75% pure, and most preferably greater than 95% pure. The polynucleotide may be provided by any means known in the art. In certain embodiments, the polynucleotide has been engineered using recombinant techniques (for a more detailed description of these techniques, please see Ausubel et al. *Current Protocols in Molecular Biology* (John Wiley & Sons, Inc., New York, 1999); *Molecular Cloning: A Laboratory Manual,* 2nd Ed., ed. by Sambrook, Fritsch, and Maniatis (Cold Spring Harbor Laboratory Press: 1989); each of which is incorporated herein by reference). The polynucleotide may also be obtained from natural sources and purified from contaminating components found normally in nature. The polynucleotide may also be chemically synthesized in a laboratory. In certain embodiments, the polynucleotide is synthesized using standard solid phase chemistry.

The polynucleotide may be modified by chemical or biological means. In certain embodiments, these modifications lead to increased stability of the polynucleotide. Modifications include methylation, phosphorylation, end-capping, etc.

Derivatives of polynucleotides may also be used in the present invention. These derivatives include modifications in the bases, sugars, and/or phosphate linkages of the polynucleotide. Modified bases include, but are not limited to, those found in the following nucleoside analogs: 2-aminoadenosine, 2-thiothymidine, inosine, pyrrolo-pyrimidine, 3-methyl adenosine, 5-methylcytidine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, 0(6)-methylguanine, and 2-thiocytidine. Modified sugars include, but are not limited to, 2'-fluororibose, ribose, 2'-deoxyribose, 3'-azido-2',3'-dideoxyribose, 2',3'-dideoxyribose, arabinose (the 2'-epimer of ribose), acyclic sugars, and hexoses. The nucleosides may be strung together by linkages other than the phosphodiester linkage found in naturally occurring DNA and RNA. Modified linkages include, but are not limited to, phosphorothioate and 5'-N-phosphoramidite linkages. Combinations of the various modifications may be used in a single polynucleotide. These modified polynucleotides may be provided by any means known in the art; however, as will be appreciated by those of skill in this art, the modified polynucleotides are preferably prepared using synthetic chemistry in vitro.

The polynucleotides to be delivered may be in any form. For example, the polynucleotide may be a circular plasmid, a linearized plasmid, a cosmid, a viral genome, a modified viral genome, an artificial chromosome, etc.

The polynucleotide may be of any sequence. In certain embodiments, the polynucleotide encodes a protein or peptide. The encoded proteins may be enzymes, structural proteins, receptors, soluble receptors, ion channels, pharmaceutically active proteins, cytokines, interleukins, antibodies, antibody fragments, antigens, coagulation factors, albumin, growth factors, hormones, insulin, etc. The polynucleotide may also comprise regulatory regions to control the expression of a gene. These regulatory regions may include, but are not limited to, promoters, enhancer elements, repressor elements, TATA box, ribosomal binding sites, stop site for transcription, etc. In certain embodiments, the polynucleotide is not intended to encode a protein. For example, the polynucleotide may be used to fix an error in the genome of the cell being transfected.

The polynucleotide may also be provided as an antisense agent or RNA interference (RNAi) (Fire et al. *Nature* 391:806-811, 1998; incorporated herein by reference). Antisense therapy is meant to include, e.g., administration or in situ provision of single- or double-stranded oligonucleotides or their derivatives which specifically hybridize, e.g., bind, under cellular conditions, with cellular mRNA and/or genomic DNA, or mutants thereof, so as to inhibit expression of the encoded protein, e.g., by inhibiting transcription and/or translation (Crooke "Molecular mechanisms of action of antisense drugs" *Biochim. Biophys. Acta* 1489(1): 31-44, 1999; Crooke "Evaluating the mechanism of action of antiproliferative antisense drugs" *Antisense Nucleic Acid Drug Dev.* 10(2):123-126, discussion 127, 2000; Methods in Enzymology volumes 313-314, 1999; each of which is incorporated herein by reference). The binding may be by conventional base pair complementarity, or, for example, in the case of binding to DNA duplexes, through specific interactions in the major groove of the double helix (i.e., triple helix formation) (Chan et al. *J. Mol. Med.* 75(4):267-282, 1997; incorporated herein by reference).

In certain embodiments, the polynucleotide to be delivered comprises a sequence encoding an antigenic peptide or protein. Nanoparticles containing these polynucleotides can be delivered to an individual to induce an immunologic response sufficient to decrease the chance of a subsequent infection and/or lessen the symptoms associated with such an infection. The polynucleotide of these vaccines may be combined with interleukins, interferon, cytokines, and adjuvants such as cholera toxin, alum, Freund's adjuvant, etc. A large number of adjuvant polymers are known; a useful compendium of many such polymers is prepared by the National Institutes of Health and can be found on the internet (www.niaid.nih.gov/daids/vaccine/pdf/compendium.pdf, incorporated herein by reference; see also Allison *Dev. Biol. Stand.* 92:3-11, 1998; Unkeless et al. *Annu. Rev. Immunol.* 6:251-281, 1998; and Phillips et al. *Vaccine* 10:151-158, 1992; each of which is incorporated herein by reference).

The antigenic protein or peptides encoded by the polynucleotide may be derived from such bacterial organisms as *Streptococccus pneumoniae, Haemophilus influenzae, Staphylococcus aureus, Streptococcus pyrogenes, Corynebacterium diphtheriae, Listeria monocytogenes, Bacillus anthracis, Clostridium tetani, Clostridium botulinum, Clostridium perfringens, Neisseria meningitidis, Neisseria gonorrhoeae, Streptococcus mutans, Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptospirosis interrogans, Borrelia burgdorferi, Camphylobacter jejuni*, and the like; from such viruses as smallpox, influenza A and B, respiratory syncytial virus, parainfluenza, measles, HIV, varicella-zoster, herpes simplex 1 and 2, cytomegalovirus, Epstein-Barr virus, rotavirus, rhinovirus, adenovirus, papillomavirus, poliovirus, mumps, rabies, *rubella*, coxsackieviruses, equine encephalitis, Japanese encephalitis, yellow fever, Rift Valley fever, hepatitis A, B, C, D, and E virus, and the like; and from such fungal, protozoan, and parasitic organisms such as *Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis, Schistosoma mansoni*, and the like.

Compositions

The present invention contemplates an inventive polymer of Formula (I), (II), (III), or (IV) as a component of a composition. Compositions, as described herein, comprising a polymer of Formula (I), (II), (III), or (IV) and an excipient of some sort may be useful in a variety of medical and non-medical applications. For example, pharmaceutical compositions comprising a polymer of Formula (I), (II), (III), or (IV) and an excipient may be useful in the delivery of an effective amount of an agent to a subject in need thereof. Nutraceutical compositions comprising a polymer of Formula (I), (II), (III), or (IV) and an excipient may be useful in the delivery of an effective amount of a nutraceutical, e.g., a dietary supplement, to a subject in need thereof. Cosmetic compositions comprising a polymer of Formula (I), (II), (III), or (IV) and an excipient may be formulated as a cream, ointment, balm, paste, film, or liquid, etc., and may be useful in the application of make-up, hair products, and materials useful for personal hygiene, etc. Compositions comprising a polymer of Formula (I), (II), (III), or (IV) and an excipient may be useful for non-medical applications, e.g., such as an emulsion or emulsifier, useful, for example, as a food component, for extinguishing fires, for disinfecting surfaces, for oil cleanup, etc.

The composition may comprise one type of a polymer of Formula (I), (II), (III), or (IV) but may also comprise any number of different types of polymers of Formula (I), (II), (III), or (IV), e.g., 1, 2, 3, 4, 5, 6, 7, 8, 9, 10 or more different types of polymers.

In certain embodiments, the composition further comprises an agent, as described herein. For example, in certain embodiments, the agent is a small molecule, organometallic compound, nucleic acid, protein, peptide, polynucleotide, metal, targeting agent, an isotopically labeled chemical compound, drug, vaccine, immunological agent, or an agent useful in bioprocessing. In certain embodiments, the agent is a polynucleotide. In certain embodiments, the polynucleotide is DNA or RNA. In certain embodiments, the RNA is RNAi, dsRNA, siRNA, shRNA, miRNA, or antisense RNA. In certain embodiments, the polynucleotide and the one or more APPLs are not covalently attached.

In certain embodiments, the one or more polymers of Formula (I), (II), (III), or (IV) are in the form of a particle. In certain embodiments, the particle is a nanoparticle or microparticle. In certain embodiments, the one or more polymers of Formula (I), (II), (III), or (IV) are in the form of liposomes or micelles. It is understood that, in certain embodiments, these polymers of Formula (I), (II), (III), or (IV) may self-assemble to provide a particle, micelle, or liposome. In certain embodiments, the particle, micelle, or liposome encapsulates an agent. The agent to be delivered by the particle, micelle, or liposome may be in the form of a gas, liquid, or solid. The polymer of Formula (I), (II), (III), or (IV) may be combined with other polymers (synthetic or natural), surfactants, cholesterol, carbohydrates, proteins, lipids etc. to form the particles. Once the complexes, micelles, liposomes, or particles have been prepared, they may be combined with one or more pharmaceutical excipients to form a pharmaceutical composition that is suitable to administer to animals including humans. As would be appreciated by one of skill in this art, the excipients may be chosen based on the route of administration as described below, the agent being delivered, time course of delivery of the agent, etc.

As used herein, the term "excipient" means a non-toxic, inert solid, semi-solid or liquid filler, diluent, encapsulating material or formulation auxiliary of any type. Some examples of materials which can serve as excipients include, but are not limited to, sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. As would be appreciated by one of skill in this art, the excipients may be chosen based on what the composition is useful for. For example, with a pharmaceutical composition or cosmetic composition, the choice of the excipient will depend on the route of administration, the agent being delivered, time course of delivery of the agent, etc., and can be administered to humans and/or to animals, orally, rectally, parenterally, intracisternally, intravaginally, intranasally, intraperitoneally, topically (as by powders, creams, ointments, or drops), bucally, or as an oral or nasal spray.

Liquid dosage forms for oral administration include pharmaceutically acceptable emulsions, microemulsions, solutions, suspensions, syrups, and elixirs. In addition to the active ingredients (i.e., microparticles, nanoparticles, liposomes, micelles, polynucleotide/lipid complexes), the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. In certain embodiments, the particles are suspended in a carrier fluid comprising 1% (w/v) sodium carboxymethyl cellulose and 0.1% (v/v) Tween 80.

The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

Compositions for rectal or vaginal administration are preferably suppositories which can be prepared by mixing the particles with suitable non-irritating excipients or carriers such as cocoa butter, polyethylene glycol, or a suppository wax which are solid at ambient temperature but liquid at body temperature and therefore melt in the rectum or vaginal cavity and release the particles.

Solid dosage forms for oral administration include capsules, tablets, pills, powders, and granules. In such solid dosage forms, the particles are mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium polymers, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like.

Dosage forms for topical or transdermal administration of an inventive pharmaceutical composition include ointments, pastes, creams, lotions, gels, powders, solutions, sprays, inhalants, or patches. The particles are admixed under sterile conditions with a pharmaceutically acceptable carrier and any needed preservatives or buffers as may be required. Ophthalmic formulation, ear drops, and eye drops are also contemplated as being within the scope of this invention.

The ointments, pastes, creams, and gels may contain, in addition to the particles of this invention, excipients such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to the particles of this invention, excipients such as lactose, talc, silicic acid, aluminum hydroxide, calcium silicates, and polyamide powder, or mixtures of these substances. Sprays can additionally contain customary propellants such as chlorofluorohydrocarbons.

Transdermal patches have the added advantage of providing controlled delivery of a polymer to the body. Such dosage forms can be made by dissolving or dispensing the microparticles or nanoparticles in a proper medium. Absorption enhancers can also be used to increase the flux of the polymer across the skin. The rate can be controlled by either providing a rate controlling membrane or by dispersing the particles in a polymer matrix or gel.

Methods of Use and Treatment

In another aspect, provided are methods of using a polymer of Formula (I), (II), (III), or (IV), or pharmaceutically acceptable salt or isomer thereof, e.g., for the treatment of a disease, disorder or condition from which a subject suffers. It is contemplated that a polymer of Formula (I), (II), (III), or (IV) will be useful in the treatment of a variety of diseases, disorders, or conditions, especially a system for delivering agents useful in the treatment of that particular disease, disorder, or condition. An exemplary disease, disorder, or condition contemplated includes, but is not limited to, a proliferative disorder, e.g., cancer.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or other non-human animals, for example mammals [e.g., primates (e.g., cynomolgus monkeys, rhesus monkeys); and commercially relevant mammals such as mice, rats, hampsters, cattle, pigs, horses, sheep, goats, cats, and/or dogs] and birds (e.g., commercially relevant birds such as chickens, ducks, geese, and/or turkeys). In certain embodiments, the subject is a non-human animal. The non-human animal may be a male or female and at any stage of development. A non-human animal may be a transgenic animal.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

As used herein, an "active ingredient" is any agent which elicits the desired biological response. Agents as described herein may also be classified as an active ingredient.

In general, the "effective amount" of an active ingredient refers to an amount sufficient to elicit the desired biological response. As will be appreciated by those of ordinary skill in this art, the effective amount of a compound of the invention may vary depending on such factors as the desired biological endpoint, the pharmacokinetics of the active ingredient, the disease being treated, the mode of administration, and the age, health, and condition of the subject. An effective amount encompasses therapeutic and prophylactic treatment.

As used herein, and unless otherwise specified, a "therapeutically effective amount" of an active ingredient is an amount sufficient to provide a therapeutic benefit in the treatment of a disease, disorder or condition, or to delay or minimize one or more symptoms associated with the disease, disorder or condition. A therapeutically effective amount of an active ingredient means an amount of the active ingredient, alone or in combination with other agents or therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, a "prophylactically effective amount" of an active ingredient is an amount sufficient to prevent a disease, disorder or condition, or one or more symptoms associated with the disease, disorder or condition, or prevent its recurrence. A prophylactically effective amount of an active ingredient means an amount of the active ingredient, alone or in combination with other agents or therapies, which provides a prophylactic benefit in the prevention of the disease, disorder or condition. The term "prophylactically effective amount" can encompass an amount that improves overall prophylaxis or enhances the prophylactic efficacy of another prophylactic agent.

The active ingredient may be administered in such amounts, time, and route deemed necessary in order to achieve the desired result. The exact amount of the active ingredient will vary from subject to subject, depending on the species, age, and general condition of the subject, the severity of the infection, the particular active ingredient, its mode of administration, its mode of activity, and the like. The active ingredient is preferably formulated in dosage unit form for ease of administration and uniformity of dosage. It will be understood, however, that the total daily usage of the active ingredient will be decided by the attending physician within the scope of sound medical judgment. The specific therapeutically effective dose level for any particular subject will depend upon a variety of factors including the disorder being treated and the severity of the disorder; the activity of the active ingredient employed; the specific composition employed; the age, body weight, general health, sex and diet of the patient; the time of administration, route of administration, and rate of excretion of the specific active ingredient employed; the duration of the treatment; drugs used in combination or coincidental with the specific active ingredient employed; and like factors well known in the medical arts.

The active ingredient may be administered by any route. In some embodiments, the active ingredient is administered via a variety of routes, including oral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, enteral, sublingual; by intratracheal instillation, bronchial instillation, and/or inhalation; and/or as an oral spray, nasal spray, and/or aerosol. In general the most appropriate route of administration will depend upon a variety of factors including the nature of the active ingredient (e.g., its stability in the environment of the gastrointestinal tract), the condition of the subject (e.g., whether the subject is able to tolerate oral administration), etc.

The exact amount of an active ingredient required to achieve a therapeutically or prophylactically effective amount will vary from subject to subject, depending on species, age, and general condition of a subject, severity of the side effects or disorder, identity of the particular compound(s), mode of administration, and the like. The amount to be administered to, for example, a child or an adolescent can be determined by a medical practitioner or person skilled in the art and can be lower or the same as that administered to an adult.

In one specific embodiment, provided is a method of treating cancer comprising administering to a subject in need thereof an effective amount of a composition comprising an a polymer of Formula (I), (II), (III), or (IV), or a pharmaceutically acceptable salt or isomer thereof, and an anti-cancer agent. In certain embodiments, the polymer of Formula (I), (II), (III), or (IV), or a pharmaceutically acceptable salt or isomer thereof encapsulates the anti-cancer agent. In certain embodiments, the polymer of Formula (I), (II), (III), or (IV), or a pharmaceutically acceptable salt or isomer thereof and the anti-cancer agent form a particle (e.g., a nanoparticle, a microparticle, a micelle, a liposome, a lipoplex).

Exemplary cancers include, but are not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarinoma), Ewing sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenstrom's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma (MM)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), Islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer and vulvar cancer (e.g., Paget's disease of the vulva).

Anti-cancer agents encompass biotherapeutic anti-cancer agents as well as chemotherapeutic agents.

Exemplary biotherapeutic anti-cancer agents include, but are not limited to, interferons, cytokines (e.g., tumor necrosis factor, interferon α, interferon γ), vaccines, hematopoietic growth factors, monoclonal serotherapy, immunostimulants and/or immunodulatory agents (e.g., IL-1, 2, 4, 6, or 12), immune cell growth factors (e.g., GM-CSF) and antibodies (e.g. HERCEPTIN (trastuzumab), T-DM1, AVASTIN (bevacizumab), ERBITUX (cetuximab), VECTIBIX (panitumumab), RITUXAN (rituximab), BEXXAR (tositumomab)).

Exemplary chemotherapeutic agents include, but are not limited to, anti-estrogens (e.g. tamoxifen, raloxifene, and megestrol), LHRH agonists (e.g. goscrclin and leuprolide), anti-androgens (e.g. flutamide and bicalutamide), photodynamic therapies (e.g. vertoporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), vinca alkaloids (e.g. vincristine, vinblastine, vindesine, and vinorelbine), taxoids (e.g. paclitaxel or a paclitaxel equivalent such as nanoparticle albumin-bound paclitaxel (ABRAXANE), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), antimetabolites, DHFR inhibitors (e.g. methotrexate, dichloromethotrexate, trimetrexate, edatrexate), IMP dehydrogenase inhibitors (e.g. mycophenolic acid, tiazofurin, ribavirin, and EICAR), ribonuclotide reductase inhibitors (e.g. hydroxyurea and deferoxamine), uracil analogs (e.g. 5-fluorouracil (5-FU), floxuridine, doxifluridine, ratitrexed, tegafur-uracil, capecitabine), cytosine analogs (e.g. cytarabine (ara C), cytosine arabinoside, and fludarabine), purine analogs (e.g. mercaptopurine and Thioguanine), Vitamin D3 analogs (e.g. EB 1089, CB 1093, and KH 1060), isoprenylation inhibitors (e.g. lovastatin), dopaminergic neurotoxins (e.g. 1-methyl-4-phenylpyridinium ion), cell cycle inhibitors (e.g. staurosporine), actinomycin (e.g. actinomycin D, dactinomycin), bleomycin (e.g. bleomycin A2, bleomycin B2, peplomycin), anthracycline (e.g. daunorubicin, doxorubicin, pegylated liposomal doxorubicin, idarubicin, epirubicin, pirarubicin, zorubicin, mitoxantrone), MDR inhibitors (e.g. verapamil), $Ca^{2+}$ ATPase inhibitors (e.g. thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEV®), gefitinib (IRESS®), imatinib (Gleevec®, CGP57148B, STI-571), lapatinib (TYKERB®, TYVERB®), lestaurtinib (CEP-701), neratinib (HKI-272), nilotinib (TASIGN®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTI®), bevacizumab (AVASTI®), rituximab (RITUXA®), cetuximab (ERBITUX®), panitumumab (VECTIBIX®), ranibizumab (Lucentis®), nilotinib (TASIGN®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine.

EXAMPLES

In order that the invention described herein may be more fully understood, the following examples are set forth. It should be understood that these examples are for illustrative purposes only and are not to be construed as limiting this invention in any manner.

Example 1

General Method.Synthesis and Characterization of α-aminoamidine Polymers

These α-aminoamidine polymers can be synthesized by combining amines, aldehydes, and isocyanides in a glass vial equipped with a stirbar and heated to 90° C. The amines chosen contain between two and five amine functionalities, while the aldehydes and isocyanides are racemic, of varying chain lengths, and feature unique functional groups and varying degrees of saturation. The reaction times vary from 24-72 hours at this temperature. Mixtures generally remain clear throughout the reaction and become noticeably viscous as the reaction progresses. Upon cooling, many become waxy solids. The extent of the reaction can be controlled by the number of equivalents of aldehydes and/or isocyanides added to the reaction mixture. For example, the amine of the formula

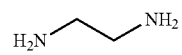

has a maximum of four points for substitution. Addition of four equivalents of aldehyde and/or isocyanide would yield an amine core with five chains linked to the α-aminoamidine backbone. Addition of three equivalents of aldehyde and/or isocyanide would yield only three chains linked to the same backbone. This can be verified by thin layer chromatography (TLC), when TLC analysis shows primarily one product existing in the crude reaction mixtures set up as described. PP1 to PP12 were synthesized following this General method.

General method for the synthesis of polymers of Formula (II): Amino alcohols or hydroxy aldehydes were reacted with corresponding diisopropylsiane chloride, phosphorus tribromide, or bis-acid chloride reagents. To a solution of aldehyde dissolved in methanol, 1 equiv. of amine followed by 1 equiv. of isocyanide was added. Finally, 0.5 equiv. of catalyst was added as a solution in methanol. The final concentration of aldehyde in this solution was always between 0.3-0.5 M. Reactions were incubated at room temperature with the reaction time dependent on the degree of polymerization desired. Polymers were purified by dialysis through a 10000 Da MWCO regenerated cellulose membrane using either methanol or a sodium acetate buffer pH 5.0.

To verify the identity of the polymers, test reactions are set up and purified by silica gel chromatography. The components of the crude reaction mixtures are separated and tested by NMR and mass spectrometry. In the case of the amine of the formula

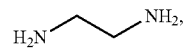

for example, three major products might be identified with two, three, and four tails. The molecular weight of each can be confirmed by mass spectrometry, and the structure can be verified by NMR. These isolated polymers are then used as standards versus selected members of the library for TLC analysis. Reactions set up to fully substitute the amine will have similar $R_f$ and staining profiles to the fully substituted standard. Reactions set up to occupy n-1 positions of the amine will have similar $R_f$ and staining profiles to n-1 standard.

| ID | Reagents used |
| --- | --- |
| PP1 | 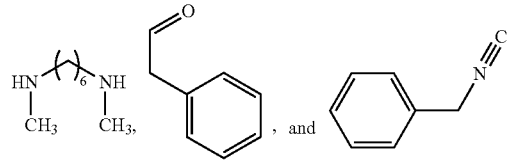 |
| PP2 | 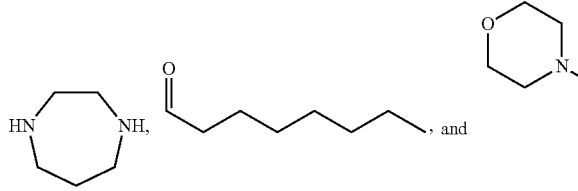 |
| PP3 | 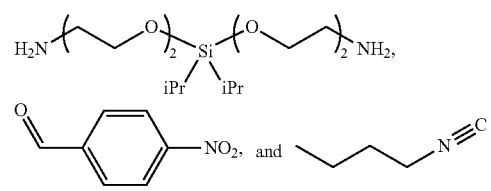 |
| PP4 | 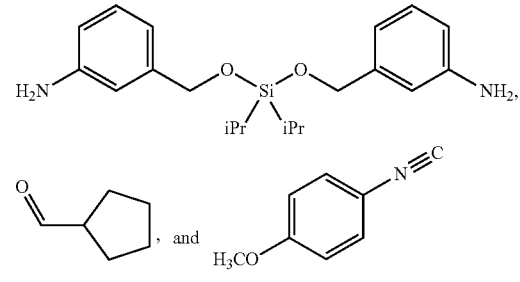 |
| PP5 | 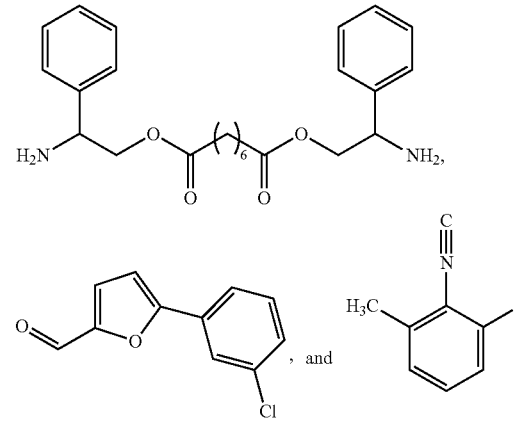 |
| PP6 | 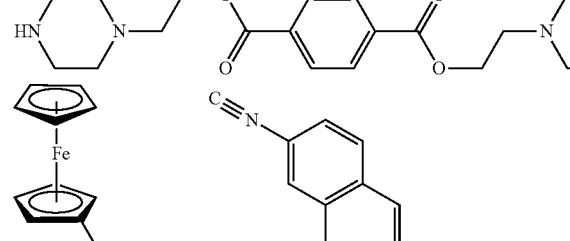 |

| ID | Reagents used |
|---|---|
| PP7 | 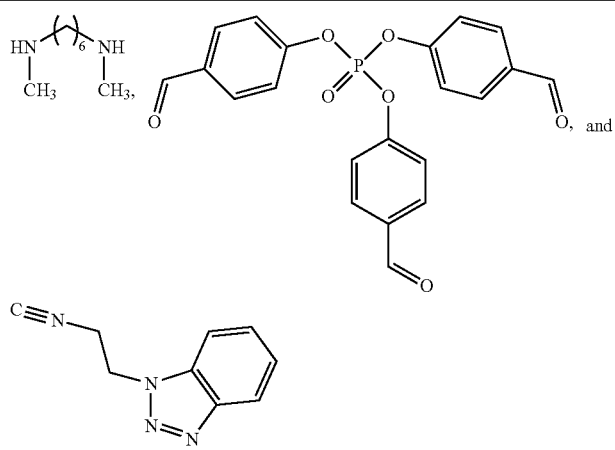 |
| PP8 | 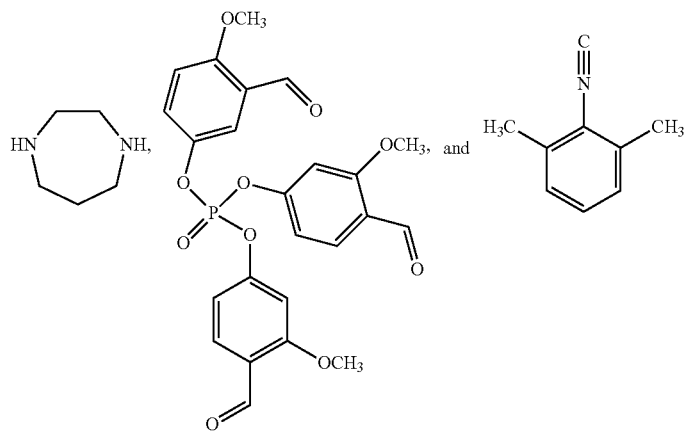 |
| PP9 | 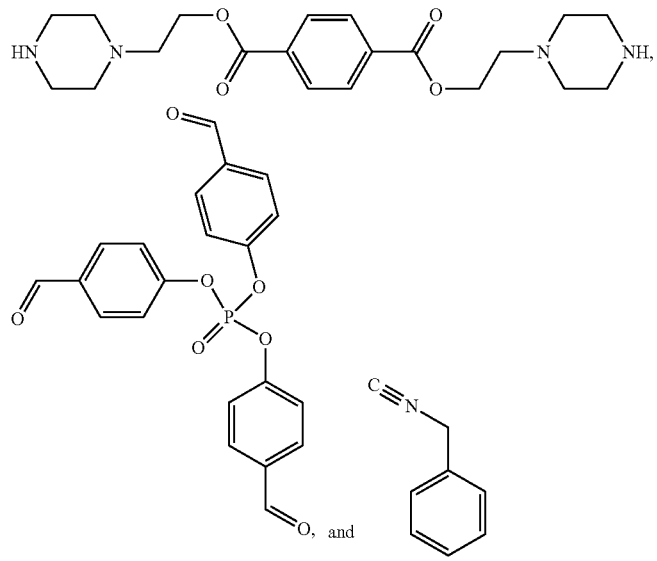 |
| PP10 | 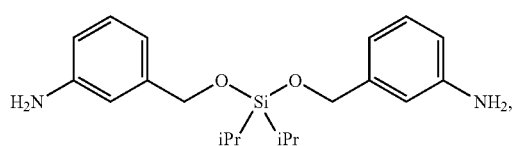 |

| ID | Reagents used |
|---|---|
| PP11 | [chemical structures: tris(4-formyl-3-methoxyphenyl) phosphate, and 4-methoxyphenyl isocyanide] |
| PP12 | [chemical structures: N,N'-dimethyl-1,6-hexanediamine, octanal, and benzyl isocyanide] |
| | [chemical structures: bis-silyl ether diamine with iPr groups, 4-nitrobenzaldehyde, and 2-morpholinoethyl isocyanide] |

Example 2

In vitro screening for RNA delivery

α-Aminoamidine polymers can be tested for their ability to deliver siRNA to a HeLa cell line that stably expresses both firefly and *Renilla* luciferase. Efficacy is determined by complexing the α-aminoamidine with siRNA specific for firefly luciferase, adding this mixture to cells and measuring the subsequent ratio of firefly to *Renilla* expression. This procedure is performed in 96-well microtiter plates to enable high throughput testing of the materials. In this assay, reduction of both firefly and *Renilla* expression indicates toxicity, while reduction of only firefly expression is an indication of specific knockdown due to siRNA. Members of a sampling of α-aminoamidine polymers are screened for the ability to transfect cells and give rise to some knockdown of firefly luciferase.

Example 3

RNA Encapsulation Efficiency

Formulation for in vitro experiments can be achieved from a simple mixing of RNA with α-aminoamidine polymers at a set ratio in buffer prior to addition to cells. In vivo formulation may require the addition of extra ingredients to facilitate circulation throughout the body. To test the ability of these α-aminoamidine polymers to form particles suitable for in vivo work, we follow a standard formulation procedure utilized in the lab. These particles may consist of various ratios of α-aminoamidine, cholesterol and PEG, such as 42% α-aminoamidine, 48% cholesterol and 10% PEG. After formation of the particle, RNA is added and allowed to integrate with the complex. The encapsulation efficiency is determined using a standard Ribogreen assay. These particles can be on the order of 100 nm after extrusion, with some achieving encapsulation efficiency of over 90%.

Example 4

HepG2 cells can be seeded, for example, at a density of 15,000 cells per well into opaque white 96-well plates (Corning-Costar, Kennebunk, Me.) 24 hours prior to transfection to allow for growth and confluence. Working dilutions of α-aminoamidines are made in 25 mM sodium acetate (pH 5) at a concentration of 0.5 mg/ml. For gene delivery experiments pCMV-Luc firefly luciferase DNA (ElimBiopharmaceuticals, South San Francisco, Calif.) is used. The α-aminoamidine:DNA complexes are formed by electrostatic interaction between positively charged α-aminoamidine molecules and negatively charged nucleic acids. By varying the volume of α-aminoamidine solution added to a constant amount of DNA, varying weight:weight ratios of α-aminoamidine to DNA are tested. α-Aminoamidine solution (75 μl) is added to DNA solution (75 μl) and mixed well. Mixtures are then incubated at room temperature for 20 minutes to allow for complexation. These complexes (30 μl) are then added to serum containing medium (200 μl) and mixed well. Growth medium is then removed from the cells and α-aminoamidine:DNA complex containing medium is immediately added. Total DNA loading is 300 ug DNA per well. Lipofectamine 2000 transfection is performed as described by the vendor. Complexes are allowed to incubate with cells for 48 hours. Luciferase expression is then quantified by Bright-Glo assay (Promega, Madison, Wis.). Briefly, 48 hours post-transfection, the α-aminoamidine:DNA complex containing growth medium is removed from cells using a 12-channel aspirating wand. 200 ul of a 1:1 mixture of Bright-Glo reagent and non-phenol red containing DMEM is added to each well of the 96-well plate with cells. After 10 minute incubation at room temperature, luminescence is measured using a luminometer.

Example 5

α-Aminoamidine siRNA formulations may comprise, for example, α-aminoamidine, cholesterol, polyethylene glycol-lipid (PEG-lipid) and siRNA. Stock solutions of α-aminoamidine, mPEG2000-DMG MW 2660 (synthesized by Alnylam), and cholesterol MW 387 (Sigma-Aldrich) can be prepared in ethanol and mixed to yield a molar ratio, for example, of 42:10:48. Mixed α-aminoamidine are added to 200 mM sodium acetate buffer pH 5.2 to yield a solution containing 35% ethanol, resulting in spontaneous formation of empty α-aminoamidine nanoparticles. Resulting nanoparticles are extruded through an 80 nm membrane (three passes). siRNA in 35% ethanol and 50 mM sodium acetate pH 5.2 is added to the nanoparticles at 10:1 (wt/wt) total α-aminoamidine: siRNA and incubated at 37° C. for 30 min. Ethanol removal and buffer exchange of siRNA-containing α-aminoamidine nanoparticles is achieved by dialysis against PBS using a 3,500 MWCO membrane. Particle size is determined using a Malvern Zetasizer NanoZS (Malvern). siRNA content and entrapment efficiency is determined by Ribogreen assay.

C57BL/6 mice (Charles River Labs) can receive either saline or siRNA in α-aminoamidine formulations via tail vein injection at a volume, for example, of 0.01 ml/g. Mice can be dosed at either 1.75 or 4 mg/kg entrapped siRNA. At 48 hours after administration, animals are anesthetized by isofluorane inhalation and blood is collected into serum separator tubes by retroorbital bleed. Serum levels of Factor VII protein are determined in samples using a chromogenic assay (Biophen FVII, Aniara Corporation) according to the manufacturer's protocols. A standard curve is generated using serum collected from saline-treated animals.

Example 6

In Vitro Screening of an α-aminoamidine Library
Polymers of an α-aminoamidine library can be synthesized according to the procedures described herein. The polymers are then screened for siRNA delivery efficacy to a cancer cell line, using a Hela-derived cell line genetically engineered to express luciferase reporter proteins. In these experiments, the ability of each material to facilitate sequence-specific gene silencing is evaluated by comparison of protein levels in treated groups to untreated controls. For each polymer, delivery experiments are performed using varying weight ratios of α-aminoamidine:siRNA.

Example 7

In Vivo Screening of Top Performing α-aminoamidines
To test siRNA delivery efficacy in vivo, a mouse model for liver delivery can be used. Factor VII, a hepatocyte-specific blood clotting factor, serves as a model protein for knockdown studies. Once produced by hepatocytes, Factor VII is released into the bloodstream, and a baseline level of expression can be determined by simple blood draw and quantification of protein levels by colorimetric assay. By delivering anti-Factor VII siRNA to hepatocytes, knockdown of this model protein can be achieved and a percentage of silencing can be determined by comparison to an untreated control.

Following the in vitro screen, polymers can be purified as detailed in Part 1. For in vivo testing, the polymers can be formulated with cholesterol and a PEG-lipid for serum stability and siRNA packaging. In these experiments, α-aminoamidines can be formulated, for example, at a 42:48:10 molar ratio of α-aminoamidine:cholesterol:PEG. The weight ratio of total lipids (α-aminoamidine+cholesterol+PEG) to siRNA can be, for example, 10:1. After each formulation, the particles are characterized for size and siRNA entrapment efficiency using dynamic light scattering and Ribogreen assay, respectively. The total dose of siRNA administered in the initial screen can vary from group to group due to the differences in entrapment efficiency of the α-aminoamidine particles. In all experiments, the dose of siRNA administered to each mouse is consistent according to body weight.

Example 8

Following the initial in vivo screening experiments, α-aminoamidine polymers can be used to conduct a dose response. In these experiments and all subsequent experiments, the siRNA dose is based on total siRNA content in the formulation, not entrapped siRNA. In addition to Factor VII measurement, the change in mouse body weight is recorded and a loss in weight is generally considered formulation induced toxicity.

Example 9

After completing the dose response, an α-aminoamidine polymer can be chosen for further investigation and optimization. In these experiments, the percent composition of the formulations can be varied to observe the effect of composition on particle size, entrapment, and efficacy.

Example 10

A second dose response can be conducted with the new percent composition parameters. The knockdown results and particle formulation/characteristics can be established. Using these results as the new benchmark, the library can be revisited and previously untested materials can be screened at 0.25 mg/kg in attempt to find other polymers which can give similar or better results.

Example 11

To further improve delivery efficacy, the percent composition of formulations can be modified incrementally. These formulations can be screened at a dose of 0.01 mg/kg to identify formulations which may perform better than the previous compositions. More efficacious delivery can be achieved by tuning the composition of the formulation.

Example 12

In vivo transfection with chiral α-aminoamidines

In vivo transfections using anti-Factor VII siRNA can be formulated with chiral α-aminoamidines in mice. At 0.01 mg/kg siRNA dosing, for example, reduction of systemic Factor VII can be assessed using either the R or S forms of the chiral α-aminoamidines.

Example 13

Formulations

Nanoparticles with α-aminoamidine polymers are prepared by nanoprecipitation. Briefly, α-aminoamidine polymer, pluronic F127 (or C14-PEG), DC cholesterol (or cholesterol), and any other formulation components that are soluble in organic solvents are dissolved and diluted in a water-miscible organic solvent (such as methanol, ethanol, dimethylsulfoxide, dimethylformamide, etc.). This organic mixture is then added to a vigorously stirred solution of nucleic acid in buffer or salt solution (such as PBS, saline, etc.). Nanoparticles form near instantaneously using this approach, and are subsequently characterized by dynamic light scattering for size and a riborgreen assay (Life Technologies) to determine percentage of nucleic acid that is entrapped in the particles. Tables 1-6 are examples of actual nanoparticle formulations made in this manner with size and entrapment characterization data.

TABLE 1

| | Formulation | | |
|---|---|---|---|
| | VNP001 | VNP002 | VNP003 |
| Polymer | 104182-H1 | 104182-H1 | 104182-H2 |
| Polymer/siRNA | 30:1 | 30:1 | 30:1 |
| Polymer:F-127*:DC-Chol wt. ratio | 1:1:1 | 1:1:1 | 1:1:1 |
| Buffer | 0.9% NaCl (by weight) | 1X PBS | 0.9% NaCl (by weight) |
| PDI | 0.564 | 0.371 | 0.331 |
| Peak 1 (nm) | 21.65 | 939.2 | 33.07 |
| Peak 1 (%) | 98.8 | 95.1 | 96.22 |
| Entrapment (%) | 96 | 95 | 94 |

*C14-PEG may be used instead of F-127

TABLE 2

| | Formulation | | |
|---|---|---|---|
| | VNP004 | VNP005 | VNP006 |
| Polymer | 104182-H3 | 104182-H5 | 104182-C2 |
| Polymer/siRNA | 30:1 | 30:1 | 30:1 |

TABLE 2-continued

| | Formulation | | |
|---|---|---|---|
| | VNP004 | VNP005 | VNP006 |
| Polymer:F-127*:DC-Chol wt. ratio | 1:1:1 | 1:1:1 | 1:1:1 |
| Buffer | 0.9% NaCl (by weight) | 0.9% NaCl (by weight) | 0.9% NaCl (by weight) |
| PDI | 0.152 | 0.366 | 0.372 |
| Peak 1 (nm) | 105 | 84.43 | 24.72 |
| Peak 1 (%) | 99.1 | 64.64 | 98.17 |
| Entrapment (%) | 96 | 98 | 96 |

*C14-PEG may be used instead of F-127

TABLE 3

| | Formulation | | | |
|---|---|---|---|---|
| | VNP007 | VNP008 | VNP009 | VNP010 |
| Polymer | 104330-B2 | 104182-H2 | 104182-H3 | 104182-H5 |
| Polymer/siRNA | 30:1 | 30:1 | 30:1 | 30:1 |
| Polymer:F-127*:DC-Chol wt. ratio | 1:1:1 | 1:1:1 | 1:1:1 | 1:1:1 |
| Buffer | 0.9% NaCl (by weight) | 1X PBS | 1X PBS | 1X PBS |
| PDI | 0.353 | 0.223 | 0.258 | 0.313 |
| Peak 1 (nm) | 31.06 | 327.7 | 168 | 88.14 |
| Peak 1 (%) | 97.99 | 91 | 100 | 100 |
| Entrapment (%) | 92 | 94 | 96 | 94 |

*C14-PEG may be used instead of F-127

TABLE 4

| | Formulation # | | |
|---|---|---|---|
| | A074 | A075 | A076 |
| Formulation Ratio | 1:1:1 | 1:1:1 | 1:1:1 |
| siRNA scale (μg) | 360.00 | 180.00 | 90.00 |
| Polymer scale (ug) | 1800 | 1800 | 1800 |
| [final siRNA] mg/mL | 0.2 | 0.1 | 0.05 |
| final volume (μL) | 1800 | 1800 | 1800 |
| Compound 1/siRNA | 5 | 10 | 20 |
| Compound 1 | 104182-H1 | 104182-H1 | 104182-H1 |
| [1] mg/mL | 60 | 60 | 60 |
| Compound 1 μL | 30 | 30 | 30 |
| Compound 2 | F-127 | F-127 | F-127 |
| [2] | 40 | 40 | 40 |
| Compound 2 μL | 45.00 | 45.00 | 45.00 |
| Compound 3 | DC-chol | DC-chol | DC-chol |
| [3] | 40 | 40 | 40 |
| Compound 3 μL | 45.000 | 45.000 | 45.000 |
| Compound 4 | | | |
| [4] | | | |
| Compound 4 μL | | | |
| MeOH (μL) | 330.00 | 330.00 | 330.00 |
| siRNA sequence | FVII | FVII | FVII |
| [siRNA] | 10 | 10 | 10 |
| siRNA μL | 36.0 | 18.0 | 9.0 |
| Buffer | .9% NaCl | .9% NaCl | .9% NaCl |
| Buffer (μL) | 1314 | 1332 | 1341 |
| PDI | 0.659 | 0.616 | 0.603 |
| size (nm) | 683 | 680 | 382 |
| % | 84.4 | 67.3 | 80.6 |
| size (nm) | 34.38 | 146.4 | 29.07 |
| % | 11.1 | 24.3 | 17.2 |
| size (nm) | 4999 | 23.63 | 5437 |
| % | 4.4 | 8.3 | 2.1 |
| entrapment | 52 | 70 | 78 |

TABLE 5

| | Formulation # | | |
|---|---|---|---|
| | A077 | A078 | A079 |
| Formulation Ratio | 1:1:1 | 1:1:1 | 1:1:1 |
| siRNA scale (μg) | 360.00 | 360.00 | 360.00 |
| Polymer scale (ug) | 1800 | 1800 | 1800 |
| [final siRNA] mg/mL | 0.2 | 0.2 | 0.2 |
| final volume (μL) | 1800 | 1800 | 1800 |
| Compound 1/siRNA | 5 | 5 | 5 |
| Compound 1 | 36-C8 | 82-H5 | 80-D12 |
| [1] mg/mL | 40 | 40 | 40 |
| Compound 1 μL | 45 | 45 | 45 |
| Compound 2 | F-127 | F-127 | F-127 |
| [2] | 40 | 40 | 40 |
| Compound 2 μL | 45.00 | 45.00 | 45.00 |
| Compound 3 | DC-chol | DC-chol | DC-chol |
| [3] | 40 | 40 | 40 |
| Compound 3 μL | 45.000 | 45.000 | 45.000 |
| Compound 4 | | | |
| [4] | | | |
| Compound 4 μL | | | |
| MeOH (μL) | 315.00 | 315.00 | 315.00 |
| siRNA sequence | FVII | FVII | FVII |
| [siRNA] | 10 | 10 | 10 |
| siRNA μL | 36.0 | 36.0 | 36.0 |
| Buffer | .9% NaCl | .9% NaCl | .9% NaCl |
| Buffer (μL) | 1314 | 1314 | 1314 |
| PDI | 0.233 | 1 | 0.702 |
| size (nm) | 265.8 | 188 | 986.9 |
| % | 98.1 | 62.7 | 87.4 |
| size (nm) | 4964 | 33.02 | 163.7 |
| % | 1.9 | 37.3 | 5.3 |
| size (nm) | | | 24.09 |
| % | | | 5.2 |
| entrapment | 89 | 30 | 38 |

TABLE 6

| | Formulation # | | |
|---|---|---|---|
| | A080 | A081 | A082 |
| Formulation Ratio | 1:1:1 | 1:1:1 | 1:1:1 |
| siRNA scale (μg) | 360.00 | 360.00 | 360.00 |
| Polymer scale (ug) | 1800 | 1800 | 1800 |
| [final siRNA] mg/mL | 0.2 | 0.2 | 0.2 |
| final volume (μL) | 1800 | 1800 | 1800 |
| Compound 1/siRNA | 5 | 5 | 5 |
| Compound 1 | 36-D3 | 81-C2 | 104336-F2 |
| [1] mg/mL | 40 | 22 | 40 |
| Compound 1 μL | 45 | 81.82 | 45 |
| Compound 2 | F-127 | F-127 | F-127 |
| [2] | 40 | 40 | 40 |
| Compound 2 μL | 45.00 | 45.00 | 45.00 |
| Compound 3 | DC-chol | DC-chol | DC-chol |
| [3] | 40 | 40 | 40 |
| Compound 3 μL | 45.000 | 45.000 | 45.000 |
| Compound 4 | | | |
| [4] | | | |
| Compound 4 μL | | | |
| MeOH (μL) | 315.00 | 278.18 | 315.00 |
| siRNA sequence | FVII | FVII | FVII |
| [siRNA] | 10 | 10 | 10 |
| siRNA μL | 36.0 | 36.0 | 36.0 |
| Buffer | .9% NaCl | .9% NaCl | .9% NaCl |
| Buffer (μL) | 1314 | 1314 | 1314 |
| PDI | 0.295 | 0.087 | 0.956 |
| size (nm) | 177.7 | 2780 | 504.8 |
| % | 96.6 | 100 | 100 |
| size (nm) | 5137 | | |
| % | 2.5 | | |
| size (nm) | 25.3 | | |
| % | 0.8 | | |
| entrapment | 101 | 77 | 89 |

OTHER EMBODIMENTS

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A polymer of Formula (I):

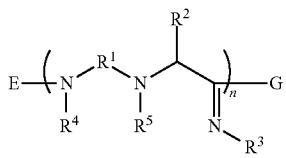

(I)

or a pharmaceutically acceptable salt or isomer thereof;
wherein:
- $R^1$ is a linking group comprising one or more combinations of substituted or unsubstituted, branched or unbranched, cyclic or acyclic $C_{1-20}$ aliphatic; substituted or unsubstituted, branched or unbranched, cyclic or acyclic $C_{1-20}$ heteroaliphatic; substituted or unsubstituted aryl; or substituted or unsubstituted heteroaryl; optionally interrupted by one or more groups independently selected from —O—, —S—, —OSi($R^7R^8$)O—, —Si$R^7R^8$—, and —N$R^{10}$—;
- $R^2$ is hydrogen; substituted or unsubstituted, branched or unbranched, cyclic or acyclic $C_{1-20}$ aliphatic; substituted or unsubstituted, branched or unbranched, cyclic or acyclic $C_{1-20}$ heteroaliphatic; substituted or unsubstituted aryl; or substituted or unsubstituted heteroaryl;
- $R^3$ is substituted or unsubstituted, branched or unbranched, cyclic or acyclic $C_{1-20}$ aliphatic; substituted or unsubstituted, branched or unbranched, cyclic or acyclic $C_{1-20}$ heteroaliphatic; substituted or unsubstituted aryl; or substituted or unsubstituted heteroaryl;
- each instance of $R^4$, $R^5$, and $R^{10}$ is, independently, hydrogen; substituted or unsubstituted, branched or unbranched, cyclic or acyclic $C_{1-20}$ aliphatic; substituted or unsubstituted, branched or unbranched, cyclic or acyclic $C_{1-20}$ heteroaliphatic; substituted or unsubstituted aryl; substituted or unsubstituted heteroaryl; acyl; sulfonyl; or a nitrogen protecting group;
- or $R^4$ and $R^1$ optionally form a cyclic structure;
- or $R^5$ and $R^1$ optionally form a cyclic structure;
- each of $R^7$ and $R^8$ is substituted or unsubstituted, branched or unbranched, cyclic or acyclic $C_{1-20}$ aliphatic; substituted or unsubstituted, branched or unbranched, cyclic or acyclic $C_{1-20}$ heteroaliphatic; substituted or unsubstituted aryl; or substituted or unsubstituted heteroaryl;
- each E is independently, hydrogen or a group of formula $R^4$ or $R^5$;
- G is

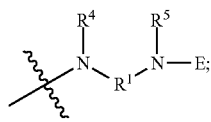

and
- n is an integer from 2 to 100, inclusive.

2. The polymer of claim 1, wherein the polymer is of the formula:

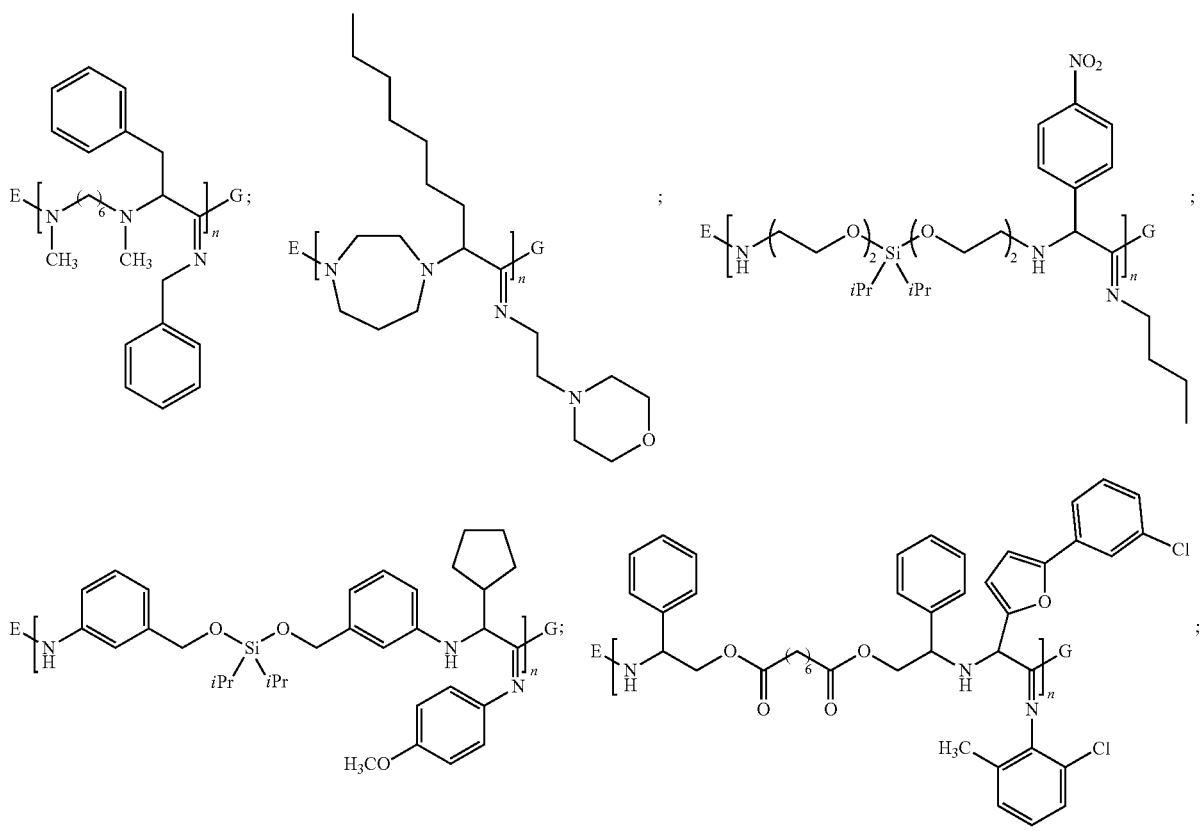

-continued
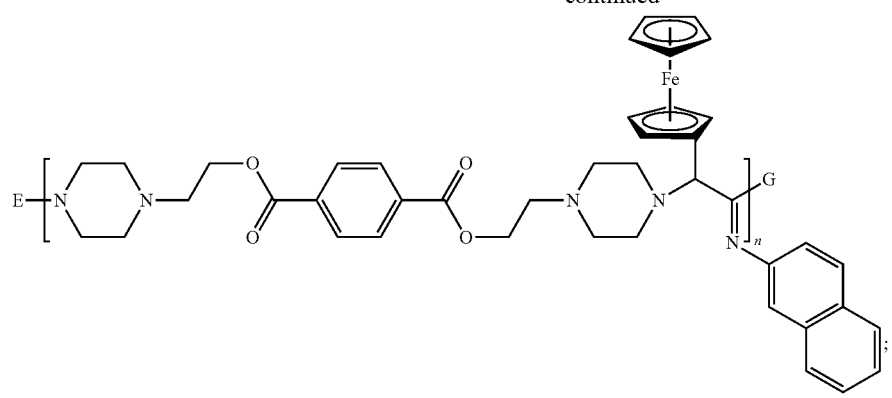
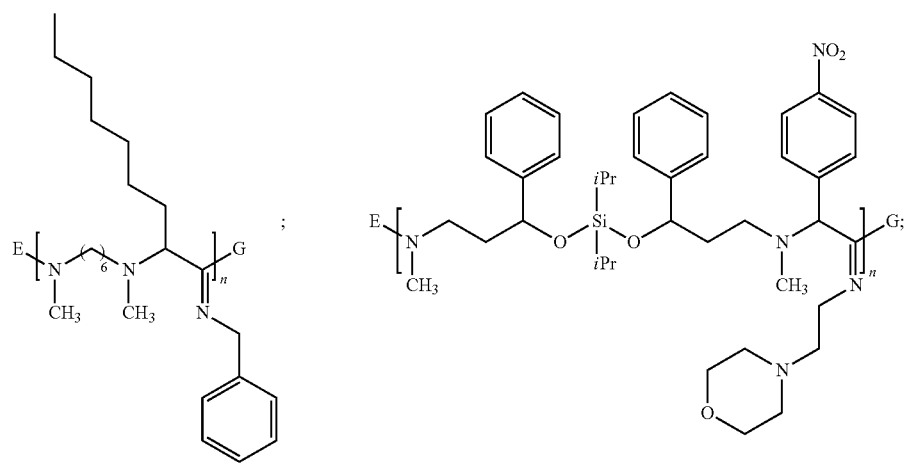
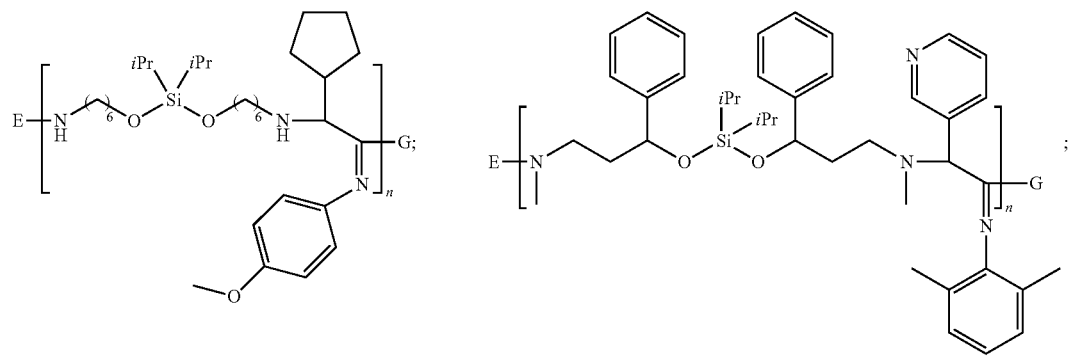
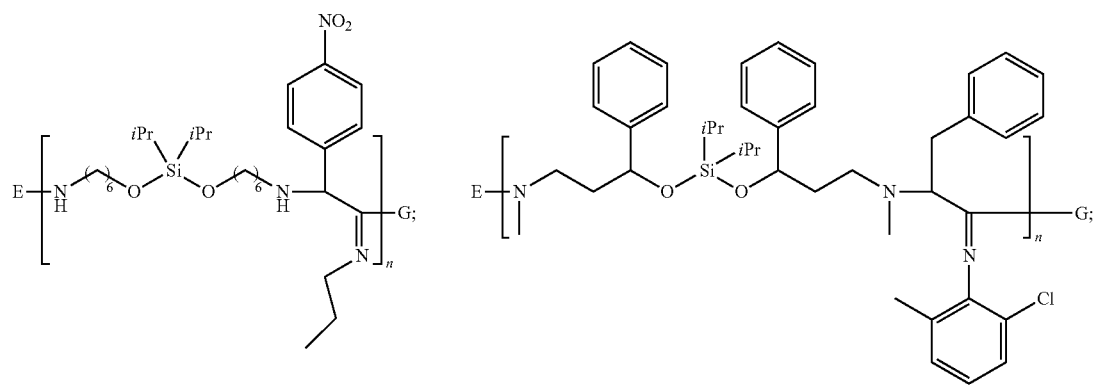

-continued

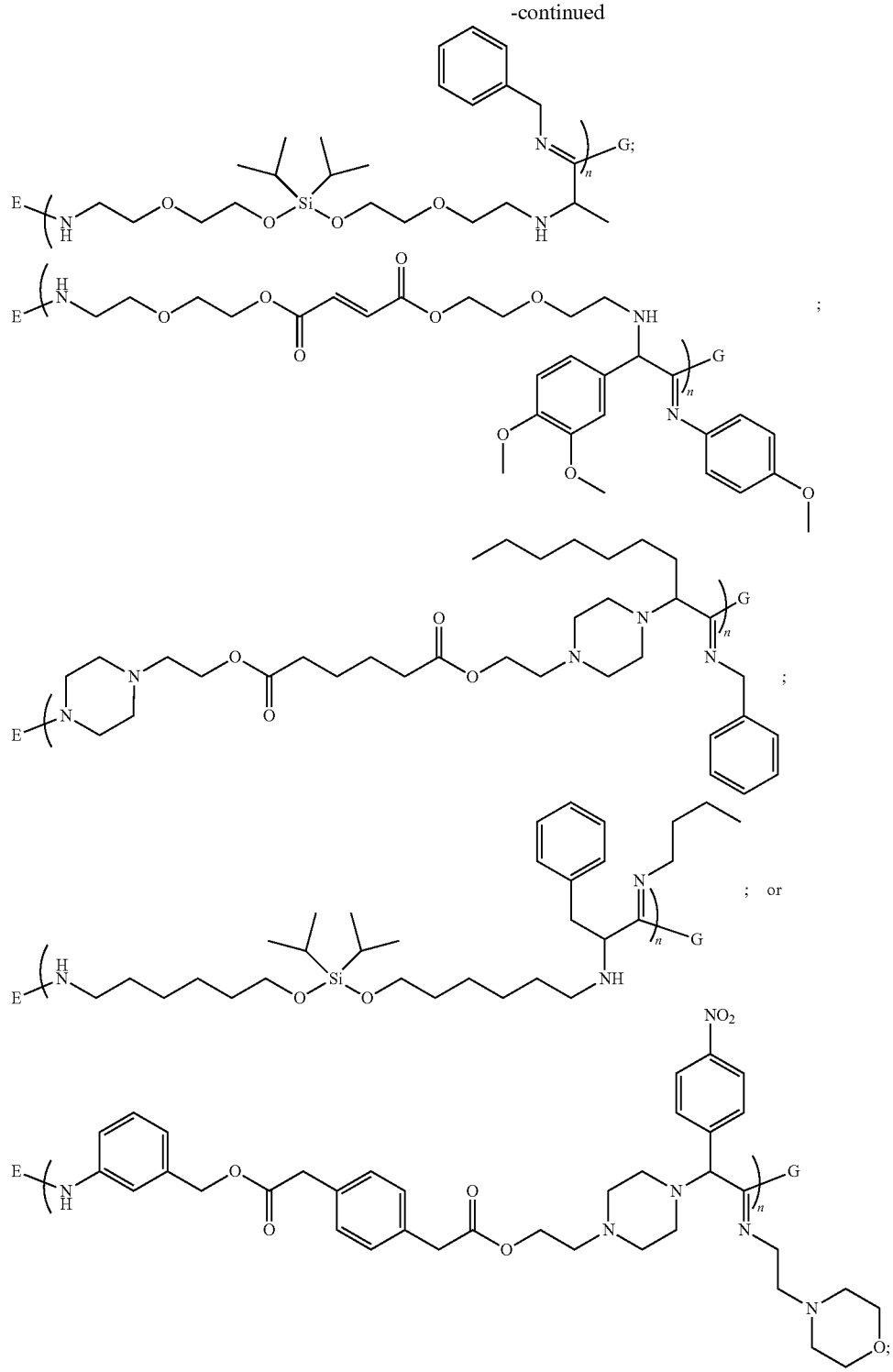

or a pharmaceutically acceptable salt or isomer thereof.

3. A particle comprising a polymer of claim 1, or a pharmaceutically acceptable salt or isomer thereof.

4. The particle of claim 3, wherein the particle further comprises one or more stabilizing agents and/or one or more amino acids.

5. The particle of claim 4, wherein the stabilizing agents are selected from the group consisting of polyethylene glycol (PEG), cholesterol, cholesterol analogs, and poloxamers.

6. The particle of claim 4, wherein the stabilizing agents are selected from the group consisting of 3β-[N-(N',N'-dimethylaminoethane)-carbamoyl]cholesterol hydrochloride (DC-cholesterol), PLURONIC® F127 (poloxamer 407), and 2-dimyristoyl-sn-glycerol methoxypolyethylene glycol (DMG-PEG).

7. The particle of claim 4, wherein the one or more amino acids comprise H (histidine).

8. A composition comprising a polymer of claim 1, or a pharmaceutically acceptable salt or isomer thereof.

9. The composition of claim 8, wherein the composition is a pharmaceutical composition, a cosmetic composition, a nutraceutical composition, or a composition with non-medical application.

10. The composition of claim 8, wherein the composition further comprises an agent.

11. The composition of claim 10, wherein the agent is an organic molecule, inorganic molecule, nucleic acid, protein, peptide, polynucleotide, targeting agent, an isotopically labeled chemical compound, vaccine, or an immunological agent.

12. The composition of claim 10, wherein the agent is a polynucleotide.

13. The composition of claim 9, wherein the composition is in the form of a particle.

14. The composition of claim 13, wherein the particle is a nanoparticle or microparticle.

15. The composition of claim 13, wherein the particle is a micelle, liposome, or lipoplex.

16. The composition of claim 13, wherein the particle encapsulates an agent.

17. A method of delivering a polynucleotide to a cell, comprising:
providing a composition comprising an polymer of claim 1, or a pharmaceutically acceptable salt or isomer thereof, and a polynucleotide; and
exposing the composition to the cell under conditions sufficient to facilitate delivery of the polynucleotide into the interior of the cell.

18. The polymer of claim 1, wherein the polymer is of the formula:

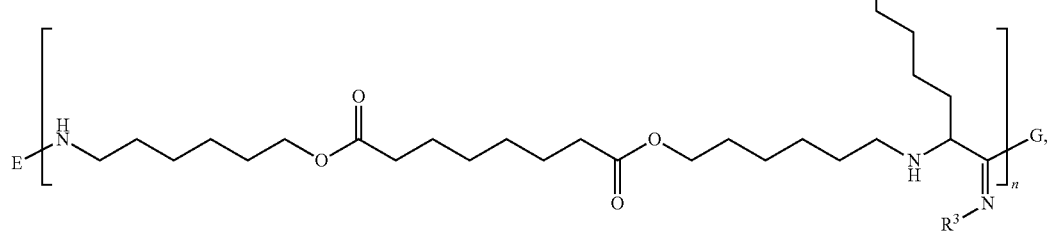

wherein $R^3$ is of the formula:

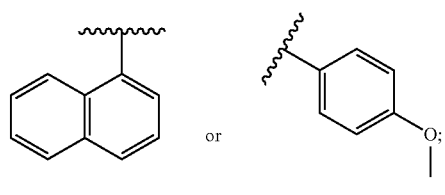

or a pharmaceutically acceptable salt or isomer thereof.

19. The polymer of claim 1, wherein the polymer is of the formula:

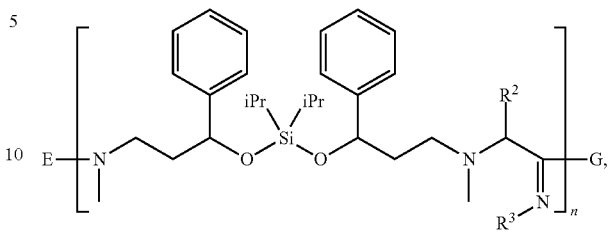

wherein:
$R^2$ is of the formula:

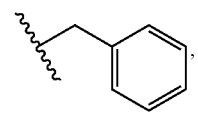 [SMILES: *Cc1ccccc1]

and $R^3$ is of the formula:

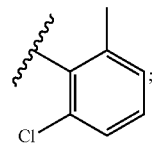 [SMILES: *c1c(C)cccc1Cl]

or $R^2$ is of the formula:

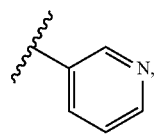

and $R^3$ is of the formula:

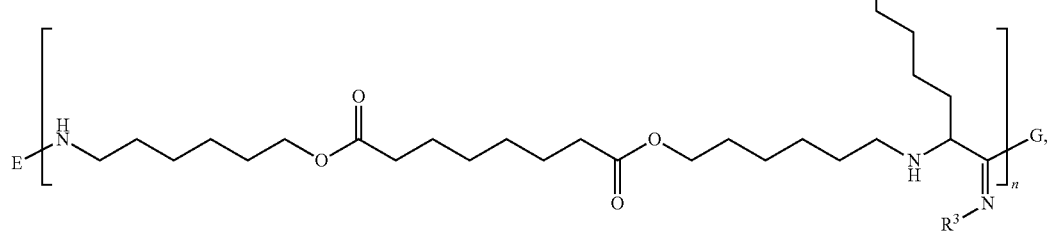

or R² is of the formula:

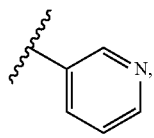

and R³ is of the formula:

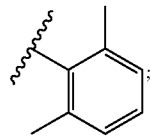 [SMILES: *c1c(C)cccc1C]

or a pharmaceutically acceptable salt or isomer thereof.

20. The polymer of claim 1, wherein the polymer is of the formula:

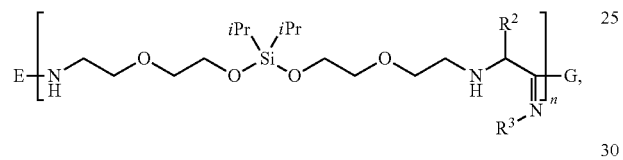

wherein:

R² is of the formula:

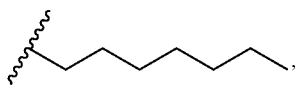 [SMILES: *CCCCCCC]

and R³ is of the formula:

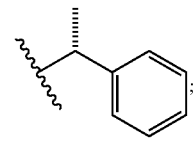 [SMILES: *[C@H](C)c1ccccc1]

or R² is of the formula:

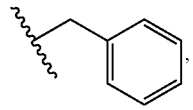

and R³ is of the formula:

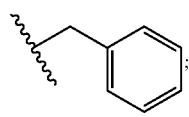 [SMILES: *Cc1ccccc1]

or R² is of the formula:

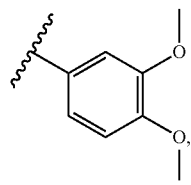 [SMILES: *c1ccc(OC)c(OC)c1]

and R³ is of the formula:

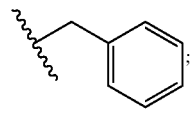 [SMILES: *Cc1ccccc1]

or R² is of the formula:

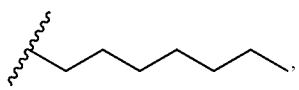 [SMILES: *CCCCCCC]

and R³ is of the formula:

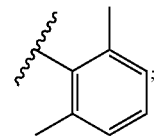 [SMILES: *c1c(C)cccc1C]

or R² is of the formula:

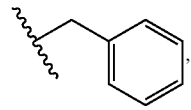 [SMILES: *Cc1ccccc1]

and R³ is of the formula:

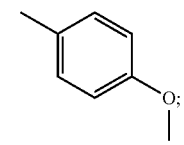

or R² is of the formula:

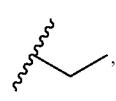

and R³ is of the formula:

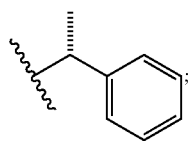 [SMILES: *[C@H](C)c1ccccc1]

or R² is of the formula:

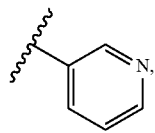 [SMILES: *c1cccnc1]

and R³ is of the formula:

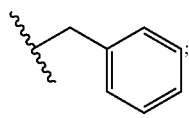 [SMILES: *Cc1ccccc1]

or R² is of the formula:

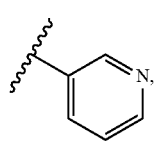 [SMILES: *c1cccnc1]

and R³ is of the formula:

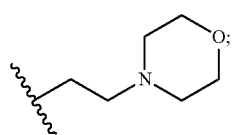 [SMILES: *CCN1CCOCC1]

or R² is of the formula:

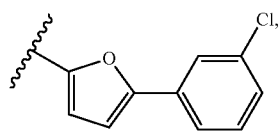 [SMILES: *c1ccc(-c2cccc(Cl)c2)o1]

and R³ is of the formula:

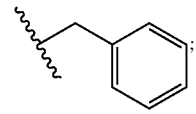

or a pharmaceutically acceptable salt or isomer thereof.

21. The polymer of claim 1, wherein the polymer is of the formula:

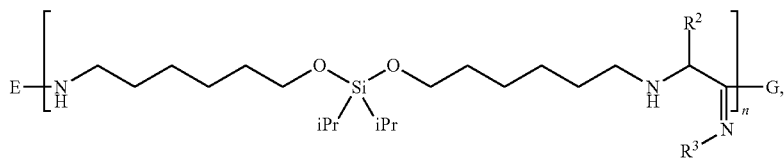

wherein:
R² is of the formula:

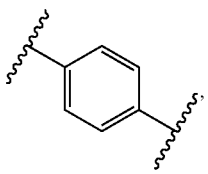 [SMILES: *c1ccc(*)cc1]

and R³ is of the formula:

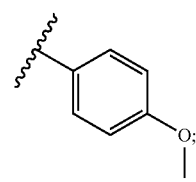 [SMILES: *c1ccc(OC)cc1]

or R² is of the formula:

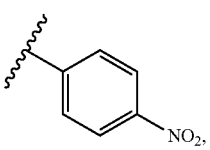 [SMILES: *c1ccc([N+](=O)[O-])cc1]

and R³ is of the formula:

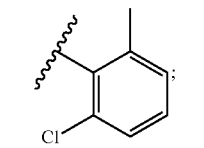

or R² is of the formula:

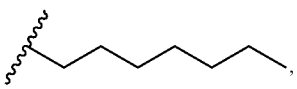

and R³ is of the formula:

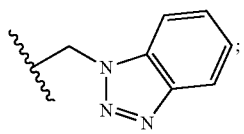 [SMILES: *Cn1nnc2ccccc21]

or R² is of the formula:

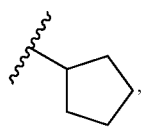 [SMILES: *C1CCCC1]

and R³ is of the formula:

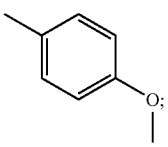

or R² is of the formula:

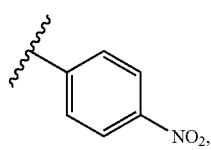

and R³ is of the formula:

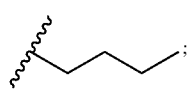 [SMILES: *CCCC]

or R² is of the formula:

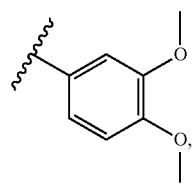 [SMILES: *c1ccc(OC)c(OC)c1]

and R³ is of the formula:

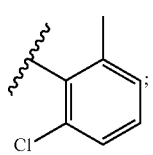 [SMILES: *c1c(C)cccc1Cl]

or R² is of the formula:

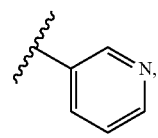

and R³ is of the formula:

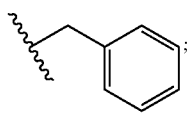 [SMILES: *Cc1ccccc1]

or a pharmaceutically acceptable salt or isomer thereof.

22. The polymer of claim 1, wherein the polymer is of the formula:

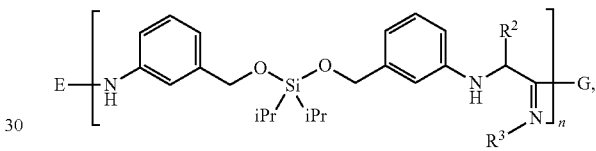

wherein:

R² is of the formula:

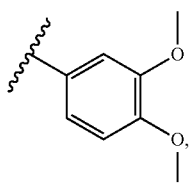 [SMILES: *c1ccc(OC)c(OC)c1]

and R³ is of the formula:

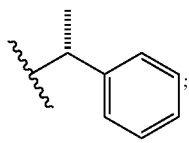 [SMILES: *[C@H](C)c1ccccc1]

or R² is of the formula:

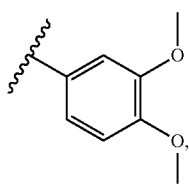 [SMILES: *c1ccc(OC)c(OC)c1]

and R³ is of the formula:

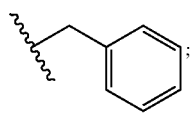 [SMILES: *Cc1ccccc1]

or R² is of the formula:

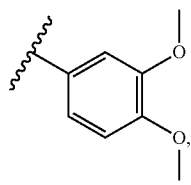

and R³ is of the formula:

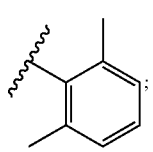 [SMILES: *c1c(C)cccc1C]

or R² is of the formula:

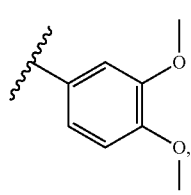 [SMILES: *c1ccc(OC)c(OC)c1]

and R³ is of the formula:

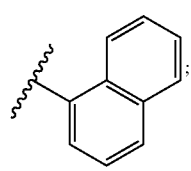 [SMILES: *c1cccc2ccccc12]

or R² is of the formula:

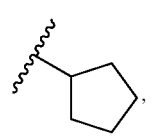 [SMILES: *C1CCCC1]

and R³ is of the formula:

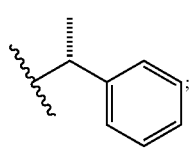 [SMILES: *[C@H](C)c1ccccc1]

or R² is of the formula:

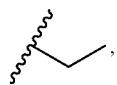

and R³ is of the formula:

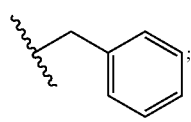

or R² is of the formula:

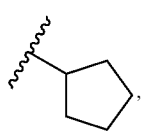 [SMILES: *C1CCCC1]

and R³ is of the formula:

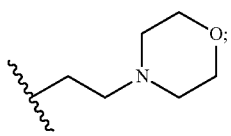 [SMILES: *CCN1CCOCC1]

or a pharmaceutically acceptable salt or isomer thereof.

23. The polymer of claim 1, wherein the polymer is of the formula:

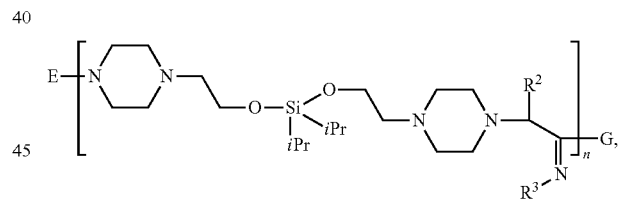

wherein:

R² is of the formula:

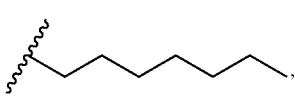 [SMILES: *CCCCCCC]

and R³ is of the formula:

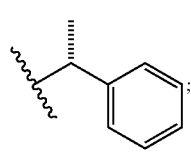 [SMILES: *[C@H](C)c1ccccc1]

$R^2$ is of the formula:
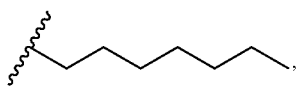
and $R^3$ is of the formula:
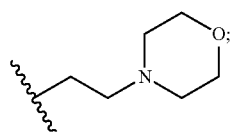 [SMILES: *CCN1CCOCC1]
or $R^2$ is of the formula:
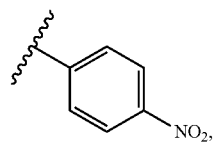 [SMILES: *c1ccc([N+](=O)[O-])cc1]
and $R^3$ is of the formula:
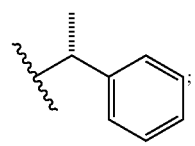 [SMILES: *[C@H](C)c1ccccc1]
or $R^2$ is of the formula:
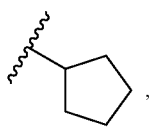 [SMILES: *C1CCCC1]
and $R^3$ is of the formula:
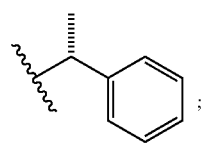 [SMILES: *[C@H](C)c1ccccc1]
or $R^2$ is of the formula:
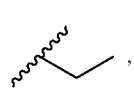
and $R^3$ is of the formula:
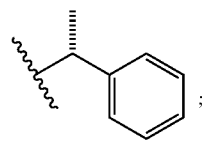 [SMILES: *[C@H](C)c1ccccc1]
or $R^2$ is of the formula:
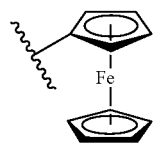
and $R^3$ is of the formula:
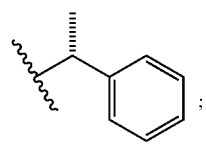 [SMILES: *[C@H](C)c1ccccc1]
$R^2$ is of the formula:
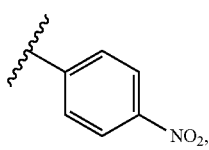 [SMILES: *c1ccc([N+](=O)[O-])cc1]
and $R^3$ is of the formula:
$R^2$ is of the formula:
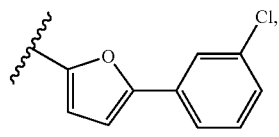 [SMILES: *c1ccc(-c2cccc(Cl)c2)o1]
and $R^3$ is of the formula:
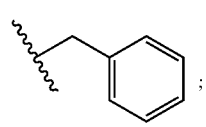 [SMILES: *Cc1ccccc1]

or R² is of the formula:

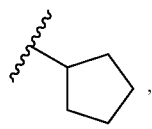 [SMILES: *C1CCCC1]

and R³ is of the formula:

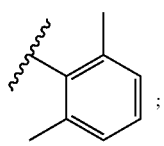 [SMILES: *c1c(C)cccc1C]

or a pharmaceutically acceptable salt or isomer thereof.

24. The composition of claim 10, wherein the agent is a polynucleotide that encodes a protein or peptide.

25. The polymer of claim 1, or a pharmaceutically acceptable salt or isomer thereof, wherein R¹ is substituted or unsubstituted, branched or unbranched, cyclic or acyclic $C_{1-20}$ aliphatic.

26. The polymer of claim 1, or a pharmaceutically acceptable salt or isomer thereof, wherein R¹ is substituted or unsubstituted, branched or unbranched, cyclic or acyclic $C_{1-20}$ aliphatic interrupted by one or more groups independently selected from —O— and —SiR⁷R⁸—.

27. The polymer of claim 1, or a pharmaceutically acceptable salt or isomer thereof, wherein R¹ is substituted or unsubstituted, branched or unbranched, cyclic or acyclic $C_{1-20}$ heteroaliphatic.

28. The polymer of claim 1, or a pharmaceutically acceptable salt or isomer thereof, wherein R¹ is a linking group comprising one or more substituted or unsubstituted, branched or unbranched, cyclic or acyclic $C_{1-20}$ heteroaliphatic, and one or more substituted or unsubstituted aryl.

29. The polymer of claim 1, or a pharmaceutically acceptable salt or isomer thereof, wherein R² is substituted or unsubstituted, branched or unbranched, cyclic or acyclic $C_{1-20}$ aliphatic.

30. The polymer of claim 1, or a pharmaceutically acceptable salt or isomer thereof, wherein R² is substituted or unsubstituted aryl, or substituted or unsubstituted heteroaryl.

31. The polymer of claim 1, or a pharmaceutically acceptable salt or isomer thereof, wherein R³ is substituted or unsubstituted, branched or unbranched, cyclic or acyclic $C_{1-20}$ aliphatic, or substituted or unsubstituted, branched or unbranched, cyclic or acyclic $C_{1-20}$ heteroaliphatic.

32. The polymer of claim 1, or a pharmaceutically acceptable salt or isomer thereof, wherein R³ is substituted or unsubstituted aryl.

33. The polymer of claim 1, or a pharmaceutically acceptable salt or isomer thereof, wherein R⁴ is hydrogen.

34. The polymer of claim 1, or a pharmaceutically acceptable salt or isomer thereof, wherein R⁴ is substituted or unsubstituted, branched or unbranched, cyclic or acyclic $C_{1-20}$ aliphatic.

35. The polymer of claim 1, or a pharmaceutically acceptable salt or isomer thereof, wherein R⁵ is hydrogen.

36. The polymer of claim 1, or a pharmaceutically acceptable salt or isomer thereof, wherein R⁵ is substituted or unsubstituted, branched or unbranched, cyclic or acyclic $C_{1-20}$ aliphatic.

37. The composition of claim 12, wherein the polynucleotide is DNA.

38. The composition of claim 12, wherein the polynucleotide is RNA.

39. The composition of claim 38, wherein the RNA is RNAi, dsRNA, siRNA, shRNA, miRNA, or antisense RNA.

40. The polymer of claim 1, wherein:
R¹ is

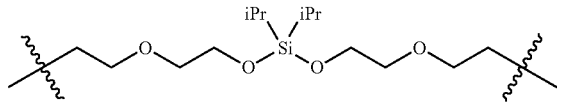 [SMILES: *CCOCCO[Si](OCCOCC*)(C(C)C)C(C)C]

R² is

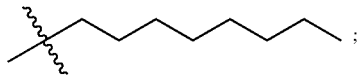 [SMILES: *CCCCCCCC]

R³ is

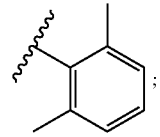

R⁴ is hydrogen; and
R⁵ is hydrogen.

* * * * *